United States Patent
Lam et al.

(10) Patent No.: US 6,503,898 B1
(45) Date of Patent: *Jan. 7, 2003

(54) SUBSTITUTED CYCLIC CARBONYLS AND DERIVATIVES THEREOF USEFUL AS RETROVIRAL PROTEASE INHIBITORS

(75) Inventors: Patrick Yuk-Sun Lam, Chadds Ford, PA (US); Prabhakar Kondaji Jadhav, Wilmington, DE (US); Charles Joseph Eyermann, Wilmington, DE (US); Carl Nicholas Hodge, Wilmington, DE (US); George Vincent De Lucca, Wilmington, DE (US); James David Rodgers, Landenberg, PA (US)

(73) Assignee: Bristol-Myers Squibb Pharma Company

( * ) Notice: Subject to any disclaimer, the term of this patent is extended or adjusted under 35 U.S.C. 154(b) by 0 days.

This patent is subject to a terminal disclaimer.

(21) Appl. No.: 09/113,905

(22) Filed: Jul. 10, 1998

Related U.S. Application Data

(60) Division of application No. 08/770,546, filed on Nov. 22, 1996, now Pat. No. 5,811,422, which is a division of application No. 08/197,630, filed on Feb. 16, 1994, now Pat. No. 5,610,294, which is a continuation-in-part of application No. 08/047,330, filed on Apr. 15, 1993, now abandoned, which is a continuation-in-part of application No. 08/023,439, filed on Feb. 26, 1993, now abandoned, which is a continuation-in-part of application No. 07/953,272, filed on Sep. 30, 1992, now abandoned, which is a continuation-in-part of application No. 07/883,944, filed on May 15, 1992, now abandoned, which is a continuation-in-part of application No. 07/776,491, filed on Oct. 11, 1991, now abandoned.

(51) Int. Cl.[7] ............ A61K 31/55; A61P 31/12; C07D 243/04

(52) U.S. Cl. ........ 514/211.08; 514/63; 514/110; 514/111; 514/218; 514/219; 514/220; 514/221; 540/487; 540/489; 540/492; 540/542; 540/545; 540/553

(58) Field of Search ............ 514/63, 110, 111, 514/218, 219, 220, 221, 211.08; 540/487, 489, 492, 542, 545, 553

(56) References Cited

U.S. PATENT DOCUMENTS

| | | | | |
|---|---|---|---|---|
| 4,644,055 A | | 2/1987 | Kettner et al. | 530/330 |
| 4,652,552 A | | 3/1987 | Kettner et al. | 514/18 |
| 5,616,578 A | * | 4/1997 | Otto | 514/218 |
| 5,683,999 A | * | 11/1997 | Jadhav et al. | 514/218 |
| 5,723,490 A | * | 3/1998 | Tung | 514/478 |
| 5,932,570 A | * | 8/1999 | Rodgers et al. | 514/218 |
| 5,945,413 A | * | 8/1999 | Tung et al. | 514/193 |
| 5,985,867 A | * | 11/1999 | Rodgers et al. | 514/218 |
| 6,100,277 A | * | 8/2000 | Tucker et al. | 514/311 |

FOREIGN PATENT DOCUMENTS

| | | |
|---|---|---|
| EP | 443848 | 8/1991 |
| WO | 87 07836 | 12/1987 |
| WO | 89 10752 | 11/1989 |
| WO | 92 09297 | 6/1992 |
| WO | 92 21647 | 12/1992 |
| WO | 93 07128 | 4/1993 |
| WO | 96 14314 | 5/1996 |

OTHER PUBLICATIONS

Mitsuya and Broder, Nature (1987) 325:773–778.

Moore et al., Biochem. Biophys. Res. Comm. (1989) 159:420–425.

Kempf et al., J. Med. Chem. (1990) 33:2687–2689.

Lam et al., (1994) Science, vol. 263, No. 5145, pp. 380–384.

* cited by examiner

Primary Examiner—Brenda Coleman

(57) ABSTRACT

This invention relates to substituted cyclic carbonyls and derivatives thereof useful as retroviral protease inhibitors, to pharmaceutical compositions comprising such compounds, and to methods of using these compounds for treating viral infection. A representative compound of the invention is the compound of formula:

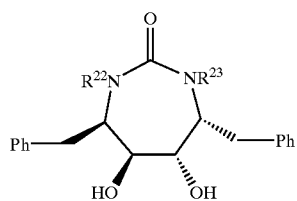

wherein $R^{22}$ and $R^{23}$ are allyl.

2 Claims, No Drawings

US 6,503,898 B1

SUBSTITUTED CYCLIC CARBONYLS AND DERIVATIVES THEREOF USEFUL AS RETROVIRAL PROTEASE INHIBITORS

CROSS-REFERENCE TO EARLIER FILED APPLICATIONS

This application is a division of U.S. patent application Ser. No. 08/770,546, filed on Nov. 22, 1996, U.S. Pat. No. 5,811,422 which is a division of U.S. patent application Ser. No. 08/197,630, filed on Feb. 16, 1994; U.S. Pat. No. 5,610,294 which is a continuation-in-part of U.S. patent application Ser. No. 08/047,330, filed Apr. 15, 1993, now abandoned which is a continuation-in-part of U.S. patent application Ser. No. 08/023,439, filed Feb. 26, 1993, now abandoned which is a continuation-in-part of U.S. patent application Ser. No. 07/953,272, filed Sep. 30, 1992, now abandoned which is a continuation-in-part of U.S. patent application Ser. No. 07/883,944, filed May 15, 1992, now abandoned which is a continuation-in-part of U.S. patent application Ser. No. 07/776,491, filed Oct. 11, 1991 now abandoned. The disclosure of these earlier filed applications is hereby incorporated herein by reference.

FIELD OF THE INVENTION

This invention relates to substituted cyclic carbonyls and derivatives thereof useful as retroviral protease inhibitors, to pharmaceutical compositions comprising such compounds, and to methods of using these compounds for treating viral infection.

BACKGROUND OF THE INVENTION

Current treatments for viral diseases usually involve administration of compounds that inhibit viral DNA synthesis. Current treatments for AIDS (Dagani, Chem. Eng. News, Nov. 23, 1987 pp. 41–49) involve administration of compounds such as 2',3'-dideoxycytidine, trisodium phosphonoformate, ammonium 21-tungsto-9-antimoniate, 1-b-D-ribofuranoxyl-1,2,4-triazole-3-carboxamide, 3'-azido-3'-deoxythymidine (AZT), and adriamycin that inhibit viral DNA synthesis; compounds such as AL-721 and polymannoacetate which may prevent HIV from penetrating the host cell; and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity, and bone marrow cytopenia.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford et al., J. Virol. 53 899 (1985); Katoh et al., Virology 145 280 (1985). Therefore, retroviral protease inhibition provides an attractive target for antiviral therapy. See Mitsuya, Nature 325 775 (1987).

Moore, Biochem. Biophys. Res. Commun., 159 420 (1989) discloses peptidyl inhibitors of HIV protease. Erickson, European Patent Application No. WO 89/10752 discloses derivatives of peptides which are inhibitors of HIV protease.

U.S. Pat. No. 4,652,552 discloses methyl ketone derivatives of tetrapeptides as inhibitors of viral proteases. U.S. Pat. No. 4,644,055 discloses halomethyl derivatives of peptides as inhibitors of viral proteases. European Patent Application No. WO 87/07836 discloses L-glutamic acid gamma-monohydroxamate as an antiviral agent.

The ability to inhibit a viral protease provides a method for blocking viral replication and therefore a treatment for viral diseases, such as AIDS, that may have fewer side effects, be more efficacious, and be less prone to drug resistance when compared to current treatments.

The present invention concerns novel substituted cyclic carbonyls and derivatives thereof, which compounds are capable of inhibiting viral protease and which compounds are believed to serve as a means of combating viral diseases, such as AIDS. The substituted cyclic carbonyls and derivatives thereof of this invention provide significant improvements over protease inhibitors that are known in the art. A large number of compounds have been reported to be inhibitors of proteases, such as renin, but these have suffered from lack of adequate bioavailability and are thus not useful as therapeutic agents, particularly if oral administration is desired. This poor activity has been ascribed to the relatively high molecular weight of most protease inhibitors, to inadequate solubility properties, and to the presence of a number of peptide bonds, which are vulnerable to cleavage by mammalian proteases in vivo and which generally cause the molecules to be extensively bound in human serum. The substituted cyclic carbonyls and derivatives described herein have a distinct advantage in this regard, in that they do not contain peptide bonds, are of low molecular weight, and can be hydrophilic yet still inhibit the viral protease enzyme.

Additionally, known inhibitors of other non-HIV proteases do not inhibit HIV protease. The structure-activity requirements of such inhibitors differ from those of HIV protease inhibitors. The substituted cyclic carbonyls and derivatives of the invention are particularly useful as inhibitors of HIV protease and similar retroviral proteases.

The compounds of the invention are of low molecular weight and may, therefore, have good oral absorption properties in mammals.

SUMMARY OF THE INVENTION

This invention provides novel substituted cyclic carbonyl compounds and derivatives thereof, of formula (I) (described below) which are useful as inhibitors of Human Immunodeficiency Virus (HIV). The compounds of the present invention inhibit the HIV protease and thereby inhibit HIV replication. The present invention also includes pharmaceutical compositions containing such compounds of formula I, and methods of using such compounds for the inhibition of HIV in a sample containing HIV, and methods of using such compounds for the treatment of HIV infection in a patient.

The present invention also includes methods of inhibiting HIV or treating HIV infection by administering a compound of formula (I) in combination with one or more second therapeutic agents selected from other inhibitors of HIV and/or therapeutic agents for the treatment of HIV-mediated disease conditions.

Also included in the present invention are pharmaceutical kits comprising one or more containers containing pharmaceutical dosage units comprising a compound of formula I, for the treatment of HIV infection.

DETAILED DESCRIPTION OF THE INVENTION

This invention provides novel substituted cyclic carbonyl compounds and derivatives thereof, of formula (I) (described below) which are useful as inhibitors of Human Immunodeficiency Virus (HIV). The compounds of the present invention inhibit the HIV protease and thereby inhibit HIV replication. The present invention also includes pharmaceutical compositions containing such compounds of formula I, and methods of using such compounds for the inhibition of HIV in a sample containing HIV, and methods of using such compounds for the treatment of HIV infection in a patient.

[1] There is provided by this invention a compound of the formula (I):

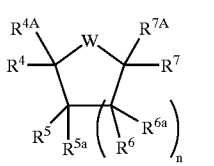

(I)

or a pharmaceutically acceptable salt or prodrug form thereof wherein:

$R^4$ and $R^7$ are independently selected from the following groups:
hydrogen;
$C_2$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or 0–3 $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$;
—$OR^{13}$; —$SR^{13}$; $CO_2R^{13}$;

$R^{4A}$ and $R^{7A}$ are independently selected from the following groups:
hydrogen;
$C_1$–$C_4$ alkyl substituted with 0–6 halogen or 0–3 $C_1$–$C_2$ alkoxy;
benzyl substituted with 0–6 halogen or 0–3 $C_1$–$C_2$ alkoxy;
—$OR^{13}$; —$SR^{13}$; $CO_2R^{13}$;

$R^4$ and $R^{4A}$ can alternatively join to form a 5–7 membered carbocyclic ring substituted with 0–2 $R^{12}$;
$R^7$ and $R^{7A}$ can alternatively join to form a 5–7 membered carbocyclic ring substituted with 0–2 $R^{12}$;
n is 0, 1, or 2;
$R^5$ is selected from H; halogen; $C_1$–$C_6$ alkyl substituted with 0–3 $R^{11}$; —$N(R^{20})_2$; —$SR^{20}$; or —$OR^{20}$, —$N_3$;
$R^6$ is independently selected from: hydrogen, halogen, $C_1$–$C_6$ alkyl substituted with 0–3 $R^{11}$, —$N(R^{20})_2$, —$SR^{20}$, or —$OR^{21}$, —$N_3$;
$R^5$ and $R^6$ can alternatively join to form an epoxide or aziridine ring; —$OCH_2SCH_2O$—; —$OC(=O)O$—; —$OCH_2O$—; —$OC(=S)O$—; —$OC(=O)C(=O)$O—; —$OC(CH_3)_2O$—; —$OC((CH_2)_3NH_2)(CH_3)O$—; —$OC(OCH_3)(CH_2CH_2CH_3)O$—; —$OS(=O)O$—; —$NHC(=O)NH$—; —$OC(=O)NH$—; —$NHC(=O)O$—; —$NHCH_2O$—; —$OCH_2NH$—; —$NHC(=S)O$—; —$OS(=O)NH$—; —$NHC(=O)C(=O)O$—; —$OC(=O)C(=O)NH$—; —$NHC(=O)C(=O)NH$—; —$NHC(CH_3)_2O$—; —$OC(CH_3)_2NH$— or any group that, when administered to a mammalian subject, cleaves to form a free dihydroxyl or diamino or hydroxyl and amino;

$R^{5a}$ is selected from hydrogen, halogen, $C_1$–$C_6$ alkyl, —$N(R^{20})_2$, —$SR^{20}$, or —$OR^{20}$;
$R^6$ a is selected from: hydrogen, halogen, $C_1$–$C_6$ alkyl, —$N(R^{20})_2$, —$SR^{20}$ or —$OR^{21}$;
$R^5$ and $R^{5a}$ can alternatively join to form =O, =S, or a ketal ring;
$R^6$ and $R^{6a}$ can alternatively join to form =O, =S, or a ketal ring;
$R^{20}$ and $R^{21}$ are independently selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
$C_1$–$C_6$ alkylaminocarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$; or
any group that, when administered to a mammalian subject, cleaves to form a free hydroxyl, amino or sulfhydryl;

$R^{11}$ is selected from one or more of the following:
H, keto, halogen, cyano, —$CH_2NR^{13}R^{14}$, —$NR^{13}R^{14}$, —$CO_2R^{13}$, —$OC(=O)R^{13}$, —$OR^{13}$, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, —$OP(O)(OR^{13})_2$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, pyridylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;
1–3 amino acids linked together via amide bonds, said amino acid being linked via the amine or carboxylate terminus;
$C_3$–$C_{10}$ cycloalkyl substituted with 0–2 $R^{12}$;
$C_1$–$C_4$ alkyl substitued with 0–2 $R^{12}$ aryl($C_1$–$C_3$ alkyl)-, substituted with 0–2 $R^{12}$;
$C_2$–$C_6$ alkoxyalkyl-, substituted with 0–2 $R^{12}$;
$C_1$–$C_4$ alkylcarbonyloxy substituted with 0–2 $R^{12}$,
$C_6$–$C_{10}$ arylcarbonyloxy substituted with 0–2 $R^{12}$,
a $C_5$–$C_{14}$ carbocyclic residue substituted with 0–3 $R^{12}$;
a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:
H, keto, halogen, cyano, —$CH_2N(R^{13A})R(^{14A})$, —$N(R^{13A})R(^{14A})$, —$CO_2H$, —$OC(=O)(C_1$–$C_3$ alkyl), —$OH$, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, aryl ($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system substituted with 0–3 $R^{12A}$.

$R^{12}$, when a substituent on carbon, is selected from one or more of the following:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_m R^{13}$, —$SO_2NR^{13}R^{14}$, —$NHSO_2R^{14}$, —$OCH_2CO_2R^{13}$, 2-(1-morpholino)ethoxy, —$C(R^{14})=N(OR^{14})$; or
  a 5- or 6-membered heterocyclic ring containing from 1 to 4 heteroatoms independently selected from oxygen, nitrogen or sulfur;
  or $R^{12}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{12}$ is attached to a saturated carbon atom, it may be =O or =S; or when $R^{12}$ is attached to sulfur it may be =O.

$R^{12}$, when a substituent on nitrogen, is selected from one or more of the following:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{12A}$, when a substituent on carbon, is selected from one or more of the following:
  phenyl, benzyl, phenethyl, phenoxy, benzyloxy, halogen, hydroxy, nitro, cyano $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, $C_1$–$C_4$ alkyl substituted with —$NH_2$, —$NH_2$, —NHMe, $C_2$–$C_6$ alkoxyalkyl optionally substituted with $Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_m$Me, —$SO_2NH_2$, —$NHSO_2$Me, —$OCH_2CO_2R^{13}$, 2-(1-morpholino)ethoxy, —$C(=NOH)NH_2$; or
  a 5- or 6-membered heterocyclic ring containing from 1 to 4 heteroatoms independently selected from oxygen, nitrogen or sulfur;
  or $R^{12A}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NH_2$; or, when $R^{12A}$ is attached to a saturated carbon atom, it may be =O or =S; or when $R^{12}$ is attached to sulfur it may be =O.

$R^{12A}$, when a substituent on nitrogen, is selected from one or more of the following:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(=NOH)NH_2$;

$R^{13}$ is selected from:
  H;
  phenyl substituted with 0–3 $R^{11A}$;
  benzyl substituted with 0–3 $R^{11A}$;
  $C_1$–$C_6$ alkyl substituted with 0–3 $R^{11A}$;
  $C_2$–$C_4$ alkenyl substituted with 0–3 $R^{11A}$;
  $C_1$–$C_6$ alkylcarbonyl substituted with 0–3 $R^{11A}$;
  $C_1$–$C_6$ alkoxycarbonyl substituted with 0–3 $R^{11A}$;
  $C_1$–$C_6$ alkylaminocarbonyl substituted with 0–3 $R^{11A}$;
  $C_3$–$C_6$ alkoxyalkyl substituted with 0–3 $R^{11A}$;
  an amine protecting group when $R^{13}$ is bonded to N;
  a hydroxy protecting group when $R^{13}$ is bonded to O;

$R^{14}$ is hydrogen, hydroxy, $C_1$–$C_6$ alkyl substituted with 0–3 groups selected from OH, $C_1$–$C_4$ alkoxy, halogen, $NH_2$, —$NH(C_1$–$C_4$ alkyl), $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

W is selected from:
  —$N(R^{22})C(=Z)N(R^{23})$—;
  —$OC(=Z)O$—;
  —$N(R^{22})C(=Z)O$—;
  —$C(R^{25})(R^{26})C(=Z)C(R^{27})(R^{28})$—;
  —$N(R^{22})C(=Z)C(R^{27})(R^{28})$—;
  —$C(R^{25})(R^{26})C(=Z)O$—;
  —$N(R^{22})C(=Z)C(=Z)N(R^{23})$—;
  —$C(R^{25})(R^{26})C(F_2)C(R^{27})(R^{28})$—;
  —$C(R^{25})(R^{26})N(CH_3)(O)C(R^{27})(R^{28})$—;
  —$C(R^{25})(R^{26})N(OR^{29})C(R^{27})(R^{28})$—;
  —$C(R^{25})(R^{26})C(=Z)S$—;
  —$N(R^{22})S(=Z')N(R^{23})$—;
  —$N(R^{22})S(=Z')_2N(R^{23})$—;
  —$N(R^{22})P(=O)(R^{24a})N(R^{23})$—;
  —$C(R^{25})(R^{26})S(=Z')C(R^{27})(R^{28})$—;
  —$C(R^{25})(R^{26})S(=Z')_2C(R^{27})(R^{28})$—;
  —$C(R^{25})(R^{26})P(=O)(R^{24a})C(R^{27})(R^{28})$—;
  —$C(R^{25})(R^{26})S(=Z')N(R^{23})$—;
  —$C(R^{25})(R^{26})S(=Z')_2N(R^{23})$—;
  —$C(R^{25})(R^{26})S(=O)_2O$—;
  —$C(R^{25})(R^{26})P(=O)(R^{24a})N(R^{23})$—;

—C($R^{25}$)($R^{26}$)P(=O)($R^{24a}$)O—;
—C($R^{25}$)C($F_2$)C(=O)N($R^{23}$)—;
—C($R^{25}$)C($F_2$)S(=O)$_2$N($R^{23}$)—;
—SC(=Z)—;
—C($R^{25}$)($R^{26}$)C($R^{34}$)($R^{35}$)C($R^{27}$)($R^{28}$)—;
—N($R^{22}$)C($R^{34}$)($R^{35}$)N($R^{23}$)—;
—N=C($R^{36}$)N($R^{23}$)—;
—N$^+$($R^{22}$)=C($R^{36}$)N($R^{23}$)—;
—N($R^{22}$)P($R^{24a}$)N($R^{23}$)—;
—C(=Z)—;
—P(=O)($R^{24a}$)—;
—S(=Z')—;
—S(=Z')$_2$—;
—N($R^{22}$)C(=C($R^{36a}$)($R^{36b}$))N($R^{23}$)—
—N($R^{22}$)C(=Z)N($R^{23}$)C(=Z)— wherein:

Z is O, S, N$R^{24}$;

Z' is O or N$R^{24}$;

$R^{22}$ and $R^{23}$ are independently selected from the following:
hydrogen; —O$R^{22a}$; —N($R^{22a}$)($R^{22b}$);
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or 0–5 $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;

$R^{22a}$ and $R^{22b}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or 0–5 $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;

$R^{24}$ is selected from: hydrogen; hydroxy; amino; $C_1$–$C_4$ alkyl; $C_1$–$C_4$ alkoxy; mono- or di-($C_1$–$C_6$ alkyl)amino; cyano; nitro; benzyloxy; —NHSO$_2$aryl, aryl being optionally substituted with ($C_1$–$C_6$)alkyl;

$R^{24a}$ is selected from: hydroxy; amino; $C_1$–$C_4$ alkyl; $C_1$–$C_4$ alkoxy; mono- or di-($C_1$–$C_6$ alkyl)amino; cyano; nitro; benzyloxy; or phenoxy;

$R^{25}$ and $R^{27}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or 0–5 $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;
—O$R^{13}$; —S$R^{13}$;

$R^{26}$ and $R^{28}$ are independently selected from:
hydrogen;
halogen;
$C_1$–$C_4$ alkyl substituted with 0–3 halogen or 0–3 $C_1$–$C_2$ alkoxy;
benzyl substituted with 0–3 halogen or 0–3 $C_1$–$C_2$ alkoxy;
—O$R^{13}$; —S$R^{13}$;

$R^{29}$ is selected from:
hydrogen;
$C_1$–$C_4$ alkyl substituted with 0–3 halogen or 0–3 $C_1$–$C_2$ alkoxy;
benzyl substituted with 0–3 halogen or 0–3 $C_1$–$C_2$ alkoxy;

alternatively, $R^{22}$, $R^{25}$, or $R^{26}$, independently, can join with $R^4$ or $R^{4A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$, $R^{27}$, or $R^{28}$, independently, can join with $R^7$ or $R^{7A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$, $R^{25}$, $R^{26}$, $R^{23}$, $R^{27}$, $R^{28}$, $R^{34}$, or $R^{35}$ can join with $R^5$ or $R^6$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$, $R^{25}$, $R^{26}$, $R^{23}$, $R^{27}$, $R^{28}$, $R^{34}$, or $R^{35}$ are taken together with $R^5$ or $R^6$ to form a direct bond);

alternatively $R^{28}$ or $R^{23}$ can join with $R^{7A}$ to form a direct bond;

alternatively $R^{26}$ or $R^{22}$ can join with $R^{4A}$ to form a direct bond;

$R^{31}$ is selected from one or more of the following:
keto, halogen, cyano, —CH$_2$N$R^{13}R^{14}$, —N$R^{13}R^{14}$, —CO$_2R^{13}$, —C(=O)$R^{11}$, —OC(=O)$R^{13}$, —O$R^{13}$, $C_2$–$C_6$ alkoxyalkyl, —S(O)$_mR^{13}$, —NHC(=NH)NH$R^{13}$, —C(=NH)NH$R^{13}$, —C(=O)N$R^{13}R^{14}$, —N$R^{14}$C(=O)$R^{13}$, =NO$R^{14}$, —N$R^{14}$C(=O)$R^{14}$, —OC(=O)N$R^{13}R^{14}$, —N$R^{13}$C(=O) N$R^{13}R^{14}$, —N$R^{13}$C(=S)N$R^{13}R^{14}$, —N$R^{14}$SO$_2$N$R^{13}R^{14}$, —N$R^{14}$SO$_2R^{13}$, SO$_2$N$R^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —N$R^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2R^{13}$, 2-(1-morpholino)ethoxy, azido, —C($R^{14}$)=N(O$R^{14}$); or 1–3 amino acids, linked together via amide bonds, said amino acid being linked via the amine or carboxylate terminus;

a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, sulfonamide, —CHO, $C_3$–$C_6$ cycloalkoxy, —$NR^{13}R^{14}$, —$C(R^{14})$=$N(OR^{14})$, $NO_2$, —$OR^{13}$, —$NR^{40}R^{41}$, —$SO_mR^{13}$, —$SO_mNR^{13}R^{14}$, —C(=O)$NR^{13}R^{14}$, —OC(=O)$NR^{13}R^{14}$, —C(=O)$R^{11}$, —OC(=O)$R^{11}$, —$OCO_2R^{13}$, phenyl, —C(=O)$NR^{13}$—($C_1$–$C_4$ alkyl)—$NR^{13}R^{14}$, —C(=O)$NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or
—C(=O) $NR^{13}C(R^{11})_2NR^{13}R^{14}$;
—C(=O)$NR^{13}C(R^{11})_2NR^{13}CO_2R^{13}$;
—C(=O)$NR^{13}$—($C_1$–$C_4$ alkyl)—$NR^{13}CO_2R^{13}$;
—C(=O)$N(R^{13})$—($C_1$–$C_4$ alkyl)—$R^{11}$; or
—C(=O)$C(R^{11})_2NR^{13}R^{14}$;
—C(=O)$C(R^{11})_2NR^{13}CO_2R^{13}$;
—C(=O)—($C_1$–$C_4$ alkyl)—$NR^{13}R^{14}$;
—C(=O)—($C_1$–$C_4$ alkyl)—$NR^{13}CO_2R^{13}$; or
$C_1$–$C_4$ alkoxy substituted with 0–4 groups selected from: $R^{11}$, $C_3$–$C_6$ cycloalkyl, —$CO_2R^{13}$, —C(=O)$NR^{13}R^{14}$, —$NR^{13}R^{14}$ or OH;
$C_1$–$C_4$ alkyl substituted with 0–4 groups selected from: $R^{11}$, =$NR^{14}$, =$NNR^{13}C(=O)NR^{13}R^{14}$, =$NNR^{13}C(=O)OR^{13}$, or —$NR^{13}R^{14}$;
$C_2$–$C_4$ alkenyl substituted with 0–4 $R^{11}$;
$C_2$–$C_4$ alkynyl substituted with 0–4 $R^{11}$;
a 5- or 6-membered heterocyclic ring containing from 1 to 4 heteroatoms independently selected from oxygen, nitrogen or sulfur, substituted with 0–2 $R^{12}$;
or $R^{32}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{32}$ is attached to a saturated carbon atom, it may be =O, =S, =NOH; or when $R^{32}$ attached to sulfur it may be =O.

$R^{32}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})$=$N(OR^{14})$;

$R^{34}$ is selected from:
hydrogen;
$OR^{13}$;
$SR^{13}$;
halogen;
$N(R^{38})(R^{39})$
$C_1$–$C_6$ alkyl substituted with 0–3 $R^{11}$;
$C_1$–$C_6$ alkoxy substituted with 0–3 $R^{11}$;
$C_1$–$C_6$ thioalkyl substituted with 0–3 $R^{11}$;

$R^{35}$ is selected from:
hydrogen;
$OR^{13}$;
$SR^{13}$;
halogen;
$N(R^{38})(R^{39})$
$C_1$–$C_6$ alkyl substituted with 0–3 $R^{11}$;
$C_1$–$C_6$ alkoxy substituted with 0–3 $R^{11}$;
$C_1$–$C_6$ thioalkyl substituted with 0–3 $R^{11}$;

$R^{34}$ and $R^{35}$ can be taken together to form a ketal ring, a 3- to 8-membered carbocyclic ring, or a 5- or 6-membered heterocyclic ring containing 1–3 heteroatoms independently selected from the group O, N, or S, said ring substituted with 0–5 $R^{11}$;

$R^{36}$ is selected from:
H
$C_1$–$C_6$ alkyl substituted with 0–3 $R^{11}$;
—$COR^{37}$;
—$NR^{38}R^{39}$;
—CN;
—$NO_2$ $R^{37}$ is selected from:
hydrogen;
$C_1$–$C_6$ alkyl substituted with 0–3 $R^{11}$;
hydroxyl;
$C_1$–$C_6$ alkoxy substituted with 0–3 $R^{11}$;
—$NR^{38}R^{39}$;

$R^{38}$ and $R^{39}$ are independently selected from:
hydrogen;
$C_1$–$C_6$ alkyl substituted with 0–3 $R^{11}$; or
an amine protecting group;

$R^{40}$ is selected from: H, $C_1$–$C_3$ alkyl;

$R^{41}$ is selected from:
—C(=O) $NR^{13}R^{14}$;
—C(=O) $NR^{13}NR^{13}R^{14}$;
—C(=O)$C(R^{11})_2NR^{13}R^{14}$;
—C(=O)$C(R^{11})_2NR^{13}NR^{13}R^{14}$;
—C(=O)$C(R^{11})_2NR^{13}CO_2R^{13}$;
—C(=O)H;
—C(=O)$R^{11}$;
—C(=O)—($C_1$–$C_4$ alkyl)—$NR^{13}R^{14}$;
—C(=O)—($C_1$–$C_4$ alkyl)—$NR^{13}CO_2R^{13}$;
1–3 amino acids linked together via amide bonds, and linked to the N atom via the carboxylate terminus;

provided that:
$R^4$, $R^{4A}$, $R^7$ and $R^{7A}$ are not all hydrogen;
when W is —OC(=Z)O—, —SC(=Z)—, —C(=Z)—, —P(=O)($R^{24a}$)—, —S(=Z')— or —S(=Z')$_2$—, $R^4$ and $R^7$ are not hydrogen;
when $R^4$, $R^{4A}$ are hydrogen, at least one of the following is not hydrogen: $R^{22}$, $R^{25}$, and $R^{26}$.

[2] Preferred compounds include those compounds described above wherein:
when W is
—C(=Z)—;
—P(=O)($R^{24a}$)—;
—S(=Z')$_2$—;
then n is 1 or 2.

[3] Preferred compounds include those compounds described above wherein:
$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
$C_3$–$C_8$ cycloalkyl substituted with 0–3 $R^{11}$;
$C_6$–$C_{10}$ bicycloalkyl substituted with 0–3 $R^{11}$;
aryl substituted with 0–3 $R^{12}$;
a $C_6$–$C_{14}$ partially unsaturated carbocyclic residue substituted with 0–3 $R^{12}$;
a 5- to 6-membered heterocyclic ring system containing 1 to 3 heteroatoms independently selected from oxygen, nitrogen or sulfur, said heterocyclic ring system being substituted with 0–2 $R^{12}$;

$R^{22}$ and $R^{23}$ are independently selected from the following:

hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
$C_3$–$C_8$ cycloalkyl substituted with 0–3 $R^{31}$;
$C_6$–$C_{10}$ bicycloalkyl substituted with 0–3 $R^{31}$;
aryl substituted with 0–5 $R^{32}$;
a $C_6$–$C_{14}$ partially unsaturated carbocyclic residue substituted with 0–3 $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;

$R^{25}$ and $R^{27}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
$C_3$–$C_8$ cycloalkyl substituted with 0–3 $R^{31}$;
$C_6$–$C_{10}$ bicycloalkyl substituted with 0–3 $R^{31}$;
aryl substituted with 0–5 $R^{32}$;
a $C_6$–$C_{14}$ partially unsaturated carbocyclic residue substituted with 0–3 $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$.

[4] Preferred compounds of this invention are those compounds described above with the proviso that when:
W is —C($R^{25}$)($R^{26}$)C(=Z)C($R^{27}$)($R^{28}$)—; and
n=0; and
Z is O;
then $R^{25}$, $R^{26}$, $R^{27}$, and $R^{28}$ are not all H.

[5] Preferred compounds of this invention are those compounds described above with the proviso that when:
W is —C($R^{25}$)($R^{26}$)S(=Z')C($R^{27}$)($R^{28}$)—; and
n=0; and
Z' is O;
then $R^{25}$, $R^{26}$, $R^{27}$, and $R^{28}$ are not all H.

[6] Preferred compounds of this invention are those compounds described above with the proviso that when:
W is —C($R^{25}$)($R^{26}$)S(=Z)$_2$C($R^{27}$)($R^{28}$)—; and
n=0; and
Z' is O or NH;
then $R^{25}$, $R^{26}$, $R^{27}$, and $R^{28}$ are not all H.

[7] Preferred compounds of this invention are those compounds described above with the proviso that when:
W is —S(=O)— or —S(=O)$_2$—; and
n=1;
then $R^6$ and $R^{6a}$ are not both H.

[8] Preferred compounds of this invention are those compounds described above with the proviso that when:
W is —C($R^{25}$)($R^{26}$)C($R^{34}$)($R^{35}$)C($R^{27}$)($R^{28}$)—; and
n=0; and
$R^{34}$ or $R^{35}$ are N($R^{38}$)($R^{39}$);
then $R^{25}$, $R^{26}$, $R^{27}$, and $R^{28}$ are not all H.

[9] Preferred compounds of this invention are compounds of the formula (I):

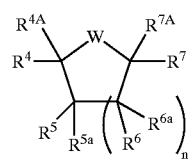

(I)

or a pharmaceutically acceptable salt or prodrug form thereof wherein:
$R^4$ and $R^7$ are independently selected from the following groups:
hydrogen;
$C_1$–$C_4$ alkyl substituted with 0–3 $R^{11}$;
$C_3$–$C_4$ alkenyl substituted with 0–3 $R^{11}$;
$C_3$–$C_4$ alkynyl substituted with 0–3 $R^{11}$;
$R^{4A}$ and $R^{7A}$ are hydrogen;
$R^5$ is selected from fluoro, —O$R^{20}$, —N($R^{20}$)$_2$;
$R^6$ is independently selected from: hydrogen, fluoro or —O$R^{21}$;
$R^5$ and $R^6$ can alternatively join to form an epoxide or aziridine ring; —OCH$_2$SCH$_2$O—; —OS(=O)O—; —OC(=O)O—; —OCH$_2$O—; —OC(=S)O—; —OC(=O)C(=O)O—; —OC(CH$_3$)$_2$O—; —OC(OCH$_3$)(CH$_2$CH$_2$CH$_3$)O—; or any group that, when administered to a mammalian subject, cleaves to form a free dihydroxyl;
$R^{5a}$ is selected from hydrogen or fluoro;
$R^{6a}$ is selected from: hydrogen or fluoro;
$R^5$ and $R^{5a}$ can alternatively join to form =O, =S, or a ketal ring;
$R^6$ and $R^{6a}$ can alternatively join to form =O, =S, or a ketal ring;
$R^{20}$ and $R^{21}$ are independently selected from:
hydrogen;
$C_1$–$C_6$ alkylcarbonyl;
$C_1$–$C_6$ alkoxycarbonyl;
benzoyl; or
any group that, when administered to a mammalian subject, cleaves to form a free hydroxyl;
$R^{11}$ is selected from one or more of the following:
H, keto, halogen, cyano, —CH$_2$N$R^{13}R^{14}$, —N$R^{13}R^{14}$, —CO$_2R^{13}$, —OC(=O)$R^{13}$, —O$R^{13}$, $C_2$–$C_4$ alkoxyalkyl, —S(O)$_m R^{13}$, $C_1$–$C_4$ alkyl, $C_2$–$C_4$ alkenyl, $C_3$–$C_{10}$ cycloalkyl;
a $C_5$–$C_{14}$ saturated or partially unsaturated carbocyclic residue substituted with 0–3 $R^{12}$;
aryl($C_1$–$C_3$ alkyl)-, substituted with 0–2 $R^{12}$;
aryl substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;
$R^{12}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, 2-(1-morpholino)ethoxy, —CO$_2$H, hydroxamic acid, hydrazide, —C($R^{14}$)=N(O$R^{14}$), cyano, boronic acid, sulfonamide, formyl, $C_3$–$C_6$ cycloalkoxy, —O$R^{13}$, $C_1$–$C_4$ alkyl substituted with —N$R^{13}R^{14}$, —N$R^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$R$^{13}$, —SO$_2$NR$^{13}$R$^{14}$, —NHSO$_2$R$^{14}$; or a 5- or 6-membered heterocyclic ring containing from 1 to 4 heteroatoms independently selected from oxygen, nitrogen or sulfur;

or R$^{12}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —NR$^{13}$R$^{14}$; or, when R$^{12}$ is attached to a saturated carbon atom, it may be =O or =S; or when R$^{12}$ is attached to sulfur it may be =O.

R$^{12}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$NR$^{13}$R$^{14}$, —NR$^{13}$R$^{14}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl, —CO$_2$H;

R$^{13}$ is H, $C_1$–$C_6$ alkyl, $C_3$–$C_6$ alkoxyalkyl, $C_2$–$C_4$ alkenyl, phenyl, or benzyl;

R$^{14}$ is OH, H, CF$_3$, $C_{1-C4}$ alkyl, $C_{1-C4}$ alkoxy, NH$_2$, $C_{2-C4}$ alkenyl, phenyl, or benzyl;

R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

W is selected from:
—N(R$^{22}$)C(=Z)N(R$^{23}$)—;
—N(R$^{22}$)C(=Z) O—;
—C(R$^{25}$)(R$^{26}$)C(=Z)C(R$^{27}$)(R$^{28}$)—;
—N(R$^{22}$)C(=Z)C(R$^{27}$)(R$^{28}$)—;
—C(R$^{25}$)(R$^{26}$)C(=Z)O—;
—N(R$^{22}$)C(=O)C(=O)N(R$^{23}$)—;
—C(R$^{25}$)(R$^{26}$)C(F$_2$)C(R$^{27}$)(R$^{28}$)—;
—C(R$^{25}$)(R$^{26}$)N(CH$_3$)(O)C(R$^{27}$)(R$^{28}$)—;
—C(R$^{25}$)(R$^{26}$)N(OR$^{29}$)C(R$^{27}$)(R$^{28}$)—;
—C(R$^{25}$)(R$^{26}$)C(=Z)S—;
—N(R$^{22}$)S(=Z')N(R$^{23}$)—;
—N(R$^{22}$)S(=Z')$_2$N(R$^{23}$)—;
—N(R$^{22}$)P(=O)(R$^{24a}$)(N(R$^{23}$)—;
—C(R$^{25}$)(R$^{26}$)S(=Z')C(R$^{27}$)(R$^{28}$)—;
—C(R$^{25}$)(R$^{26}$)S(=Z')$_2$C(R$^{27}$)(R$^{28}$)—;
—C(R$^{25}$)(R$^{26}$)P(=O)(R$^{24a}$)C(R$^{27}$)(R$^{28}$)—;
—C(R$^{25}$)(R$^{26}$)S(=Z')N(R$^{23}$)—;
—C(R$^{25}$)(R$^{26}$)S(=Z')$_2$N(R$^{23}$)—;
—C(R$^{25}$)(R$^{26}$)S(=O)$_2$O—;
—C(R$^{25}$)(R$^{26}$)P(=O)(R$^{24a}$)N(R$^{23}$)—;
—C(R$^{25}$)(R$^{26}$)P(=O)(R$^{24a}$)O—;
—C(R$^{25}$)C(F$_2$)C(=O)N(R$^{23}$)—;
—C(R$^{25}$)C(F$_2$)S(=O)$_2$N(R$^{23}$)—;
—C(R$^{25}$)(R$^{26}$)C(R$^{34}$)(R$^{35}$)C(R$^{27}$)(R$^{28}$)—;
—N=C(R$^{36}$)N(R$^{23}$)—;
—N(R$^{22}$) p(R$^{24a}$)N(R$^{23}$)—;
—C(=Z)—;
—P(=O)(R$^{24a}$)—;
—S(=Z')—;
—S(=Z')$_2$—;

wherein:
Z is O, S, N—CN, N—OH, N—OCH$_3$;
Z' is oxygen;

R$^{22}$ and R$^{23}$ are independently selected from the following:
hydrogen;
$C_1$–$C_8$ alkyl substituted with 0–3 R$^{31}$;
$C_3$–$C_8$ alkenyl substituted with 0–3 R$^{31}$;
$C_3$–$C_8$ alkynyl substituted with 0–3 R$^{31}$;
$C_3$–$C_6$ cycloalkyl substituted with 0–3 R$^{31}$;

R$^{24a}$ is selected from —OH, $C_1$–$C_4$ alkoxy, mono- or di-($C_1$–$C_6$ alkyl)amino;

R$^{25}$ and R$^{27}$ are independently selected from the following:
hydrogen;
$C_1$–$C_8$ alkyl substituted with 0–3 R$^{31}$;
$C_2$–$C_8$ alkenyl substituted with 0–3 R$^{31}$;
$C_3$–$C_8$ alkynyl substituted with 0–3 R$^{31}$;

R$^{26}$ and R$^{28}$ are hydrogen or halogen;

R$^{29}$ is selected from:
hydrogen;
$C_1$–$C_2$ alkyl substituted with 0–2 $C_1$–$C_2$ alkoxy;
benzyl substituted with 0–2 halogen or 0–2 $C_1$–$C_2$ alkoxy;

R$^{31}$ is selected from one or more of the following:
keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, $C_2$–$C_4$ alkoxyalkyl, —S(O)$_m$R$^{13}$, $C_1$–$C_4$ alkyl, $C_2$–$C_4$ alkenyl, $C_3$–$C_{10}$ cycloalkyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —NR$^{13}$R$^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, —C(R$^{14}$)=N(OR$^{14}$); or a $C_5$–$C_{14}$ saturated or partially unsaturated carbocyclic residue substituted with 0–3 R$^{32}$;

aryl substituted with 0–3 R$^{32}$; or a 5- to 10-membered heterocyclic ring system containing 1 to 4 heteroatoms independently selected from oxygen, nitrogen or sulfur, said heterocyclic ring system being substituted with 0–2 R$^{32}$;

R$^{32}$, when a substituent on carbon, is selected from one or more of the following:
phenethyl, phenoxy, $C_3$–$C_6$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —NHSO$_2$R$^{14}$, benzyloxy, halogen, 2-(1-morpholino)ethoxy, —CO$_2$R$^{13}$, hydroxamic acid, —CONR$^{13}$NR$^{13}$R$^{14}$, cyano, sulfonamide, —CHO, $C_3$–$C_6$ cycloalkoxy, —NR$^{13}$R$^{14}$, —C(R$^{14}$)=N(OR$^{14}$), —NO$_2$, —OR$^{13}$, —NR$^{40}$R$^{41}$, SO$_m$NR$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$, phenyl, —C(=O)NR$^{13}$—($C_1$–$C_4$ alkyl)—NR$^{13}$R$^{14}$, —C(=O)NR$^{40}$R$^{41}$, $C_1$–$C_4$ haloalkyl, $C_1$–$C_4$ haloalkoxy, $C_2$–$C_4$ haloalkenyl, $C_2$–$C_4$ haloalkynyl, or
—C(=O) NR$^{13}$C(R$^{11}$)$_2$NR$^{13}$R$^{14}$;
—C(=O) NR$^{13}$C(R$^{11}$)$_2$NR$^{13}$CO$_2$R$^{13}$;
—C(=O)NR$^{13}$—($C_1$–$C_4$ alkyl)—NR$^{13}$CO$_2$R$^{13}$; or
—C(=O)C(R$^{11}$)$_2$NR$^{13}$R$^{14}$;
—C(=O)C(R$^{11}$)$_2$NR$^{13}$CO$_2$R$^{13}$; —C(=O)—($C_1$–$C_4$ alkyl)—NR$^{13}$R$^{14}$;
—C(=O)—($C_1$–$C_4$ alkyl)—NR$^{13}$CO$_2$R$^{13}$; or
$C_1$–$C_4$ alkoxy substituted with 0–3 groups selected from: R$^{11}$, $C_3$–$C_6$ cycloalkyl, —CO$_2$R$^{13}$, —C(=O)NR$^{13}$R$^{14}$, —NR$^{13}$R$^{14}$ or OH;

$C_1$–$C_4$ alkyl substituted with 0–3 groups selected from:
  $R^{11}$, =$NR^{14}$, =$NNR^{13}C(=O)NR^{13}R^{14}$ or
  —$NR^{13}R^{14}$;
$C_2$–$C_4$ alkenyl substituted with 0–3 $R^{11}$;
$C_2$–$C_4$ alkynyl substituted with 0–3 $R^{11}$;
a 5- or 6-membered heterocyclic ring containing from 1 to 4 heteroatoms independently selected from oxygen, nitrogen or sulfur, substituted with 0–2 $R^{12}$;
or $R^{32}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{32}$ is attached to a saturated carbon atom, it may be =O or =S; or when $R^{12}$ is attached to sulfur it may be =O.

$R^{32}$, when a substituent on nitrogen, is selected from one or more of the following:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl, —$CO_2H$, —$C(R^{14})=N(OR^{14})$;

$R^{34}$ is selected from:
  hydrogen;
  $C_1$–$C_2$ alkyl substituted with 0–1 $R^{11}$
  $C_1$–$C_2$ alkoxy substituted with 0–1 $R^{11}$ $R^{35}$ is selected from:
  hydrogen
  $C_1$–$C_2$ alkyl substituted with 0–1 $R^{11}$
  $C_1$–$C_2$ alkoxy substituted with 0–1 $R^{11}$ $R^{34}$ and $R^{35}$ can be taken together to form a ketal ring, a 3- to 8-membered carbocyclic ring, or a 5- or 6-membered heterocyclic ring containing 1–3 heteroatoms independently selected from the group O, N, or S;

$R^{36}$ is selected from:
  $C_1$–$C_2$ alkyl substituted with 0–3 $R^{11}$;
  $COR^{37}$;
  $NR^{38}R^{39}$;
  CN;

$R^{37}$ is selected from:
  hydrogen;
  $C_1$–$C_2$ alkyl substituted with 0–1 $R^{11}$;
  hydroxyl;
  $C_1$–$C_2$ alkoxy substituted with 0–1 $R^{11}$;
  $NR^{38}R^{39}$;

$R^{38}$ and $R^{39}$ are independently selected from:
  hydrogen;
  $C_1$–$C_2$ alkyl substituted with 0–3 $R^{11}$; or
  an amine protecting group;

provided that:
  $R^4$, $R^{4A}$, $R^7$, and $R^{7A}$ are not all hydrogen;
  when W is —OC(=Z)O—, —C(=Z)—, —P(=O)($R^{24a}$)—, —S(=Z')— or —S(=Z')_2—, $R^4$ and $R^7$ are not hydrogen;
  when $R^4$ and $R^{4A}$ are hydrogen, at least one of the following is not hydrogen: $R^{22}$, $R^{25}$, and $R^{26}$.

[10] Further preferred compounds of the invention of formula (I) are compounds of formula (II):

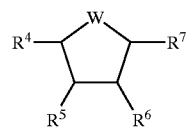

(II)

or a pharmaceutically acceptable salt or prodrug form thereof wherein:
  $R^4$ and $R^7$ are independently selected from the following groups:
    hydrogen;
    $C_1$–$C_4$ alkyl substituted with 0–3 $R^{11}$;
    $C_3$–$C_4$ alkenyl substituted with 0–3 $R^{11}$;
  $R^5$ is —$OR^{20}$;
  $R^6$ is hydrogen or —$OR^{21}$;
  $R^{20}$ and $R^{21}$ are independently hydrogen or any group that, when administered to a mammalian subject, cleaves to form a free hydroxyl;
  $R^{11}$ is selected from one or more of the following:
    H, keto, halogen, —$CH_2NR^{13}R^{14}$, —$NR^{13}R^{14}$, —$OR^{13}$, $C_2$–$C_4$ alkoxyalkyl, $C_2$–$C_4$ alkenyl, ;
    $C_3$–$C_{10}$ cycloalkyl substituted with 0–2 $R^{12}$;
    $C_1$–$C_4$ alkyl substituted with 0–2 $R^{12}$;
    aryl($C_1$–$C_3$ alkyl)-, substituted with 0–2 $R^{12}$;
    aryl substituted with 0–3 $R^{12}$; or
    a 5- to 10-membered heterocyclic ring system containing 1 to 4 heteroatoms independently selected from oxygen, nitrogen or sulfur, said heterocyclic ring system being substituted with 0–2 $R^{12}$;
  $R^{12}$, when a substituent on carbon, is selected from one or more of the following:
    phenyl, benzyl, phenethyl, phenoxy, benzyloxy, halogen, $C_1$–$C_4$ alkyl, $C_7$–$C_{10}$ arylalkyl, $C_1$–$C_4$ alkoxy, 2-(1-morpholino)ethoxy, —$CO_2H$, hydroxamic acid, hydrazide, —$C(R^{14})=N(OR^{14})$, cyano, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, methylenedioxy, $C_1$–$C_4$ haloalkyl, $C_1$–$C_4$ alkylcarbonyl, $C_1$–$C_4$ alkylcarbonylamino, hydroxymethyl; or
    a 5- or 6-membered heterocyclic ring containing from 1 to 4 heteroatoms independently selected from oxygen, nitrogen or sulfur;
  $R^{12}$, when a substituent on nitrogen, is selected from benzyl or methyl;
  $R^{13}$ is H, $C_1$–$C_4$ alkyl, $C_3$–$C_6$ alkoxyalkyl, $C_2$–$C_4$ alkenyl, or benzyl;
  $R^{14}$ is OH, H, $CF_3$, $C_1$–$C_4$ alkyl, $C_1$–$C_4$ alkoxy, $NH_2$, $C_2$–$C_4$ alkenyl, or benzyl;
  $R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

W is selected from:
  —$N(R^{22})C(=Z)N(R^{23})$—;
  —$N(R^{22})C(=Z)O$—;
  —$C(R^{25})(R^{26})C(=Z)C(R^{27})(R^{28})$—;
  —$N(R^{22})C(=Z)C(R^{27})(R^{28})$—;
  —$C(R^{25})(R^{26})C(=Z)O$—;
  —$N(R^{22})C(=O)C(=O)N(R^{23})$—;
  —$C(R^{25})(R^{26})C(=Z)S$—;
  —$N(R^{22})S(=Z')N(R^{23})$—;
  —$N(R^{22})S(=Z')_2N(R^{23})$—;
  —$N(R^{22})P(=O)(R^{24a})(N(R^{23})$—;

—C(R$^{25}$)(R$^{26}$)S(=Z')C(R$^{27}$)(R$^{28}$)—;
—C(R$^{25}$)(R$^{26}$)S(=Z')$_2$C(R$^{27}$)(R$^{28}$)—;
—C(R$^{25}$)(R$^{26}$)P(=O)(R$^{24a}$)C(R$^{27}$)(R$^{28}$)—;
—C(R$^{25}$)(R$^{26}$)S(=Z')N(R$^{23}$)—;
—C(R$^{25}$)(R$^{26}$)S(=Z')$_2$N(R$^{23}$)—;
—C(R$^{25}$)C(F$_2$)C(=O)N(R$^{23}$)—;
—C(R$^{25}$)C(F$_2$)S(=O)$_2$N(R$^{23}$)—;
—C(=Z)—;
—P(=O)(R$^{24a}$)—;
—S(=Z')—;
—S(=Z')$_2$—;
wherein:
Z is O, S, or N—CN;
Z' is O;
R$^{22}$ and R$^{23}$ are independently selected from the following:
hydrogen;
C$_1$–C$_8$ alkyl substituted with 0–3 R$^{31}$;
C$_2$–C$_6$ alkenyl substituted with 0–3 R$^{31}$;
C$_2$–C$_4$ alkynyl substituted with 0–3 R$^{31}$;
R$^{24a}$ is selected from —OH, C$_1$–C$_4$ alkoxy, mono- or di-(C$_1$–C$_6$ alkyl)amino;
R$^{25}$ and R$^{27}$ are independently selected from the following:
hydrogen;
C$_1$–C$_4$ alkyl substituted with 0–3 R$^{31}$;
C$_2$–C$_4$ alkenyl substituted with 0–3 R$^{31}$;
R$^{26}$ and R$^{28}$ are hydrogen or halogen;
R$^{31}$ is selected from one or more of the following:
keto, halogen, —CH$_2$NR$^{13}$R$^{14}$, —NR$^{13}$R$^{14}$, —OR$^{13}$, C$_2$–C$_4$ alkoxyalkyl-, C$_1$–C$_4$ alkyl, C$_2$–C$_4$ alkenyl, C$_3$–C$_{10}$ cycloalkyl, —C(R$^{14}$)=N(OR$^{14}$), —CO$_2$R$^{13}$, —S(O)$_m$R$^{13}$;
aryl substituted with 0–5 R$^{32}$; or
a 5- to 10-membered heterocyclic ring system containing 1 to 4 heteroatoms independently selected from oxygen, nitrogen or sulfur, said heterocyclic ring system being substituted with 0–2 R$^{32}$;
R$^{32}$, when a substituent on carbon, is selected from one or more of the following:
phenethyl, phenoxy, C$_3$–C$_6$ cycloalkyl, C$_3$–C$_6$ cycloalkylmethyl, C$_7$–C$_{10}$ arylalkyl, hydrazide, oxime, boronic acid, C$_2$–C$_6$ alkoxyalkyl, methylenedioxy, ethylenedioxy, C$_1$–C$_4$ alkylcarbonyloxy, —NHSO$_2$R$^{14}$, benzyloxy, halogen, 2-(1-morpholino)ethoxy, —CO$_2$R$^{13}$, hydroxamic acid, —CONR$^{13}$NR$^{13}$R$^{14}$, cyano, sulfonamide, —CHO, C$_3$–C$_6$ cycloalkoxy, —NR$^{13}$R$^{14}$, —C(R$^{14}$)=N(OR$^{14}$), —NO$_2$, —OR$^{13}$, —NR$^4$OR$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$, phenyl, —C(=O)NR$^{13}$—(C$_1$–C$_4$ alkyl)—NR$^{13}$R$^{14}$, —C(=O)NR$^{40}$R$^{41}$, C$_1$–C$_4$ haloalkyl, C$_1$–C$_4$ haloalkoxy, C$_2$–C$_4$ haloalkenyl, C$_2$–C$_4$ haloalkynyl, or
—C(=O)C(R$^{11}$)$_2$NR$^{13}$R$^{14}$; —C(=O)C(R$^{11}$)$_2$NR$^{13}$CO$_2$R$^{13}$;
—C(=O)—(C$_1$–C$_4$ alkyl)—NR$^{13}$R$^{14}$;
—C(=O)—(C$_1$–C$_4$ alkyl)—NR$^{13}$CO$_2$R$^{13}$; or
C$_1$–C$_4$ alkoxy substituted with 0–3 groups selected from: R$^{11}$, C$_3$–C$_6$ cycloalkyl, —CO$_2$R$^{13}$, —C(=O)NR$^{13}$R$^{14}$, —NR$^{13}$R$^{14}$ or OH;
C$_1$–C$_4$ alkyl substituted with 0–3 groups selected from: R$^{11}$, =NR$^{14}$, =NNR$^{13}$C(=O)NR$^{13}$R$^{14}$ or —NR$^{13}$R$^{14}$;

C$_2$–C$_4$ alkenyl substituted with 0–3 R$^{11}$;
C$_2$–C$_4$ alkynyl substituted with 0–3 R$^{11}$;
a 5- or 6-membered heterocyclic ring containing from 1 to 4 heteroatoms independently selected from oxygen, nitrogen or sulfur, substituted with 0–3 R$^{12}$;
R$^{32}$, when a substituent on nitrogen, is selected from benzyl or methyl;
R$^{34}$ is selected from:
hydrogen;
C$_1$–C$_2$ alkyl;
C$_1$–C$_2$ alkoxy;
R$^{35}$ is selected from:
hydrogen;
C$_1$–C$_2$ alkyl;
C$_1$–C$_2$ alkoxy;
R$^{34}$ and R$^{35}$ can be taken together to form a ketal ring, a 3- to 8-membered carbocyclic ring, or a 5- or 6-membered heterocyclic ring containing 1–2 heteroatoms independently selected from the group O, N, or S;
R$^{36}$ is selected from: C$_1$–C$_2$ alkyl; COR$^{37}$; NR$^{38}$R$^{39}$; CN; CCl$_3$;
R$^{37}$ is selected from:
hydrogen; C$_1$–C$_2$ alkyl substituted with 0–1 R$^{11}$;
hydroxyl; C$_1$–C$_2$ alkoxy substituted with 0–1 R$^{11}$;
NR$^{38}$R$^{39}$;
R$^{38}$ and R$^{39}$ are independently selected from:
hydrogen; C$_1$–C$_2$ alkyl substituted with 0–3 R$^{11}$; or
an amine protecting group;
provided that:
R$^4$ and R$^7$ are not both hydrogen;
when W is —C(=Z)—, —P(=O)(R$^{24a}$)—, —S(=Z')— or —S(=Z')$_2$—, R$^4$ and R$^7$ are not hydrogen;
when R$^4$ is hydrogen, at least one of the following is not hydrogen: R$^{22}$, R$^{25}$, R$^{26}$ and R$^{28}$.
[11] Preferred compounds of the present invention include compounds of formula (II) described above, wherein:
R$^4$ and R$^7$ are independently selected from the following groups:
hydrogen;
C$_1$–C$_3$ alkyl substituted with 0–1 R$^{11}$;
R$^{20}$ and R$^{21}$ are independently hydrogen or any group that, when administered to a mammalian subject, cleaves to form a free hydroxyl;
R$^{11}$ is selected from one or more of the following:
H; halogen; —OR$^{13}$;
C$_3$–C$_{10}$ cycloalkyl substituted with 0–2 R$^{12}$;
C$_1$–C$_4$ alkyl substituted with 0–2 R$^{12}$;
aryl (C$_1$–C$_3$ alkyl)-, substituted with 0–2 R$^{12}$;
aryl substituted with 0–2 R$^{12}$; or
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 R$^{12}$;
R$^{12}$, when a substituent on carbon, is selected from one or more of the following:
benzyloxy, halogen, methyl, C$_1$–C$_4$ alkoxy, CF$_3$, 2-(1-morpholino)ethoxy, —CO$_2$H, hydroxamic acid, hydrazide, —C(R$^{14}$)=N(OR$^{14}$), cyano, boronic acid, sulfonamide, formyl, C$_3$–C$_6$ cycloalkoxy, C$_1$–C$_4$ alkyl substituted with —NR$^{13}$R$^{14}$, —NR$^{13}$R$^{14}$, hydroxy, hydroxymethyl; or $R^{12}$, when a substituent on nitrogen, is methyl;
$R^{13}$ is H, $C_1$-$C_4$ alkyl, $C_2$-$C_4$ alkenyl, or benzyl;
$R^{14}$ is OH, H, $CF_3$, $C_1$-$C_4$ alkyl, $C_1$-$C_4$ alkoxy, $NH_2$, $C_2$-$C_4$ alkenyl, or benzyl;
$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;
W is selected from:
 —$N(R^{22})C(=Z)N(R^{23})$—;
 —$N(R^{22})C(=Z)O$—;
 —$C(R^{25})(R^{26})C(=Z)C(R^{27})(R^{28})$—;
 —$N(R^{22})S(=Z')N(R^{23})$—;
 —$N(R^{22})S(=Z')_2N(R^{23})$—;
 —$C(R^{25})(R^{26})C(R^{34})(R^{35})C(R^{27})(R^{28})$—;
 —$N=C(R^{36})N(R^{23})$—;
 —$C(=Z)$—;
Z is O, S, or N—CN;
Z' is O;
$R^{22}$ and $R^{23}$ are independently selected from the following:
 hydrogen;
 $C_1$-$C_8$ alkyl substituted with 0–3 $R^{31}$;
 $C_2$-$C_6$ alkenyl substituted with 0–3 $R^{31}$;
 $C_2$-$C_4$ alkynyl substituted with 0–3 $R^{31}$;
$R^{25}$ and $R^{27}$ are independently selected from the following:
 hydrogen;
 $C_1$-$C_4$ alkyl substituted with 0–3 $R^{31}$;
 $C_3$-$C_4$ alkenyl substituted with 0–3 $R^{31}$;
$R^{26}$ and $R^{28}$ are hydrogen or halogen;
$R^{31}$ is selected from one or more of the following:
 halogen, —$OR^{13}$, $C_1$-$C_4$ alkyl, $C_3$-$C_{10}$ cycloalkyl, —$C(R^{14})=N(OR^{14})$, —$CO_2R^{13}$, —$S(O)_mR^{13}$;
 aryl substituted with 0–5 $R^{32}$; or
 a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 $R^{32}$;
$R^{32}$, when a substituent on carbon, is selected from one or more of the following:
 benzyloxy, halogen, 2-(1-morpholino)ethoxy, —$CO_2R^{13}$, hydroxamic acid, —$CONR^{13}NR^{13}R^{14}$, cyano, boronic acid, —CHO, $C_3$-$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—$(C_1$-$C_4$ alkyl)—$NR^{13}R^{14}$, —$C(=O)NR^{40}R^{41}$, $C_1$-$C_4$ haloalkyl, $C_1$-$C_4$ haloalkoxy, $C_2$-$C_4$ haloalkenyl, $C_2$-$C_4$ haloalkynyl, —$C(=O)C(R^{11})_2NR^{13}R^{14}$;
 —$C(=O)C(R^{11})_2NR^{13}CO_2R^{13}$; —$C(=O)$—$(C_1$-$C_4$ alkyl)—$NR^{13}R^{14}$;
 —$C(=O)$—$(C_1$-$C_4$ alkyl)—$NR^{13}CO_2R^{13}$; or
 $C_1$-$C_4$ alkoxy substituted with 0–3 groups selected from: $R^{11}$, $C_3$-$C_6$ cycloalkyl, —$C(=O)NR^{13}R^{14}$, —$NR^{13}R^{14}$ or OH;
 $C_1$-$C_4$ alkyl substituted with 0–3 groups selected from: $R^{11}$, =$NR^{14}$, =$NNR^{13}C(=O)NR^{13}R^{14}$ or —$NR^{13}R^{14}$;
 $C_2$-$C_4$ alkenyl substituted with 0–3 $R^{11}$;
 $C_2$-$C_4$ alkynyl substituted with 0–3 $R^{11}$;
 a 5- or 6-membered heterocyclic ring containing from 1 to 4 heteroatoms independently selected from oxygen, nitrogen or sulfur, substituted with 0–2 $R^{12}$;

$R^{32}$, when a substituent on nitrogen, is methyl;
$R^{34}$ is selected from:
 hydrogen;
 $C_1$-$C_2$ alkyl;
 $C_1$-$C_2$ alkoxy;
$R^{35}$ is selected from:
 hydrogen;
 $C_1$-$C_2$ alkyl;
 $C_1$-$C_2$ alkoxy;
$R^{36}$ is selected from: $C_1$-$C_2$ alkyl; $COR^{37}$; $NR^{38}R^{39}$; CN; $CCl_3$;
$R^{37}$ is selected from:
 hydrogen;
 $C_1$-$C_2$ alkyl substituted with 0–1 $R^{11}$;
 hydroxyl;
 $C_1$-$C_2$ alkoxy substituted with 0–1 $R^{11}$;
 —$NR^{38}R^{39}$;
$R^{38}$ and $R^{39}$ are independently selected from:
 hydrogen;
 $C_1$-$C_2$ alkyl substituted with 0–3 $R^{11}$; or
 an amine protecting group;
provided that:
 $R^4$ and $R^7$ are not both hydrogen;
 when W is —$C(=Z)$—, $R^4$ and $R^7$ are not hydrogen;
 when $R^4$ is hydrogen, at least one of the following is not hydrogen: $R^{22}$, $R^{25}$, $R^{26}$ and $R^{28}$.
[12] Preferred compounds of the present invention are compounds of formula (II) described above, wherein:
 $R^4$ and $R^7$ are selected from benzyl, fluorobenzyl, pyrrolylmethyl, methoxybenzyl, isobutyl, nitrobenzyl, aminobenzyl, thienylmethyl, hydroxybenzyl, pyridylmethyl, naphthylmethyl;
 $R^5$ is —OH;
 $R^6$ is hydrogen or —OH;
 $R^{13}$ is H, $C_1$-$C_4$ alkyl, $C_2$-$C_4$ alkenyl, or benzyl;
 $R^{14}$ is OH, H, $CF_3$, $C_1$-$C_4$ alkyl, $C_1$-$C_4$ alkoxy, $NH_2$, $C_2$-$C_4$ alkenyl, or benzyl;
 $R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;
W is selected from:
 —$N(R^{22})C(=O)N(R^{23})$—;
 —$N(R^{22})C(=N$—$CN)N(R^{23})$—;
 —$N(R^{22})S(=O)_2N(R^{23})$—;
 —$C(=O)$—;
 —$N(R^{22})C(=S)N(R^{23})$—; or
 —$C(=N$—$CN)$—;
$R^{22}$ and $R^{23}$ are independently selected from the following:
 hydrogen;
 $C_1$-$C_8$ alkyl substituted with 0–2 $R^{31}$;
 $C_2$-$C_6$ alkenyl substituted with 0–2 $R^{31}$;
 $C_2$-$C_4$ alkynyl substituted with 0–2 $R^{31}$;
$R^{31}$ is selected from one or more of the following:
 halogen, —$OR^{13}$, $C_1$-$C_4$ alkyl, $C_3$-$C_{10}$ cycloalkyl, —$C(R^{14})=N(OR^{14})$, —$CO_2R^{13}$, —$S(O)_mR^{13}$;
 aryl substituted with 0–5 $R^{32}$; or
 a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0–2 $R^{32}$;

$R^{32}$, when a substituent on carbon, is selected from one or more of the following:
—CONH$_2$, —CO$_2$H, —CHO, —CH$_2$NHOH, —CH$_2$NR$^{13}$R$^{14}$, —NR$^{13}$R$^{14}$, hydroxy, hydroxymethyl, —C(R$^{14}$)=N(OR$^{14}$), halogen, methoxy, methyl, nitro, cyano, allyloxy, —CO$_2$CH$_3$, —NHCHO, —NHCOCH$_3$, —OCO$_2$CH$_3$, —CH=NCH$_2$CH$_2$OH, —OCONHCH$_2$C$_6$H$_5$, —OCONHCH$_3$, oxazolidinyl, —C≡C—CH$_2$OH, —COCH$_3$, hydroxyethyl, C$_1$–C$_3$ alkyl (said alkyl substituted with 0–4 halogen, or OH), tetrazolyl, —OCH$_2$CONH$_2$, —CONHNH$_2$, —CH=NNHCONH$_2$, —CONHOCH$_3$, —CH$_2$CH(OH)CH$_2$OH, adamantamido, hydroxyethoxy, dihydroxyethyl, —C(NH$_2$)=NH, —CONHCH$_3$, —B(OH)$_2$, benzyloxy, —CONHCH$_2$CH$_3$, —CON(CH$_2$CH$_3$)$_2$, methylthio, —SO$_2$CH$_3$, —NHCONH$_2$, —NHCONHCH$_3$, —NHCOCH$_2$N(CH$_3$)$_2$, —NHCOCH$_2$NHCH$_3$, —NHCOCH$_2$NHCO$_2$CH$_2$C$_6$H$_5$, —NHCOCH$_2$NH$_2$, —NHCOCH(CH$_3$)NHCO$_2$CH$_2$C$_6$H$_5$, —NHCOCH(CH$_2$C$_6$H$_5$)NHCO$_2$CH$_2$C$_6$H$_5$, —NHCOCH(CH$_3$)NH$_2$, —NHCOCH(CH$_2$C$_6$H$_5$)NH$_2$, —CO$_2$CH$_2$CH$_3$, —CONHCH$_2$CH$_2$CH$_3$, —CONHCH(CH$_3$)$_2$, —CH$_2$-imidazole, —COC(CH$_3$)$_3$, —CH(OH)CF$_3$, —CO-imidazole, —CO-pyrazolyl, oxadiazolidinonyl, —COCF$_3$, —COCH$_2$CH$_3$, —COCH$_2$CH$_2$CH$_3$, pyrazolyl, —SO$_2$NH$_2$, —C(CH$_2$CH$_3$)=N(OH) or —C(CF$_3$)=N(OH), phenyl, acetoxy, hydroxyamino, —N(CH$_3$)(CHO), cyclopropylmethoxy, —CONR$^{13}$R$^{14}$, —CONHOH, (diethylaminoethyl)aminocarbonyl, (N-ethyl,N-methylaminoethyl)aminocarbonyl, (4-methylpiperazinylethyl)aminocarbonyl, pyrrolidinylethyl)aminocarbonyl, (piperidinylethyl)aminocarbonyl, —NHCOCH$_2$NHCH$_3$, N-(2-(4-morpholino)ethyl)aminocarbonyl, N-(2-(N,N-dimethylamino)ethyl)aminocarbonyl;

$R^{32}$, when a substituent on nitrogen, is methyl.

[13] Also preferred are compounds of the formula:

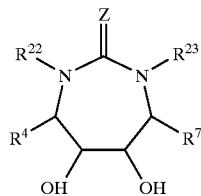

wherein:

Z is ), S, or N—CN;

$R^4$ and $R^7$ are independently selected from: benzyl, fluorobenzyl, pyrrolylmethyl, methoxybenzyl, isobutyl, nitrobenzyl, aminobenzyl, thienylmethyl, hydroxybenzyl, pyridylmethyl, naphthylmethyl;

$R^{22}$ and $R^{23}$ are independently selected from the group consisting of:
hydrogen, allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H$_2$NC(=O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl—NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl, (H$_2$NC(=NOH))benzyl, (H$_2$NC(=NOH))fluorobenzyl, benzimidazolylmethyl, benzotriazolylmethyl, indazolylmethyl, benzoxazolinylmethyl, benzisoxazolylmethyl, thienylmethyl, furylmethyl.

[14] Also preferred are compounds of formula (IIa):

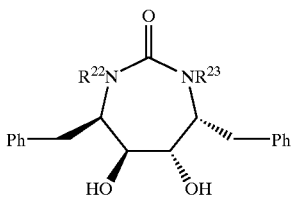

(IIa)

wherein $R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N,N-dimethylaminocarbonylbenzyl, $(HOCH_2CH(OH)CH_2O)$-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy) pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, $(CH_3CH_2NHC(=O))$-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl) benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, $(H_2NSO_2)$-benzyl, dihydroxyethylbenzyl, (MeHNC(=O)NH)-benzyl, $(H_2NC(=O)NH)$-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, $(CH_3CH_2C(=NOH))$-benzyl, (trifluorohydroxyethyl)benzyl, $(CF_3C(=NOH))$-benzyl, (N-methylglycyl) aminobenzyl, ((4-morpholino)ethyl) aminocarbonylbenzyl, (N,N-dimethylaminoethyl) aminocarbonylbenzyl, (N,N-diethylaminoethyl) aminocarbonylbenzyl, (4-methylpiperazin-1-ylethyl) aminocarbonylbenzyl, (benzyl-NHC(=O)O)benzyl, $(CH_3NHC(=O)O)$benzyl, $(NH_2C(=O)CH_2O)$benzyl, $(NH_2C(=NH))$benzyl, ((N-phenylmethoxycarbonyl) glycylamino)benzyl, (imidazolylmethyl)benzyl, $((CH_3)_3C-C(=O))$benzyl, (N-methyl-N-ethylaminoethyl)aminocarbonylbenzyl, (pyrrolidinylethyl)aminocarbonylbenzyl, (piperidinylethyl)aminocarbonylbenzyl, $(H_2NC(=NOH))$benzyl, $(H_2NC(=NOH))$fluorobenzyl, benzimidazolylmethyl, benzotriazolylmethyl, indazolylmethyl, benzoxazolinylmethyl, benzisoxazolylmethyl, thienylmethyl, furylmethyl.

[15] Specifically preferred are compounds of formula (IIa):

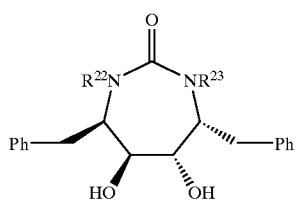

(IIa)

selected from the group consisting of:

the compound of formula (IIa) wherein $R^{22}$ is allyl and $R^{23}$ is allyl;

the compound of formula (IIa) wherein $R^{22}$ is propyl and $R^{23}$ is propyl;

the compound of formula (IIa) wherein $R^{22}$ is cyclopropylmethyl and $R^{23}$ is cyclopropylmethyl;

the compound of formula (IIa) wherein $R^{22}$ is n-hexyl and $R^{23}$ is n-hexyl;

the compound of formula (IIa) wherein $R^{22}$ is n-butyl and $R^{23}$ is n-butyl;

the compound of formula (IIa) wherein $R^{22}$ is $CH_2CH=C(CH_3)_2$ and $R^{23}$ is $CH_2CH=C(CH_3)_2$;

the compound of formula (IIa) wherein $R^{22}$ is $CH_2CH=C(CH_3)_2$ and $R^{23}$ is H;

the compound of formula (IIa) wherein $R^{22}$ is i-pentyl and $R^{23}$ is i-pentyl;

the compound of formula (IIa) wherein $R^{22}$ is 2-methallyl and $R^{23}$ is 2-methallyl;

the compound of formula (IIa) wherein $R^{22}$ is n-pentyl and $R^{23}$ is n-pentyl;

the compound of formula (IIa) wherein $R^{22}$ is benzyl and $R^{23}$ is benzyl;

the compound of formula (IIa) wherein $R^{22}$ is i-hexyl and $R^{23}$ is i-hexyl;

the compound of formula (IIa) wherein $R^{22}$ is allyl and $R^{23}$ is isoprenyl;

the compound of formula (IIa) wherein $R^{22}$ is 1-cinnamyl and $R^{23}$ is 1-cinnamyl;

the compound of formula (IIa) wherein $R^{22}$ is 4-fluorobenzyl and $R^{23}$ is 4-fluorobenzyl;

the compound of formula (IIa) wherein $R^{22}$ is cyclopropylmethyl and $R^{23}$ is benzyl;

the compound of formula (IIa) wherein $R^{22}$ is allyl and $R^{23}$ is benzyl;

the compound of formula (IIa) wherein $R^{22}$ is $CH_2CH=C(CH_3)_2$ and $R^{23}$ is cyclopropylmethyl;

the compound of formula (IIa) wherein $R^{22}$ is 2-naphthylmethyl and $R^{23}$ is 2-napthylmethyl;

the compound of formula (IIa) wherein $R^{22}$ is n-butyl and $R^{23}$ is benzyl;

the compound of formula (IIa) wherein $R^{22}$ is allyl and $R^{23}$ is cyclopropylmethyl;

the compound of formula (IIa) wherein $R^{22}$ is n-butyl and $R^{23}$ is cyclopropylmethyl;

the compound of formula (IIa) wherein $R^{22}$ is $CH_2CH=C(CH_3)_2$ and $R^{23}$ is benzyl;

the compound of formula (IIa) wherein $R^{22}$ is benzyl and $R^{23}$ is ethyl;

the compound of formula (IIa) wherein $R^{22}$ is benzyl and $R^{23}$ is 4-pyridinylmethyl;

the compound of formula (IIa) wherein $R^{22}$ is cyclopropylmethyl and $R^{23}$ is 4-pyridinylmethyl;

the compound of formula (IIa) wherein $R^{22}$ is benzyl and $R^{23}$ is cyclopentylmethyl;

the compound of formula (IIa) wherein $R^{22}$ is cyclopropylmethyl and $R^{23}$ is cyclopentylmethyl;

the compound of formula (IIa) wherein $R^{22}$ is benzyl and $R^{23}$ is n-propyl;

the compound of formula (IIa) wherein $R^{22}$ is cyclopropylmethyl and $R^{23}$ is cinnamyl;

the compound of formula (IIa) wherein $R^{22}$ is cyclopropylmethyl and $R^{23}$ is 2-naphthylmethyl;

the compound of formula (IIa) wherein $R^{22}$ is cyclopentylmethyl and $R^{23}$ is 2-naphthylmethyl;

the compound of formula (IIa) wherein $R^{22}$ is benzyl and $R^{23}$ is 2-naphthylmethyl;

the compound of formula (IIa) wherein $R^{22}$ is cyclopropylmethyl and $R^{23}$ is 2-pyridinylmethyl;

the compound of formula (IIa) wherein $R^{22}$ is 3-cyanobenzyl and $R^{23}$ is 3-cyanobenzyl;

the compound of formula (IIa) wherein $R^{22}$ is allyl and $R^{23}$ is 2-naphthylmethyl;

the compound of formula (IIa) wherein $R^{22}$ is n-propyl and $R^{23}$ is 2-naphthylmethyl;

the compound of formula (IIa) wherein $R^{22}$ is n-butyl and $R^{23}$ is 2-naphthylmethyl;

the compound of formula (IIa) wherein $R^{22}$ is hydrogen and $R^{23}$ is 2-naphthylmethyl;

the compound of formula (IIa) wherein $R^{22}$ is 4-pyridinylmethyl and $R^{23}$ is 2-naphthylmethyl;

the compound of formula (IIa) wherein $R^{22}$ is allyl and $R^{23}$ is cyclopentylmethyl;

the compound of formula (IIa) wherein $R^{22}$ is allyl and $R^{23}$ is 2-quinolinylmethyl;

the compound of formula (IIa) wherein $R^{22}$ is 3-pyridinylmethyl and $R^{23}$ is cyclopropylmethyl;

the compound of formula (IIa) wherein $R^{22}$ is 3-pyridinylmethyl and $R^{23}$ is 2-naphthylmethyl;

the compound of formula (IIa) wherein $R^{22}$ is 3-hydroxybenzyl and $R^{23}$ is 3-hydroxybenzyl;

the compound of formula (IIa) wherein $R^{22}$ is vinylbenzyl and $R^{23}$ is vinylbenzyl;

the compound of formula (IIa) wherein $R^{22}$ is 3-allyloxybenzyl and $R^{23}$ is 3-hydroxybenzyl;

the compound of formula (IIa) wherein $R^{22}$ is 3-pyridinylmethyl and $R^{23}$ is 3-pyridinylmethyl;

the compound of formula (IIa) wherein $R^{22}$ is 2-naphthylmethyl and $R^{23}$ is 4-fluorobenzyl;

the compound of formula (IIa) wherein $R^{22}$ is 4-hydroxybenzyl and $R^{23}$ is 4-hydroxybenzyl;

the compound of formula (IIa) wherein $R^{22}$ is 3-hydroxymethylbenzyl and $R^{23}$ is 3-hydroxymethylbenzyl;

the compound of formula (IIa) wherein $R^{22}$ is 3-carbomethoxybenzyl and $R^{23}$ is 3-carbomethoxybenzyl;

the compound of formula (IIa) wherein $R^{22}$ is 4-hydroxymethylbenzyl and $R^{23}$ is 4-hydroxymethylbenzyl;

the compound of formula (IIa) wherein $R^{22}$ is 3-formylbenzyl and $R^{23}$ is 3-formylbenzyl;

the compound of formula (IIa) wherein $R^{22}$ is 4-cyanobenzyl and $R^{23}$ is 4-cyanobenzyl;

the compound of formula (IIa) wherein $R^{22}$ is 4-formylbenzyl and $R^{23}$ is 4-formylbenzyl;

the compound of formula (IIa) wherein $R^{22}$ is 4-hydroxybenzyl and $R^{23}$ is 2-propyl;

the compound of formula (IIa) wherein $R^{22}$ is 3-hydroxybenzyl and $R^{23}$ is 2-propyl;

the compound of formula (IIa) wherein $R^{22}$ is 3-carboxybenzyl and $R^{23}$ is 3-carboxybenzyl;

the compound of formula (IIa) wherein $R^{22}$ is 3-formaldoximebenzyl and $R^{23}$ is 3-formaldoximebenzyl;

the compound of formula (IIa) wherein $R^{22}$ is cyclopropylmethyl and $R^{23}$ is 3-hydroxybenzyl;

the compound of formula (IIa) wherein $R^{22}$ is cyclopropylmethyl and $R^{23}$ is 4-hydroxybenzyl;

the compound of formula (IIa) wherein $R^{22}$ is cyclobutylmethyl and $R^{23}$ is cyclobutylmethyl;

the compound of formula (IIa) wherein $R^{22}$ is cyclopentylmethyl and $R^{23}$ is cyclopentylmethyl;

the compound of formula (IIa) wherein $R^{22}$ is n-butyl and $R^{23}$ is $CH_2CH=C(CH_3)_2$;

the compound of formula (IIa) wherein $R^{22}$ is n-butyl and $R^{23}$ is cyclopentylmethyl;

the compound of formula (IIa) wherein $R^{22}$ is benzyl and $R^{23}$ is H;

the compound of formula (IIa) wherein $R^{22}$ is 3-fluorobenzyl and $R^{23}$ is 3-fluorobenzyl;

the compound of formula (IIa) wherein $R^{22}$ is 3-methoxybenzyl and $R^{23}$ is 3-methoxybenzyl;

the compound of formula (IIa) wherein $R^{22}$ is 3,4-difluorobenzyl and $R^{23}$ is 3,4-difluorobenzyl;

the compound of formula (IIa) wherein $R^{22}$ is 4-methylbenzyl and $R^{23}$ is 4-methylbenzyl;

the compound of formula (IIa) wherein $R^{22}$ is 4-chlorobenzyl and $R^{23}$ is 4-chlorobenzyl;

the compound of formula (IIa) wherein $R^{22}$ is cyclopropylmethyl and $R^{23}$ is 4-fluorobenzyl;

the compound of formula (IIa) wherein $R^{22}$ is 3-chlorobenzyl and $R^{23}$ is 3-chlorobenzyl;

the compound of formula (IIa) wherein $R^{22}$ is 3-nitrobenzyl and $R^{23}$ is 3-nitrobenzyl;

the compound of formula (IIa) wherein $R^{22}$ is 3-methylbenzyl and $R^{23}$ is 3-methylbenzyl;

the compound of formula (IIa) wherein $R^{22}$ is 3-bromobenzyl and $R^{23}$ is 3-bromobenzyl;

the compound of formula (IIa) wherein $R^{22}$ is 4-fluorobenzyl and $R^{23}$ is H;

the compound of formula (IIa) wherein $R^{22}$ is cyclopropylmethyl and $R^{23}$ is 3-chlorobenzyl;

the compound of formula (IIa) wherein $R^{22}$ is 3-aminobenzyl and $R^{23}$ is 3-aminobenzyl;

the compound of formula (IIa) wherein $R^{22}$ is 4-aminobenzyl and $R^{23}$ is 4-aminobenzyl;

the compound of formula (IIa) wherein $R^{22}$ is 3-nitrobenzyl and $R^{23}$ is H;

the compound of formula (IIa) wherein $R^{22}$ is 3-(NHCHO)benzyl and $R^{23}$ is 3-(NHCHO)benzyl;

the compound of formula (IIa) wherein $R^{22}$ is 3-(NHCOCH$_3$)benzyl and $R^{23}$ is 3-(NHCOCH$_3$)benzyl;

the compound of formula (IIa) wherein $R^{22}$ is 3,4-dihydroxybenzyl and $R^{23}$ is 3,4-dihydroxybenzyl;

the compound of formula (IIa) wherein $R^{22}$ is 3-formaldoximebenzyl and $R^{23}$ is 3-(N-hydroxy)aminomethylbenzyl;

the compound of formula (IIa) wherein $R^{22}$ is 3-(N-hydroxy)aminomethylbenzyl and $R^{23}$ is 3-(N-hydroxy)aminomethylbenzyl;

the compound of formula (IIa) wherein $R^{22}$ is 3-(CH$_3$O(=O)O—)benzyl and $R^{23}$ is 3-(CH$_3$O(=O)O—)benzyl;

the compound of formula (IIa) wherein $R^{22}$ is 3-(1-hydroxyethyl)benzyl and $R^{23}$ is 3-(1-hydroxyethyl)benzyl;

the compound of formula (IIa) wherein $R^{22}$ is 3-(HOCH$_2$CH$_2$N=CH)benzyl and $R^{23}$ is 3-(HOCH$_2$CH$_2$N=CH)benzyl;

the compound of formula (IIa) wherein $R^{22}$ is 3-(HOCH$_2$CH$_2$N=CH)benzyl and $R^{23}$ is 3-(2-oxazolidinyl)benzyl;

the compound of formula (IIa) wherein $R^{22}$ is 3-(C$_6$H$_5$CH$_2$NHC(=O)O)benzyl and $R^{23}$ is 3-(C$_6$H$_5$CH$_2$NHC(=O)O)benzyl;

the compound of formula (IIa) wherein $R^{22}$ is 3-(CH$_3$NHC(=O)O)benzyl and $R^{23}$ is 3-(CH$_3$NHC(=O)O)benzyl;

the compound of formula (IIa) wherein $R^{22}$ is 3-(HOCH$_2$CC)benzyl and $R^{23}$ is 3-bromobenzyl;

the compound of formula (IIa) wherein $R^{22}$ is 3-acetylbenzyl and $R^{23}$ is 3-bromobenzyl;

the compound of formula (IIa) wherein $R^{22}$ is 3-acetylbenzyl and $R^{23}$ is 3-acetylbenzyl;

the compound of formula (IIa) wherein $R^{22}$ is 3-(CH$_3$C(=NOH))benzyl and $R^{23}$ is 3-(CH$_3$C(=NOH))benzyl;

the compound of formula (IIa) wherein $R^{22}$ is 3-(1-hydroxyethyl)benzyl and $R^{23}$ is 3-bromobenzyl;

the compound of formula (IIa) wherein $R^{22}$ is 3-(chloromethyl)benzyl and $R^{23}$ is 3-(chloromethyl)benzyl;

the compound of formula (IIa) wherein $R^{22}$ is 3-(5-tetrazolyl)benzyl and $R^{23}$ is cyclopropylmethyl;

the compound of formula (IIa) wherein $R^{22}$ is 3-cyanobenzyl and $R^{23}$ is 3-formylbenzyl;

the compound of formula (IIa) wherein $R^{22}$ is 4-acetoxybenzyl and $R^{23}$ is 4-hydroxybenzyl;

the compound of formula (IIa) wherein $R^{22}$ is 3-aminocarbonylbenzyl and $R^{23}$ is 3-aminocarbonylbenzyl;

the compound of formula (IIa) wherein $R^{22}$ is 3-(H$_2$NCOCH$_2$O)benzyl and $R^{23}$ is 3-(H$_2$NCOCH$_2$O)benzyl;

the compound of formula (IIa) wherein $R^{22}$ is 3-hydroxybenzyl and $R^{23}$ is H;

the compound of formula (IIa) wherein $R^{22}$ is 3-methylbenzyl and $R^{23}$ is 3-hydroxybenzyl;

the compound of formula (IIa) wherein $R^{22}$ is 2-naphthylmethyl and $R^{23}$ is 3-hydroxybenzyl;

the compound of formula (IIa) wherein $R^{22}$ is 3-(H$_2$NNHC(=O))-benzyl and $R^{23}$ is 3-(H$_2$NNHC(=O))-benzyl;

the compound of formula (IIa) wherein $R^{22}$ is 4-(H$_2$NNHC(=O))-benzyl and $R^{23}$ is 4-(H$_2$NNHC(=O))-benzyl;

the compound of formula (IIa) wherein $R^{22}$ is 4-hydroxymethylbenzyl and $R^{23}$ is 3-hydroxybenzyl;

the compound of formula (IIa) wherein $R^{22}$ is 3-(H$_2$NC(=O)NHN=CH)-benzyl and $R^{23}$ is 3-(H$_2$NC(=O)NHN=CH)-benzyl;

the compound of formula (IIa) wherein $R^{22}$ is 3-[(N-methoxy)aminocarbonyl]-benzyl and $R^{23}$ is 3-[(N-methoxy)aminocarbonyl]-benzyl;

the compound of formula (IIa) wherein $R^{22}$ is 4-[(N-methoxy)aminocarbonyl]-benzyl and $R^{23}$ is 4-[(N-methoxy)aminocarbonyl]-benzyl;

the compound of formula (IIa) wherein $R^{22}$ is 3-(HOCH$_2$CH(OH)CH$_2$O)benzyl and $R^{23}$ is 3-(HOCH$_2$CH(OH)CH$_2$O)benzyl;

the compound of formula (IIa) wherein $R^{22}$ is 3-(2-hydroxyethoxy)benzyl and $R^{23}$ is 3-(2-hydroxyethoxy)benzyl;

the compound of formula (IIa) wherein $R^{22}$ is 3-(1,2-dihydroxyethyl)benzyl and $R^{23}$ is 4-(1,2-dihydroxyethyl)benzyl;

the compound of formula (IIa) wherein $R^{22}$ is 3-aminocarbonylbenzyl and $R^{23}$ is 3-(H$_2$NC(=NH))benzyl;

the compound of formula (IIa) wherein $R^{22}$ is 4-hydroxybenzyl and $R^{23}$ is 3-formyl-4-hydroxybenzyl;

the compound of formula (IIa) wherein $R^{22}$ is 3-carbomethoxybenzyl and $R^{23}$ is 3-(N-methylaminocarbonyl)benzyl;

the compound of formula (IIa) wherein $R^{22}$ is 3-(N-methylaminocarbonyl)benzyl and $R^{23}$ is 3-(N-methylaminocarbonyl)benzyl;

the compound of formula (IIa) wherein $R^{22}$ is benzyl and $R^{23}$ is 3-hydroxybenzyl;

the compound of formula (IIa) wherein $R^{22}$ is 2-naphthylmethyl and $R^{23}$ is 4-hydroxymethylbenzyl;

the compound of formula (IIa) wherein $R^{22}$ is 3-(1,2-dihydroxyethyl)benzyl and $R^{23}$ is 3-(1,2-dihydroxyethyl)benzyl;

the compound of formula (IIa) wherein $R^{22}$ is 4-(1,2-dihydroxyethyl)benzyl and $R^{23}$ is 4-(1,2-dihydroxyethyl)benzyl;

the compound of formula (IIa) wherein $R^{22}$ is 3-hydroxymethylbenzyl and $R^{23}$ is 3-(N-methylaminocarbonyl)benzyl;

the compound of formula (IIa) wherein $R^{22}$ is 4-hydroxymethylbenzyl and $R^{23}$ is hydrogen;

the compound of formula (IIa) wherein $R^{22}$ is 3-(boronic acid)benzyl and $R^{23}$ is 3-(boronic acid)benzyl;

the compound of formula (IIa) wherein $R^{22}$ is 3-nitrobenzyl and $R^{23}$ is 3-benzyloxybenzyl;

the compound of formula (IIa) wherein $R^{22}$ is 3-aminobenzyl and $R^{23}$ is 3-hydroxybenzyl;

the compound of formula (IIa) wherein $R^{22}$ is 3-(N-ethylaminocarbonyl)benzyl and $R^{23}$ is 3-(N-ethylaminocarbonyl)benzyl;

the compound of formula (IIa) wherein $R^{22}$ is 3-carbomethoxybenzyl and $R^{23}$ is 3-(N,N-diethylaminocarbonyl)benzyl;

the compound of formula (IIa) wherein $R^{22}$ is 3-carbomethoxybenzyl and $R^{23}$ is 3-(N-ethylaminocarbonyl)benzyl;

the compound of formula (IIa) wherein $R^{22}$ is 6-hydroxy-1-hexyl and $R^{23}$ is hydrogen;

the compound of formula (IIa) wherein $R^{22}$ is 6-hydroxy-1-hexyl and $R^{23}$ is 6-hydroxy-1-hexyl;

the compound of formula (IIa) wherein $R^{22}$ is cyclopropylmethyl and $R^{23}$ is 6-hydroxy-1-hexyl;

the compound of formula (IIa) wherein $R^{22}$ is 5-carboxy-1-pentyl and $R^{23}$ is 5-carboxy-1-pentyl;

the compound of formula (IIa) wherein $R^{22}$ is 3-iodobenzyl and $R^{23}$ is 3-iodobenzyl;

the compound of formula (IIa) wherein $R^{22}$ is benzyl and $R^{23}$ is 2-(hydroxymethyl)-cyclopropylmethyl;

the compound of formula (IIa) wherein $R^{22}$ is 3-(thiomethyl)benzyl and $R^{23}$ is 3-(thiomethyl)benzyl;

the compound of formula (IIa) wherein $R^{22}$ is 3-(methylsulfonyl)benzyl and $R^{23}$ is 3-(methylsulfonyl)benzyl;

the compound of formula (IIa) wherein $R^{22}$ is 6-hexenyl and $R^{23}$ is 6-hexenyl;

the compound of formula (IIa) wherein $R^{22}$ is 6-bromo-5-hydroxy-1-hexyl and $R^{23}$ is 6-bromo-5-hydroxy-1-hexyl;

the compound of formula (IIa) wherein $R^{22}$ is 5-hydroxy-1-pentyl and $R^{23}$ is 5-hydroxy-1-pentyl;

the compound of formula (IIa) wherein $R^{22}$ is 3-aminobenzyl and $R^{23}$ is 4-hydroxymethylbenzyl;

the compound of formula (IIa) wherein $R^{22}$ is 3-($H_2NC(=O)NH$)benzyl and $R^{23}$ is 3-($H_2NC(=O)NH$)benzyl;

the compound of formula (IIa) wherein $R^{22}$ is 3-(N-methylamino)benzyl and $R^{23}$ is 3-(N-methylamino)benzyl;

the compound of formula (IIa) wherein $R^{22}$ is cyclopropylmethyl and $R^{23}$ is 3-aminobenzyl;

the compound of formula (IIa) wherein $R^{22}$ is cyclopropylmethyl and $R^{23}$ is 3-nitrobenzyl;

the compound of formula (IIa) wherein $R^{22}$ is 3-(N,N-dimethylamino)benzyl and $R^{23}$ is 3-(N,N-dimethylamino)benzyl;

the compound of formula (IIa) wherein $R^{22}$ is 3-nitrobenzyl and $R^{23}$ is 4-hydroxymethylbenzyl;

the compound of formula (IIa) wherein $R^{22}$ is 3-aminobenzyl and $R^{23}$ is 3-($CH_3NHC(=O)NH$)benzyl;

the compound of formula (IIa) wherein $R^{22}$ is 3-($CH_3NHC(=O)NH$)benzyl and $R^{23}$ is 3-($CH_3NHC(=O)NH$)benzyl;

the compound of formula (IIa) wherein $R^{22}$ is 3-(N-methylamino)benzyl and $R^{23}$ is 4-hydroxymethylbenzyl;

the compound of formula (IIa) wherein $R^{22}$ is 3-((N,N-dimethylaminoglycyl)amino)benzyl and $R^{23}$ is 3-((N,N-dimethylaminoglycyl)amino)benzyl;

the compound of formula (IIa) wherein $R^{22}$ is 3-((N-methylaminoglycyl)amino)benzyl and $R^{23}$ is 3-((N-methylaminoglycyl)amino)benzyl;

the compound of formula (IIa) wherein $R^{22}$ is 3-((N,N-dimethylaminoglycyl)amino)benzyl and $R^{23}$ is 4-hydroxymethylbenzyl;

the compound of formula (IIa) wherein $R^{22}$ is 3-((N-phenylmethoxycarbonylaminoglycyl)amino)benzyl and $R^{23}$ is 3-((N-phenylmethoxycarbonylaminoglycyl)amino)benzyl;

the compound of formula (IIa) wherein $R^{22}$ is 3-(glycylamino)benzyl and $R^{23}$ is 3-(glycylamino)benzyl;

the compound of formula (IIa) wherein $R^{22}$ is 3-(glycylamino)benzyl and $R^{23}$ is 4-hydroxymethylbenzyl;

the compound of formula (IIa) wherein $R^{22}$ is 3-((N-phenylmethoxycarbonylamino-L-alanyl)amino)benzyl and $R^{23}$ is 3-((N-phenylmethoxycarbonylamino-L-alanyl)amino)benzyl;

the compound of formula (IIa) wherein $R^{22}$ is 3-((N-phenylmethoxycarbonylamino-L-phenylalanyl)amino)benzyl and $R^{23}$ is 3-((N-phenylmethoxycarbonylamino-L-phenylalanyl)amino)benzyl;

the compound of formula (IIa) wherein $R^{22}$ is 3-(L-alanyl)amino)benzyl and $R^{23}$ is 3-(L-alanyl)amino)benzyl;

the compound of formula (IIa) wherein $R^{22}$ is 3-(L-phenylalanyl)amino)benzyl and $R^{23}$ is 3-(L-phenylalanyl)amino)benzyl;

the compound of formula (IIa) wherein $R^{22}$ is 5-hydroxy-1-pentyl and $R^{23}$ is hydrogen;

the compound of formula (IIa) wherein $R^{22}$ is 5-hydroxy-1-pentyl and $R^{23}$ is 2-naphthylmethyl;

the compound of formula (IIa) wherein $R^{22}$ is 5-hydroxy-1-pentyl and $R^{23}$ is benzyl;

the compound of formula (IIa) wherein $R^{22}$ is 5-hydroxy-1-pentyl and $R^{23}$ is 4-hydroxymethylbenzyl;

the compound of formula (IIa) wherein $R^{22}$ is 6-hydroxy-1-hexyl and $R^{23}$ is 2-naphthylmethyl;

the compound of formula (IIa) wherein $R^{22}$ is 5-hydroxy-1-pentyl and $R^{23}$ is 3-hydroxybenzyl;

the compound of formula (IIa) wherein $R^{22}$ is 5-hydroxy-1-pentyl and $R^{23}$ is (5-methylsulfonyl)-1-pentyl;

the compound of formula (IIa) wherein $R^{22}$ is 5-hydroxy-1-pentyl and $R^{23}$ is 5-($CH_3S(O)$)-1-pentyl;

the compound of formula (IIa) wherein $R^{22}$ is 5-hydroxy-1-pentyl and $R^{23}$ is cyclopropylmethyl;

the compound of formula (IIa) wherein $R^{22}$ is 5-hydroxy-1-pentyl and $R^{23}$ is 5-methoxy-1-pentyl;

the compound of formula (IIa) wherein $R^{22}$ is 5-hydroxy-1-pentyl and $R^{23}$ is 3-cyanobenzyl;

the compound of formula (IIa) wherein $R^{22}$ is 5-hydroxy-1-pentyl and $R^{23}$ is 3-carboethoxybenzyl;

the compound of formula (IIa) wherein $R^{22}$ is 4-hydroxy-1-hexyl and $R^{23}$ is 4-hydroxy-1-hexyl;

the compound of formula (IIa) wherein $R^{22}$ is 4-hydroxy-1-hexyl and $R^{23}$ is 2-naphthylmethyl;

the compound of formula (IIa) wherein $R^{22}$ is 4-oxime-1-hexyl and $R^{23}$ is 4-oxime-1-hexyl;

the compound of formula (IIa) wherein $R^{22}$ is 5-hydroxy-1-pentyl and $R^{23}$ is 3-hydroxymethylbenzyl;

the compound of formula (IIa) wherein $R^{22}$ is 6-amino-1-hexyl and $R^{23}$ is 4-hydroxymethylbenzyl;

the compound of formula (IIa) wherein $R^{22}$ is 3-(N,N-diethylaminocarbonyl)benzyl and $R^{23}$ is 3-(N,N-diethylaminocarbonyl)benzyl;

the compound of formula (IIa) wherein $R^{22}$ is 3-carbomethoxybenzyl and $R^{23}$ is 3-(N,N-diethylaminocarbonyl)benzyl;

the compound of formula (IIa) wherein $R^{22}$ is 3-carbomethoxybenzyl and $R^{23}$ is 3-(N-ethylaminocarbonyl)benzyl;

the compound of formula (IIa) wherein $R^{22}$ is 3-hydroxymethylbenzyl and $R^{23}$ is hydrogen;

the compound of formula (IIa) wherein $R^{22}$ is 3-hydroxymethylbenzyl and $R^{23}$ is 3-(N,N-diethylaminocarbonyl)benzyl;

the compound of formula (IIa) wherein $R^{22}$ is 3-hydroxymethylbenzyl and $R^{23}$ is 3-(N-ethylaminocarbonyl)benzyl;

the compound of formula (IIa) wherein $R^{22}$ is 3-(N-propylaminocarbonyl)benzyl and $R^{23}$ is 3-(N-propylaminocarbonyl)benzyl;

the compound of formula (IIa) wherein $R^{22}$ is 3-($HO_2C$)benzyl and $R^{23}$ is 3-(N-isopropylaminocarbonyl)benzyl;

the compound of formula (IIa) wherein $R^{22}$ is 3-($HO_2C$)benzyl and $R^{23}$ is 3-(N-propylaminocarbonyl)benzyl;

the compound of formula (IIa) wherein $R^{22}$ is 3-($HO_2C$)benzyl and $R^{23}$ is benzyl;

the compound of formula (IIa) wherein $R^{22}$ is 3-($HO_2C$)benzyl and $R^{23}$ is cyclopropylmethyl;

the compound of formula (IIa) wherein $R^{22}$ is 4-hydroxymethylbenzyl and $R^{23}$ is 3-($HO_2C$)benzyl;

the compound of formula (IIa) wherein $R^{22}$ is 3-hydroxymethylbenzyl and $R^{23}$ is 3-pyridinylmethyl;

the compound of formula (IIa) wherein $R^{22}$ is 4-hydroxymethylbenzyl and $R^{23}$ is 3-aminocarbonylbenzyl;

the compound of formula (IIa) wherein $R^{22}$ is 3-aminobenzyl and $R^{23}$ is 2-naphthylmethyl;

the compound of formula (IIa) wherein $R^{22}$ is cyclopropylmethyl and $R^{23}$ is 3-aminocarbonylbenzyl;

the compound of formula (IIa) wherein $R^{22}$ is 3-aminocarbonylbenzyl and $R^{23}$ is hydrogen;

the compound of formula (IIa) wherein $R^{22}$ is 3-hydroxymethylbenzyl and $R^{23}$ is 3-(N-ethylaminocarbonyl)benzyl;

the compound of formula (IIa) wherein $R^{22}$ is 3-hydroxymethylbenzyl and $R^{23}$ is 3-(N-methylamino)benzyl;

the compound of formula (IIa) wherein $R^{22}$ is 3-(N-methylamino)benzyl and $R^{23}$ is 2-naphthylmethyl;

the compound of formula (IIa) wherein $R^{22}$ is 4-formylbenzyl and $R^{23}$ is 4-hydroxymethylbenzyl;

the compound of formula (IIa) wherein $R^{22}$ is 3-(1-hydroxy-1-ethyl)benzyl and $R^{23}$ is 3-(1-hydroxyethyl)benzyl;

the compound of formula (IIa) wherein $R^{22}$ is 3-pyridinylmethyl and $R^{23}$ is 4-hydroxymethylbenzyl;

the compound of formula (IIa) wherein $R^{22}$ is 3-(N-imidazolylmethyl)benzyl and $R^{23}$ is 3-(N-imidazolylmethyl)benzyl;

the compound of formula (IIa) wherein $R^{22}$ is 3-(2,2-dimethyl-1-propionyl)benzyl and $R^{23}$ is 3-(2,2-dimethyl-1-propionyl)benzyl;

the compound of formula (IIa) wherein $R^{22}$ is 3-(2,2,2-trifluoro-1-hydroxyethyl)benzyl and $R^{23}$ is 3-(2,2,2-trifluoro-1-hydroxyethyl)benzyl;

the compound of formula (IIa) wherein $R^{22}$ is 3-(2-imidazolyl-C(=O))benzyl and $R^{23}$ is 3-(2-imidazolyl-C(=O))benzyl;

the compound of formula (IIa) wherein $R^{22}$ is 3-(3-hydroxy-1-propyn-1-yl)benzyl and $R^{23}$ is 3 (3-hydroxy-1-propyn-1-yl)benzyl;

the compound of formula (IIa) wherein $R^{22}$ is 3-(2,2,2-trifluoroacetyl)benzyl and $R^{23}$ is 3-(2,2,2-trifluoroacetyl)benzyl;

the compound of formula (IIa) wherein $R^{22}$ is 3-propionylbenzyl and $R^{23}$ is 3-propionylbenzyl;

the compound of formula (IIa) wherein $R^{22}$ is 3-(4-pyrazolyl)benzyl and $R^{23}$ is 3-(4-pyrazolyl)benzyl;

the compound of formula (IIa) wherein $R^{22}$ is 3-($CH_3CH_2C$(=N-OH))benzyl and $R^{23}$ is 3-($CH_3CH_2C$(=N-OH))benzyl;

the compound of formula (IIa) wherein $R^{22}$ is 3-sulfonamidobenzyl and $R^{23}$ is 3-sulfonamidobenzyl;

the compound of formula (IIa) wherein $R^{22}$ is 3-($CF_3CH_2C$(=N-OH))benzyl and $R^{23}$ is 3-($CF_3CH_2C$(=N-OH))benzyl;

the compound of formula (IIa) wherein $R^{22}$ is 4-fluoromethylbenzyl and $R^{23}$ is 4-fluoromethylbenzyl;

the compound of formula (IIa) wherein $R^{22}$ is 4-(1-hydroxyethyl)benzyl and $R^{23}$ is 4-(1-hydroxyethyl)benzyl;

the compound of formula (IIa) wherein $R^{22}$ is 3-(5-methyl-1,2,3-oxadiazolyl)benzyl and $R^{23}$ is 3-(5-methyl-1,2,3-oxadiazolyl)benzyl;

the compound of formula (IIa) wherein $R^{22}$ is 3-($H_2NC$(=NOH))benzyl and $R^{23}$ is 3-($H_2NC$(=NOH))benzyl;

the compound of formula (IIa) wherein $R^{22}$ is 3-($H_2NC$(=NOH))-4-fluorobenzyl and $R^{23}$ is 3-($H_2NC$(=NOH))-4-fluorobenzyl;

the compound of formula (IIa) wherein $R^{22}$ is 5-benzotriazolylmethyl and $R^{23}$ is 5-benzotriazolylmethyl;

the compound of formula (IIa) wherein $R^{22}$ is 5-benzimidazolylmethyl and $R^{23}$ is 5-benzimidazolylmethyl;

the compound of formula (IIa) wherein $R^{22}$ is 5-benzimidazolylmethyl and $R^{23}$ is 5-benzimidazolylmethyl;

the compound of formula (IIa) wherein $R^{22}$ is 5-benzotriazolylmethyl and $R^{23}$ is 4-hydroxymethylbenzyl;

the compound of formula (IIa) wherein $R^{22}$ is 5-benzotriazolylmethyl and $R^{23}$ is 3-(3-pyrazolyl)benzyl;

the compound of formula (IIa) wherein $R^{22}$ is 5-indazolylmethyl and $R^{23}$ is 5-indazolylmethyl;

the compound of formula (IIa) wherein $R^{22}$ is 3-chloro-5-indazolylmethyl and $R^{23}$ is 3-chloro-5-indazolylmethyl;

the compound of formula (IIa) wherein $R^{22}$ is 3-methylamino-5-indazolylmethyl and $R^{23}$ is 3-methylamino-5-indazolylmethyl;

the compound of formula (IIa) wherein $R^{22}$ is 3-ethylamino-5-indazolylmethyl and $R^{23}$ is 3-ethylamino-5-indazolylmethyl;

the compound of formula (IIa) wherein $R^{22}$ is 6-indazolylmethyl and $R^{23}$ is 6-indazolylmethyl;

the compound of formula (IIa) wherein $R^{22}$ is 3-amino-5-benzisoxazolylmethyl and $R^{23}$ is 3-amino-5-benzisoxazolylmethyl;

the compound of formula (IIa) wherein wherein $R^{22}$ is 5-(2-amino)benzoxazolyl and $R^{23}$ is 5-(2-amino)benzoxazolyl.

[16] Also preferred are compounds of formula (IIaa):

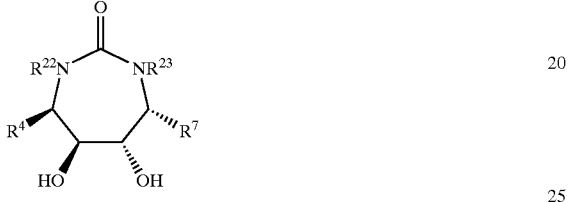

(IIaa)

or a pharmaceutically acceptable salt or prodrug form thereof wherein:

$R^4$ and $R^7$ are independently selected from: benzyl, fluorobenzyl, pyrrolylmethyl, methoxybenzyl, isobutyl, nitrobenzyl, aminobenzyl, hydroxybenzyl, thienylmethyl, pyridylmethyl, naphthylmethyl;

$R^{22}$ and $R^{23}$ are independently selected from:
hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylm-ethylboronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)-benzyl, (trifluorohydroxyethyl)benzyl, ($CF_3C(=NOH)$)-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC(=O)O$)benzyl, ($NH_2C(=O)CH_2O$)benzyl, ($NH_2C(=NH)$)benzyl, ((N-phenylmethoxycarbonyl)glycylamino)benzyl, (imidazolylmethyl)benzyl, (($CH_3)_3C-C(=O)$)benzyl, (N-methyl-N-ethylaminoethyl)aminocarbonylbenzyl, (pyrrolidinylethyl)aminocarbonylbenzyl, (piperidinylethyl)aminocarbonylbenzyl, ($H_2NC(=NOH)$)benzyl, ($H_2NC(=NOH)$)fluorobenzyl, benzimidazolylmethyl, benzotriazolylmethyl, indazolylmethyl, benzoxazolinylmethyl, benzisoxazolylmethyl, thienylmethyl, furylmethyl.

[17] Specifically preferred are compounds of formula (IIaa):

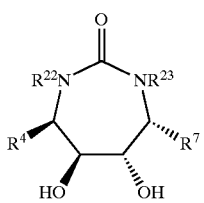

(IIaa)

selected from the group consisting of:

the compound of formula (IIaa) wherein $R^4$ and $R^7$ are isobutyl, $R^{22}$ and $R^{23}$ are cyclopropylmethyl;

the compound of formula (IIaa) wherein $R^4$ and $R^7$ are isobutyl, $R^{22}$ and $R^{23}$ are allyl;

the compound of formula (IIaa) wherein $R^4$ is 4-nitrobenzyl, $R^7$ is 2-nitrobenzyl, $R^{22}$ and $R^{23}$ are cyclopropylmethyl;

the compound of formula (IIaa) wherein $R^4$ and $R^7$ are 4-nitrobenzyl, $R^{22}$ and $R^{23}$ are cyclopropylmethyl;

the compound of formula (IIaa) wherein $R^4$ is 4-nitrobenzyl, $R^7$ is 2-nitrobenzyl, $R^{22}$ and $R^{23}$ are n-butyl;

the compound of formula (IIaa) wherein $R^4$ is 4-aminobenzyl, $R^7$ is 2-aminobenzyl, $R^{22}$ and $R^{23}$ are cyclopropylmethyl;

the compound of formula (IIaa) wherein $R^4$ and $R^7$ are 4-fluorobenzyl, $R^{22}$ and $R^{23}$ are 3-hydroxybenzyl;

the compound of formula (IIaa) wherein $R^4$ and $R^7$ are 4-fluorobenzyl, $R^{22}$ and $R^{23}$ are cyclopropylmethyl;

the compound of formula (IIaa) wherein $R^4$ and $R^7$ are 4-fluorobenzyl, $R^{22}$ and $R^{23}$ are 4-hydroxymethylbenzyl;

the compound of formula (IIaa) wherein $R^4$ and $R^7$ are 4-fluorobenzyl, $R^{22}$ and $R^{23}$ are 3-aminocarbonylbenzyl;

the compound of formula (IIaa) wherein $R^4$ and $R^7$ are 4-fluorobenzyl, $R^{22}$ and $R^{23}$ are 3-acetylbenzyl;

the compound of formula (IIaa) wherein $R^4$ and $R^7$ are 4-fluorobenzyl, $R^{22}$ and $R^{23}$ are 3-butyrylbenzyl;

the compound of formula (IIaa) wherein $R^4$ and $R^7$ are 4-fluorobenzyl, $R^{22}$ and $R^{23}$ are 3-hydroxymethylbenzyl;

the compound of formula (IIaa) wherein $R^4$ and $R^7$ are 4-fluorobenzyl, $R^{22}$ and $R^{23}$ are 3-($CH_3C$(=NOH)) benzyl;

the compound of formula (IIaa) wherein $R^4$ and $R^7$ are 3-methoxybenzyl, $R^{22}$ and $R^{23}$ are benzyl.

the compound of formula (IIaa) wherein $R^4$ and $R^7$ are 4-fluorobenzyl, $R^{22}$ and $R^{23}$ are 3-($H_2NC$(=NOH)benzyl;

the compound of formula (IIaa) wherein $R^4$ and $R^7$ are 4-fluorobenzyl, $R^{22}$ and $R^{23}$ are 3-($H_2NC$(=NOH)-4-fluorobenzyl;

the compound of formula (IIaa) wherein $R^4$ and $R^7$ are 3-methoxybenzyl, $R^{22}$ and $R^{23}$ are cyclopropylmethyl;

the compound of formula (IIaa) wherein $R^4$ and $R^7$ are 3-methoxybenzyl, $R^{22}$ and $R^{23}$ are 4-hydroxymethylbenzyl;

the compound of formula (IIaa) wherein $R^4$ and $R^7$ are 3-methoxybenzyl, $R^{22}$ and $R^{23}$ are 3-methoxybenzyl;

the compound of formula (IIaa) wherein $R^4$ and $R^7$ are 3-hydroxybenzyl, $R^{22}$ and $R^{23}$ are 3-hydroxybenzyl.

the compound of formula (IIaa) wherein $R^4$ and $R^7$ are 4-methoxybenzyl, $R^{22}$ and $R^{23}$ are cyclopropylmethyl;

the compound of formula (IIaa) wherein $R^4$ and $R^7$ are 4-methoxybenzyl, $R^{22}$ and $R^{23}$ are benzyl;

the compound of formula (IIaa) wherein $R^4$ and $R^7$ are 4-methoxybenzyl, $R^{22}$ and $R^{23}$ are 2-naphthylmethyl;

the compound of formula (IIaa) wherein $R^4$ and $R^7$ are 4-methoxybenzyl, $R^{22}$ and $R^{23}$ are 4-hydroxymethylbenzyl;

the compound of formula (IIaa) wherein $R^4$ and $R^7$ are 4-hydroxybenzyl, $R^{22}$ and $R^{23}$ are benzyl;

the compound of formula (IIaa) wherein $R^4$ and $R^7$ are 4-methoxybenzyl, $R^{22}$ and $R^{23}$ are allyl;

the compound of formula (IIaa) wherein $R^4$ and $R^7$ are 4-(2-hydroxyethoxy)benzyl, $R^{22}$ and $R^{23}$ are benzyl;

the compound of formula (IIaa) wherein $R^4$ and $R^7$ are 4-(2-morpholinylethoxy)benzyl, $R^{22}$ and $R^{23}$ are benzyl;

the compound of formula (IIaa) wherein $R^4$ and $R^7$ are 3-($H_2NC$(=O)$CH_2O$)benzyl, $R^{22}$ and $R^{23}$ are n-butyl;

the compound of formula (IIaa) wherein $R^4$ and $R^7$ are 3,4-difluorobenzyl, $R^{22}$ and $R^{23}$ are 3-hydroxymethylbenzyl;

the compound of formula (IIaa) wherein $R^4$ and $R^7$ are 3,4-difluorobenzyl, $R^{22}$ and $R^{23}$ are 4-hydroxymethylbenzyl;

the compound of formula (IIaa) wherein $R^4$ and $R^7$ are 3,4-difluorobenzyl, $R^{22}$ and $R^{23}$ are 3-($H_2NC$(=O)) benzyl;

the compound of formula (IIaa) wherein $R^4$ and $R^7$ are 3,4-difluorobenzyl, $R^{22}$ and $R^{23}$ are 3-($H_2NC$(=NOH))benzyl;

the compound of formula (IIaa) wherein $R^4$ and $R^7$ are 2-naphthylmethyl, $R^{22}$ and $R^{23}$ are benzyl;

the compound of formula (IIaa) wherein $R^4$ and $R^7$ are 2-naphthylmethyl, $R^{22}$ and $R^{23}$ are cyclopropylmethyl;

the compound of formula (IIaa) wherein $R^4$ and $R^7$ are 2-thienylmethyl, $R^{22}$ and $R^{23}$ are cyclopropylmethyl;

the compound of formula (IIaa) wherein $R^4$ and $R^7$ are 2-thienylmethyl, $R^{22}$ and $R^{23}$ are 3-($H_2NC$(=NOH)) benzyl;

the compound of formula (IIaa) wherein $R^4$ and $R^7$ are 4-methylthiobenzyl, $R^{22}$ and $R^{23}$ are benzyl;

the compound of formula (IIaa) wherein $R^4$ and $R^7$ are isopropyl, $R^{22}$ and $R^{23}$ are n-hexyl;

the compound of formula (IIaa) wherein $R^4$ and $R^7$ are 4-pyridylmethyl, $R^{22}$ and $R^{23}$ are benzyl.

[18] Also preferred in the present invention are compounds of formula (IIb):

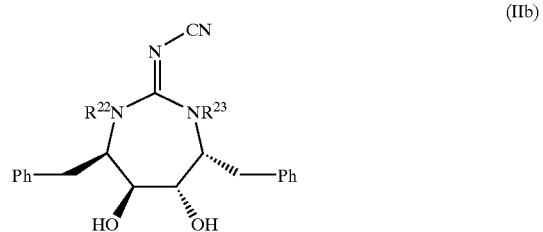

or a pharmaceutically acceptable salt or prodrug form thereof wherein:

$R^{22}$ and $R^{23}$ are independently selected from the group consisting of:

hydrogen, allyl, methyl, ethyl, propyl, cyclopropylmethyl, n-butyl, i-butyl, $CH_2CH$=C$(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H₂NC(=O))-benzyl, carbomethoxybenzyl, carboethoxybenzyl, tetrazolylbenzyl, and dimethylallyl, aminomethylbenzyl, (O-benzyl-formaldoxime) benzyl, (O-methyl-formaldoxime)benzyl, (CH₃O₂CO)-benzyl, (HOCH₂CH₂N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, (CH₃C(=NOH))-benzyl, (H₂NNHC(=O))-benzyl, (H₂NC(=O)NHN=CH)-benzyl, (CH₃ONHC(=O))-benzyl, (HONHC(=O))-benzyl, (CH₃NHC(=O))-benzyl, N,N-dimethylaminocarbonylbenzyl, (HOCH₂CH(OH)CH₂O)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, (CH₃CH₂NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl) benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, (H₂NSO₂)-benzyl, dihydroxyethylbenzyl, (MeHNC(=O)NH)-benzyl, (H₂NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH₃CH₂C(=NOH))-benzyl, (trifluorohydroxyethyl)benzyl, (CF₃C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH₃NHC(=O)O) benzyl, (NH₂C(=O)CH₂O)benzyl, (NH₂C(=NH)) benzyl, ((N-phenylmethoxycarbonyl)glycylamino) benzyl, (imidazolylmethyl)benzyl, ((CH₃)₃C—C(=O))benzyl, (N-methyl-N-ethylaminoethyl) aminocarbonylbenzyl, (pyrrolidinylethyl) aminocarbonylbenzyl, (piperidinylethyl) aminocarbonylbenzyl, (H₂NC(=NOH))benzyl, (H₂NC(=NOH))fluorobenzyl, benzimidazolylmethyl, benzotriazolylmethyl, indazolylmethyl, benzoxazolinylmethyl, benzisoxazolylmethyl, thienylmethyl, furylmethyl.

[19] Specifically preferred are compounds of formula (IIb):

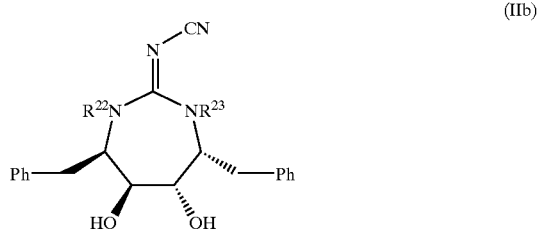

selected from the group consisting of:
the compound of formula (IIb) wherein $R^{22}$ is 4-hydroxybenzyl and $R^{23}$ is 4-hydroxybenzyl;
the compound of formula (IIb) wherein $R^{22}$ is cyclopentylmethyl and $R^{23}$ is cyclopentylmethyl;
the compound of formula (IIb) wherein $R^{22}$ is n-butyl and $R^{23}$ is n-butyl;
the compound of formula (IIb) wherein $R^{22}$ is 3-hydroxybenzyl and $R^{23}$ is 3-hydroxybenzyl;
the compound of formula (IIb) wherein $R^{22}$ is 3-aminobenzyl and $R^{23}$ is 3-aminobenzyl;
the compound of formula (IIb) wherein $R^{22}$ is cyclohexylmethyl and $R^{23}$ is cyclohexylmethyl;
the compound of formula (IIb) wherein $R^{22}$ is cyclobutylmethyl and $R^{23}$ is cyclobutylmethyl;
the compound of formula (IIb) wherein $R^{22}$ is 3-hydroxymethylbenzyl and $R^{23}$ is 3-hydroxymethylbenzyl;
the compound of formula (IIb) wherein $R^{22}$ is 3-formylbenzyl and $R^{23}$ is 3-formylbenzyl;
the compound of formula (IIb) wherein $R^{22}$ is 3-formaldoximebenzyl and $R^{23}$ is 3-formaldoximebenzyl.

[20] Also preferred in the present invention are compounds of the formula (Ibb):

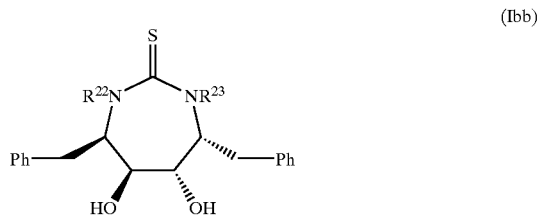

or a pharmaceutically acceptable salt or prodrug form thereof wherein:
$R^{22}$ and $R^{23}$ are independently selected from the group consisting of:
hydrogen, allyl, methyl, ethyl, propyl, cyclopropylmethyl, n-butyl, i-butyl, CH₂CH=C(CH₃)₂, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyloxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime) benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl) benzyl, (imidazolyl-C(=O))-benzyl, (pyrazolyl-C (=O))-benzyl, (pyridylmethylaminocarbonyl) benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)-benzyl, (trifluorohydroxyethyl)benzyl, ($CF_3C(=NOH)$)-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC(=O)O$) benzyl, ($NH_2C(=O)CH_2O$)benzyl, ($NH_2C(=NH)$) benzyl, ((N-phenylmethoxycarbonyl)glycylamino) benzyl, (imidazolylmethyl)benzyl, (($CH_3)_3C-C(=O)$)benzyl, (N-methyl-N-ethylaminoethyl) aminocarbonylbenzyl, (pyrrolidinylethyl) aminocarbonylbenzyl, (piperidinylethyl) aminocarbonylbenzyl, ($H_2NC(=NOH)$)benzyl, ($H_2NC(=NOH)$)fluorobenzyl, benzimidazolylmethyl, benzotriazolylmethyl, indazolylmethyl, benzoxazolinylmethyl, benzisoxazolylmethyl, thienylmethyl, furylmethyl.

[21] Specifically preferred are compounds of formula (Ibb):

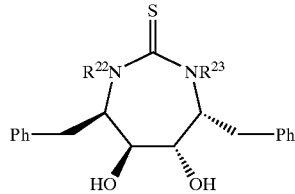

(Ibb)

selected from the group consisting of:

the compound of formula (Ibb) wherein $R^{22}$ is benzyl and $R^{23}$ is hydrogen;

the compound of formula (Ibb) wherein $R^{22}$ is cyclopropylmethyl and $R^{23}$ is cyclopropylmethyl;

the compound of formula (Ibb) wherein $R^{22}$ is benzyl and $R^{23}$ is benzyl;

the compound of formula (Ibb) wherein $R^{22}$ is 3-hydroxybenzyl and $R^{23}$ is 3-hydroxybenzyl.

the compound of formula (Ibb) wherein $R^{22}$ is 3-hydroxymethylbenzyl and $R^{23}$ is 3-hydroxymethylbenzyl;

the compound of formula (Ibb) wherein $R^{22}$ is 4-hydroxybenzyl and $R^{23}$ is 4-hydroxybenzyl;

the compound of formula (Ibb) wherein $R^{22}$ is 3-methoxybenzyl and $R^{23}$ is 3-methoxybenzyl;

the compound of formula (Ibb) wherein $R^{22}$ is 3-(H2NC(=NOH))benzyl and $R^{23}$ is 4-hydroxymethylbenzyl;

the compound of formula (Ibb) wherein $R^{22}$ is 3-(H2NC(=NOH))benzyl and $R^{23}$ is 3-(H2NC(=NOH)) benzyl;

the compound of formula (Ibb) wherein $R^{22}$ is 3-(H2NC(=NOH))-4-fluorobenzyl and $R^{23}$ is 3-(H2NC(=NOH))-4-fluorobenzyl;

[22] Also preferred in the present invention are compounds of the formula (Ic):

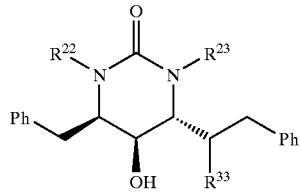

(Ic)

or a pharmaceutically acceptable salt or prodrug form thereof wherein:

$R^{33}$ is OH, halogen, H, $N_3$ or can alternatively be taken together with $R^{23}$ to form a direct bond;

wherein $R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime) benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl) benzyl, (imidazolyl-C(=O))-benzyl, (pyrazolyl-C(=O))-benzyl, (pyridylmethylaminocarbonyl) benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)-benzyl, (trifluorohydroxyethyl)benzyl, ($CF_3C(=NOH)$)-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC(=O)O$) benzyl, ($NH_2C(=O)CH_2O$)benzyl, ($NH_2C(=NH)$) benzyl, ((N-phenylmethoxycarbonyl)glycylamino) benzyl, (imidazolylmethyl)benzyl, (($CH_3$)$_3$C—C(=O))benzyl, (N-methyl-N-ethylaminoethyl) aminocarbonylbenzyl, (pyrrolidinylethyl) aminocarbonylbenzyl (piperidinylethyl) aminocarbonylbenzyl, ($H_2NC(=NOH)$)benzyl, ($H_2NC(=NOH)$)fluorobenzyl, benzimidazolylmethyl, benzotriazolylmethyl, indazolylmethyl, benzoxazolinylmethyl, benzisoxazolylmethyl, thienylmethyl, furylmethyl.

[23] Specifically preferred are compounds of formula (Ic):

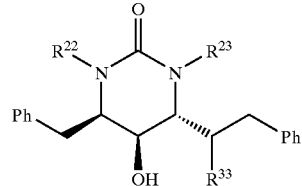

(Ic)

selected from the group consisting of:
the compound of formula (Ic) wherein $R^{22}$ is 3-hydroxybenzyl, $R^{23}$ is 3-hydroxybenzyl and $R^{33}$ is hydrogen;
the compound of formula (Ic) wherein $R^{22}$ is 3-acetylbenzyl, $R^{23}$ is 3-acetylbenzyl and $R^{33}$ is hydrogen;
the compound of formula (Ic) wherein $R^{22}$ is 3-hydroxymethylbenzyl, $R^{23}$ is 3-hydroxymethylbenzyl and $R^{33}$ is hydrogen.
the compound of formula (Ic) wherein $R^{22}$ is 3-($H_2NC(=O)$)benzyl, $R^{23}$ is 3-($H_2NC(=O)$)benzyl and $R^{33}$ is hydrogen.
the compound of formula (Ic) wherein $R^{22}$ is 3-($H_2NC(=NOH)$)benzyl, $R^{23}$ is 3-($H_2NC(=NOH)$)benzyl and $R^{33}$ is hydrogen.
the compound of formula (Ic). wherein $R^{22}$ is 3-($H_2NC(=O)$)-4-fluorobenzyl, $R^{23}$ is 3-($H_2NC(=O)$)-4-fluorobenzyl and $R^{33}$ is hydrogen.
the compound of formula (Ic) wherein $R^{22}$ is 3-($H_2NC(=NOH)$)-4-fluorobenzyl, $R^{23}$ is 3-($H_2NC(=NOH)$)-4-fluorobenzyl and $R^{33}$ is hydrogen.

[24] Also preferred are compounds of formula (IId):

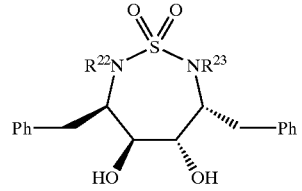

(IId)

or a pharmaceutically acceptable salt or prodrug form thereof wherein:
$R^{22}$ and $R^{23}$ are independently selected from the group consisting of:
hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime) benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, (HONHC(=O))-benzyl, ($CH_3NHC(=O)$)-benzyl, N,N-dimethylaminocarbonylbenzyl, ($HOCH_2CH(OH)CH_2O$)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl) benzyl, (imidazolyl-C(=O))-benzyl, (pyrazolyl-C(=O))-benzyl, (pyridylmethylaminocarbonyl) benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)-benzyl, (trifluorohydroxyethyl)benzyl, ($CF_3C(=NOH)$)-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC(=O)O$) benzyl, ($NH_2C(=O)CH_2O$)benzyl, ($NH_2C(=NH)$) benzyl, ((N-phenylmethoxycarbonyl)glycylamino) benzyl, (imidazolylmethyl)benzyl, (($CH_3)_3C-C(=O)$)benzyl, (N-methyl-N-ethylaminoethyl) aminocarbonylbenzyl, (pyrrolidinylethyl) aminocarbonylbenzyl, (piperidinylethyl) aminocarbonylbenzyl, ($H_2NC(=NOH)$)benzyl, ($H_2NC(=NOH)$)fluorobenzyl, benzimidazolylmethyl, benzotriazolylmethyl, indazolylmethyl, benzoxazolinylmethyl, benzisoxazolylmethyl, thienylmethyl, furylmethyl.

[25] Specifically preferred are compounds of formula (IId):

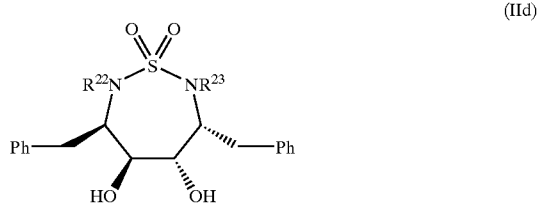

selected from the group consisting of:

the compound of formula (IId) wherein $R^{22}$ is 4-hydroxymethylbenzyl and $R^{23}$ is 4-hydroxymethylbenzyl;

the compound of formula (IId) wherein $R^{22}$ is 3-hydroxybenzyl and $R^{23}$ is 3-hydroxybenzyl;

the compound of formula (IId) wherein $R^{22}$ is cyclopropylmethyl and $R^{23}$ is cyclopropylmethyl;

the compound of formula (IId) wherein $R^{22}$ is 2-naphthylmethyl and $R^{23}$ is 2-naphthylmethyl;

the compound of formula (IId) wherein $R^{22}$ is 4-hydroxybenzyl and $R^{23}$ is 4-hydroxybenzyl;

the compound of formula (IId) wherein $R^{22}$ is 3-aminobenzyl and $R^{23}$ is 3-aminobenzyl;

the compound of formula (IId) wherein $R^{22}$ is 3-hydroxymethylbenzyl and $R^{23}$ is 3-hydroxymethylbenzyl;

the compound of formula (IId) wherein $R^{22}$ is 3-($Me_2NCH_2C(=O)NH$)-benzyl and $R^{23}$ is 3-($Me_2NCH_2C(=O)NH$)-benzyl;

the compound of formula (IId) wherein $R^{22}$ is 3-formaldoximebenzyl and $R^{23}$ is 3-formaldoximebenzyl;

the compound of formula (IId) wherein $R^{22}$ is 3-($CH_3C(=NOH)$)-benzyl and $R^{23}$ is 3-($CH_3C(=NOH)$)-benzyl;

the compound of formula (IId) wherein $R^{22}$ is 3-(2-amino-4-thienyl)benzyl and $R^{23}$ is 3-(2-amino-4-thienyl)benzyl;

the compound of formula (IId) wherein $R^{22}$ is 5-hydroxypentyl and $R^{23}$ is 5-hydroxypentyl;

the compound of formula (IId) wherein $R^{22}$ is 6-hydroxypentyl and $R^{23}$ is 6-hydroxypentyl;

the compound of formula (IId) wherein $R^{22}$ is 5-hydroxypentyl and $R^{23}$ is 2-naphthylmethyl;

the compound of formula (IId) wherein $R^{22}$ is 5-hydroxypentyl and $R^{23}$ is 4-hydroxymethylbenzyl;

the compound of formula (IId) wherein $R^{22}$ is 5-hydroxypentyl and $R^{23}$ is 3-hydroxymethylbenzyl.

[52] Also included in the present invention are compounds, or a pharmaceutically acceptable salt form thereof, selected from the following formulae:

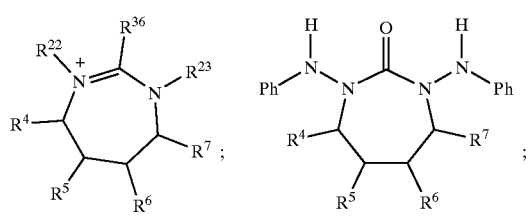

-continued

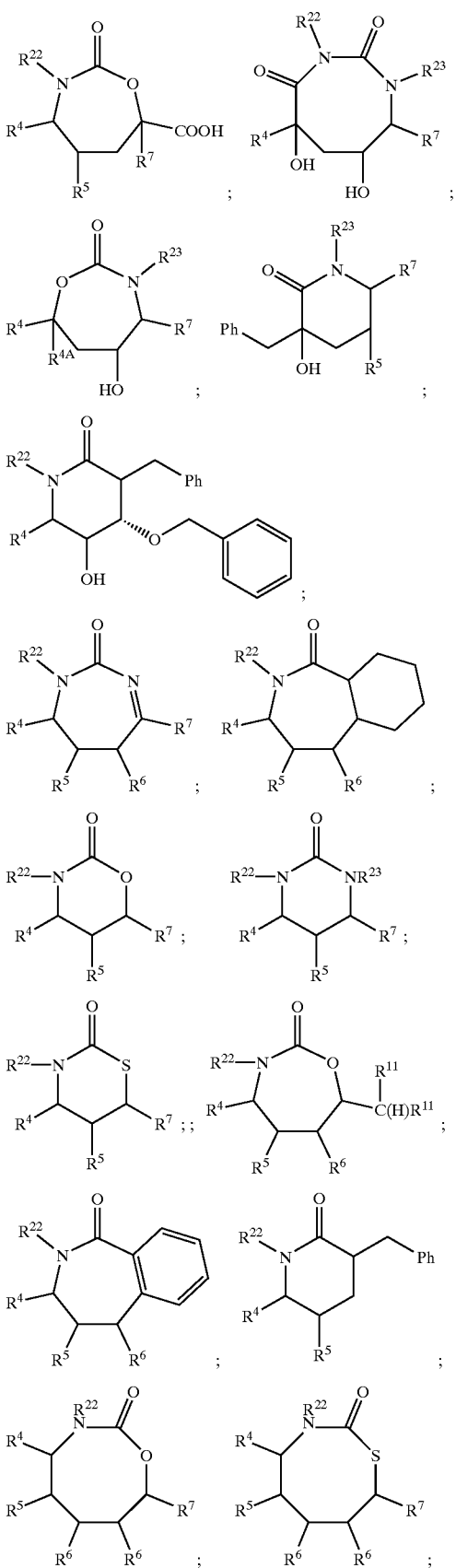
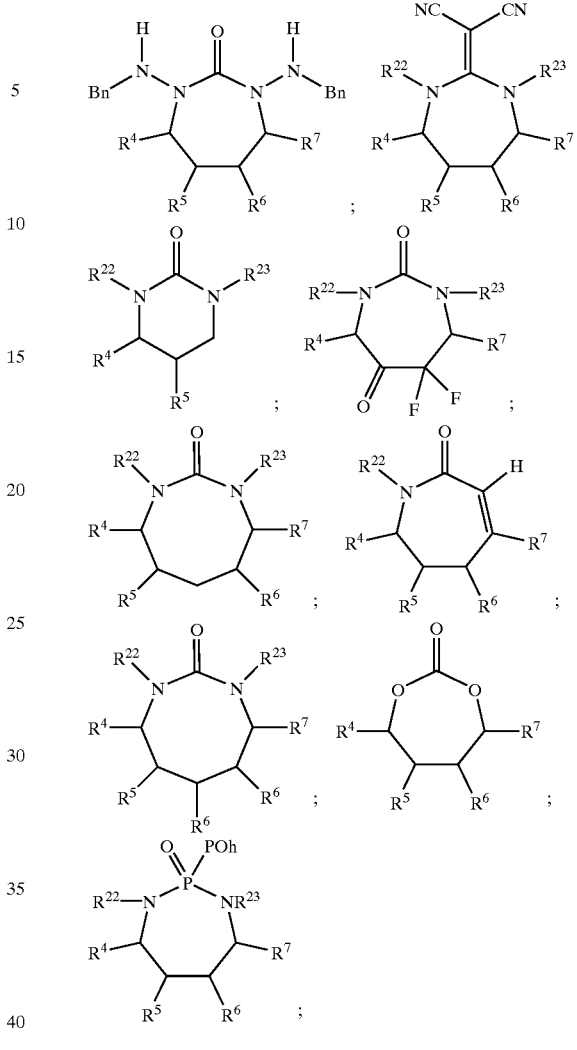

wherein:
R⁴ and R⁷ are independently selected from the following groups:
hydrogen; $C_1$–$C_3$ alkyl substituted with 0–1 $R^{11}$;
$R^5$ is —$OR^{20}$;
$R^6$ is hydrogen or —$OR^{21}$;
$R^{20}$ and $R^{21}$ are independently hydrogen or any group that, when administered to a mammalian subject, cleaves to form a free hydroxyl;
$R^{11}$ is selected from one or more of the following:
H; halogen; —$OR^{13}$;
$C_3$–$C_{10}$ cycloalkyl substituted with 0–2 $R^{12}$;
$C_1$–$C_4$ alkyl substituted with 0–2 $R^{12}$;
aryl($C_1$–$C_3$ alkyl) substituted with 0–2 $R^{12}$;
aryl substituted with 0–2 $R^{12}$; or
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;
$R^{12}$, when a substituent on carbon, is selected from one or more of the following:
benzyloxy, halogen, methyl, $C_1$–$C_4$ alkoxy, $CF_3$, 2-(1-morpholino)ethoxy, —$CO_2H$, hydroxamic acid, hydrazide, —C(R$^{14}$)=N(OR$^{14}$), cyano, boronic acid, sulfonamide, formyl, C$_3$–C$_6$ cycloalkoxy, C$_1$–C$_4$ alkyl substituted with —NR$^{13}$R$^{14}$, —NR$^{13}$R$^{14}$, hydroxy, hydroxymethyl; or R$^{12}$, when a substituent on nitrogen, is methyl;

R$^{13}$ is H, C$_1$–C$_4$ alkyl, C$_2$–C$_4$ alkenyl, or benzyl;

R$^{14}$ is OH, H, CF$_3$, C$_1$–C$_4$ alkyl, C$_1$–C$_4$ alkoxy, NH$_2$, C$_2$–C$_4$ alkenyl, or benzyl;

R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

R$^{15}$ is H or CH$_3$;

R$^{22}$ and R$^{23}$ are independently selected from the following:
  hydrogen;
  C$_1$–C$_8$ alkyl substituted with 0–3 R$^{31}$;
  C$_2$–C$_6$ alkenyl substituted with 0–3 R$^{31}$;
  C$_2$–C$_4$ alkynyl substituted with 0–3 R$^{31}$;

R$^{31}$ is selected from one or more of the following:
  halogen, —OR$^{13}$, C$_1$–C$_4$ alkyl, C$_3$–C$_{10}$ cycloalkyl, —C(R$^{14}$)=N(OR$^{14}$), —CO$_2$R$^{13}$, —S(O)$_m$R$^{13}$;
  aryl substituted with 0–5 R$^{32}$; or
  a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 R$^{32}$;

R$^{32}$, when a substituent on carbon, is selected from one or more of the following:
  benzyloxy, halogen, 2-(1-morpholino)ethoxy, —CO$_2$R$^{13}$, hydroxamic acid, —CONR$^{13}$NR$^{13}$R$^{14}$, cyano, boronic acid, sulfonamide, —CHO, C$_3$–C$_6$ cycloalkoxy, —NR$^{13}$R$^{14}$, —C(R$^{14}$)=N(OR$^{14}$), NO$_2$, —OR$^{13}$, —NR$^{40}$R$^{41}$, —SO$_m$R$^{13}$, —SO$_m$NR$^{13}$R$_{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$, phenyl, —C(=O)NR$^{13}$—(C$_{1-C4}$ alkyl)-NR$^{13}$R$^{14}$, —C(=O)NR$^{40}$R$^{41}$, C$_1$–C$_4$ haloalkyl, C$_1$–C$_4$ haloalkoxy, C$_2$–C$_4$ haloalkenyl, C$_1$–C$_4$ haloalkynyl, —C(=O)NR$^{13}$R$^{14}$; —C(=O)C(R$^{11}$)$_2$NR$^{13}$R$^{14}$; —C(=O)C(R$^{11}$)$_2$NR$^{13}$NR$^{14}$; —C(=O)C(R$^{11}$)$_2$NR$^{13}$CO$_2$R$^{13}$; —C(=O)—(C$_1$–C$_4$ alkyl)—NR$^{13}$R$^{14}$; —C(=O)—(C$_1$–C$_4$ alkyl)—NR$^{13}$CO$_2$R$^{13}$; or
  C$_1$–C$_4$ alkoxy substituted with 0–3 groups selected from: R$^{11}$, C$_3$–C$_6$ cycloalkyl, —C(=O)NR$^{13}$R$^{14}$, —NR$^{13}$R$^{14}$ or OH;
  C$_1$–C$_4$ alkyl substituted with 0–3 groups selected from: R$^{11}$, =NR$^{14}$, =NNR$^{13}$C(=O)NR$^{13}$R$^{14}$ or —NR$^{13}$R$^{14}$;
  C$_2$–C$_4$ alkenyl substituted with 0–3 R$^{11}$;
  C$_2$–C$_4$ alkynyl substituted with 0–3 R$^{11}$;
  a 5- or 6-membered heterocyclic ring containing from 1 to 4 heteroatoms independently selected from oxygen, nitrogen or sulfur substituted with 0–2 R$^{12}$;

R$^{32}$, when a substituent on nitrogen, is methyl;

m is 0, 1, or 2;

R$^{36}$ is selected from: C$_1$–C$_2$ alkyl; COR$^{37}$; NR$^{38}$R$^{39}$; CN; CCl$_3$;

R$^{37}$ is selected from:
  hydrogen;
  C$_1$–C$_2$ alkyl substituted with 0–1 R$^{11}$;
  hydroxyl;
  C$_1$–C$_2$ alkoxy substituted with 0–1 R$^{11}$;
  —NR$^{38}$R$^{39}$;

R$^{38}$ and R$^{39}$ are independently selected from:
  hydrogen;
  C$_1$–C$_2$ alkyl substituted with 0–3 R$^{11}$; or
  an amine protecting group;

R$^{40}$ is selected from: H, C$_1$–C$_3$ alkyl;

R$^{41}$ is selected from:
  —C(=O)NR$^{13}$R$^{14}$;
  —C(=O)NR$^{13}$NR$^{14}$;
  —C(=O)C(R$^{11}$)$_2$NR$^{13}$R$^{14}$;
  —C(=O)C(R$^{11}$)$_2$NR$^{13}$NR$^{14}$;
  —C(=O)C(R$^{11}$)$_2$NR$^{13}$CO$_2$R$^{13}$;
  —C(=O)H;
  —C(=O)R$^{11}$;
  —C(=O)—(C$_1$–C$_4$ alkyl)-NR$^{13}$R$^{14}$;
  —C(=O)—(C$_1$–C$_4$ alkyl)-NR$^{13}$CO$_2$R$^{13}$;
  1–3 amino acids linked together via amide bonds, and linked to the N atom via the carboxylate terminus.

[53] Another aspect of the invention is a process for preparing cyclic compounds of formula (I):

(I)

wherein:

W is selected from:
  —N(R$^{22}$)C(=O)N(R$^{23}$)—;
  —N(R$^{22}$)C(=S) N(R$^{23}$)—;
  —N(R$^{22}$)S(=O)$_2$N(R$^{23}$)—;

R$^{22}$ and R$^{23}$ are as defined above, provided that at least one of R$^{22}$ or R$^{23}$ must be H;

R$^4$, R$^{4A}$, R$^7$, R$^{7A}$, R$^{5a}$, and R$^{6a}$ are as defined above;

n is 0, 1, or 2;

R$^{20}$ and R$^{21}$ are as defined above and may in addition be selected from a hydroxyl protecting group;

said process comprising the step of reacting an acyclic diamine compound of the formula (III):

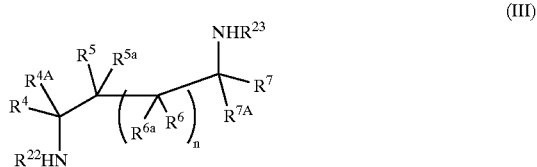

(III)

with a suitable cyclizing reagent in a suitable solvent, said solvent optionally comprising a base, thereby to form a compound of formula (I).

For compounds of formula (I) wherein W is —N(R$^{22}$)C(=O)N(R$^{23}$)—, the suitable cyclizing reagent may be selected from, but is not limited to, phenyl chloroformate, phenyl tetrazoylformate, urea, phosgene, triphosgene, oxalyl chloride, N,N'-disuccinimidyl carbonate, 1,1'-carbonyldiimidazole, trichloromethyl chloroformate, and 2(S),3-pyridinediyl thiocarbonate. A preferred cyclizing reagent is 1,1'-carbonyl diimidazole.

For compounds of formula (I) wherein W is —N(R$^{22}$)C(=S)N(R$^{23}$)—, the suitable cyclizing reagent may be selected from, but is not limited to, 1,1'-thiocarbonyl diimidazole or carbon disulfide. Preferably, the cyclizing reagent is 1,1'-thiocarbonyldiimidazole.

For compounds of formula (I) wherein W is —N($R^{22}$)S(=O)$_2$N($R^{23}$)—, the suitable cyclizing reagent may be selected from, but is not limited to, sulfamide.

A base may optionally be included in the above-described method in order to account for the lability of the $R^{20}$ and $R^{21}$ hydroxyl protecting groups to the cyclization conditions. The base may be selected from organic bases which include, but are not limited to, pyridine, diisopropylethylamine, and triethylamine. The base may alternatively be selected from inorganic bases which include but are not limited to sodium hydroxide.

The above-described reaction is carried out in a suitable solvent, for example, in an organic solvent or in a biphasic suspension of water and an organic solvent. Suitable solvents include chlorinated organic solvents which include, but are not limited to, chloroform, methylene chloride, tetrachloroethane, butyl chloride and dichloroethane. A preferrable chlorinated organic solvent is chloroform. The non-chlorinated organic solvents useful in the method of the invention include, but are not limited to tetrahydrofuran, N,N-dimethylformamide and toluene. A preferrable non-chlorinated organic solvent is toluene.

The reaction can be conducted at a temperature of from about 0° C. to about the boiling point of the solvent selected, 153° C. in the case of N,N-dimethylformamide. Preferably, the temperature of the reaction is about 0° C. to about room temperature.

The time required for completion of the reaction can range from about 1 hour to about 5 days, depending on the combination of cyclizing reagent, solvent, base and stereoisomer of compound (III) selected. The reaction can be run under nitrogen or other inert atmosphere, provided that any changes in concentration and integrity of the reagents due to decomposition are compensated for.

As used herein, the term "hydroxyl protecting group" means any group known in the art of organic synthesis for the protection of hydroxyl groups. Such protecting groups include those listed in Greene and Wuts, "Protective Groups in Organic Synthesis", John Wiley & Sons, New York (1991), the disclosure of which is hereby incorporated by reference. The hydroxyl protecting groups are base-stable and can include, but are not limited to acyl types, aromatic carbamate types and alkyl types. Exemplary are methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

[55] Another aspect of the invention is a process for preparing cyclic compounds of formula (Icc):

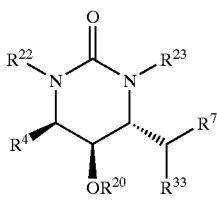

(Icc)

wherein:

$R^4$, $R^7$, $R^{20}$, $R^{22}$, $R^{23}$ are as defined above, and $R^{33}$ is hydrogen or halogen;

with the proviso that neither $R^{22}$ or $R^{23}$ are hydrogen.

said process comprising the step of reacting a cyclic urea of formula (IIaaa)

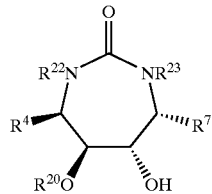

(IIaaa)

with a reagent capable of converting the free hydroxy in the compound of formula (IIaaa) to a suitable leaving group and, at the same time, providing in situ a suitable nucleohilic species to bring about a ring contraction, in a suitable solvent, thereby to form a compound of formula (Icc).

The above reagent may be selected from, but is not limited to, 2-acetoxyisobutyryl bromide, DAST, or a combination of triphenylphosphine/DEAD/chloroacetic acid. The preferred reagent when $R^{20}$ and $R^{33}$ are hydrogen is 2-acetoxyisobutyryl bromide.

The above-described reaction is carried out in a suitable solvent, for example, in an organic solvent. Suitable solvents include chlorinated organic solvents which include, but are not limited to, chloroform, methylene chloride, tetrachloroethane, butyl chloride and dichloroethane. A preferrable chlorinated organic solvent is dichloromethane. The non-chlorinated organic solvents useful in the method of the invention include, but are not limited to tetrahydrofuran, diethyl ether and toluene. A preferrable non-chlorinated organic solvent is tetrahydrofuran.

The reaction can be conducted at a temperature of from about 0° C. to 50° C. Preferably, the temperature of the reaction is about 0° C. to about room temperature.

The time required for completion of the reaction can range from about 5 min to about 24 hr, depending on the combination of solvent, and substitution on compound (IIaaa) selected. The reaction can be run under nitrogen or other inert atmosphere, provided that any changes in concentration and integrity of the reagents due to decomposition are compensated for.

For compounds of Formula (1cc) wherein $R^{33}$ is hydrogen, a second step comprising reacting a compound of formula (1cc), wherein $R^{33}$ is bromo, with a suitable dehalogenation reagent is required. Suitable dehalogenation reagents may be selected from but are not limited to tri-n-butyltin hydride or zinc dust. Preferred reagents are tri-n-butyltin hydride or zinc. Suitable solvents in the case of tri-n-butyltin hydride include toluene, tetrahydrofuran or benzene, with the preferred solvent being toluene. The reaction may be carried out at a temperature of from about 50° C. to about 120° C. Preferably, the temperature of the reations is from 80° C. to 120° C. The time required for completion of the reaction is from about 30 min to about 6 hr. In the case where the reagent used is zinc dust, then the preferred solvent is glacial acetic acid, the prefferred temperature is room temperature, and the time required for completion of reaction is from about 1 hr to about 48 hr.

Hereby incorporated herein by reference is copending commonly assigned U.S. patent application Ser. No. of Jadhav and Emmett 08/040,146 filed Mar. 30, 1993.

In the present invention it has been discovered that the compounds of formula (I) above are useful as inhibitors of HIV protease and similar retroviral proteases, and for the inhibition of HIV and the treatment of HIV infection and similar retrovirus infections.

The present invention also provides methods for the treatment of HIV infection by administering to a host infected with HIV a pharmaceutically or therapeutically effective or acceptable amount of a compound of formula (I) as described above. By therapeutically effective amount, it is meant an amount of a compound of the present invention effective to inhibit HIV infection or treat the symptoms of HIV infection in a host.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral replication and/or HIV protease, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV protease, the compounds of the present invention may also be useful as diagnostic reagents in diagnostic assays for the detection of HIV protease. Thus, inhibition of the protease activity in an assay (such as the assays described herein) by a compound of the present invention would be indicative of the presence of HIV protease and HIV virus.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, $R^1$ through $R^{41}$, $R^{4A}$ and $R^{7A}$, m, n, W, Z, etc.) occurs more than one time in any constituent or in formula (I) or (II), or any other formula herein, its definition on each occurrence is independent of its definition at every other occurrence. Thus, for example, if a group is shown to be substituted with 0–3 $R^{11}$, then said group may optionally be substituted with up to three $R^{11}$ and $R^{11}$ at each occurrence is selected independently from the defined list of possible $R^{11}$. Also, for example, in $—N(R^{20})_2$, each of the $R^{20}$ substituents may be independently selected from the list of possible $R^{20}$ groups defined. Also, combinations of substituents and/or variables are permissible only if such combinations result in stable compounds. Similarly, by way of example, for the group $—C(R^{11})_2—$, each of the two $R^{11}$ substituents on C is independently selected from the defined list of possible $R^{11}$.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example $—C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon. bonds which may occur in any stable point along the chain, such as ethynyl, propynyl and the like.

The terms "-(alkyl)-" n, "-(alkyenyl)-", "-(phenyl)-", and the like, refer to alkyl, alkenyl, and phenyl groups, respectively, which are connected by two bonds to the rest of the structure of Formula I. Such groups may alternatively and equivalently be denoted as "alkylene", "alkenylene", "phenylene", and the like, respectively.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl) aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridinyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, or isatinoyl. Also included are fused ring and spiro compounds containing, for example, the above heterocycles. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

When a bond to a substituent is shown to cross the bond connecting two atoms in a ring, then such substituent may be bonded to any atom on the ring. When a substituent is listed without indicating the atom via which such substituent is bonded to the rest of the compound of formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of formula (I) via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that an one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, the term "any group that, when administered to a mammalian subject, cleaves to form a free hydroxyl, amino or sulfhydryl" means any group bonded to an O, N, or S atom, respectively, which is cleaved from the O, N, or S atom when the compound is administered to a mammalian subject to provide a compound having a remaining free hydroxyl, amino, or sulfhydryl group, respectively. Examples of groups that, when administered to a mammalian subject, are cleaved to form a free hydroxyl, amino or sulfhydryl, include but are not limited to, phosphate esters, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, or heteroarylcarbonyl. Examples of groups that, when administered to a mammalian subject, are cleaved to form a free hydroxyl, amino or sulfhydryl, may include hydroxy, amine or sulfhydryl protecting groups, respectively.

As used herein, the term "amine protecting group" means any group known in the art of organic synthesis for the protection of amine groups. Such amine protecting groups include those listed in Greene and Wuts, "Protective Groups in Organic Synthesis" John Wiley & Sons, New York (1991) and "The Peptides: Analysis, Synthesis, Biology", Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) fair, and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

By a "ketal ring" or "ketal" group is meant any ketal protecting group which can be hydroyzed to form a carbonyl. Such ketal rings or ketal protecting groups are well known in the art of organic synthesis and typically include, for example, substituted or unsubstituted carbocyclic diethers, dithioethers, or mixed ethers. Such ketal protecting groups include those listed in Greene and Wuts, "Protective Groups in Organic Synthesis" John Wiley & Sons, New York (1991).

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, 9-phenylproline, tert-leucine, 4-aminocyclohexylalanine, N-methylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the compounds of formula (I); phosphate esters, dimethylglycine esters, aminoalkylbenzyl esters, aminoalkyl esters and carboxyalkyl esters of alcohol and phenol functional groups in the compounds of formula (I); and the like.

The pharmaceutically acceptable salts of the compounds of formula (I) include the conventional non-toxic salts or the quaternary ammonium salts of the compounds of formula (I) formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of formula (I) which contain a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

As used herein, "W" is not intended to be a symbol for tungsten.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below.

The compounds of the present invention may be synthesized using the general synthetic procedures described below. Each of the references cited below are hereby incorporated herein by reference. All the temperatures are reported herein in degrees Celsius.

Compounds of the invention wherein:

W is —N($R^{22}$)C(=Z)N($R^{23}$)— or —N($R^{22}$)C(=O)C(=O)N($R^{23}$)— or —N($R^{22}$)S(=Z')N($R^{23}$)— or —N($R^{22}$)S(=Z')$_2$N($R^{23}$)— or —N($R^{22}$)P(=O)($R^{24a}$)N($R^{23}$)— or —N($R^{22}$)C($F_2$)C(=O)N($R^{23}$)— or —N($R^{22}$)C($F_2$)S(=O)N($R^{23}$)—;

$R^5$ is —$OR^{20}$ or H;

$R^6$ is —$OR^{21}$ or H; and n is 1; can be formed from diamines of formula (III):

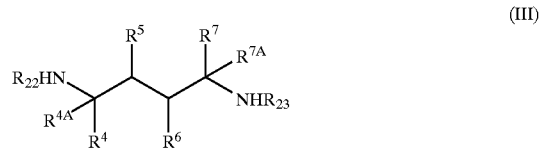

(III)

The diamines of formula (III) can be synthesized as described in copending commonly assigned patent application Jadhav et al. U.S. Ser. No. 07/714,042, filed May. 31, 1991. Alternative methods which can be used to synthesize the compounds of structure (III) above are described in European Patent Application Publication Number 402646A1, U.S. Pat. No. 4,837,204, and Canadian Patent Application 2,026,832.

The compounds of formula (III) can be cyclized to form compounds of formula (IV) under conditions normally used to form cyclic ureas, as is known to one skilled in the art. Reagents J—(C=Z)—J', where J and J' are leaving groups, are employed, preferably under relatively dilute conditions (for example, less than about 0.1 M), to effect ring closure to provide compounds of formula (I). Many examples of J and J' are known; preferred are carbonyl diimidazole, thiocarbonyldiimidazole, phosgene, thiophosgene, diphenyl carbonate, or diphenyl thiocarbonate. Additionally, for compounds wherein W is —N($R^{22}$)C(=O)C(=O)N($R^{23}$)—, compounds of formula (III) can be reacted with activated derivatives of oxalic acid, preferably oxalyl chloride, under the above conditions to form the diamide.

For compounds of the invention where $R^{20}$ or $R^{21}$ is —OH, it is advantageous to protect the free hydroxyl before cyclization. Protecting groups used can include any of those listed in Greene and Wuts, *Protective Groups in Organic Synthesis*, Chapter 2, Wiley, NY (1991). The preferred protecting groups are trimethylsilylethoxymethyl (SEM), methoxyethoxymethyl (MEM), or methoxymethyl (MOM).

Cyclization of compounds of formula (III) results in structure (IV) (i.e., structure (I) wherein W is —N($R^{22}$)C(=O)C(=O)N($R^{23}$)— and n is 1).

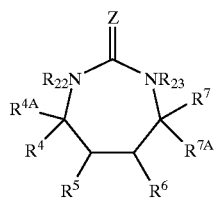

(IV)

Another, preferred method to form compounds of formula (IV), in cases wherein $R^{22}$ and $R^{23}$ are linked to their respective nitrogens by a $CH_2$ residue, is to cyclize a compound of structure (III) where $R^{22}$ and $R^{23}$ are hydrogen, and to alkylate the nitrogens using a base, a phase transfer catalyst, and an alkylating agent, using methods well known in the art. The preferred base is sodium hydride, and the preferred alkylating agents are $R^{22}Y$ and $R^{23}Y$, wherein Y is a halogen, triflate, or mesylate, preferably a bromide or iodide. Preferred conditions are in polar aprotic solvents between 0 and 100° C.

Cleavage of protecting groups, if employed, yields structures of formula (I) wherein $R^5$ and $R^6$ are hydroxyl.

When $R^5$ and $R^6$ are other than $OR^{20}$ and $OR^{21}$, some chemical manipulation of functional groups may need to be performed in the preparation of the compounds of formula (III) or (IV), as is appreciated by one of skill in the art of organic synthesis. Described below are examples of such procedures.

Methods for obtaining compounds wherein $R^5$ is OH and $R^6$ is $OR^{21}$ include protection of nitrogen, if necessary, followed by reaction of the diol with one equivalent of base and one equivalent of acyl halide, alkyl halide, alkoxyalkyl halide, alkoxycarbonyl halide, benzoyl halide, diphenyl carbonate or phenylisocyanate, and purification by column chromatography of the unwanted bis-alkylated and unreacted material.

Methods for obtaining compounds wherein $R^5$ is OH and $R^6$ is H include protection of nitrogen, if necessary, and reduction of the diol to the monool using techniques known in the art (see, for example, *Chem. Comm.* 1971, 1097; *J. Org. Chem.* 1969, 3923). The preferred method is formation of cyclic diol ester and reduction using hydride. Deprotection of nitrogen, if necessary, results in the desired compound.

Methods for obtaining compounds wherein $R^5$ is OH and $R^6$ is F include protection of nitrogen, if necessary, followed by formation of mono-protected diol as described above. Reaction with a fluorinating agent, preferably diethylaminosulfurtrifluoride (DAST) (*Reagents for Organic Synthesis*, Vol. 13, p. 110, Wiley Interscience, NY, 1988), provides the alkyl fluoride. Deprotection of nitrogen, if necessary, and hydroxyl results in the desired compound.

Methods for obtaining compounds wherein $R^5$ is OH and $R^6$ is =O include protection of nitrogen, if necessary, and standard conditions for oxidizing glycols to pinacols. The preferred oxidant is one equivalent of pyridinium dichromate in dichloromethane, or one equivalent of NaOCl in HOAc. Deprotection of nitrogen, if necessary, results in the desired compound. Alternatively, a monohydroxy compound described above can be oxidized to the ketone under standard conditions, preferably Swern oxidation using oxalyl chloride, DMSO and $Et_3N$, followed by alpha-hydroxylation of the ketone (see *Tet. Lett.* 1981, 607; *Tet. Lett.* 1982, 2917).

Methods for obtaining compounds wherein $R^5$ is OH and $R^6$ is difluoro include protection of nitrogen, if necessary, and hydroxyl of the above obtained pinacol, followed by reaction of the carbonyl with a fluorinating reagent, such as DAST. Deprotection of hydroxyl and nitrogen, if necessary, results in the desired compound.

Methods for obtaining compounds wherein $R^5$ and $R^6$ join to form an epoxide include protection of nitrogen, if necessary, followed by standard conditions for the formation of an epoxide from a glycol (see, for example, *J. Org. Chem.* 1981, 3361). Preferred is the reaction of the glycol with more than 2 equivalents of base and one equivalent of an activating group, such as methanesulfonyl chloride. Deprotection if necessary results in the desired compound.

Methods for obtaining compounds wherein $R^5$ is OH and $R^6$ is $C_1$–$C_3$ alkyl include protection of nitrogen, if necessary, and reaction of the epoxide prepared above with $C_1$–$C_3$ alkylmetal reagents. Preferred is the reaction of lithium dialkyl cuprates in aprotic solvents at low temperatures (–78 to –40° C.) (see Carruthers, *Some Modern Methods in Organic Synthesis*, p. 64, Cambridge University Press, 1978).

With a judicious selection of reagents, as is well appreciated to one skilled in the art, these manipulations can be performed in a straightforward manner to yield the claimed combinations of $R^5$ and $R^6$.

Compounds of the invention wherein:

W is —N($R^{22}$)C(=Z)N($R^{23}$)— or —N($R^{22}$)C(=O)C(=O)N($R^{23}$)—or —N($R^{22}$)S(=Z')N($R^{23}$)— or —N($R^{22}$)S(=Z)$_2$N($R^{23}$)— or —N($R^{22}$)P(=O)($R^{24a}$)N($R^{23}$)— or —N($R^{22}$)C($F_2$)C(=O)N($R^{23}$)— or —N($R^{22}$)C($F_2$)S(=O)N($R^{23}$)— or —N($R^{22}$)P(—Z)N($R^{23}$)—, and n is 0;

can be synthesized from diamines of formula (V):

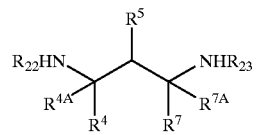

which can in turn be synthesized as described in European Patent Application Publication Number 402 646 A1.

Protection, if necessary, cyclization, and functional group manipulation if desired is performed as described above to obtain compounds of structure (VI):

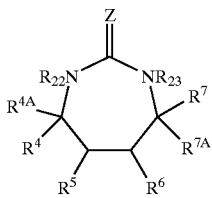

(VI)

Compounds of the invention wherein:

W is —OC(=O)O— or —C(=Z)— or —C($R^{25}$)($R^{26}$)P(=O)($R^{24a}$)C($R^{27}$)($R^{28}$)— or —P(=O)($R^{24a}$)— and n is 1;

can be formed from diols of structure (VII):

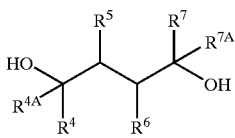

(VII)

which can in turn be synthesized as described in copending, commonly assigned U.S. patent application Jadhav et al. U.S. Ser. No. 07/714,042, filed May. 31, 1991.

Functional group manipulation, if desired, may be performed as described above, followed by cyclization to the carbonate using standard conditions, preferably phosgene or thiophosgene in the presence of 2 equivalents of a base such as potassium hydride, to obtain compounds of structure (I).

Compounds of the invention wherein:

W is —N($R^{22}$)C(=Z)O— or N($R^{22}$)P(=O)($R^{24a}$)C($R^{27}$)($R^{28}$)— or —C($R^{25}$)($R^{26}$)P(=O))($R^{24a}$)O— and n is 1;

can be formed from aminoalcohol of structure (VIII):

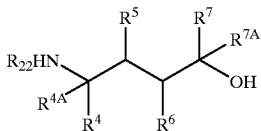

(VIII)

which can in turn be synthesized as described in a copending, commonly assigned U.S. patent application Jadhav et al. U.S. Ser. No. 07/714,042, filed May. 31, 1991, by employing a single equivalent of azide in the reaction of the diol of formula (VII) to obtain the azidoalcohol, followed by reduction as described in U.S. Ser. No. 07/714,042, to form the aminoalcohol.

Protection, if necessary, and functional group manipulation, if desired, is performed as described above, followed by cyclization to the carbamate using standard conditions, preferably phosgene or thiophosgene in the presence of 2 equivalents of a base, such as potassium hydride, to obtain compounds of structure (I).

Compounds of the invention wherein:
W is —OC(=Z)O— and n is 0;
can be formed from the diol of structure (IX):

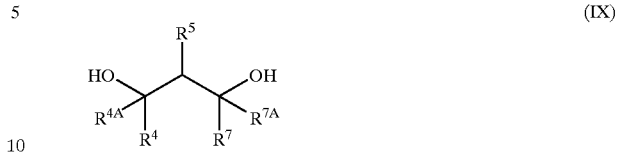

(IX)

which can in turn be synthesized by the reaction of $R^4$CHO with the lithium anion of 1,3 dithiane, followed by the reaction of $R^7$CHO with the anion of the product (see Carruthers, *Some Modern Methods in Organic Synthesis*, p. 45, Cambridge University Press, 1978). Cleavage of the dithiane with mercuric ion yields the acyclic alpha, alpha' dihydroxyketone.

Functional group manipulation, if desired, is performed as described above, followed by cyclization to the carbonate using standard conditions, preferably phosgene or thiophosgene, in the presence of 2 equivalents of a base such as potassium hydride, to obtain compounds of structure (I).

Compounds of the invention wherein:
W is —N($R^{22}$)C(=Z)O— and n is 0;
can be formed from aminoalcohol of structure (X):

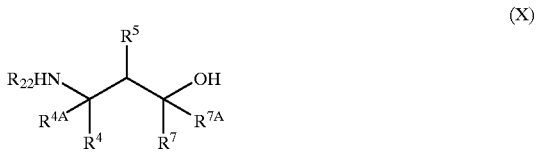

(X)

which can in turn be synthesized by the techniques described in European Patent Application Publication Number 402 646 A1 for the synthesis of compounds of structure (V), above; however, in place of azide, in opening the oxirane (shown below), an oxygen nucleophile, such as acetate or hydroxide ion, is reacted in the presence of a polar aprotic solvent, such as DMSO.

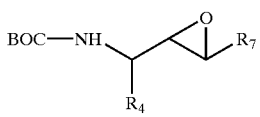

Alternatively, the oxirane is treated with a catalytic amount of a strong acid in water and a cosolvent, if necessary, which technique also removes the BOC protecting group.

Protection, if necessary, and functional group manipulation, if desired, is performed as described above, followed by cyclization to. the carbamate using standard conditions, preferably phosgene or thiophosgene in the presence of 2 equivalents of a base such as potassium hydride, to obtain compounds of structure (I).

Compounds of the present invention wherein:
W is —C($R^{25}$)($R^{26}$)N(CH$_3$)(O)C($R^{27}$)($R^{28}$)—;
can be synthesized from aminoalcohols (VIII) and (X) by the following steps: protection of nitrogen, if necessary, preferably with a benzyloxycarbonyl group; activation of the alcohol to displacement, preferably with a sulfonate derivative, such as mesyl chloride; removal of the nitrogen protecting group, preferably with hydrogen in the presence of a catalyst, such as palladium on carbon; and heating under dilute conditions in the presence of a base such as triethylamine to effect cyclization.

The secondary cyclic amine is then methylated, preferably with formic acid/formaldehyde, and oxidized, preferably with a peracid, such as MCPBA, to form compounds of formula (I), wherein W is —C($R^{25}$)($R^{26}$)N($CH_3$)(O)C($R^{27}$)($R^{28}$)—. The secondary cyclic amine can alternatively be directly oxidized to form structure (I), where W is —C($R^{25}$)($R^{26}$)N(O$R^{29}$)C($R^{27}$)($R^{28}$)—.

Compounds wherein:

W is —C($R^{25}$)($R^{26}$)C(=Z)C($R^{27}$)($R^{28}$)— and n is 0; can be prepared by the alkylation of protected cyclohexanedione (XI) with the required $R^4$-LG and $R^7$-LG, and optionally $R^{4A}$-LG and $R^{7A}$-LG groups, wherein LG represents a leaving group such as halogen or sulfonate ester.

(XI)

Reduction of the ketone to the alcohol, preferably with $LiAlH_4$, or manipulation to other values of $R^5$ as described above, is followed by cleavage of the ketal (see Greene and Wuts, *Protective Groups in Organic Synthesis*, Chapter 2, Wiley, NY, 1991). Protection of the alcohol or other reactive groups, followed by alkylation ketone and deprotection, provides compounds of structure (I), wherein W is —C($R^{25}$)($R^{26}$)C(=Z)C($R^{27}$)($R^{28}$)— and n is 0.

Compounds wherein:

W is —C($R^{25}$)($R^{26}$)C(=Z)C($R^{27}$)($R^{28}$)— and n is 1; can be prepared from the protected hydroxyketones described immediately above by ring expansion, for example via the Tiffeneau-Demyanov reaction (March, *Advanced Organic Chemistry*, p. 965, Wiley, NY, 1985), or by treatment with dimethylsulfonium ylide to form the spiro-epoxide, followed by acid-catalyzed ring expansion to the cycloheptanone (ibid., pp. 871, 966).

The above routes have the advantage of producing a number of stereoiomers which, upon purification, can be evaluated for the best combination of potency, safety and in vivo availability.

Compounds wherein:

W is —C($R^{25}$)($R^{26}$)C($F_2$)C($R^{27}$)($R^{28}$)— and n is 0 or 1; can be obtained from the above-described protected hydroxyketone by treatment with a fluorinating reagent, preferably DAST, as described above.

Compounds wherein:

W is —N($R^{22}$)C(=Z)C($R^{27}$)($R^{28}$)— and n is 0; can be obtained by cyclization of compound (XII) to the lactam using techniques known in the art (March, *Advanced Organic Chemistry*, p. 371, Wiley, NY, 1985).

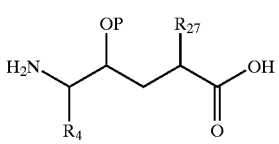

(XII)

Compounds of structure (XII) can in turn be obtained as described in European Patent Application Publication Number 434 365 A2, European Patent Application Publication Number 386 611 A2, European Patent Application Publication Number 389 127 A1, and CA 2005337, each of which are hereby incorporated by reference. OP in structure (XII) designates protected oxygen. Hydroxyl can be protected by the use of any of a number of groups as described in Greene and Wuts, *Protective Groups in Organic Synthesis*, Chapter 2, Wiley, NY (1991).

If desired, the resulting lactam (XIII):

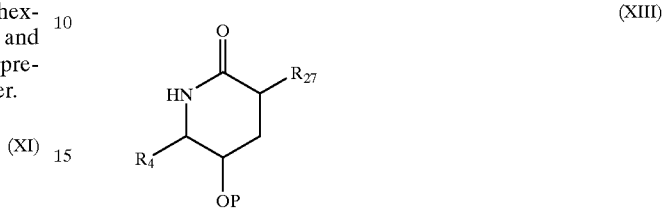

(XIII)

can be further functionalized, for example by the following techniques: the lactam nitrogen can be alkylated with an $R^{22}$-LG group, preferably employing sodium hydride in DMF; an $R^{4A}$, $R^7$ or $R^{7A}$ group can be added by deprotection and oxidation of the alcohol, followed by alkylation of the enolate using $R^{4A}$-LG, $R^7$-LG or $R^{7A}$-LG; and reduction of the ketone to hydroxyl or otherwise functionalizing to obtain the $R^5$ group of choice as described above.

Compounds wherein:

W is —N($R^{22}$)C(=Z)C($R^{27}$)($R^{28}$)— and n is 1; can be obtained through techniques known in the art from ketones of structure (I) wherein W is —C($R^{25}$)($R^{26}$)C(=Z)C($R^{27}$)($R^{28}$)— and n is 0, preferably via the Beckmann rearrangement (March, *Advanced Organic Chemistry*, p. 987, Wiley, NY, 1985). Manipulation of the $R^5$ group, if desired, as described above provides $R^5$ and $R^6$-substituted examples of (I), wherein W=—N($R^{22}$)C(=Z)C($R^{27}$)($R^{28}$)— and n=1.

Compounds wherein:

W is —C($R^{25}$)($R^{26}$)C(=Z)O— and n is 0 or 1; can be obtained from compounds of structure (I), wherein W=—N($R^{22}$)C(=Z)C($R^{27}$)($R^{28}$)—, n=0 or 1, and $R^{22}$=H. for example, by hydrolysis of the lactam, followed by displacement of the primary amine by hydroxyl, and closure to the lactone (March, *Advanced Organic Chemistry*, p. 348, Wiley, NY, 1985).

Similarly, compounds wherein:

W is —C($R^{25}$)($R^{26}$)C(=Z)S— and n is 0 or 1; can be obtained from compounds of structure (I), wherein W=—N($R^{22}$)C(=Z)C($R^{27}$)($R^{28}$)—, n=0 or 1, and $R^{22}$=H, for example, by hydrolysis of the lactam, followed by conversion of the primary amine to the diazonium salt, displacement by NaSH, and closure to the thiolactone (March, *Advanced Organic Chemistry*, p. 601, Wiley, NY, 1985).

Compounds of structure (I) described above wherein Z=0 can be converted to the thio derivatives, Z=S, using standard conditions (March, *Advanced Organic Chemistry*, p. 792, Wiley, NY, 1985); preferred is the use of the disulfide described in *Bull. Soc. Chim. Belges* 1978, 223.

Structures (I) described above wherein Z=0 can be converted to the imino derivatives, Z=N$R^{24}$, using standard conditions. When $R^{24}$ is OH or O-alkyl, the oximes can be formed and alkylated if desired as described in March, *Advanced Organic Chemistry*, pp. 359, 805, Wiley, NY, 1985. The hydrazones and imines can be formed similarly (ibid, pp. 533, 797).

The compounds of the formula (I) where in W=—N($R^{22}$)P(O)($R^{24a}$)N($R^{23}$)— and n=1, and $R^{24a}$ is ethyl, can be synthesized by cyclization of diamine III under conditions normally used to form cyclic phosphoric amides, as exemplfied by Patois et al. in Heteroatom. Chem. 1(5), 369–374, (1990), wherein ethyl phosphorodichloridate in presence of trialkylamine, such as triethylamine, was used to cyclize a diimino derivative. Similarly, other diimines could be cyclized to form cyclic phosphoric amide derivatives.

It is expected that the compounds of the invention can also be prepared as shown in Scheme 1 (shown below). The intra-molecular coupling of the N-substituted or unsubstituted dialdehydes may be achieved by organometal reagents derived from vanadium, titanium, samarium etc. The dialdehyde precursors can be prepared from the commercially available materials by the methods known to those skilled in the art of organic synthesis, preferably by the techniques disclosed in copending commmonly assigned U.S. patent application, Hodge, U.S. Ser. No. 07/659,442, filed Feb. 21, 1991.

Compounds wherein W is $-N(R^{22})C(=O)N(R^{23})-$ and n is 2 can be synthesized as shown in Scheme 2 (below). The eight-membered cyclic urea in Scheme 2 can be protected, if necessary, and manipulated as described above to yield the desired compounds.

Compounds wherein W is $-N(R^{22})C(=O)N(R^{23})-$ and n is 1 can likewise be synthesized as shown in Schemes 3, 4, 6, 7 (below). If necessary, intermediates described herein can be manipulated by methods known to those skilled in the art of organic synthesis to provide compounds within the scope of the invention.

Compounds wherein W is $-N(R^{22})C(=N-OR)N(R^{23})-$ or $-N(R^{22})C(=S)N(R^{23})-$ and n is 1 can be synthesized as shown in Scheme 5 (below). If necessary, intermediates described herein can be manipulated by methods known to those skilled in the art of organic synthesis to provide compounds within the scope of the invention.

Compounds wherein W is $-N(R^{22})C(=O)N(R^{23})-$ and n is 0 can likewise be synthesized as shown in Scheme 8 (below). If necessary, intermediates described herein can be manipulated by methods known to those skilled in the art of organic synthesis to provide compounds within the scope of the invention.

Compounds wherein W is $-N(R^{22})C(=O)N(R^{23})-$, n is 0 and $R^{23}$ and $R^{33}$ are combined to be a direct bond, can be synthesized as shown in Scheme 9. Compounds of (XXXIIa) were treated under strongly ionizing conditions to produce compounds where W is $-N(R^{22})C(=O)N(R^{23})-$, n is 0, and $R^{23}$ is H, $R^{33}$ is $-O_2C$-alkyl. Treatment of compound (XXXIIa) with hydrogen and palladium catalyst provided $R^{33}$ is H, whereas treatment with gaseous hydrogen bromide provided $R^{33}$ is Br. Another route to these compounds was developed (Scheme 10). If necessary, intermediates described herein can be manipulated by methods known to those skilled in the art of organic synthesis to provide compounds within the scope of the invention.

Compounds wherein W is $-N(R^{22})S(=O)_2N(R^{23})-$, n is 1 could be synthesized as shown in Scheme 11. Diamines of structure (III) were treated with sulfamide to give the cyclic sulfamides. Alkylation using a metal hydride base gave the bisalkylated products. The monoalkylated products could be obtained by selective alkylation using techniques known to one skilled in the art of orgainc synthesis and further described in this invention.

Compounds wherein W is $-C(R^{25})(R^{26})SC(R^{27})(R^{28})-$, $-C(R^{25})(R^{26})S(=Z')C(R^{27})(R^{28})-$ and $-C(R^{25})(R^{26})S(=Z')_2C(R^{27})(R^{28})-$, n is 1, and Z' is defined above can be synthesized as shown in Scheme 12. Asymmetric epoxidation of muconic acid (Sharpless et al., *J. Org. Chem.* 57, 2768 (1992)); followed by benzylation (Seebach, D. and Wasmuth, D. *Helv. Chim. Acta* 63, 197 (1980)) provides a secondary diol, which can be converted to primary diol (XXXVIIa) by protection and reduction with lithium aluminum hydride. Further elaboration by the methods of Dugger et al. (*Tetrahedron Letters* 33, 6763 (1992)) and Trost et al. (*Tetrahedron Letters*, 22, 1287 (1981)) provide the sulfoxide shown. Further oxidation using a stronger oxidizing agent such as m-chloroperbenzoic acid would provide the corresponding sulfone (W is $-C(R^{25})(R^{26})S(=O)_2C(R^{27})(R^{28})-$). The intermediates described therein can be manipulated by methods known to those skilled in the art of organic synthesis to provide compounds within the scope of the invention.

Compounds wherein W is $-C(R^{25})(R^{26})C(=Z)C(R^{27})(R^{28})-$, n is 1, and Z is defined above can be synthesized as shown in Scheme 13. Compound XXXVIIa could be converted to the corresponding dibromide using carbon tetrabromide/triphenylphosphine. Dithiane anion, formed according to the method of Seebach, as reported in *Org. Syn.*, Coll. Vol. 6, 316 (1988), could be alkylated with this dibromide. The seven-membered ring ketone (Z is O), upon liberation with aqueous mercuric ion, could be alkylated according to methods reported in the literature. Imines (Z is $NR^{24}$) and thiocarbonyls (Z is S) can be prepared by one skilled in the art of organic synthesis using methods described in the literature.

Compounds wherein W is $-C(=Z)-$, n is 1, and Z is defined above can be synthesized as shown in Scheme 14. Secondary diol (VII) could be converted to the dibromide using such as described previously. Dithiane alkylation followed by deprotection with mercury ion would produce the five-membered ring ketone. Alkylation of the alpha-carbons would provide for substitution at $R^{4A}$ and $R^{7A}$. Thiocarbonyls and imines of the carbonyl could be prepared using methods described in the literature.

Compounds wherein W is $-C(R^{25})(R^{26})P(=O)(R^{24a})N(R^{23})-$ or $-C(R^{25})(R^{26})P(=O)(R^{24a})O-$ and n is 1, could be prepared as shown in Scheme 15. Aminoalcohol (VIII) could be converted to the corresponding bromide using the method of Morin and Sawaya (*Synthesis*, (1987), 479) and displaced with lithiophosphinate according to the method of Corey and Kwiatkowski (*J. Amer. Chem. Soc.*, (1966), 88, 5654). Deprotection of the amine protecting group would be followed by phosphoramide formation according to the method described by Patel et al., (*Tet Lett.*, (1990), 31, 5591). Alkylation with strong base would lead to the compounds where W is $-C(R^{25})(R^{26})P(=O)(R^{24a})N(R^{23})-$. Similarly, diazotization and nucleophilic displacement with hydroxide would lead to the compounds where W is $-C(R^{25})(R^{26})P(=O)(R^{24a})O-$ after cyclization.

Compounds wherein W is $-C(R^{25})(R^{26})P(=O)(R^{24a})C(R^{27})(R^{28})-$ or $-P(=O)(R^{24a})-$ and n is 1, could be prepared as shown in Scheme 16. Secondary diol (VII) could be brominated by the method of Morin and Sawaya to give (XXXVIa), which could be elaborated to (XXXVIIIa) via earlier described (XXXVIIa). Grignard coupling with methyl dichlorophosphate using the method of Polniaszek and Foster (*J. Org. Chem.*, 1991, 56, 3137) would lead to a cyclic phosphinate. Alkylation with strong base based on methods described in the literature (ie., see Polniaszek above) would provide the desired products.

Compounds of formula (I) wherein W is $-(R^{22})N^+=C(R^{36})N(R^{23})-$ and $-N=C(R^{36})N(R^{23})-$ and n=1 can be prepared according to Scheme 17. Intermediate (XXXIXa) can be cyclized under standard amidine reaction conditions, based on method known in the art. Quaternary salt formation with alkyl halide leads to compounds of the formula (XXXIXd) and (XXXIXe), which can be acid-deprotected according to method described herein.

Synthesis of intermediate (XLa) is described in Scheme 18a, and use thereafter is described in Schemes 18b–18c. N-Cbz-Phenylalaninal (XLb') is prepared from optically-active phenylalanine (XLa') by the route previously described. Compound (XLc') can be prepared by the reaction of (XLb') with an appropriate acetic acid anion equivalent such as a Reformatsky reagent derived from ethyl bromoacetate (prepared from bromoethyl acetate and zinc metal). Other acetic acid Ad anion equivalents are contemplated and are recognized by those possessing skill in the art. Compound (XLd') can be prepared by reacting (XLc') with an acyl anion equivalent such as a dithiane anion (such as that derived from 1,3-dithiane upon reaction with butyllithium). Other acyl anion equivalents are contemplated and are recognized by those possessing skill in the art. The conversion of (XLc') to (XLd') can also incorporate the use of either or both oxygen-protecting groups and nitrogen-protecting groups. A suitable oxygen-protecting group is the SEM (trimethylsilylethyloxymethyl) ether and a suitable nitrogen-protecting group is the Cbz (carbobenzyloxy) carbamate. Other protecting groups are contemplated including those described in Protecting Groups in Organic Synthesis, Second Edition by T. W. Greene and P. G. M. Wuts, John Wiley & Sons Inc., 1991. Compound (XLa) can be obtained by the hydrolysis of (XLd') with acid or base.

Alternatively, (XLa) can be obtained as follows: (XLe') can be prepared by reaction of (XLb') with a pyruvic acid anion equivalent such as a Reformatsky reagent. Other pyruvic acid anion equivalents are contemplated and are recognized by those possessing skill in the art. (XLf') is prepared by the reaction of (XLe') with an alkyl or aryl derived nucleophile such as a Grignard reagent or an organolithium reagent (such as benzylmagnesium bromide or phenyllithium). Other organometallic species are contemplated and are recognized by those possessing skill in the art. Intermediate (XLa) can be obtained by reaction of (XLf') under hydrolytic conditions needed to induce ester cleavage and/or conditions necessary to remove any or all protecting groups.

Intermediates (XLa)–(XLk) can be derived from (L)-phenylalanine, for example, although all other naturally-occurring and other unnatural amino acids are also contemplated.

Intermediate (XLb) can be prepared by the reaction of a methylene chloride solution of compound (XLa) with SEM-Cl (trimethylsilylethyloxymethyl chloride) in the presence of an amine base (such as diisopropylethylamine). Intermediate (XLc) can be obtained by the reaction of (XLb) with a carboxylic acid activating reagent such as dicyclohexylcarbodiimide (DCC). Other peptide-forming conditions and reagents are contemplated and are recognized by those possessing skill in the art. Intermediate (XLd) can be obtained by the reaction of (XLc) with an appropriately protected (if needed) hydroxymethylbenzyl halide followed by the removal of the SEM protecting groups via reaction with fluoride ion (tetrabutylammonium fluoride) in a suitable solvent (tetrahydrofuran).

Intermediate (XLe) is obtained by the reaction of (XLa) with SEM-Cl under conditions to avoid/suppress bis-alkylation such as limiting molar equivalents of SEM-Cl and/or using lower reaction temperatures. Intermediate (XLf) can be obtained reaction of (XLe) with phosgene in the presence of a suitable base. Phosgene equivalents and various amine bases are also contemplated and are recognized by those possessing skill in the art. Compounds of the formula (XLg) can be obtained by the same methodology described above for the preparation of (XLd) from compound (XLc).

Compounds (XLh) can be obtained by reacting (XLb) with Cbz-Cl (carbobenzyloxy chloride) in the presence of a base. Intermediate (XLi) can be obtained by reacting (XLh) with a carboxylic acid activating reagent in the presence of an amine such as ammonia. Other methods are contemplated and are recognized by those possessing skill in the art. Compound (XLj) is obtained by the reaction of (XLi) with a carbon monoxide equivalent such as phosgene in the presence of an amine base as previously described for the conversion of (XLe) to (XLf). Compounds of the formula (XLk) can obtained by N-alkylation and removal of protecting group(s) as described for the conversion of (XLc) to (XLd).

A more detailed description of the general formulas is provided in Scheme 18c.

Compounds such as lactam (XLIm) with an alkoxy substituent could be synthesized as shown in Scheme 19. The alcohol (XLIh) obtained using the procedure of S. Thaisrivongs, et al (*J. Med. Chem.* 1991, 34, 2344–2356) can be alkylated with benzyl bromide using standard procedures to give (XLIi). Treatment with catalytic p-toluenesulfonic acid in methanol cleaves the oxazolidine to give the free alcohol (XLIj) which can be then converted to the acid (XLIk) using the procedure described by S. Thaisrivongs, et al (*J. Med. Chem.* 1991, 34, 2344–2356). Protection of the alcohol as the t-butyldimethylsilyl ether and cyclization to the lactam is analogous to that described in Scheme 23.

Compounds such as the cyclohexane fused 7-membered ring lactam (XLIIh) could be synthesized as outlined in Scheme 20. The acid (XLIIa) is obtained following the procedure of J. A. Martin and G. J. Thomas (EP 0 512 343 A2). This can be treated with methanol and catalytic p-toluenesulfonic acid to give the free alcohol which can be protected as the t-butyldimethylsilyl ether to give the acid (XLIIc). The cyclization to the fused lactam (XLIIf) followed by an alkylation deprotection sequence can lead to (XLIIh)

Compounds of formula (XLIII) can be converted to a variety of cyclic structures and the general outline of useful routes is detailed in Schemes 21, 21a and 21b. Advanced intermediates (XLIIIh) and (XLIIIn) are known and details of their preparation are described in WO9301166-A (published 21 January 1993), herein incorporated by reference. The conversion of (XLIIIa) via known methodology and that described herein, to a 6-memebered cyclic structure (XLIIIg), wherein P denotes a suitable hydroxyl protecting group (for example 2-(trimethylsilyl)ethoxymethyl (SEM), 2-methoxyethyl (MEM)) and X can be NH, O. R and R' are similar to $R^4$ and $R^7$. Further alkylation of the nitrogens can be performed. Conversion of (XLIIIh) to a 7-membered cyclic structure via known synthetic transformations is described, wherein P denotes a suitable protecting group (for example SEM, MEM) and R and R' are similar to $R^4$ and $R^7$. X and X' can be any nucleophile (nucleophilic carbon, nitrogen, oxygen, sulfur). Conversion of intermediate (XLIIIn) to an 8-membered cyclic structure (XLIIIs) is described. P denotes-an appropriate protecting group; R and R' are similar to $R^4$ and $R^7$ and X can be any nucleophile; X' can be NH, O.

Compounds such as the benzo-fused 7-membered ring lactam (XLIVh) can be synthesized as outlined in Scheme 22. The acid (XLIVa) is obtained following the procedure of M. Hammond and S. W. Kaldor (EP 0 526 009 A1). The free alcohol can be protected as the t-butyldimethylsilyl ether to give the acid (XLIVc). The cyclization to the fused lactam (XLIVf) followed by an alkylation deprotection sequence can generate (XLIVh) by analogy to that described for Scheme 23.

Compounds of Formula (I) wherein, W is $N(R^{22})C(=O)C(R^{27})(R^{28})$, n is 0 and $R^7$ is hydrogen, and $R^4$ and $R^{27}$ are benzyl can be synthesized according to Scheme 23. Conversion of N-Boc-phenylalanine by an 8 step procedure can give intermediates of the formula (XLVa). Hydrolysis of the lactone, followed by activation of the acid functionality using methods known in peptide chemistry, followed by deprotection of the amine protecting group and intramolecular cyclization can give lactam (XLVe). Standard alkyation and alcohol liberation provide compounds of the formula stated above.

The preparation of compounds of the formula (XLVId) is shown in Scheme 24. The Wittig product from the first step is reduced to the allylic alcohol using DIBAL-H in methylene chloride at –78° C. This alcohol can be epoxidized using m-chloroperbenzoic acid or using Sharpless epoxidation methodology to give the epoxy alcohol (XLVIa). The epoxide can be opened selectively using $TMSN_3$ (Sharpless, K. B. *J. Org. Chem* (1988) 53 5185) to give the desired 1,2-diol. Exhaustive silylation followed by selective deprotection of the primary silyl ether gives compound (XLVIb). Standard primary tosylate formation followed by displacement with sodium azide can give the diazide (XLVIc). Reduction of the diazide using catalytic hydrogenation and cyclization using carbonyl diimidazole would give the 6-membered cyclic urea. Alkylation as described herein and deprotection would give the final product (XLVId). The diazide (XLVIc) can be manipulated to give a variety of cyclic structures as previously shown.

Compounds of the formula (I), wherein $W=-R^{22}NC(=O)NR^{23}$—, n is 1, $R^5$ is OH or =O and $R^6=R^{6a}$ is fluorine, can be synthesized as shown in Scheme 25. Compound (XLVIIa) can be oxidized to the corresponding ketone by Jones oxidation (Org. Syn. Coll., Vol. V, 866) followed by reaction of the carbonyl with a fluorinating agent such as DAST. Deprotection, cyclization, alkylation and removal of hydroxyl protecting groups (such as MEM) can give (XLVIIg), which can be further oxidized to (XLVIIh) using the method of Gallina & Giordano (*Synthesis* 1989, 466).

The preparation of compounds of the formula (XLVIIIc) is shown in Scheme 26. Starting from the known hydroxy ketone (XLVIIIa) (WO 92/00956, published Jan. 23, 1992) the alcohol can be protected and the amine function deprotected to give diamine (XLVIIIb). Cyclization and introduction of the $R^{22}$ and $R^{23}$ can be accomplished as described herein. Reduction of the ketone and deprotection can give the desired diol (XLVIIIc). Hydroxy ketone (XLVIIIa) can be converted to the triol (XLVIIIe). After alcohol protection, a second hydroxyl group can be introduced a to the ketone using standard chemical procedures known to one skilled in the art. After protecting this hydoxyl, the amines can be deprotected to give diamine (XLVIIId).

Using similar chemistry as discussed previously, the triol (XLVIIIe) can be prepared as shown in Scheme 26a. The mono-ol (XLVIIIj) can be prepared starting from the aldehyde (XLVIIIf) and an organometallic reagent (XLVIIIg). Both of these compounds can be prepared from amino acids using standard chemical procedures known to one skilled in the art. The alcohol (XLVIIIh) can be protected and manipulated as discussed previously to give the desired mono-ol (XLVIIIj).

The cyclic carbonates of the formula (XLIXb) can be prepared, as shown on Scheme 27, starting from commercially available 3,4-O-Isopropylidene-D-mannitol. Primary tosylate formation and base treatment can provide the diepoxide which can be opened with numerous nucleophiles to give compounds of the formula (XLIXa). Cyclization and deprotection would give the desired diol (XLIXb).

Compounds wherein W is $-N(R^{22})P(O)(R^{24a})N(R^{23})-$, n=1 and $R^{24a}$ is phenoxy or OH, can be synthesized as described earlier and as shown in Scheme 28. Diamine III could be cyclized with phenyldichlorophosphate using the method of Patois et al. (Heteroatom. Chem. 1990, 1, 369) to give the cyclic phosphoric amide. Alkylation with strong base and removal of the protecting groups using methods known to one skilled in the art would give the desired products.

Compounds of the formula (I) wherein W is $-N(R^{22})C(=O)N(R^{23})-$, and $R^{22}$ and $R^{23}$ are $NH(R^{22a})$ and $NH(R^{23a})$, respectively, can be prepared as shown in Scheme 29. Intermediate (XXIc) can be treated with chloramine to yield dihydrazine (LIa) according to the method of S. R. Sandler and W. Karo (Organic Functional Group Preparations, Vol 1, Academic Press, N.Y., 1983, p. 445), herein incorporated by reference. Cyclization using phosgene can give cyclic urea (LIb). Standard procedure for alkylation and deprotection can provide alkylated dihydrazine (LIc). Alternatively, (XXIc) can be treated with chloroaminobenzene, according to the method of S. R. Sandler and W. Karo above, to yield dihydrazine (LId). Cyclization using phosgene, followed by alkylation of the product as described previously, can provide compounds of the formula (LIe).

Compounds of the formula (I), wherein W is $-N(R22)C(=C(CN)2)N(R23)-$ and n=1, can be prepared as shown in Scheme 30. Intermediate (XXIc) can be treated with 1,1'-bismethylthio-2,2'biscyanoethylene in acetonitrile, followed by the standard procedure of alkylation and deprotection to give compounds of the formula (LIIa).

Compounds of the formula (I), wherein W is $-N(R^{22})C(=S)N(R^{23})-$, $R^{22}$ and $R^{23}$ are not hydrogen, and n=1, can be prepared as shown in Scheme 31. Mono-alkylated intermediate (XXVIIb) can be further reacted with a alkyl bromide under refluxing reaction conditions (to facilitate the removal of byproduct methyl bromide) to give dialkylated thiocarbonyl compound (LIIIa), which can be acid-deprotected as described previously.

Compounds of the formula (I), wherein W is $-N(R^{22})C(=O)C(R^{27})-$, n=1, and R28 and R7a are taken to form a bond can be prepared as shown in Scheme 32. The aldehydes required for coupling can be prepared by methods known to one of skill in the art. Acetylation after coupling can provide diacetate (LIVa). Amine protecting group modification can lead to (LIVb), afterwhich liberation of the carbonyl (LIVb) and Wittig olefination using stabilized Wittig can provide (LIVc), after separation of the geometric isomers. Liberation of the amine protecting group can provide (LIVd), which upon modification of the ester for standard amino-acid type coupling (via LIVe) can lead to compounds of formula (LIVf).

The synthesis of compounds of the invention is described in further detail below.

PROCEDURE 1

Preparation of di-N-CBZ Protected 1,4-Diamino-2,3-diols (XIX)

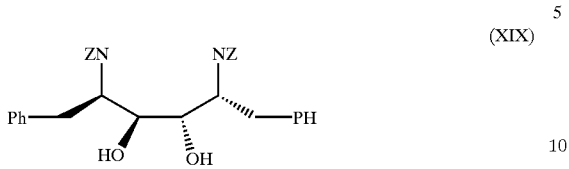

(XIX)

Detailed experimental procedures for the synthesis of compound (XIX) are described in copending commonly assigned patent application Jadhav et al. U.S. Ser. No. 07/714,042, filed May. 31, 1991.

PROCEDURE 2

Preparation of di-O Protected di-N-CBZ 1,4-Diamino Diols (XXa) and (XXb)

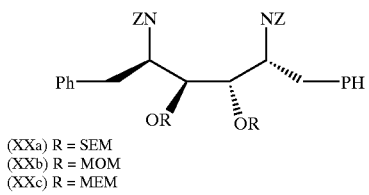

(XXa) R = SEM
(XXb) R = MOM
(XXc) R = MEM

A. Protection as 2-(trimethylsilyl) Ethoxy Methyl (SEM) ether (XXa):

Compound (XIX) (60 g, 105 mmol) was dissolved in dry DMF (600 mL). Diisopropylethylamine (75 mL) and SEMCl (66.8 g, 400 mmol) were added and the mixture stirred for 16 h at room temperature under $N_2$. The solution was diluted with water (1 L) and extracted with hexane (400 mL). The organic layer was separated and washed with water (2×100 mL). The aqueous layers were combined and extracted with hexane (2×300 mL). The organic layers were combined, washed with water (2×100 mL), dried over $MgSO_4$, filtered and evaporated. The residue was chromatographed on $SiO_2$ and eluted with 10–30% ethyl acetate/hexane to afford a white solid (91 g, 100%). NMR ($CDCl_3$): δ 7.0–7.4 (m, 20H, Ph), 5,01 (br s, 4H, $PhCH_2CO$), 4.5–4.95 (m, 6H, NH, $OCH_2O$), 3.6–4.25 (m, 4H, C$\underline{H}OCH_2$, C$\underline{H}NH$), 3.5 (s, 4H, $OCH_2CH_2$), 2.76 (br d, 4H, $PhCH_2$), 0.8–1.0 (m, 4H, $SiCH_2$). MS: 846 (M+$NH_4$, 100), 695 (M–SEM, 40).

B. Protection as Methoxymethyl (MOM) Ether (XXb).

Compound (XIX) (0.50 g, 0.88 mmol) was dissolved in dry DMF (10 mL). Diisopropylethylamine (0.46 mL, 2.64 mmol) and methoxymethyl bromide (0.165 mL, 2.02 mmol) were added and the solution stirred at 40° C. under nitrogen for four h. TLC (50/50 ethyl acetate/methylene chloride) showed that the reaction was complete. The mixture was partitioned between methylene chloride (50 mL) and 5% HCl (30 mL). The organic layer was separated, washed with water (5×20 mL), brine (20 mL), dried over $MgSO_4$, filtered and evaporated to a light yellow oil. Chromatography on $SiO_2$ and elution with 1–20% ethyl acetate/methylene chloride afforded (XXb) as a clear oil (0.29 g, 53%).

NMR ($CDCl_3$): δ .95–7.42 (m, 20H, Ph), 5.1–3.8 (m, complex), 3.35 (s, 6H, $OCH_3$), 2.8–2.95 (m, 4H, $PhCH_2$). MS: 657 (13, M+1), 674 (21, M+$NH_4$), 522 (84), 414 (100), 370 (34).

PROCEDURE 3

Deprotection of Amines (XXa) and (XXb) Via Hydrogenation to Afford (XXIa) and (XXIb)

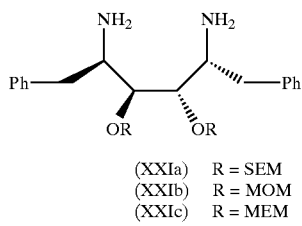

(XXIa) R = SEM
(XXIb) R = MOM
(XXIc) R = MEM

A. Hydrogenation of SEM ether (XXa).

Compound (XXa) (90 g, 108.5 mmol) was dissolved in absolute ethanol (2.5 L). 5% Pd/C (6.5 g) was added and the solution was stirred under hydrogen for 1.5 h until hydrogen uptake ceased. TLC (20/80 ethyl acetate/hexane) showed that the reaction was complete. The solution was filtered through Celite and evaporated at reduced pressure to give XXIa as a colorless gum (60 g, 99%). NMR ($CDCl_3$): δ 7.1–7.35 (m, 10H, Ph), 4.72 (br d, 4H, $OCH_2O$), 3.5–3.9 (m, 6H, $NH_2$, C$\underline{H}OCH_2$), 3.15 (m, 2H, C$\underline{H}NH_2$), 2.55–2.95 (m, 4H, $PhCH_2$), 0.95 (m, 4H, $SiCH_2$).

B. Hydrogenation of MOM Ether (XXb).

Compound (XXb) (0.29 g, 0.441 mmol) was dissolved in ethyl acetate (6 mL) and methanol (3 mL). 10% Pd/C (70 mg) was added and the solution stirred under hydrogen until $H_2$ uptake ceased. TLC (20/80 methanol/ethyl acetate) showed that the reaction was complete. The solution was filtered through Celite and evaporated at reduced pressure to afford XXIb as a clear oil (0.132 g, 77.4%). NMR ($CDCl_3$): δ 7.1–7.35 (m, 10H, Ph), 4.58 (s, 4H, $OCH_2O$), 3.75 (br s, 2H, C$\underline{H}OCH_2$), 3.3–3.5 (m, 2H, C$\underline{H}NH_2$), 3.23 (s, 6H, $OCH_3$), 2.85 (br d, 4H, $PhCH_2$). MS: 389 (M+1, 100), 345 (3.7), 280 (1.8), 120 (6.1).

PROCEDURE 4

Formation of Cyclic Ureas (XXIIa), (XXIIb) and (XXIIc)

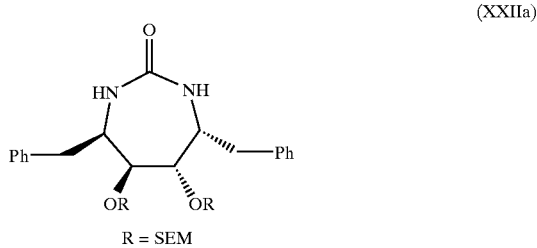

(XXIIa)

R = SEM

A. Cyclization of SEM Ether (XXIa).

Compound (XXIa) (40 g, 71.3 mmol) was dissolved in methylene chloride (200 mL). Carbonyl diimidazole (13.87 g, 85.6 mmol) was dissolved in methylene chloride (200 mL) in a separate flask. Each solution was then pumped into dry methylene chloride (6 L) at a rate of 90 mL/h. The mixture was then stirred for 18 h at room temperature under nitrogen. TLC (60/40 ethyl acetate/hexane) showed the reaction was complete. The solvent was removed at reduced pressure and residue chromatographed on $SiO_2$ and eluted with 1–50% ethyl acetate/hexane to afford (XXIIa) as a white solid (38.82 g, 93%). mp: 75–76° C. NMR (CDCl$_3$): δ 7.05–7.4 (m, 10H, Ph), 4.6–4.8 (dd, 4H, OCH$_2$O), 4.08 (s, 2H, CHOCH$_2$), 3.5–3.91 (m, 8H, NH, CHNH, OCH$_2$CH$_2$), 2.86, (br d, 4H, PhCH$_2$), 0.8–0.95 (m, 4H, SiCH$_2$). MS: 587 (M+1, 100).

B. Cyclization of MOM Ether (XXIb).

Compound (XXIb) (0.53 g, 1.364 mmol) was dissolved in dry methylene chloride (20 mL). In a separate flask, carbonyl diimidazole (0.265 g, 1.64 mmol) was dissolved in methylene chloride (20 mL). To a third flask containing pyridine (0.22 mL, 2.73 mmol) in methylene chloride (100 mL) at room temperature under nitrogen were added the first two solutions via syringe pump at a rate of 1.7 mL/h. The solution was stirred overnight at room temperature. TLC (50/50 ethyl acetate/methylene chloride) showed that the reaction was complete. The solution was washed with 5% HCl (50 mL), NaHCO$_3$ (50 mL), brine (50 mL), dried over MgSO$_4$, filtered and evaporated. The residue was chromatographed on SiO$_2$ and eluted with 50–75% ethyl acetate/methylene chloride to afford (XXIb) as a colorless gum (198 mg, 35%). NMR (CDCl$_3$): δ 7.1–7.4 (m, 10H, Ph), 4.65 (q, 4H, OCH$_2$O), 4.13 (s, 2H, NH), 3.89 (t, 2H, CHNH), 3.59 (s, 2H, CHOCH$_2$), 3.18 (s, 6H, OCH$_3$), 2.87 (m, 4H, PhCH$_2$). MS: 415 (M+1, 100), 102 (11).

Synthesis of Dimem DiZ Intermediate (XXc)

DiZ Diol (XIX) 507 g (0.89 mol) was stirred in 4 L of dichloromethane. To the slurry was added N,N-Diisopropylethylamine 780 g (6.05 mol) in one portion at room temperature followed by the dropwise addition of 2-methoxyethoxymethyl choride 500 g (4 mol) (1 hour addition, exothermic). Heated the solution at reflux for 12 hours. TLC (10:1:10 EtOAc:EtOH:Hexanes, Rf=0.56) indicated a complete reaction. The solution was worked up by quenching with ice water (3L). Washed the dichloromethane extract with water (2×2L) and dried over magnesium sulfate. The filtrate was taken to dryness. The resultant semi-solid was dissolved in chlorobutane (1L). Passed the solution through a four inch pad of silica gel to remove most of the intense red color. To the chlorobutane extract was added hexane (2L) to precipitate the desired DiZ Dimem intermediate (XXc). Washed the white solid with hexanes (3×350 ml). Dried at room temperature. Recovered the desired DiZ Dimem intermediate as a white solid in a yield of 525 g (79% yield). m.p. 52–54 C, 1H NMR (CDCl$_3$): δ 2.80 (m, 4H)—CH$_2$Ph, 3.38 (s, 6H)—OCH$_3$, 3.58 (m, 8H)—OCH$_2$CH$_2$O—, 3.80 (m, 2H), 4.20 (m, 2H), 4.6–5.2 (m, 10H)NH, H$_2$CCO$_2$, —OCH$_2$O—, 7.25 (m, 20H)C$_6$H$_5$ Synthesis of Cyclic Urea Intermediate (XXIc)

DiZ Dimem (XXc) 20 g (26.8 mmol) was dissolved in 200 ml of tetrahydrofuran. To the solution was added 2 g of 10% Palladium on Carbon and the suspension stirred for 7 hours under hydrogen (1 atm). TLC (10:1:10 EtOAc:EtOH:Hex, Rf=0.05) indicated a complete reaction. The suspension was filtered through a bed of Celite to remove the catalyst. Washed the Celite bed with 150 ml of tetrahydrofuran. Transferred the THF solution to a 500 ml round bottom flask. To the THF solution was added 5.5 g (33.3 mmol) 1,1'-Carbonyldiimidazole in several portions as a solid. Stirred at room temperature for 12 hrs. TLC (10:1:10 EtOAc:EtOH:Hex, Rf=0.26) indicated a complete reaction. The mixture was worked up by quenching with ice-cold 0.5N HCl (150 ml) and extracting with diethyl ether (2×50 ml). The organic extract was washed with water (2×100 ml) and dried over magnesium sulfate. The filtrate was taken to dryness. The residue was purified on silica gel (200 g; 1:1 EtOAc:Hex followed by 10:1:10 EtOAc:EtOH:Hex) to provide 10.2 g (75.7% yield over two steps) of the desired cyclic urea intermediate (XXIIc) as a colorless oil. 1H NMR (CDCl$_3$): 2.90 (m, 4H)—CH$_2$Ph, 3.36 (s, 6H)—OCH$_3$, 3.40 (m, 8H)—OCH$_2$CH$_2$O—, 3.60 (m, 2H), 3.90 (t, 2H), 4.10 (s, 2H)NH, 4.80 (q, 4H)—OCH$_2$O—, 7.30 (m, 10H)C$_6$H$_5$

PROCEDURE 5

General Alkylation/hydrolysis Procedure

Compound (XXIIa) (1 mmol) in dry DMF (5 mL) was added to a flask containing sodium hydride (10 mmol, that had been washed with hexane, 3×20 mL) in DMF (5 mL). The solution was stirred at room temperature under nitrogen for 5 min. Evolution of hydrogen gas was observed. The appropriate alkyl bromide (5 mmol) was added and the solution was stirred at room temperature under nitrogen for 1 h. Hindered alkyl bromides required heating at 40–70° C. for up to 5 h. TLC (40/60 ethyl acetate/hexane) was used to ensure that no starting material remained. The solution was quenched with methanol (1 mL), partitioned between ether (60 mL) and water (50 mL) and the organic layer was removed. The aqueous layer was washed with ether (50 mL), the organic layers combined and washed with water (4×30 mL), brine (30 mL), dried over MgSO$_4$, filtered and evaporated. In cases where the alkyl bromide contained basic nitrogen, 1 N NaOH was used in place of water.

The crude product was hydrolyzed directly in methanol (10 mL) and 4 N HCl/dioxane (5 mL) for up to 16 h at room temperature. The solution was evaporated and chromatographed directly on SiO$_2$ to afford the bis-alkylated cyclic ureas. Where nitrogen was present, the solutions were first basified with 1 N NaOH and extracted with ethyl acetate, dried over MgSO$_4$, filtered, evaporated and chromatographed. Hydrolysis can also be carried out using saturated hydrogen chloride in methanol with shorter reaction times.

Hydrolysis of (XXIIb) under the same conditions gave 67% yield of the N,N-unsubstituted cyclic urea Example 1A, mp 170–174° C.

EXAMPLE 1G

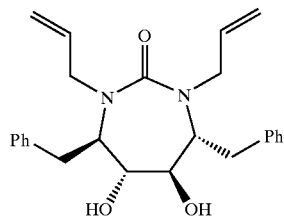

The experimental procedure is similar to the synthesis of Example 1E. The isomer, (2R,3R,4R,5R)-2,5-diamino-1,6-diphenyl-3,4-hexanediol, needed for the synthesis was isolated from the vanadium trichloride coupling reaction, as described in copending commonly assigned patent application Jadhav et al. U.S. Ser. No. 07/714,042, filed May 31, 1991 (see Procedure 1 above).

Example 1G: $^{13}$C NMR (CDCl$_3$): (75.48 Hz) 37.387, 51.51, 65.136, 72.779, 118.649, 126.540, 128.409, 129.714, 134.618, 137.757, 162.705.

Synthesis of Monoalkyl Cyclic Urea

The intermediate from previous step 2 g (4 mmol) was dissolved in 25 ml toluene and placed in a 100 ml round bottom flask. To the solution was added 85% KOH 0.82 g (12 mmol) and polyethylene glycol (M.W.=1000) 0.20 g. With a Dean Stark trap in place the mixture was refluxed for 4 hours until the theoretical amount of water (0.20 ml) was collected. Cooled to room temperature and added (bromomethyl)cyclopropane 1.78 g (13.2 mmol). Stirred at 75 C for 17 hours. TLC(10:1:10 EtOAc:EtOH:Hex, Rf=0.52) indicated that the reaction was complete. Worked up by quenching with aqueous ammonium chloride (50 ml) and extracting with ethyl acetate (2×35 ml). Washed the organic layer with water (2×35 ml) and dried over magnesium sulfate. The filtrate was taken to dryness. The residue was purified on silica gel (150 g, 2:3 EtOAc:Hex) to provide 1.55 g (70% yield) of the desired monoalkyl cyclic urea as a colorless oil. C13 NMR (CDCl$_3$): 3.331, 4.000, 10.619, 32.877, 34.159, 55.677, 58.294, 58.972, 64.085, 67.361, 67.437, 71.723, 71.753, 76.576, 78.023, 96.347, 96.519, 126.224, 126.316, 128.366, 128.563, 129.400, 129.447, 139.475, 139.555, 161.558. For reactive alkylating agents, e.g. m-nitrobenzyl chloride, the reactions are carried out lower temperatures, such as room temperature.

An alternative procedure to make the monoalkylated cyclic urea involved using the procedure described previously for formation of the dialkylated cyclic urea, however, varying the amount of sodium hydride to 1.5 equivalents and alkylating agent to 1.0 equivalents. Silica gel chromatography provided the desired product, as well as dialkylated cyclic urea and unreacted starting material.

Examples 1A–1Z, 1AA–1AZ, and 1BA–1BD

The compounds listed in Table 1a (Examples 1A–1Z, 1AA–1AZ, and 1BA–1BD) were synthesized using the above-described procedures.

TABLE 1a

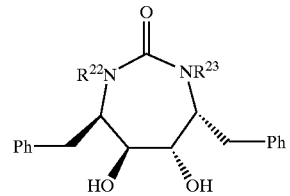

| Example Number | Stereo-isomer (2,3,4,5) | $R^{22}$ | $R^{23}$ | Ki |
|---|---|---|---|---|
| 1A | RSSR | H | H | + |
| 1B | SRRS | H | H | + |
| 1C | RSSR | CH$_2$CH=CH$_2$ | CH$_2$CH=CH$_2$ | +++ |
| 1D | SRRS | CH$_2$CH=CH$_2$ | CH$_2$CH=CH$_2$ | + |
| 1E | SSSS | H | H | + |
| 1F | RRSR | CH$_2$CH=CH$_2$ | CH$_2$CH=CH$_2$ | |
| 1G | RRRR | CH$_2$CH=CH$_2$ | CH$_2$CH=CH$_2$ | ++ |
| 1H | SSSS | CH$_2$CH=CH$_2$ | CH$_2$CH=CH$_2$ | + |
| 1I | SRRS | CH$_2$Ph | CH$_2$Ph | + |
| 1J | SRRS | (CH$_2$)$_2$O(CH$_2$)$_2$OMe | (CH$_2$)$_2$O(CH$_2$)$_2$OMe | + |
| 1K | SRRS | 1-geranyl | 1-geranyl | + |
| 1L | SRRS | CH$_2$CH$_2$OH | CH$_2$CH$_2$NHCH(CH(CH$_3$)$_2$)—C(=O)O-benzyl | + |
| 1M | SRRS | CH$_2$CH$_2$(CH$_2$CH$_2$O)$_2$OCH$_3$ | CH$_2$CH$_2$(CH$_2$CH$_2$O)$_2$OCH$_3$ | + |
| 1N | SRRS | 3,7-dimethyl-1-octyl | 3,7-dimethyl-1-octyl | ++ |
| 1O | RSSR | CH$_3$OCH$_2$CH$_2$OCH$_2$CH2 | CH$_3$OCH$_2$CH$_2$OCH$_2$CH2 | + |
| 1P | RSSR | 3,7-dimethyl-1-octyl | 3,7-dimethyl-1-octyl | ++ |
| 1Q | RSSR | 3,7-dimethyl-1-octyl | H | ++ |
| 1R | RSSR | CH$_3$(OCH$_2$CH$_2$)$_3$ | H | + |
| 1S | RSSR | CH$_3$(OCH$_2$CH$_2$)$_3$ | CH$_3$(OCH$_2$CH$_2$)$_3$ | |
| 1T | RSSR | HOCH$_2$CH$_2$ | CH$_2$CH$_2$NHCH(CH(CH$_3$)$_2$)—C(=O)O-benzyl | ++ |
| 1U | SRRS | CH$_2$CH$_2$NHCH(CH(CH$_3$)$_2$)—C(=O)O-benzyl | CH$_2$CH$_2$NHCH(CH(CH$_3$)$_2$)—C(=O)O-benzyl | + |
| 1V | RSSR | propyl | propyl | +++ |
| 1W | RSSR | methyl | methyl | + |
| 1X | RSSR | cyclopropyl-methyl | cyclopropyl-methyl | +++ |
| 1Y | RSSR | n-hexyl | n-hexyl | +++ |
| 1Z | RSSR | n-butyl | n-butyl | +++ |
| 1AA | RSSR | N-morpholinoethyl | N-morpholinoethyl | + |
| 1AB | RSSR | n-heptyl | n-heptyl | ++ |
| 1AC | RSSR | CH$_2$CH=C(CH$_3$)$_2$ | CH$_2$CH=C(CH$_3$)$_2$ | +++ |
| 1AD | RSSR | ethyl | ethyl | ++ |
| 1AE | RSSR | CH$_2$CH=C(CH$_3$)$_2$ | H | +++ |
| 1AF | RSSR | propyl | propyl | +++ |
| 1AG | RSSR | CH$_3$ | CH$_3$ | + |
| 1AH | RSSR | i-pentyl | i-pentyl | +++ |
| 1AI | RSSR | 4-pyridylmethyl | 4-pyridylmethyl | ++ |
| 1AJ | RSSR | 2-methallyl | 2-methallyl | +++ |
| 1AK | RSSR | n-pentyl | n-pentyl | +++ |
| 1AL | RSSR | i-octyl | i-octyl | ++ |
| 1AM | RSSR | i-hexyl | i-hexyl | +++ |

TABLE 1a-continued

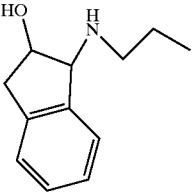

| Example Number | Stereo-isomer (2,3,4,5) | R²² | R²³ | Ki |
|---|---|---|---|---|
| 1AN | RSSR | i-heptyl | i-heptyl | ++ |
| 1AO | RSSR | i-butyl | i-butyl | ++ |
| 1AP | RSSR | 3-propargyl | 3-propargyl | ++ |
| 1AQ | RSSR | benzyl | benzyl | +++ |
| 1AR | RSSR | 2-pyridylmethyl | 2-pyridylmethyl | ++ |
| 1AS | RSSR | phenylpropyl | phenylpropyl | ++ |
| 1AT | RSSR | allyl | isoprenyl | +++ |
| 1AU | RSSR | 1-cinnamyl | 1-cinnamyl | +++ |
| 1AV | | methyl | cyclopropyl-methyl | |
| 1AW | RSSR | allyl | cyclopropyl-methyl | +++ |
| 1AX | | $CH_2CH_2N(CH_2)_2$ | allyl | |
| 1AY | RSSR | methyl | benzyl | ++ |
| 1AZ | | N-pyrrolylethyl | N-pyrrolylethyl | |
| 1BA | | 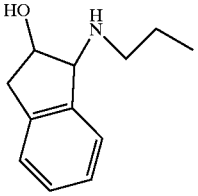 | | |
| 1BB | | 2-furylmethyl | 2-furylmethyl | |
| 1BC | | $CH_2CH_2OCH(CH_2)_2$ | $CH_2CH_2OCH(CH_2)_2$ | |
| 1BD | RSSR | isoprenyl | methyl | ++ |

The $K_i$ values in Table 1 were determined using the assay conditions described below under HIV Protease Inhibtion Assay. The $K_i$ values are indicated as follows: +++=<10 nM; ++=10 nM to 1 μM; +=>1 mM.

Listed below are physical data for representative compounds of the invention.

Example 1W: mp 170–174° C. (67% yield). MS: 355 (M+1, 100). NMR (CDCl₃) d 7.1–7.35 (m, 10H, Ph), 4.03 (s, 2H, CHHOH), 3.5 (d, 2H, NCH), 2.8–3.1 (m, 6H, PhCH₂, OH), 2.58 (s, 6H, NH₃).

Example 1AD: mp 214–215° C. MS: 383 (M+1, 100). NMR (CDCl₃) d 7.1–7.35 (m, 10H, Ph), 3.95 (s, 2H, CHOH), 3.5 (d, 2H, NCH), 2.8–3.1 (m, 4H, PhCH₂, OH), 2.7 (br s, 2H, OH), 2.3 (m, 2H, NCH), 0.95 (t, 6H, CH₃).

Example 1AF: mp 180–182° C. MS: 411 (M+1, 100). NMR (CDCl₃) d 7.05–7.3 (m, 10H, Ph), 4.0 (s, 2H, CHOH), 3.68 (m, 2H, NCH₂), 3.52 (d, 2H, NCH), 3.05 (m, 4H, PhCH₂), 2.1 (m, 2H, NCH₂), 1.6 (s, 2H, OH), 1.4 (m, 4H, MeCH₂), 0.79 (t, 6H, CH₃).

Example 1Z: HRMS: Calc. 439.2960. Found: 439.2959.

Example 1AK: mp 125–127° C. MS: 467 (M+1, 100). NMR (CDCl₃) d 7.15–7.35 (m, 10H, Ph), 3.95 (s, 2H, CHOH), 3.68 (m, 2H, NCH₂), 3.55 (d, 2H, NCH), 2.9–3.15 (m, 4H, PhCH₂), 2.75 (s, 2H, OH), 2.18 (m, 2H, NCH₂), >8–1.45 (m, complex, pentyl).

Example 1Y: mp 110–112° C. MS: 495 (M+1, 100). NMR (CDCl₃) d 7.1–7.35 (m, 10H, Ph), 4.0 (s, 2H, CHOH), 3.65 (m, 2H, NCH—H), 3.52 (d, 2H, NCH), 2.8–3.2 (m, 4H, PhCH₂), 2.15 (m, 2H, OH), 0.9–1.45 (m, 11H, hexyl).

Example 1AB: mp 100–101° C. MS: 523 (M+1, 100). NMR (CDCl₃) d 7.1–7.35 (m, 10H, Ph), 3.95 (s, 2H, CHOH), 3.65 (m, 2H, NCH—H), 3.5 (d, 2H, NCH), 2.9–3.1 (m, 4H, PhCH₂), 2.6 (s, 2H, OH), 2.15 (m, 2H, NCH), 0.8–1.4 (m, complex, heptyl).

Example 1I: MS: 507 (M+1, 100). NMR (CDCl₃) d 7.05–7.4 (m, 20H, Ph), 4.91 (d, 4H, PhCH₂N), 3.5–3.65 (m, 4H, NCH, CHOH), 3.05 (m, 4H, PhCH₂), 2.35 (br s, 2H, OH).

Example 5i (R²² and R²³=allyl; R²⁰ and R²¹=C(=O)CH₃): mp 164–166° C. MS: 407 (M+1, 100). NMR (CDCl₃) d 7.1–7.4 (m, 10H, Ph), 5.65 (m, 2H, CH₂CH), 5.01 (m, 4H, CH₂CH), 4.26 (m, 4H, NCH₂), 3.91 (s, 2H, CHOH), 3.59 (d, 2H, CHN), 3.1 (m, 4H, PhCH₂), 2.7 (m, 2H, CHCH₂), 2.41 (s, 2H, OH).

Example 1AO: MS 439 (M+1, 100). NMR (CDCl₃) d 7.15–7.35 (m, 10H, Ph), 4.05 (s, 2H, CHOH), 3.7 (m, 2H, NCH₂), 3.55 (d, 2H, NCH), 3.0–3.2 (m, 4H, PhCH₂), 2.65 (s, 2H, OH), 1.78 (m, 2H, NCH), 1.6 (s, 2H, CH₂CHH), 0.82 (d, 12H, CHMe₂).

Example 1AH: mp 194–195° C. MS: 467 (M+1, 100). NMR (CDCl₃) d 7.15–7.35 (m, 10H, Ph), 3.95 (s, 2H, CHOH), 3.65 (m, 2H, NCH), 3.49 (d, 2H, NCH), 2.9–3.1 (m, 4H, PhCH₂), 2.61 (s, 2H, OH), 2.2 (m, 2H, NCH), 1.1–1.5 (m, complex), 0.9 (m, 12H, CHMe₂).

Example 1AM: mp 120–122° C. MS: 495 (M+1, 100). NMR (CDCl₃) d 7.1–7.35 (m, 10H, Ph), 3.95 (s, 2H, NCH), 3.45–3.7 (m, 4H, NCH₂, NCH), 2.9–3.2 (m, 4H, PhCH₂), 2.1 (m, 2H, NCH₂), 0.78–1.45 (m, complex, hexyl).

Example 1AN: mp 105–107° C. MS: 523 (M+1, 100). NMR (CDCl$_3$) d 7.18–7.31 (m, 10H, Ph), 3.95 (s, 2H, CHOH), 3.7 (m, 2H, NCH$_2$), 3.56 (d, 2H, NCH), 2.9–3.15 (m, 4H, PhCH$_2$), 2.18 (m, 2H, NCH$_2$), 0.9–1.45 (m, complex, hexyl).

Example 1AL: mp 144–145° C. MS: 551 (M+1, 100). NMR (CDCl$_3$) d 7.15–7.35 (m, 10H, Ph), 3.95 (s, 2H, CHOH), 3.65 (m, 2H, NCH$_2$), 3.55 (d, 2H, NCH), 2.9–3.15 (m, 6H, PhCH$_2$, OH), 2.15 (m, 2H, NCH$_2$), 0.9–1.5 (m, complex, heptyl).

Example 1AC: mp 160–163° C. MS: 463 (M+1, 100). NMR (CDCl$_3$) d 7.15–7.35 (m, 10H, Ph), 5.06 (br t, 2H, NCH$_2$C$\underline{H}$), 4.1 (dd, 2H, NCH$_2$), 3.9 (s, 2H, CHOH), 3.5 (d, 2H, NCH), 2.8–3.1 (m, 4H, PhCH$_2$), 1.65 (s, 6H, CHC$\underline{H}_3$), 1.38 (s, 6H, CHC$\underline{H}_3$).

Example 1AJ: mp 205–207° C. MS: 435 (M+1, 100). NMR (CDCl$_3$) d 7.1–7.35 (m, 10H, Ph), 4.85 (s, 2H, C=CH), 4.58 (s, 2H, C=CH), 4.28 (d, 2H, NCH$_2$), 3.95 (s, 2H, CHOH), 3.7 (br d, 2H, CHOH), 2.9–3.2 (m, 4H, PhCH$_2$), 2.5 (d, 2H, NCH$_2$), 1.75 (s, 6H, CH$_3$).

Example 1AI: MS: 509 (M+1, 100). NMR (CDCl$_3$) d 7.0–8.4 (m, 18H, Ph, pyr.), 4.8–5.0 (m, 4H, NCH$_2$), 3.7 (s, 2H, CHOH), 3.5 (d, 2H, NCH), 2.9–3.2 (m, 8H, PhCH$_2$, pyrCH$_2$).

Example 1AP: mp 198–200° C. MS: 403 (M+1, 100). NMR (CDCl$_3$) d 7.2–7.35 (m, 10H, Ph), 4.5 (s, 2H, CCH), 4.42 (s, 2H, NCH), 4.1 (s, 2H, CHOH), 3.8 (d, 2H, NCH), 2.9–3.2 (m, 4H, PhCH$_2$), 2.7–2.85 (m, 4H, NCH$_2$).

Example 1O: mp 105–106° C. MS: 531 (M+1, 100). NMR (CDCl$_3$) d 7.1–7.35 (m, 10H, Ph), 3.0–4.15 (m, complex), 2.25 (m, 2H, OH).

Example 1S: MS: 619 (M+1, 100). NMR (CDCl$_3$) d 7.18–7.3 (m, 10H, Ph), 3.0–4.2 (m, complex), 2.25 (m, 2H, OH).

Example 1P: mp 80–82° C. MS: 607 (M+1, 100), 257 (9.6). NMR (CDCl$_3$) d 7.05–7.35 (m, 10H, Ph), 3.95 (s, 2H, CHOH), 3.4–3.75 (m, 4H, NCH, NCH$_2$), 2.9–3.15 (m, 4H, PhCH$_2$), 2.1 (m, 2H, OH), 0.85–1.6 (m, complex).

Example 1AA: mp 70–75° C. MS: 553 (M+1, 100). NMR (CDCl$_3$) d 7.05–7.4 (m, 10H, Ph), 3.4–4.25 (m, complex), 2.9–3.15 (m, 4H, PhCH$_2$), 2.2–2.8 (m, complex).

Example 1X: mp 210–212° C. MS: 435 (M+1, 100). NMR (CDCl$_3$) d 7.18–7.35 (m, 10H, Ph), 4.06 (s, 2H, CHOH), 3.68 (br d, 2H, NCH), 3.55 (q, 2H, NCHC$\underline{H}$), 3.1 (m, 4H, PhCH$_2$), 2.55 (s, 2H, OH), 2.05 (q, 2H, CHC$\underline{H}$), 0.9 (m, 2H, NCH$_2$C$\underline{H}$), 0.42 (m, 4H, —CH$_2$—), 0.008 (m, 4H, —CH$_2$—).

| Example Number | MS (M + 1) |
| --- | --- |
| 1B | 327.9 |
| 1D | 406.5 |
| 1H | 407 |
| 1J | 531 |
| 1K | 463 |
| 1L | 604.5 |
| 1M | 619 |
| 1N | 607 |
| 1O | 467 |
| 1R | 473 |
| 1T | 604 |
| 1U | 793 |
| 1V | 411 |
| 1AE | 395 |
| 1AG | 355 |
| 1AS | 563 |
| 1AT | 435 |
| 1BD | 409 |
| 1AQ | 507.26 |
| 1AU | 559.29 |
| 1BE | 457.2 |
| 1BF | 557.5 |
| 1BG | 593.4 |

Example 1AR: mp 85–87° C.

Example 1C: mp 164–166° C.

Example 1A: mp 170–174°C.

Using the above-described techniques or variations thereon appreciated by those of skill in the art of chemical synthesis, the compounds of Tables 1b can be prepared.

TABLE 1b

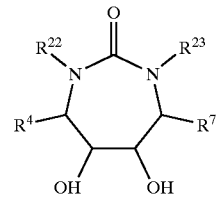

| Example Number | R22 | R23 | R4 | R7 |
| --- | --- | --- | --- | --- |
| 1BE | methyl | phenylmethyl | 4-F-phenylmethyl | 4-F-phenylmethyl |
| 1BF | allyl | cyclopropyl-methyl | 4-F-phenylmethyl | 4-F-phenylmethyl |
| 1BG | allyl | cyclopropyl-methyl | 4-Cl-phenylmethyl | 4-Cl-phenylmethyl |
| 1BH | allyl | cyclopropyl-methyl | 1-pyrolyl-methyl | 1-pyrolyl-methyl |
| 1BI | allyl | ethyl | 4-F-phenylmethyl | 4-F-phenylmethyl |

TABLE 1b-continued

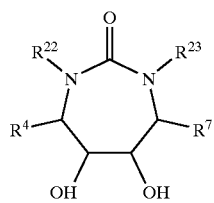

| Example Number | R22 | R23 | R4 | R7 |
|---|---|---|---|---|
| 1BJ | isoprenyl | isoprenyl | 1-pyrrolyl-methyl | 1-pyrrolyl-methyl |
| 1BK | n-butyl | n-butyl | 4-hydroxy-benzyl | 4-hydroxy-benzyl |
| 1BL | N-2-acetoamido-3-methyl-butane | cyclopropyl-methyl | benzyl | 1-pyrazolyl-methyl |
| 1BM | benzyl | cyclopropyl-methyl | benzyl | 1-pyrazolyl-methyl |
| 1BN | cyclopropyl-methyl | cyclopropyl-methyl | 4-phenyl-benzyl | 1-pyrrolyl-methyl |
| 1BO | cyclopropyl-methyl | cyclopropyl-methyl | benzyl | 1-imidazolyl-methyl |
| 1BP | cyclopropyl-methyl | cyclopropyl-methyl | benzyl | 1-pyrrolyl-methyl |
| 1BQ | n-butyl | cyclopropyl-methyl | benzyl | 1-pyrrolyl-methyl |
| 1BR | cyclopropyl-methyl | cyclopropyl-methyl | benzyl | 1-pyrazolyl-methyl |
| 1BR1 | H | cyclopropyl-methyl | 1-pyrrolyl-methyl | 1-pyrrolyl-methyl |
| 1BR2 | allyl | allyl | benzyl | 4-pyridinyl-methyl |
| 1BR3 | N-butyl | cyclopropyl-methyl | benzyl | 4-pyridinyl-methyl |

Synthesis of Cyclic Guanidines

Cyclic guanidine compounds of the invention wherein W=NH(C=N-CN)NH, differ from the cyclic urea compounds of the invention wherein W=NH(C=O)NH.

Described below are representative methods for the preparation of cyclic quanidine compounds of the invention.

Synthesis of Cyclic Guanidines

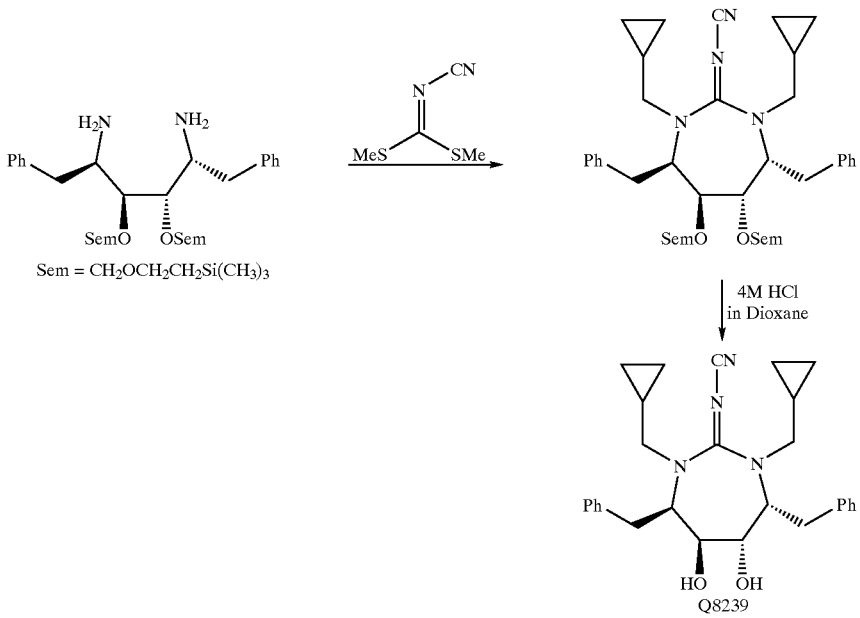

The structures of the Examples below are shown in Table 1c.

EXAMPLE 1BS

Synthesis of Intermediate A

Diamino Disem 561 mg (1 mmol) was dissolved in 2 ml pyridine and to this solution was added 175 mg (1.2 mmol) Dimethyl N-cyanodithioiminocarbonate. The contents were refluxed in a 125° C. oil bath for 2 hours. (Caution: Methyl mercaptan is a by-product and the reaction should be vented to a Clorox scrubber). TLC(1:2 EtOAc:Hexane Rf=0.4) indicated a complete reaction. The reaction was diluted with 100 ml dichloromethane. The organic layer was washed with 1N HCL (2×25 ml) followed by sat. sodium bicarbonate solution (25 ml). It was separated and dried over magnesium sulfate and the filtrate taken to dryness. The residue was purified on $SiO_2$ gel (55 g; using 1:3 followed by 1:2 EtOAc:Hexane) to provide 372 mg (60.9% yield) of the desired intermediate A as a colorless oil.

Synthesis of Intermediate B

Intermediate A 305 mg (0.5 mmol) was dissolved in 2 ml dimethylformamide and to this solution, cooled in a 0° C. ice bath, was added NaH (60% in oil) 80 mg (2 mmol) slowly. The contents were stirred at room temperature for 30 minutes. The mixture was cooled in a 0° C. ice bath and (bromomethyl)cyclopropane 0.19 ml (2 mmol) was added via syringe and stirred at room temperature for 18 hours. TLC(1:4 EtOAc:Hexane Rf=0.31) indicated a complete reaction. The reaction was worked up by diluting with water (50 ml) and extracting with diethylether (2×25 ml). The organic layer was dried over magnesium sulfate and the filtrate taken to dryness. The residue was purified on $SiO_2$ gel (33 g; 1:5 followed by 1:4 EtOAc:Hexane) to provide 243 mg (67.6% yield) of the desired intermediate B as a colorless oil.

Synthesis of Example 1BS

Intermediate B 110 mg (0.153 mmol) was placed in a 10 ml R.B. Flask and cooled in a 0° C. ice bath. To the flask was added 4M HCl in dioxane 1 ml (4 mmol) and the mixture stirred at room temperature for 15 minutes. TLC(1:1 EtOAc:Hexane Rf=0.15) indicated a complete reaction. The mixture was worked up by quenching in sat. sodium bicarbonate (25 ml) and extracting with dichloromethane (2×25 ml). The organic extracts were dried over magnesium sulfate and the filtrated taken to dryness. The residue was purified on $SiO_2$ gel (33 g; 1:1 EtOAc:Hexane followed by 10:1:10 EtOAc:EtOH:Hexane) to provide 27 mg (38.5% yield) of the desired Q8239 as a white solid. m.p.211.2° C.

EXAMPLE 1BT

Synthesis of Intermediate C

Intermediate A 1.515 g (2.48 mmol) was dissolved in 7.5 ml dimethylformamide and to this solution, cooled in a 0° C. ice bath, was added NaH (60% in oil) 397 mg (9.92 mmol) slowly. The contents were stirred at room temperature for 30 minutes. The mixture was cooled in a 0° C. ice bath and p-benzyloxybenzyl chloride 2.308 g (9.92 mmol) was added as a solid and the mixture stirred at room temperature for 18 hours. TLC(1:4 EtOAc:Hexane Rf=0.31) indicated a complete reaction. The reaction was worked up by diluting with water (100 ml) and extracting with diethylether (2×50 ml). The organic layer was dried over magnesium sulfate and the filtrate taken to dryness. The residue was purified on $SiO_2$ gel (130 g; 1:4 followed by 1:3 EtOAc:Hexane)to provide 2.068 g (83.1% yield) of the desired intermediate C as a colorless foam.

Synthesis of Example 1BT

Intermediate C 1.928 g (1.92 mmol) was placed in a 100 ml R.B. flask and cooled in a 0° C. ice bath. To the flask was added 4M HCl in dioxane 15 ml (60 mmol) and the mixture stirred at room temperature for 15 minutes. TLC(1:1 EtOAc:Hexane Rf=0.25) indicated a complete reaction. The mixture was worked up by quenching in 0.5N sodium hydroxide solution (100 ml) and washing with sat.sodium bicarbonate (50 ml) and extracting with dichloromethane (3×50 ml). The organic extracts were dried over magnesium sulfate and the filtrate taken to dryness. The residue was purified on $SiO_2$ gel (130 g; 1:1 EtOAc:Hexane) to provide 1.284 g (89.9% yield) of the desired product as a white solid. m.p. 90.1° C.

EXAMPLE 1BU

Synthesis of Example 1BU

Example Number 1BT 1.161 g (1.56 mmol) was dissolved in 15 ml of ethanol. To the mixture was added 1.1 g of 5% Palladium on Carbon and the suspension stirred for 18 hours under hydrogen (1 atm). TLC indicated an incomplete reaction. The mixture was treated with 1.1 g of 10% Palladium Hydroxide on Carbon and stirred for 2 hours under hydrogen (1 atm). TLC(10:1:10 EtOAc:Hexane Rf=0.31) indicated a complete reaction. The suspension was filtered through a celite pad and the filtrate taken to dryness. The residue was purified on $SiO_2$ gel (130 g; 10:1:10 followed by 10:2:10 EtOAc:EtOH:Hexane) to provide 458 mg (52.2% yield) of the desired product as a white solid. m.p. 103.3° C.

TABLE 1c

![Structure: 7-membered ring with two N atoms bearing R groups, C=N-CN imino group, two CH-CH2-Ph substituents, and two OH groups]

| Example Number | R | Ki | IC90 | M + H (M + NH4) | m.p. (° C.) |
|---|---|---|---|---|---|
| 1BS | cyclopropylmethyl | ++ | +++ | 459 | 211.2 |
| 1BT | CH2(C6H4)-p-OCH2C6H5 | ++ | + | 743 | 90.1 |
| 1BU | CH2(C6H4)-p-OH | +++ | +++ | 563 | 103.3 |
| 1BV | cyclopentylmethyl | +++ | +++ | 515 | 99.7 |
| 1BW | allyl | ++ | ++ | 431 | 70.2 |
| 1BX | n-butyl | +++ | +++ | 463 | 58.3 |
| 1BY | Beta-napthylmethyl | ++ | + | 631 | 111.1 |
| 1BZ | benzyl | ++ | +++ | 531 | 94.0 |
| 1CA | CH2(C6H4)-m-OCH2C6H5 | ++ | + | 743 | 75.2 |
| 1CB | p-nitrobenzyl | ++ | ++ | 621 | 130.3 |
| 1CC | m-nitrobenzyl | | | | 114 |
| 1CD | CH2(C6H4)-m-OH | +++ | +++ | 563 | 124 |
| 1CE | p-aminobenzyl | ++ | +++ | 561 | 226.3 |
| 1CF | m-aminobenzyl | +++ | +++ | 561 | 114.4 |
| 1CG | p-nitrilobenzyl | ++ | +++ | 581 | |
| 1CH | m-nitrilobenzyl | ++ | +++ | (598) | 108.5 |
| 1CI | dimethylallyl | ++ | +++ | 487 | 72.9 |
| 1CJ | cyclohexylmethyl | +++ | +++ | 543 | 96.4 |
| 1CK | cyclobutylmethyl | +++ | +++ | 487 | 235.5 |
| 1CL | propyl | ++ | +++ | 435 | 216.6 |
| 1CM | 3-methyl-1-butyl | ++ | +++ | 491 | 76.1 |
| 1CN | CH2(C6H4)-p-CH2OH | ++ | +++ | 591 | 100.9 |
| 1CO | CH2(C6H4)-m-CH2OH | +++ | +++ | 591 | 193.8 |
| 1CP | CH2(C6H4)-m-CHO | +++ | +++ | 587 | |
| 1CQ | CH2(C6H4)-m-CH=N—OH | +++ | +++ | 617 | 121.2 |

The structures of the Examples below are shown in Tables 1d and 1e.

EXAMPLE 7F

A solution of Example 1X (120 mg, 0.27 mmol) in methylene chloride (25 mL) was cooled in an ice bath at 0° C. and treated with triethylamine (110 mg, 1.1 mmol). Then a solution of thionyl chloride (150 mg, 1.3 mmol) in methylene chloride (10 mL) was added dropwise. The mixture was stirred for 10 minutes and then washed with sat'd NaHCO3 (aq), brine, and dried over MgSO4. The solution is filtered and the solvent removed on a rotary evaporator and the resulting residue is HPLC chromatographed on silica gel (50% EtOAc/Hexanes) to give 100 mg of a white foam. HRMS calculated for $C_{27}H_{32}N_2O_4S$: 481.2161; found: 481.2152.

EXAMPLE 7G

A solution of Example 1X (120 mg, 0.27 mmol) in methylene chloride (25 mL) was cooled in an ice bath at 0° C. and treated with triethylamine (80 mg, 0.8 mmol). Then a solution of trichloromethyl chloroformate (DIPHOSGENE) (53 mg, 0.27 mmol) in methylene chloride (5 mL) was added dropwise. The mixture was stirred for 60 minutes and then washed with sat'd NaHCO3 (aq), brine, and dried over MgSO4. The solution is filtered and the solvent removed on a rotary evaporator and the resulting residue is chromatographed on silica gel (50% EtOAc/Hexanes) to give 90 mg of a white foam. MS (NH3) 461 (M+H)+.

EXAMPLE 7I

A solution of Ex. 1X (500 mg, 1.15 mmol) in THF (25 mL) was treated with thiocarbonyldiimidazole (410 mg, 2.3 mmol) and heated to reflux for 1.5 hours. The solvent is removed on a rotary evaporator and the resulting residue is chromatographed on silica gel (50% EtOAc/Hexanes) to give 320 mg of a white solid. MS (NH3) 477.3 (M+H)+.

EXAMPLE 7H AND 7U

A solution of Example 7I (220 mg, 0.46 mmol) in dry toluene (25 mL) was heated to reflux and treated with Bu3SnH (0.4 mL, 1.5 mL) and 20 mg of AIBN. The mixture was heated at reflux for 2.5 hours. The solvent is removed on a rotary evaporator and the resulting residue is chromatographed on silica gel (20% EtOAc/Hexanes) to give 70 mg of 7H as a white solid. MS (NH3) 447.2. (M+H)+. A later fraction gave 30 mg of Example 7U as a white solid. MS 419.2 (M+H)+.

EXAMPLE 7V

A solution of Ex. 1X (112 mg, 0.26 mmol) in methylene chloride (5 mL) was cooled in an ice bath at 0° C. and treated with DAST (110 mg, 1.1 mmol). The mixture was stirred for 10 minutes and then washed with sat'd NaHCO3 (aq), brine, and dried over MgSO4. The solution is filtered and the solvent removed on a rotary evaporator and the resulting residue is HPLC chromatographed on silica gel (65% EtOAc/Hexanes) to give 40 mg of a colorless residue. HRMS calculated for $C_{27}H_{33}N_2O_2F$: 437.2604; found: 437.2593.

EXAMPLE 7O

A solution of Ex. 3U (600 mg, 1.9 mmol) in pyridine (10 mL) is treated with methanesulfonyl chloride (170 mg, 1.5 mmol) and stirred at room temperature for 3 hours. The mixture is quenched with 5 mL of methanol. The solution is concentrated on a rotary evaporator and the resulting residue is dissolved in ethyl acetate and then washed with dilute HCl (aq), brine, and dried over $MgSO_4$. The solution is filtered and the solvent removed on a rotary evaporator and the resulting residue is chromatographed on silica gel (40% EtOAc/Hexanes) to give Example 7O (420 mg) as a white solid. MS 685 $(M+H)^+$.

EXAMPLE 7Y

A solution of Example 7O (100 mg, 0.15 mmol) in DMF (4 mL) was treated with $NaN_3$ (100 mg, 1.5 mmol) and heated at 80° C. for 2 hrs and then stirred overnight at 40° C. The solution was diluted with water and the resulting white solid is extracted into ethyl acetate. The organic extract is washed with water, brine, and dried over $MgSO_4$. The solution is filtered and the solvent removed on a rotary evaporator and the resulting residue is HPLC chromatographed on silica gel (50% EtOAc/Hexanes) to give Example 7Y (80 mg) as a white solid. MS 632 $(M+H)^+$. IR $(CHCl_3)$ 2214 $cm^{-1}$ for $N_3$.

EXAMPLE 7J AND 7K

A solution of Ex. 3U (100 mg, 0.165 mmol) in pyridine (3 mL) is treated with acetic anhydride (84 mg, 0.824 mmol) and stirred at room temperature for 2 hours. The mixture is quenched with 5 mL of methanol. The solution is concentrated on a rotary evaporator and the resulting residue is dissolved in ethyl acetate and then washed with dilute HCl (aq), brine, and dried over $MgSO_4$. The solution is filtered and the solvent removed on a rotary evaporator and the resulting residue is HPLC chromatographed on silica gel (40% EtOAc/Hexanes) to give Example 7J (24 mg) as a white solid. HRMS: $(M+H)^+$ calculated for $C_{45}H_{43}N_2O_5$: 691.317198; found: 691.316252. Also gives as a later fraction Example 7K (27 mg) as a white solid. HRMS: $(M+H)^+$ calculated for $C_{43}H_{41}N_2O_4$: 649.306633; found: 649.304918.

EXAMPLE 7R

A solution of Ex. 3U (100 mg, 0.165 mmol) in methylene chloride (5 mL) is treated with 2,2dimethoxy propane (174 mg, 1.65 mmol), p-toluenesulfonic acid (10 mg) and stirred at room temperature for overnight. The mixture is diluted with methylene chloride and washed with saturated $NaHCO_3$, brine, and dried over $MgSO_4$. The solution is filtered and the solvent removed on a rotary evaporator and the resulting residue is HPLC chromatographed on silica gel (50% EtOAc/Hexanes) to give Example 7R (73 mg) as a white solid. HRMS: $(M+H)^+$ calculated for $C_{44}H_{43}N_2O_3$: 647.327369; found: 647.327531.

EXAMPLE 7P

A solution of Ex. 3U (200 mg, 0.33 mmol) in methylene chloride (5 mL) is treated with oxalyl chloride (249 mg, 2.0 mmol) and stirred at room temperature for overnight. The solvent removed on a rotary evaporator and the resulting residue is HPLC chromatographed on silica gel (50% EtOAc/Hexanes) to give a tan solid. This was recrystallized from $CH_2Cl_2$/hexane to give Example 7P (80 mg) as a white solid. MS: 661.4 $(M+H)^+$.

EXAMPLE 7S

A solution of Ex. 3U (100 mg, 0.165 mmol) in methylene chloride (5 mL) is treated with trimethylorthobutyrate (244 mg, 1.65 mmol) p-toluenesulfonic acid (10 mg) and stirred at room temperature for 30 minutes. The mixture is diluted with methylene chloride and washed with saturated $NaHCO_3$, brine, and dried over $MgSO_4$. The solution is filtered and the solvent removed on a rotary evaporator and the resulting residue is HPLC chromatographed on silica gel (50% EtOAc/Hexanes) to give Ex. 7S. MS: 691.5 $(M+H)^+$.

EXAMPLE 7B

A solution of the Di-MEM protected Ex. 1C (550 mg, 0.94 mmol) in pyridine (11 mL) is treated with $P_2S_5$ (420 mg, 0.94 mmol) and heated to reflux for 3 hrs. The pyridine is evaporated off on a rotary evaporator and the residue is taken up in methylene chloride and washed with water, $NaHCO_3$, and brine. The solution is dried over $MgSO_4$, filtered and the solvent removed on a rotary evaporator and the resulting residue is chromatographed on silica gel (40% EtOAc/Hexanes) to give Example 7B (120 mg) as a clear oil. HRMS: $(M+H)^+$ calculated for $C_{27}H_{33}N_2O_3S$: 465.221190; found: 465.220899.

EXAMPLE 7A

A solution of Example 1C (330 mg, 0.8 mmol) in pyridine (5 mL) is treated with acetic anhydride (160 mg, 1.6 mmol) and stirred at room temperature for 4 hours. The mixture is quenched with 5 mL of methanol. The solution is concentrated on a rotary evaporator and the resulting residue is dissolved in ethyl acetate and then washed with dilute HCl (aq), brine, and dried over $MgSO_4$. The solution is filtered and the solvent removed on a rotary evaporator and the resulting residue is chromatographed on silica gel (50% EtOAc/Hex) to give Example 7A (120 mg) as a white solid. MS: (CI, $NH_3$) 449.1 $(M+H)^+$.

EXAMPLE 7W

A solution of example 1C (160 mg, 0.39 mmol) in methylene chloride (5 mL) was cooled in an ice bath at 0° C. and treated with DAST (63 mg, 0.4 mmol). The mixture was stirred for 10 minutes and then washed with sat'd $NaHCO_3$ (aq), brine, and dried over $MgSO_4$. The solution is filtered and the solvent removed on a rotary evaporator and the resulting residue is HPLC chromatographed on silica gel (50% EtOAc/Hex) to give 80 mg of a colorless residue. HRMS calculated for $C_{25}H_{30}N_2O_2F$: 409.2291; found: 409.2291.

EXAMPLE 7X

A solution of example 3U (100 mg, 0.16 mmol) in methylene chloride (5 mL) was cooled in an ice bath at 0° C. and treated with DAST (26 mg, 0.16 mmol). The mixture was stirred for 10 minutes and then washed with sated $NaHCO_3$ (aq), brine, and dried over $MgSO_4$. The solution is filtered and the solvent removed on a rotary evaporator and the resulting residue is HPLC chromatographed on silica gel (50% EtOAc/Hex) to give 35 mg of a white foam. HRMS calculated for $C_{41}H_{38}N_2O_2F$: 609.2917; found: 609.2911.

EXAMPLE 8A

A solution of example 1X (2.06 g, 4.74 mmol) in methylene chloride was treated with diisopropylethylamine (1.53 g, 11.8 mmol), MEM-Cl (0.71 g, 5.7 mmol) and heated to reflux for 5 hours and let stir overnight at rt. The solution is concentrated on a rotary evaporator the residue is HPLC chromatographed on silica gel (5% MeOH/CHCl$_3$) to give 1.3 g of the mono-MEM mono-ol intermediate. MS: (CI, NH$_3$) 523.4 (M+H)$^+$.

A solution of mono-MEM mono-ol intermediate from above (1.0 g, 1.9 mmol) in THF was treated with triphenylphosphine (1.0 g, 3.8 mmol), diethylazadicarboxylate (DEAD) (0.7 g, 4.0 mmol), and chloroacetic acid (0.4 g, 4.2 mmol). The solution is stirred overnight at rt. The solvent is evaporated and the resulting residue is chromatographed on silica gel (50% EtOAc/Hex) to give 0.9 g of the chloroacetate intermediate. MS: (CI, NH$_3$) 599.3 (100%, (M+H)$^+$); 600 (39%).

The chloroacetate intermediate (0.9 g, 1.5 mmol) was dissolved in MeOH (15 ml) and treated with NaOH$_{(aq)}$ (4 ml, 1N) and stirred at rt for 15 min. The solution was evaporated to dryness and the residue partitioned between water and ethyl acetate. The organic layer was washed with water and brine and then dried over MgSO$_4$. The solution is the filtered, concentrated and the residue is HPLC chromatographed on silica gel (85% EtOAc/Hex) to give 400 mg of example 8A. MS: (CI, NH$_3$) 523.4 (M+H)$^+$.

EXAMPLE 7Z

A solution of example 8A (100 mg, 0.2 mmol) in MeOH is cooled in an ice bath and treated with HCl $_{(g)}$ for 20 min and then stirred for an additional 40 min at 0° C. The solution is then evaporated to dryness at rt and the residue is HPLC chromatographed on silica gel (80% EtOAc/Hex) to give 48 mg of example 7Z as a white foam. MS: (CI, NH$_3$) 435.2 (M+H)$^+$.

EXAMPLE 8C

A solution of example 8A (160 mg, 0.3 mmol) in methylene chloride (10 ml) is cooled to 0° C. in an ice bath and treated with DAST (50 mg, 0.3 mmol). The solution is stirred at rt for 15 min and then quenched with water. The organic layer is washed with water and brine and dried over MgSO$_4$. The solution is filtered, the solvent evaporated and the residue HPLC chromatographed on silica gel (50% EtOAc/Hex) to give 100 mg of example 8C. MS: (CI, NH$_3$) 525.4 (M+H)$^+$.

EXAMPLE 8B

A solution of example 8C (70 mg, 0.13 mmol) in MeOH is cooled in an ice bath and treated with HCl $_{(g)}$ for 20 min and then stirred for an additional 40 min at 0° C. The solution is then evaporated to dryness at rt and the residue is HPLC chromatographed on silica gel (80% EtOAc/Hex) to give 40 mg of example 8B as a white foam. MS: (CI, NH$_3$) 437.3 (M+H)$^+$.

EXAMPLE 7AA

To a stirred suspension of 750 mg (1.72 mmol) of the diol (1×) in 35 mL of methylene chloride was added 445 mg (3.45 mmol) of diisopropylethylamine and 322 mg (2.59 mmol) of MEM chloride. After stirring 5 days the resulting solution was washed with dilute HCl, brine and was dried with anhydrous MgSO$_4$. The solvent was removed under reduced pressure and the residue was chromatographed on silica gel. Elution with 50% ethyl acetate in hexanes gave 430 mg (48%) of the mono protected ether (XXVa). MS: 523 (M+1, 100); NMR (CDCl$_3$): d 7.20 (m, 10H), 4.96 (s, 2H), 4.08 (m, 1H), 3.90 (m, 2H), 3.61 (m, 7H), 3.42 (s, 3H), 3.13 (m, 4H), 1.99 (m, 2H), 0.88 (m, 2H), 0.40 (m, 4H), 0.06 (m, 4H), To a stirred solution of 78 mg (0.15 mmol) of Compound (XXVa) in 3 ml of methylene chloride was added 60 mg (0.74 mmol) of sodium acetate and 95 mg (0.44 mmol) of PCC. The resulting suspension was stirred 3 days and was diluted with ether and filtered through florisil. The solvent was removed under reduced pressure and the residue was chromatographed on silica gel. Elution with 2.5% methanol in methylene chloride gave 68 mg (885) of example 7AA. MS: 521 (M+1, 100); NMR (CDCl$_3$): d 7.21 (m, 10H), 4.90 (d, 1H), 4.70 (dd, 2H), 4.10 (t, 1H), 3.80–3.37 (m, 8H), 3.36 (s, 3H), 3.26–2.82 (m, 4H), 2.22 (q, 1H), 1.03 (m, 2H), 0.51 (m, 4H), 0.20 (m, 4H), Oxidation of Monoprotected Diol: Preparation of (XXVb)

To a stirred solution of 51 mg (0.10 mmol) of example 7AA in 4 mL of methanol was added 1 mL of concentrated HCl. The resulting solution was stirred 5 h and the product was precipitated by adding water. The suspension was extracted with methylene chloride and the combined organic layers were dried with anhydrous MgSO$_4$. The solvent was removed under reduced pressure and the residue was chromatographed on silica gel. Elution with 33% ethyl acetate in hexanes gave 34 mg (80%) of the ketol (XXVb). MS: 433 (M+1, 100); NMR (CDCl$_3$): d 7.21 (m, 10H), 4.82 (m, 1H), 4.24 (t, 1H), 3.85 (m, 1H), 3.74 (d, 1H), 3.44 (m, 3H), 3.22–2.73 (m, 4H), 2.27 (q, 1H), 1.01 (m, 2H), 0.51 (m, 4H), 0.20 (m, 4H),

EXAMPLE 7AC

To a stirred solution of 37 mg (0.09 mmol) of the ketol (XXVb) in 4 mL of ethanol and 2 mL of water was added 40 mg (0.48 mmol) of methoxylamine hydrochloride. The resulting solution was stirred overnight and the product was precipitated by adding water. The suspension was extracted with methylene chloride and the combined organic layers were dried with anhydrous MgSO$_4$. The solvent was removed under reduced pressure to give 40 mg (100%) of example 7AC. MS: 462 (M+1, 100); NMR (CDCl$_3$) d 7.20 (m, 10H), 5.30 (m, 2H), 4.80 (t, 1H), 4.24 (t, 1H), 3.77 (m, 4H), 3.40 (m, 3H), 2.90 (m, 4H), 2.25 (dd, 1H), 1.03 (m, 2H), 0.48 (m, 4H), 0.23 (m, 2H), 0.12 (m, 2H).

EXAMPLE 7AB

By substituting hydroxylamine hydrochloride in the above procedure, the desired product can be obtained: MS: 448 (M+1, 100); NMR (CDCl$_3$): d 8.13 (s, 1H), 7.20 (m, 10H), 5.42 (t, 1H), 4.83 (t, 1H), 3.75 (m, 2H), 3.40 (m, 3H), 2.94 (m, 4H), 2.22 (dd, 1H), 1.17 (m, 1H), 0.90 (m, 1H), 0.47 (m, 4H), 0.23 (m, 2H), 0.11 (m, 2H).

EXAMPLE 7AD

To a stirred solution of 98 mg (0.23 mmol) of ketol (XXVb) in 5 mL of butanol was added 57 mg (0.71 mmol) of formamidine hydrochloride and 40 mg (0.75 mmol) of sodium methoxide. The resulting suspension was stirred 30 min and was refluxed overnight. The butanol was removed under reduced pressure and water was added. The suspension was extracted with methylene chloride and the combined organic layers were dried with anhydrous MgSO$_4$. The solvent was removed under reduced pressure and the residue was chromatographed on silica gel. Elution with 25% ethyl acetate in hexanes gave 28 mg (28%) of example 7AD. MS: 442 (M+1, 100); NMR (CDCl$_3$): d 7.58 (s, 1H), 7.20 (m, 10H), 4.55 (m, 2H), 3.51 (m, 2H), 3.24 (m, 2H), 3.05 (m, 2H), 2.53 (q, 1H), 2.27 (q, 1H), 0.91 (m, 2H), 0.45 (m, 4H), 0.11 (m, 4H).

EXAMPLES 7AE AND 7AF

To a stirred solution of 65 mg (0.15 mmol) of the diol (1x) in 1mL of DMF was added 5.5 mg (0.18 mmol) of 80% sodium hydride. The resulting suspension was stirred 20 min. and 68 mg (0.48 mmol) of methyl iodide was added. After stirring overnight, the suspension was quenched with water, extracted with ethyl acetate, and the combined organic layers were dried with anhydrous MgSO$_4$. The solvent was removed under reduced pressure and the residue was chromatographed on silica gel. Elution with 25% ethyl acetate in hexanes gave 19 mg (28%) of example 7AE along with 25 mg (37%) of Example 7AF.

Example 7AE: MS: 449 (M+1, 100); NMR (CDCl$_3$): d 7.26 (m, 10H), 4.05 (dd, 1H), 3.84 (m, 1H), 3.67 (m, 2H), 3.60 (s, 3H), 3.53 (m, 2H), 3.13 (m, 3H), 2.90 (m, 2H), 1.94 (dt, 2H), 0.89 (m, 2H), 0.41 (m, 4H), 0.04 (m, 4H), Example 7AF: MS: 463 (M+1, 100); NMR (CDCl$_3$): d 7.21 (m, 10H), 3.67 (m, 4H), 3.62 (s, 6H), 3.58 (s, 2H), 3.10 (m, 4H), 1.92 (dd, 2H), 0.83 (m, 2H), 0.41 (m, 4H), 0.04 (m, 4H).

EXAMPLES 7AG and 7AH

By substituting benzyloxymethyl chloride in the above procedure, example 7AG and 7AH were obtained.

Example 7AG: MS: 615 (M+1, 100); $^1$H NMR (CDCl$_3$): d 7.50–7.06 (m, 20H), 4.88 (ab, 4H), 3.92 (s, 2H), 3.56 (m, 2H), 3.47 (dd, 2H), 3.14 (m, 4H), 1.88 (dd, 2H), 0.62 (m, 2H), 0.34 (m, 4H), 0.05 (m, 4H).

Example 7AH: MS: 525 (M+1, 100); $^1$H NMR (CDCl$_3$): d 7.45–7.10 (m, 15H), 4.74 (ab, 2H), 4.13 (dd, 1H), 3.82–3.50 (m, 5H), 3.09 (m, 4H), 2.76 (s, 1H), 1.95 (dt, 2H), 0.92 (m, 2H), 0.40 (m, 4H), 0.03 (m, 4H).

EXAMPLES 7AI AND 7AJ

By substituting allyl bromide in the above procedure, example 7AI and 7AJ were obtained.

Example 7AI: $^1$H NMR (CDCl$_3$) d 7.26 (m, 10H), 6.05 (m, 2H), 5.30 (dd, 4H), 4.28 (m, 2H), 3.76 (s, 2H), 3.60 (m, 4H), 3.10 (m, 4H), 1.93 (dd, 2H), 0.86 (m, 2H), 0.40 (m, 4H), 0.01 (m, 4H).

Example 7AJ: MS: 475 (M+1, 100); $^1$H NMR (CDCl$_3$) d 7.27 (m, 10H), 6.01 (m, 1H), 5.32 (dd, 2H), 4.34 (dd, 1H), 4.18 (dd.1H), 4.66 (m, 5H), 3.10 (m, 4H), 2.82 (s, 1H), 1.95 (m, 2H), 0.85 (m, 2H), 0.40 (m, 4H), 0.04 (m, 4H).

EXAMPLE 8E

A solution of Example 5F (500 mg, 0.7 mmol) in methylene chloride (10 ml) is cooled to 0° C. in an ice bath and treated with DAST (112 mg, 0.7 mmol). The solution is stirred at 0° C. for 15 min and then quenched with sat'd NaHCO$_3$. The organic layer is washed with water and brine and dried over MgSO$_4$. The solution is filtered, the solvent evaporated and the residue HPLC chromatographed on silica gel (50% EtOAc/Hex) to give 250 mg of example 8E as a white foam. MS: (CI, NH$_3$) 721 (M+H)$^+$.

EXAMPLE 8F

A solution of example 8E (200 mg, 0.28 mmol) in MeOH is cooled in an ice bath and treated with gaseous HCl for 20 min and then stirred for an additional 40 min at 0° C. The solution is then evaporated to dryness at rt and the residue is HPLC chromatographed on silica gel (5% MeOH/CHCl$_3$) to give 120 mg of example 8F as a white foam. MS: (CI, NH$_3$) 541 (M+H)$^+$.

EXAMPLE 8G (via Alkene Intermediate XXIX)

A solution of Example 7Q (150 mg, 0.22 mmol) in DMF was treated with sodium iodide (160 mg, 1.1 mmol) and heated at 90° C. for 2 hrs. The mixture is cooled to room temperature, diluted with water and the precipitate is extracted into CH$_2$Cl$_2$. The extract is washed with water and brine, dried over MgSO$_4$ and evaporated to give a yellow oil. This is HPLC chromatographed on silica gel (50% EtOAc/Hex) to give 50 mg of alkene intermediate (XXIX) as a white solid. MS: (CI, NH$_3$) 589 (M+H)$^+$.

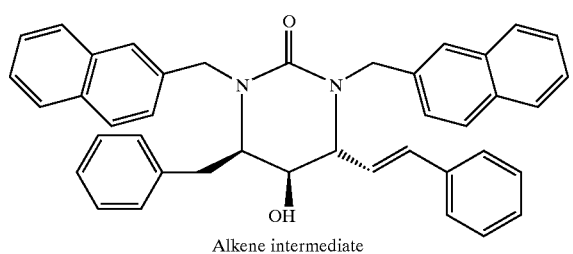

(XXIX)

Alkene intermediate

A solution of alkene intermediate (XXIX) (40 mg, 0.07 mmol) in THF was treated with 20 mg of 10% Pd/C and hydrogenated in a Parr Hydrogenator at 50 psi overnight. The catalyst was filtered off and the filtrate concentrated. The resulting residue was HPLC chromatographed on silica gel (70% EtOAc/Hex) to give 10 mg of Example 8G as a white solid. MS: (CI, NH$_3$) 591.5 (M+H)$^+$.

Method 2 (As outlined in Scheme 10):

A suspension of Example 3U (2.0 g, 0.0033 mol) in methylene chloride was treated at room temperature with 2-acetoxyisobutryl bromide (2.09 g, 0.01 mol) and stirred for 1 hour until the solution became clear. The reaction was quenched with a solution of sat'd sodium bicarbonate and the organic layer was washed with water and brine. The solution was dried over magnesium sulfate, concentrated and chromatographed on silica gel (30% EtOAc/Hexane elution) to give 1.3 g of the corresponding bromoacetate intermediate as a white solid. MS: (CI, NH$_3$) 713.4 (M+H)$^+$.

A solution of the bromo acetate intermediate (0.45 g, 0.63 mmol) in acetic acid was treated with 1 g of zinc dust and stirred at room temperature until TLC analysis showed no starting material remained. The mixtured was diluted with ethyl acetate and filtered. The filtrate was concentrated and the resulting residue was dissolved in methanol and treated with 1N aq. NaOH and stirred overnight. The solution was concentrated and the residue was dissolved in methylene chloride, washed with water and brine, dried over magnesium sulfate, and concentrated. The residue was chromatographed on silica gel (50% EtOAc/Hexane elution) to give 170 mg of Example 8G as a white solid. MS: (CI, NH$_3$) 591.5 (M+H)+.

EXAMPLE 8H

Method 1.

A. Synthesis of 6-Membered Ring Cyclic Urea (XXX)

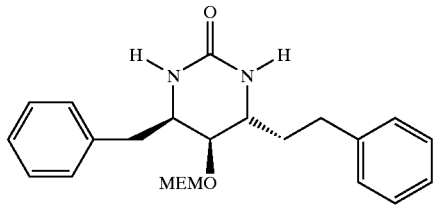

The synthesis of the six-membered cyclic urea (XXX) is outlined in Scheme 8. A solution of N-Cbz-D-phenylalanine N,O-dimethylhydroxylamide (33.5 g, 0.098 mol) in ether was cooled to 0° C. and treated with 300 mL of a 1 M solution of vinyl magnesium bromide in THF. The mixture was stirred for 30 mins and then poured into an ice cold solution of 1 N HCl (500 mL). The mixture was extracted into ether and the extracts washed with water and brine. The organic layer was dried over $MgSO_4$, filtered and concentrated to give the desired vinyl ketone as a thick, light yellow residue which was used without further purification. MS: (CI, $NH_3$) 310 (77%, $(M+H)^+$); 327.1 (100%, $(M+NH_4)^+$).

The crude ketone was dissolved in methanol (350 mL) and treated with cerium trichloride heptahydrate (37.2 g, 0.1 mol) and cooled in an ice bath. While stirring vigorously sodium borohydride (3.78 g 0.1 mol) was added slowly, a small portion at a time, over a period of 30 min. After the addition was complete the mixture was allowed to warm to room temperature and stirred for an additional 1 hr. The solvent was removed under vacuum on a rotorary evaporator and the residue was partitioned between 1 N HCl and methylene chloride. The organic layer was washed with water, brine, and then dried over $MgSO_4$, filtered and concentrated to give the desired allylic alcohol as an off-white solid which was used without further purification.

A solution of the crude allylic alcohol and diisopropylethylamine (30 g, 0.23 mol) in methylene chloride was cooled in an ice bath and treated dropwise with methanesulfonyl chloride (28 g, 0.24 mol). The solution was stirred for 30 mins, then washed sequentially with 1 N HCl, water, brine and dried over $MgSO_4$. The solution was filtered and concentrated to give the crude mesylate as a thick oil. To a flamed-dried flask was added copper cyanide (12 g, 0.144 mol) and 100 mL of THF. The flask was cooled to −78° C. under nitrogen atmosphere. A solution of benzylmagnesium chloride (360 mL, 2M in THF, 0.72 mol) was added via syringe and the resulting thick solution was stirred at −60° C. for 20 mins and at 0° C. for 30 mins. The solution was then cooled to −78° C. and a solution of the mesylate in 130 mL of THF was added via syringe. The solution was stirred at −60° C. for 45 mins and then poured into a mixture of 1 N HCl/ice. This was extracted into ethyl acetate and the organic layer was washed sequentially with $NH_4Cl$ (aq), $NH_4OH$, brine, dried over $MgSO_4$, filtered and concentrated. The resulting residue is chromatographed on silica gel (hexane, then 10% EtOAc/Hex) to give 11.7 g of the desire alkene as a white solid. MS: (CI, $NH_3$) 386.3 (98%, $(M+H)^+$); 403.2 (100%, $(M+NH_4)^+$).

A solution of the above alkene (11.0 g, 0.029 mol) in methylene chloride (75 mL) was cooled to 0° C. in an ice bath and treated with 60% m-chloroperbenzoic acid (14.0 g, 0.049 mol). The solution was stirred 0° C. for 7 hrs until TLC analysis showed no starting material remained. A precipitate formed during this time. The suspension was diluted with methylene chloride and washed sequentially with 1 N $Na_2S_2O_3$, 1 N sodium hydroxide, water, brine, dried over $MgSO_4$, filtered and concentrated to give the epoxide as a thick oil which was used without further purification.

To solution of crude epoxide in 80 mL of DMF was added sodium azide (20 g, 0.3 mol), ammonium chloride (2.5 g, 0.047 mol) and 20 mL of water. The mixture was heated at 90° C. for 3 hrs and then stirred at rt overnight. The solvent was removed under high vacuum on a rotorary evaporator and the residue was partitioned between water and methylene chloride. the organic layer was washed with water and brine, dried over $MgSO_4$, filtered and concentrated to give a residue. This was then chromatographed on silica gel (20% EtOAc/Hex) to give 7.4 g of the azide alcohol as a white solid. MS: (CI, $NH_3$) 445.0 (25%, $(M+H)^+$); 462.2 (100%, $(M+NH_4-BnOH)^+$).

A solution of the azide alcohol above (7.2 g, 0.016 mol) in methylene chloride was treated with diisopropylethylamine (4.2 g, 0.032 mol) and MEM-Cl (4.0 g 0.032 mol) and heated to reflux overnight (18 hrs). The mixture was concentrated and the residue chromatographed on silica gel (20% EtOAc/Hex—35% EtOAc/Hex) to give 7.7 g of the MEM protected azido alcohol as a colorless oil. MS: (CI, $NH_3$) 533.2 (100%, $(M+H)^+$).

To a solution of MEM protected azido alcohol (5.7 g 0.0107 mol) in ethyl acetate was added 2 mL of acetic acid and 1 g of Pearlman's catalyst (10% $Pd(OH)_2$ on Carbon) and the solution was hydrogenated at 55 psi for 22 hrs. The solution was filtered through Celite and the filtrate was extracted with 1 N HCl (organic layer turn orange). The acidic aqueous extract was made basic with 50% NaOH (while cooling in an ice bath) and the precipitate is extracted into ethyl acetate. The organic layer is washed with water, brine, dried over $MgSO_4$, filtered and concentrated to give 2.5 g of the MEM protected diamino alcohol as a colorless oil. MS: (CI, $NH_3$) 373.1 (100%, $(M+H)^+$).

To a solution of the MEM protected diamino alcohol (2.5 g 0.0067 mol) in THF was added 1,1-carbonyldiimidazole (1.1 g, 0.0067 mol) and stirred over night at room temperature. The solution was concentrated and the residue partitioned between 1 N HCl and $CH_2Cl_2$. The organic layer is washed with brine, dried over $MgSO_4$, filtered and concentrated. The residue is HPLC chromatographed on silica gel (5% $MeOH/CHCl_3$) to give 1.2 g of the MEM protected 6-membered ring cyclic urea (XXX) as a white solid. MS: (CI, $NH_3$) 399.1 (100%, $(M+H)^+$).

B. The MEM protected 6-membered ring cyclic urea (XXX) (100 mg, 0.27 mmol) was alkylated with cyclopropylmethylbromide (250 mg, 1.8 mmol) followed by removal of the MEM group, as described in general procedure 5, to give after chromatography on HPLC (silica gel, 10% $MeOH/CHCl_3$) 20 mg of Example 8H as a clear, viscous residue. MS: (CI, $NH_3$) 419.4 (100%, $(M+H)^+$).

Method 2.

A solution of Example 8A (160 mg, 0.3 mol) and thiocarbonyldiimidazole (55 mg, 0.3 mmol) in THF was heated to reflux for 4 hrs. The mixture was evaporated and the residue chromatographed on silica gel (50% EtOAc/Hex) to give 34 mg (0.055 mmol) of the corresponding thiocarbamate. The thiocarbamate was dissolved in 2 mL of toluene and heated to reflux. To the refluxing solution was added tributyltin hydride (32 mg, 0.1 mmol) and 2 mg of AIBN. The mixture was refluxed for 1 hour, concentrated, and the residue chromatography on HPLC (silica gel, 65% EtOAc/Hex) to give 20 mg of clear colorless oil. The oil was dissolved in MeOH, cooled in an ice bath and gaseous HCl was bubbled through the solution for 30 mins. The solution was then stirred at room temperature overnight, concentrated and the residue chromatography on HPLC (silica gel, 10% MeOH/CHCl$_3$) to give 10 mg of Example 8H as a clear, viscous residue. MS: (CI, NH$_3$) 419.2 (100%, (M+H)$^+$).

EXAMPLE 8AA

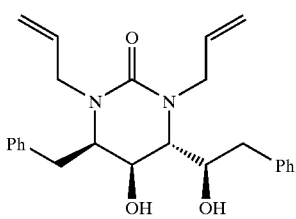

Compound (XXIIb) (0.85 g) was heated with mixture of acetic acid (9.5 mL) and water (0.5 mL) at 85° C. for 4 h. After extraction with dichloromethane, followed by washing the organic extract with saturated sodium bicarbonate and brine, a mixture was provided which, on separation by column chromatography, furnished (XXIIb) (TLC 1:10 ethyl acetate/hexane Rf=0.4; 0.54 g), the desired mono-alcohol intermediate (TLC 1:10 ethyl acetate/hexane Rf=0.1; 0.13 g), and overhydrolysed diol (0.05 g).

The above mono-alcohol intermediate 0.25 g (0.466 mmol), triphenylphosphine 183 mg (0.7 mmol), diethylazadicarboxyalte 0.11 mL (0.7 mmol), and chloroacetic acid 66 mg (0.7 mmol) were stirred in 5 mL anhydrous tetrahydrofuran at 0° C. for 15 minutes and then at room temperature for 18 h. The excess reagents were quenched with 0.5 mL methanol and the mixture allowed to stir for 20 minutes. The mixture was purified by silica gel column chromatography to provide the desired chloroacetate intermediate with inversion of configuration. $^{13}$C NMR (CDCl$_3$): (75.48 Hz) −1.373, 14.413, 14.487, 18.253, 25.591, 33.851, 35.741, 40.505, 48.824, 49.962, 57.507, 58.234, 66.589, 67.885, 73.179, 77.423, 95.454, 117.296, 118.554, 126.588, 126.887, 128.518, 128.610, 129.117, 129.199, 129.479, 133.686, 134.168, 136.324, 138.285, 155.698, 166.323.

The above chloroacetate intermediate 73 mg (0.12 mmol) in 2 mL dry methanol was treated with 0.25 mL (0.5M) sodium methoxide and stirred for 30 minutes at room temperature. The contents were then treated with 0.3 mL (4% HCl in methanol) and stirred for 4.5 h at room temperature. The residue after removal of solvent was purified on silica gel column to provide Example 8AA. $^{13}$C NMR (CDCl$_3$): (75.48 Hz) 34.075, 37.672, 48.941, 48.985, 58.071, 60.640, 65.861, 73.212, 177.975, 118.669, 126.535, 126.858, 128.603, 128.815, 129.225, 133.605, 134.172, 137.637, 138.273, 155.497.

EXAMPLE 8R

A solution of the bromoacetate intermediate from Example 8G (0.10 g, 0.14 mmol) in methanol was treated dropwise with sodium hydroxide solution (1N, 1 mL) and stirred at room temperature for 1 hour. The solution was diluted with water, acidified with 1N HCl (aq) and extracted into methylene chloride. The extract was washed with water, brine and dried over magnesium sulfate. The solution was filtered and concentrated to give 90 mg of Example 8R as white solid. MS: (CI, NH$_3$) 671.2 (72%, (M+H)$^+$); 669.2 (67%).

TABLE 1d

| Ex. No. | R$^{22}$ = R$^{23}$ | X | Y | stereo 2:3:4:5 | K$_i$ | IC$_{90}$ | MS (M + H) |
|---|---|---|---|---|---|---|---|
| 7A | allyl | OH | OAc | RSSR | + | +++ | 449.1 |
| 7B | allyl | \_O—S—O\_ (cyclic) | | RSSR | − | ++ | 465.2 |
| 7C | allyl | O—S(=O)—O | | RSSR | +++ | +++ | 453.2 |
| 7D | R$^{22}$ = n-butyl R$^{23}$ = allyl | O—S(=O)—O | | RSSR | +++ | ++ | 469.2 |

TABLE 1d-continued

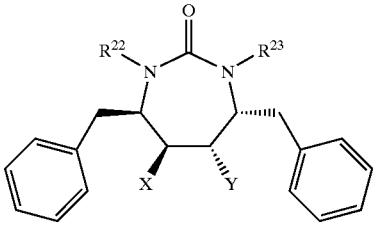

| Ex. No. | R²² = R²³ | X | Y | stereo 2:3:4:5 | $K_i$ | $IC_{90}$ | MS (M + H) |
|---|---|---|---|---|---|---|---|
| 7E | R²² = n-butyl<br>R²³ = allyl |  carbonate | | RSSR | ++ | +++ | 449.2 |
| 7F | cyclopropyl methyl |  sulfite | | RSSR | +++ | +++ | 481.2 |
| 7G | cyclopropyl methyl |  carbonate | | RSSR | ++ | +++ | 461 |
| 7H | cyclopropyl methyl |  methylenedioxy | | RSSR | + | ++ | 447.2 |
| 7I | cyclopropyl methyl |  thiocarbonate | | RSSR | ++ | +++ | 477.2 |
| 7J | 2-naphthyl methyl | OAc | OAc | RSSR | ++ | + | 691.3 |
| 7K | 2-naphthyl methyl | OH | OAc | RSSR | ++ | + | 649.3 |
| 7L | 2-naphthyl methyl |  carbonate | | RSSR | ++ | + | 633.2 |
| 7M | 2-naphthyl methyl |  sulfite | | RSSR | +++ | +++ | 653.2 |
| 7N | 2-naphthyl methyl |  thiocarbonate | | RSSR | + | + | 649.2 |

TABLE 1d-continued

[Structure: seven-membered ring with two N atoms bearing R22 and R23, a carbonyl (C=O) between them, and two benzyl substituents on adjacent ring carbons; X and Y substituents on the other two ring carbons]

| Ex. No. | R22 = R23 | X | Y | stereo 2:3:4:5 | $K_i$ | $IC_{90}$ | MS (M + H) |
|---|---|---|---|---|---|---|---|
| 7O | 2-naphthyl methyl | OMs | OH | RSSR | ++ | +++ | 685 |
| 7P | 2-naphthyl methyl | O—C(=O)—C(=O)—O (oxalate cyclic diester) | | RSSR | +++ | +++ | 661 |
| 7Q | 2-naphthyl methyl | O—CH₂—O (methylenedioxy) | | RSSR | ++ | ++ | 619 |
| 7R | 2-naphthyl methyl | O—C(CH₃)₂—O (isopropylidenedioxy) | | RSSR | + | + | 647.3 |
| 7S | 2-naphthyl methyl | O—C(CH₃O)(CH₂CH₂CH₃)—O | | RSSR | + | ++/+ | 691 |
| 7T | 2-naphthyl methyl | OH | H | RSSR | +++ | + | 591 |
| 7U | cyclopropyl methyl | OH | H | RSSR | +++ | +++ | 419 |

TABLE 1d (continued)

| Ex. No. | R22 R23 | X | Y | stereo 2:3:4:5 | HPLC $K_i$ | Mass Spec M + H |
|---|---|---|---|---|---|---|
| 7AA | cyclopropyl methyl | OMEM | O= | RS-R | + | 521 |
| 7AB | cyclopropyl methyl | hydroxy | HO—N= | RS-R | + | 448 |
| 7AC | cyclopropyl methyl | hydroxy | MeO—N= | RS-R | ++ | 462 |
| 7AD | cyclopropyl methyl | oxazole | oxazole | R-R | ++ | 442 |
| 7AE | cyclopropyl methyl | methoxy | hydroxy | RSSR | ++ | 449 |
| 7AF | cyclopropyl methyl | methoxy | methoxy | RSSR | + | 463 |
| 7AG | cyclopropyl methyl | benzyloxy | benzyloxy | RSSR | + | 615 |
| 7AH | cyclopropyl methyl | benzyloxy | hydroxy | RSSR | + | 525 |
| 7AI | cyclopropyl methyl | allyloxy | allyloxy | RSSR | | — |
| 7AJ | cyclopropyl methyl | allyloxy | hydroxy | RSSR | ++ | 475 |
| 7AK | 2-naphthyl | OCH₂OH | H | RR-R | +++ | 621 |
| 7AL | 3-hydroxymethylbenzyl | OH | H | RSSR | +++ | +++ |
| 7AM | 3-carbomethoxybenzyl | OH | H | RSSR | ++ | +++ |
| 7AN | benzyl | OH | H | RSSR | +++ | +++ |
| 7AO | benzyl | OH | N₃ | | ++ | |
| 7AP | benzyl | OH | NH₂ | | | |

TABLE 1e

| Ex. No. | R | X | Y | Ki | IC$_{90}$ | Mass Spec (M + H) | Notes |
|---|---|---|---|---|---|---|---|
| 7V | cyclopropylmethyl | F | OH | ++ | +++ | 437.26 | |
| 7W | allyl | F | OH | ++ | ++ | 409.23 | |
| 7X | 2-naphthylmethyl | F | OH | ++ | + | 609.29 | |
| 7Y | 2-naphthylmethyl | N$_3$ | OH | ++ | + | 632 | |
| 7Z | cyclopropylmethyl | OH | OH | ++ | +++ | 435.2 | |
| 8A | cyclopropylmethyl | OH | OMEM | | | 523.4 | |
| 8B | cyclopropylmethyl | F | OH | ++ | +++ | 437.3 | |
| 8C | cyclopropylmethyl | F | OMEM | + | ++ | 525.4 | |
| 8D | 2-naphthylmethyl | F | OMEM | ++ | | 697.5 | |
| 8E | 3-benzyloxy benzyl | F | OH | ++ | | 721 | |
| 8F | 3-hydroxybenzyl | F | OH | ++ (HPLC) | +++ | 541.0 | |
| 8G | 2-naphthylmethyl | H | OH | ++ (HPLC) | ++/+ | 591.5 | |
| 8H | cyclopropylmethyl | H | OH | +++ (HPLC) | +++ | 419.1 | |
| 8I | 3-hydroxybenzyl | H | OH | +++ (HPLC) | +++ | 523.2 | |
| 8J | 4-chloromethy benzyl | H | OH | ++ (HPLC) | | 587.2 | |
| 8K | 3-hydroxybenzyl/ 4-chloromethy benzyl | H | OH | ++ (HPLC) | | 569.2 | |
| 8L | 3-hydroxybenzyl/ 4-chloromethyl benzyl | H | OH | ++ (HPLC) | | 569.2 | |
| 8M | 4-hydroxymethyl benzyl | H | OH | +++ (HPLC) | | 551 | |
| 8N | cyclopropylmethyl | F | H | + (HPLC) | +++ | 421.2 | |
| 8O | 3-cyanobenzyl | H | OH | ++ | +++ | 541.3 | |
| 8P | <image of 3-ethylphenyl ketone substituent> | H | OH | +++ | +++ | 575.3 | |
| 8Q | benzyl/H | OH | OH | ++ | ++ | 417.0 | 1 |
| 8R | 2-naphthylmethyl | Br | OH | ++ | ++/+ | 671.2 | 2 |
| 8S | 3-hydroxybenzyl/ H | H | OH | +++ | +++ | 417.1 | 4 |
| 8T | N-methylamino benzyl | Br | OH | ++ | +++ | 629.2 | 2 |
| 8U | 3-cyanobenzyl | H | OH | ++ | +++ | 577.2 | 2, 3 |
| 8V | 3-hydroxymethyl benzyl | Br | OH | ++ | +++ | 631.2 | 2 |
| 8W | N-methylamino benzyl | H | OH | +++ | +++ | 549.3 | 2 |
| 8X | <image of 5-CF$_3$-3-(3-ethylphenyl)-1,2,4-oxadiazole substituent> | H | OH | ++ | ++ | 763.4 | 2 |
| 8Y | 3-carbomethoxy benzyl | H | OH | +++ | ++ | 607.3 | 2 |
| 8Z | 3-hydroxymethyl | H | OH | +++ | +++ | 551.4 | 4 |

TABLE 1e-continued

| Ex. No. | R | X | Y | Ki | IC$_{90}$ | Mass Spec (M + H) | Notes |
|---|---|---|---|---|---|---|---|
| 8AA | benzyl allyl | OH | OH | ++ | | | |
| 8AB | 3-carbomethoxy benzyl | H | H | + | +++ | 623.3 | |
| 8AC | 4-hydroxymethyl benzyl | H | H | ++ | +++ | 535.2 | |
| 8AD | benzyl | H | OH | ++ | +++ | 491.2 | |
| 8AE | 3-(H$_2$NC(O)) benzyl | H | OH | +++ | +++ | 577.2 | |
| 8AF | 3-(H$_2$NC(=NOH)) benzyl | H | OH | +++ | +++ | 607.3 (ESI) | |
| 8AG | 3-(H$_2$NC(=NOH)) benzyl | H | OH | +++ | +++ | 643.3 (ESI) | 3 |
| 8AH | 3-(H$_2$NC(O)) benzyl | H | OH | +++ | +++ | 613.2 | 3 |
| 8AI | 3(H$_2$NC(O))-4-fluorobenzyl | H | OH | +++ | +++ | 613.5 | |
| 8AJ | 3-(H$_2$NC(=NOH))-4-fluorobenzyl | H | OH | +++ | +++ | 643.2 (ESI) | |
| 8AK | 3-(H$_2$NC(O)) benzyl | H | OH | +++ | +++ | 649.2 | 5 |
| 8AL | 3-(H$_2$NC(=NOH)) benzyl | H | OH | +++ | +++ | 679 | 5 |
| 8AM | 3-(3-pyrazolyl)-benzyl | H | OH | | | 623.3 | |
| 8AN | 3-cyanobenzyl | H | OH | + | + | 541.2 | 6 |
| 8AO | 3-(H$_2$NC(=NOH)) benzyl | H | OH | ++ | + | 607.0 | 6 |
| 8AP | 3-(H$_2$NC(O)) benzyl | H | OH | + | + | 577.3 | 6 |
| 8AQ | 3-carbomethoxy benzyl | H | OH | + | + | 607.4 | 6 |
| 8AR | 3-hydroxymethyl benzyl | H | OH | ++ | + | 551.4 | 6 |

Notes
1. As in Scheme 9: CF$_3$COOH opening of aziridine followed by hydrolysis of the diester.
2. As in Scheme 10.
3. The unsubstituted benzyls in the title structure are replaced with p-fluorobenzyls.
4. As in Scheme 9A: Hydrolysis of monoacetate followed by catalytic hydrogenolysis of aziridine ring.
5. The unsubstituted benzyls in the title structure are replaced with 3,4-difluorobenzyls.
6. SSS isomer Using the above-described techniques or variations thereon appreciated by those of skill in the art of chemical synthesis, the compounds of Tables 3–13 (shown below) can also be prepared.

Prodrugs

For compounds of the present invention having reduceded water solubility it may be advantageous to prepare prodrugs to enhance the solubility and bioavailability of these compounds. For example, the addition of ionizable groups by derivatization of free hydroxy groups of compounds of formula (I) with bioreversible esters resulted in greatly improved water solubility. Solubility studies were performed by mixing an excess of solid compound in water or aqueous medium for at least 4 hours. Solubility was assessed either visually, if a weighed amount clearly dissolved in a measured volume of solvent (method A), or by HPLC assay of filtrates of saturated solutions (method B). Solubility results are summarized in Table A below.

TABLE A

| Ex. No. | Solvent | Method | Solubility (mg/ml) |
|---|---|---|---|
| 5U | water | B | 0.01 |
| 29A | water | B | 2.25 |
| 29B | water | A | >100 |
| 29C | 0.1M citric acid | A | >20 |
| 29D | water | A | >200 |

For such prodrugs of the present invention to be useful therapeutic agents (assuming that the intact esters have relatively little inherent pharmacologic activity), the ester must be hydrolyzed after dosing to yield the parent hydroxy compound. Compounds 29A–29E are hydrolyzed to parent compound 5U in biological fluids in vitro. This was shown as follows. Plasma was collected from rats, dogs, or human volunteers, and was used within 24 hours. Prodrug was added to plasma, which had been warmed to 37° C., at concentrations of 2–10 μg/ml. After various times of incubation at 37° C., the hydrolysis reaction was quenched with the addition of an organic solvent. The organic solvent was used for extraction of 5U, and concentrations of 5U in the plasma aliquots were determined using HPLC after extraction. Concentrations of 5U were thus measured vs. time of incubation of the prodrug in plasma at 37° C. Similar studies were performed using a homogenate of rat intestinal tissue (10% w/v) as the hydrolysis medium. Results for in vitro hydrolysis of prodrug 29B in dog plasma and rat intestinal homogenate (10% w/v) are given in Table B. Results for in vitro hydrolysis of prodrug 29C in rat, dog and human plasma are given in Table C. Prodrugs 29B, 29C, and 29E were shown to readily convert to parent 5U when exposed to plasma or intestinal enzymes in vitro. These results indicate that these prodrugs will convert to; 5U in vivo. Other salt forms of these compounds, such as prodrugs 29A and 29D, will be similar to their free acid or free base forms.

TABLE B

| Time (min) | % Converted to 5U (Dog plasma) | % Converted to 5U (Rat intestine homogenate) |
|---|---|---|
| 0 | 3.4 | 16.0 |
| 5 | 4.9 | 16.6 |
| 15 | 5.5 | 22.7 |
| 60 | 9.3 | 46.0 |
| 120 | 19.9 | 47.1 |

TABLE C

| Time (min) | % converted to 5U (rat plasma) | % converted to 5U (dog plasma) | % converted to 5U (human plasma) |
|---|---|---|---|
| 0 | 29.4 | 1.8 | 6.7 |
| 5 | 69.0 | 3.1 | 12.9 |
| 10 | 74.6 | 3.3 | |
| 15 | | | 12.9 |
| 20 | 77.6 | 5.0 | |
| 30 | 81.6 | 6.7 | 14.5 |
| 60 | 90.6 | 10.1 | 31.3 |
| 120 | 100 | 15.7 | 45.8 |
| 240 | 100 | 31.0 | 73.4 |
| 360 | | | 74.9 |

Improved water solubility can result in increasing the extent of oral bioavailability. Oral bioavailability studies were performed in fasted beagle dogs. Compounds were dosed orally using a solution vehicle or the solid drug powder filled into hard gelatin capsules. Periodic blood samples were taken from each dog and plasma was separated. Plasma drug concentrations were determined using extraction and HPLC analysis. Generally, after the administration of 5U or its prodrugs 29A–E, the plasma concentrations of 5U were determined, rather than unchanged prodrug concentrations. Oral bioavailability was estimated by comparing the dose-normalized area under the plasma 5U concentration vs. time curve (AUC) after oral dosing with the AUC after intravenous administration of 5U. Oral bioavailability is expressed as the percentage of the oral dose absorbed.

Compound 5U has reduced water soluble, and when administered as the solid powder gave low oral bioavailability. Therefore, in order to attain improved oral bioavailability, 5U was administered using a solution with polyethylene glycol 400 or propylene glycol as the vehicle. However, as the dose of 5U was increased, oral bioavailability was reduced, due to precipitation of 5U from the glycol vehicle upon mixing with the aqueous contents of the gastrointestinal tract. Improved oral bioavailability was attained when the water soluble prodrugs were administered in the solid form, with no added excipients or solvents. One advantage of these water soluble prodrugs is that they can be formulated in conventional solid oral dosage forms, whereas 5U gave low oral bioavailability when dosed in solid form. The advantage of the water soluble prodrugs is especially clear at high doses. Both prodrugs 29B and 29D yielded good oral bioavailability at relatively high doses, whereas the administration of a similar dose of 5U in a non-aqueous vehicle resulted in relatively poor oral bioavailability.

Prodrug 29E resulted in lower bioavailability then prodrugs 29B–D. Additional assays of the plasma samples for intact ester (total of mono and bis ester) was performed by treating plasma with NaOH to hydrolyze any intact esters. Samples were then extracted again and assayed for 5U concentration. The AUC of intact esters was approximately 2 fold greater than that of 5U. Thus, plasma levels of both intact prodrug and hydrolysis product can be attained using these water soluble prodrugs. The results of the comparison of the oral bioavailability in dogs of 5U and its water soluble prodrugs are shown in Table D.

TABLE D

| Ex. No. | Excipients | Dose (mg/kg, 5U eq.) | % Oral Bioavailability of 5U (Mean ± SE) |
|---|---|---|---|
| 5U | glycol | 10–15 | 50 ± 20 |
| 5U | glycol | 40 | 5 ± 2 |
| 29B | none | 8 | 29 ± 2 |
| 28B | none | 27 | 27 ± 6 |
| 29D | none | 31 | 40 ± 12 |
| 29E | none | 8 | 12 ± 2 |

Utility

The compounds of this invention possess retroviral protease inhibitory activity, in particular, HIV inhibitory efficacy, as evidenced by their activity in the assays, as described below. The compounds of formula (I) possess HIV protease inhibitory activity and are therefore useful as antiviral agents for the treatment of HIV infection and associated diseases. The compounds of formula (I) possess HIV protease inhibitory activity and are effective as inhibitors of HIV growth.

The protease inhibitory activity of the compounds of the present invention is demonstrated using standard assays of protease activity, for example, using the assay described below for assaying inhibitors of HIV protease activity. The ability of the compounds of the present invention to inhibit viral growth or infectivity is demonstrated in standard assay of viral growth or infectivity, for example, using the assays described below. The compounds of the present invention inhibit HIV-protease activity in vivo as demonstrated using the animal models for HIV protease inhibition described below. The compounds of the present invention demonstrate in vivo HIV inhibitory activity, as shown in the animal models described below. The HIV inhibitory activity in the animal models described below indicates that the presently claims compounds are useful for the treatment of HIV infection in humans.

As discussed above, the compounds provided by this invention are also useful as standards and reagents for use in tests or assays for determining the ability of a potential pharmaceutical to inhibit HIV protease and/or HIV growth, such as the assays described herein below. Thus, the compounds of the present invention may be provided in commercial kits or containers comprising a compound of this invention, for use pharmaceutical research.

Since the compounds of the present invention inhibit HIV growth and infectivity, they may be used as HIV antivirals for the inhibition of HIV in a biological sample which contains HIV or is suspected to contain HIV or to be exposed to HIV.

As used herein "$\mu g$" denotes microgram, "mg" denotes milligram, "g" denotes gram, "$\mu L$" denotes microliter, "mL" denotes milliliter, "L" denotes liter, "nM" denotes nanomolar, "$\mu M$" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 1 mM for the inhibition of HIV protease or HIV viral growth or infectivity.

HIV Protease Inhibition Assay—Spectroscopic Method

Materials:

Protease: Inclusion bodies of E. coli harboring plasmid containing HIV protease under the control of an inducible T7 promoter were prepared according to Cheng et. al (1990) Gene 87: 243. Inclusion bodies were solubilized in 8 M urea, 50 mM tris pH 8.0. Protease activity was recovered by dilution 20-fold into buffer containing 50 mM sodium acetate pH 5.5, 1 mM EDTA, 10% glycerol and 5% ethylene glycol. Enzyme was used at a final concentration of 1.0–10 ug/ml.

Substrate: Peptide of sequence: Ala-Thr-His-Gln-Val-Tyr-Phe($NO_2$)-Val-Arg-Lys-Ala, containing p-nitrophenylalanine (Phe($NO_2$)), was prepared by solid phase peptide synthesis as previously described by Cheng et al. (1990) Proc. Natl. Acad. Sci. USA 87: 9660. Stock solutions of 10 mM were prepared in DMSO.

Inhibitory compounds were dissolved in sufficient DMSO to make 2.5 or 25 mM stock solutions. All further dilutions were done in DMSO.

Reactions:

Compound (1–5 uL) and HIV protease were mixed in buffer containing 50 mM MES, pH 6.5, 1 M NaCl, 1 mM EDTA, 1 mM dithiothreitol, 10% glycerol. Reactions were initiated by the addition of peptide substrate to a final concentration of 240 uM, and absorbance at 300 nM monitored for 10 min. Values of Ki for inhibitor binding were determined from percent activity measurements in the presence and absence of known concentration of inhibitor, using a value of 0.07 mM for the Km of the substrate (Cheng et al. (1990) Proc. Natl. Acad. Sci. USA 87: 9660).

The HIV-1 protease inhibitory activity of representative compounds of the invention is shown in Table 1 and 2.

HIV Protease Inhibition Assay—HPLC Method

Materials:

Protease: Inclusion bodies of E. coli harboring plasmid containing plasmid T1718R with a synthetic gene coding for a single-chain tethered dimer of HIV protease were prepared as described in Cheng et al. (Proc. Natl. Acad. Sci. USA, 87, 9660–9664, 1990). Active protease was prepared as described therein by extraction with 67% acetic acid, dilution 33-fold with water, dialysis against water and then against a "refolding buffer" consisting of 20 mM MES, 1 mM dithiothreitol and 10% glycerol. Protease was stored as a stock preparation at 10 uM in refolding buffer.

Substrate: Peptide of sequence: aminobenzoyl-Ala-Thr-His-Gln-Val-Tyr-Phe($NO_2$)-Val-Arg-Lys-Ala containing p-nitrophenylalanine, was prepared by solid phase synthesis as previously described Cheng et al., op. cit. Stock solutions of 2 mM substrate were prepared in DMSO.

Inhibitory compounds were dissolved in sufficient DMSO to make 3 mM stock solutions. All further dilutions were prepared in "assay buffer": 1 M NaCl, 50 mM MES, pH 5.5, 1 mM EDTA, 1 mM DTT, 20% glycerol.

Reactions:

Enzyme reaction: In a 2 ml screw-cap centrifuge tube were added 50 ul protease (final concentration 0.25 nM) and 0.1 ml inhibitory compound (final concentration 0.1–12, 500). After 15 min preincubation at room temperature, the reaction was started with the addition of 0.05 ml substrate (final concentration 5 uM). Incubation was carried out at 30 C. for 1 hr. The reaction was stopped with 1 ml 0.1 M ammonium hydroxide.

HPLC measurement of product formation: The product (aminobenzoyl-Ala-Thr-His-Gln-Val-Tyr) was separated from substrate on a Pharmacia MonoQ anion exchange column. The injection volume was 0.2 ml. The mobile phases were: A (20 mM trisHCl, pH 9.0, 0.02% sodium Azide, 10% acetonitrile), B (20 mM tris HCl, pH 9.0, 0.02% sodium azide, 0.5 M ammonium formate, 10% acetonitrile). The mobile phases were pumped at 1 ml/min, with a gradient from 0 to 30% B in 5 min, 100% B for 4 min to wash the column, and a re-equilibration for 4 min. The retention time of the product was 3.6 min. Detection with a Shimadzu model RF535 fluorescence monitor was at 330 nm (excitation) and 430 (emission). The Ki was calculated from the formula $Ki=I/(((Km+S-FA*S)/(FA*Km))-1)$ where I=inhibitory concentration, S=substrate concentration, FA=fractional activity=cm peak height with inhibitor/cm peak height without inhibitor, and Km=Michaelis constant=20 uM.

HIV RNA Assay

DNA Plasmids and In Vitro RNA Transcripts:

Plasmid pDAB 72 containing both gag and pol sequences of BH10 (bp 113–1816) cloned into PTZ 19R was prepared according to Erickson-Viitanen et al. AIDS Research and Human Retroviruses 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the $A_{260}$.

Probes:

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, Tet. Lett. 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5° CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 µM stocks in 2×SSC (0.3 M NaCl, 0.03 M sodium citrate), 0.05 M Tris pH 8.8, 1 mg/mL BSA. The biotinylated capture probes were prepared as 100 µM stocks in water.

Streptavidin Coated Plates:

Nunc-immunomodule microtiter plate strips were coated by addition of 200 µL of streptavidin (30 µg/mL, Scripps, La Jolla, Calif.) in freshly prepared 10 mM sodium carbonate (pH 9.6). Plates were incubated overnight at 4° C. Streptavidin solution was aspirated from the wells and a blocking buffer composed of phosphate buffered saline (PBS), 20 mg/mL bovine serum albumin (crystalline, nuclease and protease free, Calbiochem) and 100 mg/mL lactose (Sigma) was added to the plates for 3 hrs at room temperature. Blocking buffer was removed from the wells, which were allowed to dry overnight at room temperature and subsequently stored at 4° C. in zip lock bags with desiccant. For the majority of the compound evaluation experiments, streptavidin coated plates were obtained from Du Pont Biotechnology Systems (Boston, Mass.).

Cells and Virus Stocks:

MT-2, CEM, and H9 cells were maintained in RPMI 1640 supplemented with 5% fetal calf serum (FCS), 2 mM L-glutamine and 50 µg/mL gentamycin, all from Gibco. Laboratory strains of HIV-1 (RF, MN and IIIB) were propagated in H9 cells in the same medium. Virus stocks were prepared approximately 1 month after acute infection of H9 cells by clarification of the tissue culture medium and storage of aliquots at −70° C. Infectious titers of HIV-1(RF) stocks were $1-3\times10^7$ PFU (plaque forming units)/mL as measured by plaque assay on MT-2 cells (see below). Each aliquot of virus stock used for infection was thawed only once. In some cases, infected H9 cells were shifted to Dulbecco's modified Eagle's medium 3–10 days before collection of virus in order to generate virus stocks in medium with low biotin content. Clinical isolates of HIV that had been passaged once in MT-2 cells were used to infect fresh MT-2 cells in RPMI medium. Three days after infection, cells were pelleted, resuspended and culture continued in Dulbecco's modified Eagle's medium as above. Virus stocks of clinical isolates were prepared 10–15 days after infection when cytopathic effects were apparent in the culture.

For evaluation of antiviral efficacy, cells to be infected were subcultured one day prior to infection. On the day of infection, cells were resuspended at $5\times10^5$ cells/mL in RPMI 1640, 5% FCS for bulk infections or at $2\times10^6$/mL in either Dulbecco's modified Eagles medium, or RPMI 1640 medium minus biotin (Gibco, custom formulation) with 5% FCS for infection in microtiter plates. Virus was added and culture continued for 3 days at 37° C. In some experiments, virus was removed after an initial adsorption period.

Preparation of HIV-1 Infected Cell Lysates:

HIV-1 infected cells were pelleted by centrifugation. After removal of the supernatant the cells were resuspended at a concentration of $1\times10^7$ cells/mL in 5 M guanidinium isothiocyanate solution (GED: 5 M guanidinium isothiocyanate (Sigma), 0.1 M EDTA, 10% dextran sulfate). Alternately, cells grown in biotin free tissue culture medium were mixed with 5 M GED to a final concentration of 3 M guanidinium isothiocyanate, 0.06 M EDTA and 6% dextran sulfate.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed microfuge tubes or in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 µl of a hybridization cocktail containing 4×SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer d (2.5 M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of $5\times10^5$ per mL ($1\times10^5$ per well). Cells were incubated with compounds for 30 minutes at 37° C. in a $CO_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 µL of medium/well was removed from the HIV infected plates. Thirty seven µL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~3×10$^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 μg/mL. Finally, the plateau level of viral RNA produced by an effective protease inhibitor should be less than 10% of the level achieved in an uninhibited infection.

For antiviral potency tests, all manipulations in microtiter plates, following the initial addition of 2X concentrated compound solution to a single row of wells, were performed using a Perkin Elmer/Cetus ProPette. The HIV inhibitory activity of representative compounds of the present invention in the RNA assay described above is shown in TABLE 3. The $IC_{90}$ values in TABLE 3 were determined using the assay conditions described above under HIV RNA Assay. The $IC_{90}$ values are indicated as follows: +++=<10 ug/mL; ++=10 to 100 ug/mL; +=>100 ug/mL. The ++/+ is used in the cases where an $IC_{90}$ was determined to be >50 ug/mL.

HIV Yield Reduction Cell Assay

Materials: MT-2, a human T-cell line, was cultured in RPMI medium supplemented with 5% (v/v) heat inactivated fetal calf serum (FCS), L-glutamine and gentamycin. Human immunodeficiency virus strains, HIV (3B) and HIV (RF) were propagated in H-9 cells in RPMI with 5% FCS. Poly-L-lysine (Sigma) coated cell culture plates were prepared according to the method of Harada et al. (1985) Science 229: 563–566. MTT, 3-(4,5-dimethyl-thiazol-2yl)-2,5-diphenyltetrazolium bromide, was obtained from Sigma.

Method: Test compounds were dissolved in dimethylsulfoxide to 5 mg/mL and serially diluted into RPMI medium to ten times the desired final concentration. MT-2 cells (5×10$^5$/mL) in 2.3 mL were mixed with 0.3 ml of the appropriate test compound solution and allowed to sit for 30 minutes at room temperature. HIV (3B) or HIV (RF) (~5× 10$^5$ plaque forming units/mL) in 0.375 ml was added to the cell and compound mixtures and incubated for one hour at 36° C. The mixtures were centrifuged at 1000 rpm for 10 minutes and the supernatants containing unattached virus were discarded. The cell pellets were suspended in fresh RPMI containing the appropriate concentrations of test compound and placed in a 36° C., 4% $CO_2$ incubator. Virus was allowed to replicate for 3 days. Cultures were centrifuged for 10 minutes at 1000 rpm and the supernatants containing cell free progeny virus were removed for plaque assay.

The virus titers of the progeny virus produced in the presence or absence of test compounds were determined by plaque assay. Progeny virus suspensions were serially diluted in RPMI and 1.0 mL of each dilution was added to 9 ml of MT-2 cells in RPMI. Cells and virus were incubated for 3 hours at 36° C. to allow for efficient attachment of the virus to cells. Each virus and cell mixture was aliquoted equally to two wells of a six well poly-L-lysine coated culture plate and incubated overnight at 36° C., 4% $CO_2$. Liquid and unattached cells were removed prior to the addition of 1.5 mL of RPMI with 0.75% (w/v) Seaplaque agarose (FMC Corp.) and 5% FCS. Plates were incubated for 3 days and a second RPMI/agarose overlay was added. After an additional 3 days at 36° C., 4% $CO_2$, a final overlay of phosphate-buffered saline with 0.75% Seaplaque agarose and 1 mg MTT/mL was added. The plates were incubated overnight at 36° C. Clear plaques on a purple background were counted and the number of plaque forming units of virus was calculated for each sample. The antiviral activity of test compounds was determined by the percent reduction in the virus titer with respect to virus grown in the absence of any inhibitors.

HIV Low Multiplicity Assay

Materials: MT-2, a human T-cell line, was cultured in RPMI medium supplemented with 5% (v/v) heat inactivated fetal calf serum (FCS), L-glutamine and gentamycin (GIBCO). Human immunodeficiency virus strains HIV (3B) and HIV (RF) were propagated in H-9 cells in RPMI with 5% FCS. XTT, benzene-sulfonic acid, 3,3'-[1-[(phenylamino)carbonyl]-3,4-tetrazolium]bis(4-methoxy-6-nitro)-, sodium salt, was obtained from Starks Associates, Inc.

Method: Test compounds were dissolved in dimethylsulfoxide to 5 mg/ml and serially diluted into RPMI medium to ten times the desired final concentration. MT-2 cells (5×10$^4$/0.1 mL) were added to each well of a 96 well culture plate and 0.02 mL of the appropriate test compound solution was added to the cells such that each compound concentration was present in two wells. The cells and compounds were allowed to sit for 30 minutes at room temperature. HIV(3B) or HIV(RF) (~5×10$^5$ plaque forming units/mL) was diluted in medium and added to the cell and compound mixtures to give a multiplicity of infection of 0.01 plaque forming unit/cell. The mixtures were incubated for 7 days at 36° C., during which time the virus replicated and caused the death of unprotected cells. The percentage of cells protected from virus induced cell death was determined by the degree of metabolism of the tetrazolium dye, XTT. In living cells, XTT was metabolized to a colored formazan product which was quantitated spectrophotometrically at 450 nm. The amount of colored formazan was proportional to the number of cells protected from virus by the test compound. The concentration of compound protecting either 50% ($IC_{50}$) or 90% ($IC_{90}$) with respect to an uninfected cell culture was determined.

The HIV inhibitory activity of representative compounds of the present invention in the whole cell infectivity assay described above is shown in Table E.

TABLE E

| Example Number | $IC_{90}$ |
| --- | --- |
| 1C | +++ |
| 1X | +++ |
| 1Z | +++ |
| 1AC | +++ |
| 1AF | +++ |

TABLE E-continued

| Example Number | IC$_{90}$ |
|---|---|
| 1AH | +++ |
| 1AQ | +++ |

The IC$_{90}$ values in Table 2 are indicated as: +++=<10 ug/mL.

In the Tables herein the Ki values were determined using the assay conditions described above under HIV Protease Inhibtion Assay. The Ki values are indicated as follows: +++=<10 nM; ++=10 nM to 1 $\mu$M; +=>1 $\mu$M.

In the Tables herein the IC$_{90}$ values were determined using the assay conditions described above under HIV RNA Assay. The IC$_{90}$ values are indicated as follows: +++=<10 $\mu$g/mL; ++=10 to 100 $\mu$g/mL; +=>100 $\mu$g/mL. The ++/+ is used in the cases where an IC$_{90}$ was determined to be >50 $\mu$g/mL.

HIV-1/CEM Mouse Xenotransplant Animal Model

The HIV inhibitory activity of the presently claimed compounds in an animal was demonstrated in an animal model wherein HIV-1 infected human CEM lymphcyte cells were xenotransplanted in nude mice and the growth of HIV in vivo in such xenotransplanted CEM cells was monitored. The in vivo assay using this model consisted of testing compound in a prophylactic manner, whereby the daily dose of agent was administered to a group of mice one day prior to HIV challenge. The test and control animals were followed with drug for a period of 25 days. Upon the experiment termination and animal sacrifice, serum p24 antigen levels, and relative percent indirect immunofluorescence assay (IFA) positive cell numbers were determined as the experimental endpoint (as described below).

Cell Line and HIV Culture: CCRF-CEM or CEM, a well characterized tumorigenic and HIV permissive cell line, was obtained from the American Type Culture Collection, Rockville, Md. (AYCC CCL 119) and maintained in RPMI 1640 medium with 15% heat inactivated fetal calf serum and 50 $\mu$g/ml gentamicin as described by Wetherall (In: Schellekens and Horzinek, eds., *Animal Models in AIDS*, Elsevier, Amsterdam, 1990, pp 291–302). The cells were propagated at 37° C. in a humid 5% CO$_2$ atmosphere. Stocks of the HIV-1 isolate HTLV-III$_B$ were acquired from Dr. Neal T. Wetherall, Vanderbilt University, and were harvested from cultures of chronically-infected CCRF-CEM (CEM) cells obtained from the American Type Culture Collection. For routine propagation, virus containing culture fluids were clarified of cells by low speed centrifugation and passed through 0.45 $\mu$m filters. Infectious virions were quantitated on MT-2 cells in microculture using cytopathic effect (CPE) as the end point for infection.(Scudiero et al., Cancer Res. 1988, 48, 4827–4833). The 50% tissue culture infectious dose (TCID$_{50}$) was calculated by the method of Reed and Muench (Amer J. Hygiene, 1938, 27, 493–497). CCRF-CEM cells used for virus xenotransplantation were acutely infected with a stock dilution of HIV-1 at a MOI (input multiplicity of infection) of 0.01 followed by adsorption for 1 h at 37° C.

Animals and Cell/HIV Transplantation: Sprague Dawley 21+2 day old female nude (nu/nu) mice were exposed to 450 Rad's of $^{137}$Cs irradiation. Twenty-four hours later, the drug dosing was started. CEM cell cultures, both HIV infected or uninfected, were harvested and washed with serum free media and reharvested. Cells of a specified number were suspended in 0.2 ml media and injected subcutaneously (s.c.) into the intrascapular region of the mice, 24 h after drug dosing commenced. The mice were observed the following day and at least three times a week for the duration of the experiment. At each of these time points the animal group weight is determined, and the inoculation site is gently palpated to determine the date of gross tumor onset. At the termination of an experiment, the animals were anesthesized and euthanized by exsanguination.

p24 Enzyme Immunoassay: The p24 enzyme immunoassay (EIA) used was the unmodified procedure commercially available from Coulter Corporation (Hialeah, Fla.), which uses a murine monoclonal antibody to the HIV core protein coated onto microwell strips. The assay detects p24 gag antigen in culture supernatants, plasma, and serum. Non-specific cross reactions with mouse serum are not seen with this assay.

Indirect Immunofluorescence Assay (IFA): HIV-1 antigen-expressing cells are detected by IFA using the method described by Montefiori and Mitchell (Virology 1986, 155, 726–731). Slides were prepared by air drying and fixing in a 50:50 mixture of acetone/methanol for 30 minutes, followed by adding a 1:200 dilution in PBS-BSA (phosphate buffered saline containing 0.1% globin-free bovine serum albumin) of high-titer serum from pooled HIV-1 positive individuals (positive by Western immunoblot for all HIV-1 antigens).

Anti-HIV IgG then will be detected using a 1:200 dilution of fluorescein-conjugated, IgG fraction of goat anti-human IgG (heavy and light chains specific, Cappel) containing Evan's blue counter stain. Slides were mounted using 50% glycerol and cells examined for fluorescence using a Zeiss KF-2 Epi-fluorescence microscope.

Preparation and Administration of Compounds: Compounds were mixed with 0.25% (wt/v) methylcellulose solution, warmed to 37° C., and homogenized. One drop of Tween 80 was added to the stock suspension (1 drop/10–20 ml) and mixed by vortexing. Dilutions of the stock suspension were made in methylcellulose/Tween 80 and stored at 4,C for no more than one week. The suspensions were gently warmed and vortexed after removal from the refrigerator and prior to injection to ensure proper suspension. The compounds were administered BID, i.p. at doses of 30, 100, and 300 mg/kg or 60, 200, and 600 mg/kg/day.

The HIV inhibitory activity in vivo in the HIV/CEM mouse xenotransplant animal model for a representative compound of the invention is shown in Table F below. Data in the p24 EIA and IFA is expressed as a percent of the control untreated levels.

TABLE F

| Compound | Dose | p24 EIA | IFA |
|---|---|---|---|
| Ex. 5I | 300 mg/kg bid ip | 37.8 | 51.5 |
| Ex. 5I | 100 mg/kg bid ip | 76.4 | 111.3 |
| Ex. 5I | 30 mg/kg bid ip | 61.5 | 116.7 |

HIV-1 Protease Transgenic Mouse Model

The in vivo HIV protease inhibitory activity of the presently claimed compounds was also demonstrated using a transgenic animal model system wherein the HIV-1 protease protein was expressed in the mouse lens using a transgene where the HIV-1 protease coding sequence was placed under the transcriptional control of the mouse alpha A-crystallin promoter. Such transgenic animals were found to display a HIV protease-mediated cataract phenotype. The HIV protease inhibitory activity of the presently claimed compounds was measured in this animal system as a delay or prevention of the onset of cataract appearance in the test animals.

Plasmid Construction: The mammalian expression vector pMSG (Pharmacia) was modified by replacing the MMTV LTR promoter with the 412-bp Bgl II-BamHI mouse alpha A-crystallin promoter fragment (Chepelinsky et al. Proc. Natl. Acad. Sci. USA, 1985, 82, 2334–2338). The SV40 early splice and polyadenylation signals were retained and this plasmid was renamed pCSV 19. A single chain, tethered dimeric form of the active HIV-1 protease gene (BAA; Cheng et al., Proc. Natl. Acad. Sci. USA, 1990, 87, 9660–9664 and Cheng et al., Gene, 1990, 87, 243–248) was modified for mammalian cell expression by replacing nucleotides 7 to 90 with CGTAATAGAAGGAGATATAAC-CATGGAG. The gene was cut with EcoRI and Hind III and after blunt-end repair cloned into the Sma I site of the PCSV 19, thus producing pCSV 19-BAA. The mutant form of the construct (BA*A*) was produced by site directed mutagenesis (GAT to GGT) resulting in the change of aspartic acid (25th residue) to glycine in both monomers resulting in an inactive form of the protease.

Construction of Transgenic Mice: 2.5 kb Hind III fragments from the pCSV 19-BAA and PCSV 19-BA*A* plasmids were isolated (modified from Sambrook at al., *Molecular Cloning, A Laboratory Manual*, 2nd Ed., 1989, Cold Spring Harbor Laboratory) and used for the construction of transgenic mice using the pronuclei injection method (Hogan et al., *Manipulating the Mouse Embryo. A Laboratory Manual*, 1986, Cold Spring Harbor Laboratory). Mice were screened for the HIV-1 protease transgene by either Southern blot or Polymerase Chain Reaction (PCR) methods. Mice of the FVB/N strain (Taketo et al., Proc. Natl. Acad. Sci. USA, 1991, 88, 2065–2069) were used for the construction and breeding of these transgenic mice, and were originally obtained from Dr. Carl Hansen (NIH) and bred in our facility. Subsequently, the mice were purchased from Charles River Laboratory (Portage, Mich.).

Identification of Transgenic Mice: Southern blot analysis (Sambrook et al. vide supra) was performed on DNA purified from tail biopsies (Hogan et al. vide supra) using the 2.5 kb Hind III fragment from pCSV 19-BAA as the probe ($^{32}$p labeled). DNA for PCR was prepared from tail biopsies by overnight digestion with 0.5 mg of Proteinase K (Boehringer-Manheim GmbH) in 100 $\mu$l of water and 0.025% SDS. PCR primers specific for the mouse c-fos gene and and the transgene's SV40 segment were used as an internal control in some samples. Each PCR reaction contained 1–2 $\mu$l of tail digest, 60 $\mu$g of each primer, 200 $\mu$M of Perkin Elmer Cetus DATP, dCTP, dGTP, TTP (buffered at pH 8.8) and up to 5 units of Perkin Elmer Cetus Ampli/Taq polymerase. The reactions were run on a Perkin Elmer DNA Thermal Cycler as follows: 1 min at 94° C., 3 min at 67° C. (2 sec extension/cycle) for 35 cycles. The PCR products were analyzed by gel electrophoresis (1% agarose,0.5 $\mu$g/ml of ethidium bromide), and tail samples with a 625 PCR fragment (SV40 specific) were considered positive for the transgene. Mice bearing the active HIV-1 protease transgene were also identified by their cataract phenotype. Progeny of homozygous parent(s) were 100% positive for the transgene and did not require Southern/PCR analysis.

Dosing Regimen: Compounds to be tested were pulverized by manual grinding with mortar and pestle. Just prior to dosing of mice, the compound was suspended in 0.25% methylcellulose/Tween 80 solution, homogenized in a manual Dounce homogenizer and sonicated for 10 min in a sonicating water bath. The volume of suspension was adjusted so that the amount of compound required for dosing one mouse was 0.1–0.2 mL. In order to maintain the required mg/kg dose, an average mouse weight for each group was determined twice a week and the amount of compound adjusted accordingly. Intraperitoneal (ip) and oral (po) dosing was performed using 25 G ⅝ in. injection and 20 G 1½ in. feeding needles, respectively. The dosing was performed twice a day (bid) and the doses were administered 6–8 h apart. Eyes of control and dosed animals were examined daily by up to 3 individuals, and the day when cataracts became visible to the naked eye was recorded as the experimental end point (days after birth). Because cataracts do not always develop in both eyes of individual mice on the same day, each eye was scored as an independent observation. Results from individual eyes were used to calculate the average (mean) day of cataract development and its standard deviation for each group.

Eye Histology: Eyes were dissected from euthanized mice and fixed with 10% neutral buffered formalin. Eye histology was performed at the Experimental Pathology Laboratories (EPL), Inc., Sterling, Va.

Characterization of HIV-1 Protease Transgenic Mice:

Gross appearance: Three lines of mice with the active (BAA) and three lines with the mutant (BA*A*) form of HIV-1 protease gene were established. The eyes of mice with the mutant gene appear identical to those of normal mice (FIG. 1A), but bilateral cataracts develop in the eyes of mice with the active gene. This phenotype is easily detected even by an untrained observer because the inside of cataract eye is opaque and white/gray in color (FIG. 1B). Cataracts appear similar in all transgenic lines.

Time of cataract development: The time when cataract develops varies among the three transgenic lines bearing the active HIV-1 protease gene (BAA, Appendix 2). Mice of the Tg 61 line develop the phenotype prenatally (day 18 in utero). Mice of the remaining two lines (Tg 62, and 72) develop the cataracts postnatally (at 24–30 days). Among the mice of each individual line, the time difference in cataract development is less than one week. None of the mice bearing the mutant form of the gene (BA*A*) have developed cataract. Based on this genetic evidence that cataracts develop only in transgenic mice with the active but not inactive form of HIV-1 protease we conclude this phenotype is caused by the protease's enzymatic activity.

Method:

A single homozygous male mouse (Tg 72-110) was mated with three non-transgenic FVB/N females. From each litter, 4–5 mice were used as controls, i.e., were dosed with vehicle only (ip or po route). The remaining mice of each litter (5–7) were dosed (ip or po) with test compound. When mice were 15 days old, dosing began in two groups of 5 mice each with ip injections of 100 mg/kg/BID. The compound was administered ip to the mice in the first group until all had bilateral cataracts. For the second group, the compound was administered ip for 5 days only and from day 20 via the po route until cataracts appeared. A third group (7 mice) was dosed ip starting on day 15 but with 400 mg/kg/bid. On day 41, when no cataracts had yet developed in this last group, three were removed from treatment, and the remaining four were dosed until day 52. All mice were observed daily for cataract formation.

The results for representative compounds of the present invention in the above HIV-1 transgenic mouse model are shown in Table G below. The results show that the representative compounds of the present invention effectively inhibit HIV protease activity in vivo.

TABLE G

| Ex. No. | Dose/Route | Mouse | Cataract Density (% of control) | Delay in Cataract (relative to control) |
|---|---|---|---|---|
| 1AQ | 60 mg/kg ip preg days 11–18 | Tg 61 | 46.6 | |
| 1AQ | 85 mg/kg ip preg days 11–18; 17–18 | Tg 61 | 20.6 | |
| 1X | 15 mg/kg ip preg days 11–18 | Tg 61 | 28.8 | |
| 1X | 5 mg/kg ip preg days 11–18 | Tg 61 | 39.8 | |
| 5I | 80 mg/kg bid ip days 15–19/ po days 20 & ff | Tg 72 | | 6 days |
| 5I | 50 mg/kg bid ip days 15–20/ po days 21 & ff | Tg 72 | | 3.6 days |
| 5U | 100 mg/kg bid ip | Tg 72 | | 5 days |
| 5U | 400 mg/kg bid ip days 15–42 | Tg 72 | | |

Dosage and Formulation

The antiviral compounds of this invention can be administered as treatment for retroviral infections by any means that produces contact of the active agent with the agent's site of action, the retroviral protease, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The compounds of the present invention can be administered in oral dosage forms as tablets, capsules (each of which includes sustained release or timed release formulations), pills, powders, granules, elixirs, tinctures, suspensions, syrups, and emulsions. The compounds of the present invention may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed for the inhibition of HIV and the treatment of HIV infection.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses may range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention may also be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Dosage forms (compositions suitable for administration contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension:

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of formula (I) of the present invention may be administered in combination with a second therapeutic agent, such as a second HIV inhibitory agent or other therapeutic agent for treatment of HIV associated disease conditions. The compound of formula (I) and such second therapeutic agent can be administered separately or as a physical combination in a single dosage unit, in any dosage form and by various routes of administration, as described above. The compound of formula (I) may be formulated together with the second therapeutic agent in a single dosage unit (that is, combined together in one capsule, tablet, powder, or liquid, etc.). When the compound of formula (I) and the second therapeutic agent are not formulated together in a single dosage unit, the compound of formula (I) and the second therapeutic agent may be administered essentially at the same time, or in any order; for example the compound of formula (I) may be administered first, followed by administration of the second agent. When not administered at the same time, preferably the administration of the compound of formula (I) and the second therapeutic agent occurs less than about one hour apart, more preferably less than about 5 to 30 minutes apart.

The present invention also includes pharmaceutical kits useful, for example, for the treatment of HIV infection, which comprise one or more containers containing a pharmaceutical composition comprising a therapeutically effective amount of a compound of formula I. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

The Tables below provide representative compounds of formula (I) of the present invention. Specifically incorporated herein by reference is the disclosure of PCT International Application Publication Number WO 93/07128, including Examples Number 1-5763, which are listed in Tables 3–12 of such reference.

Tables 2A through 2C and 2d through 2q below set forth representative compounds of the present invention.

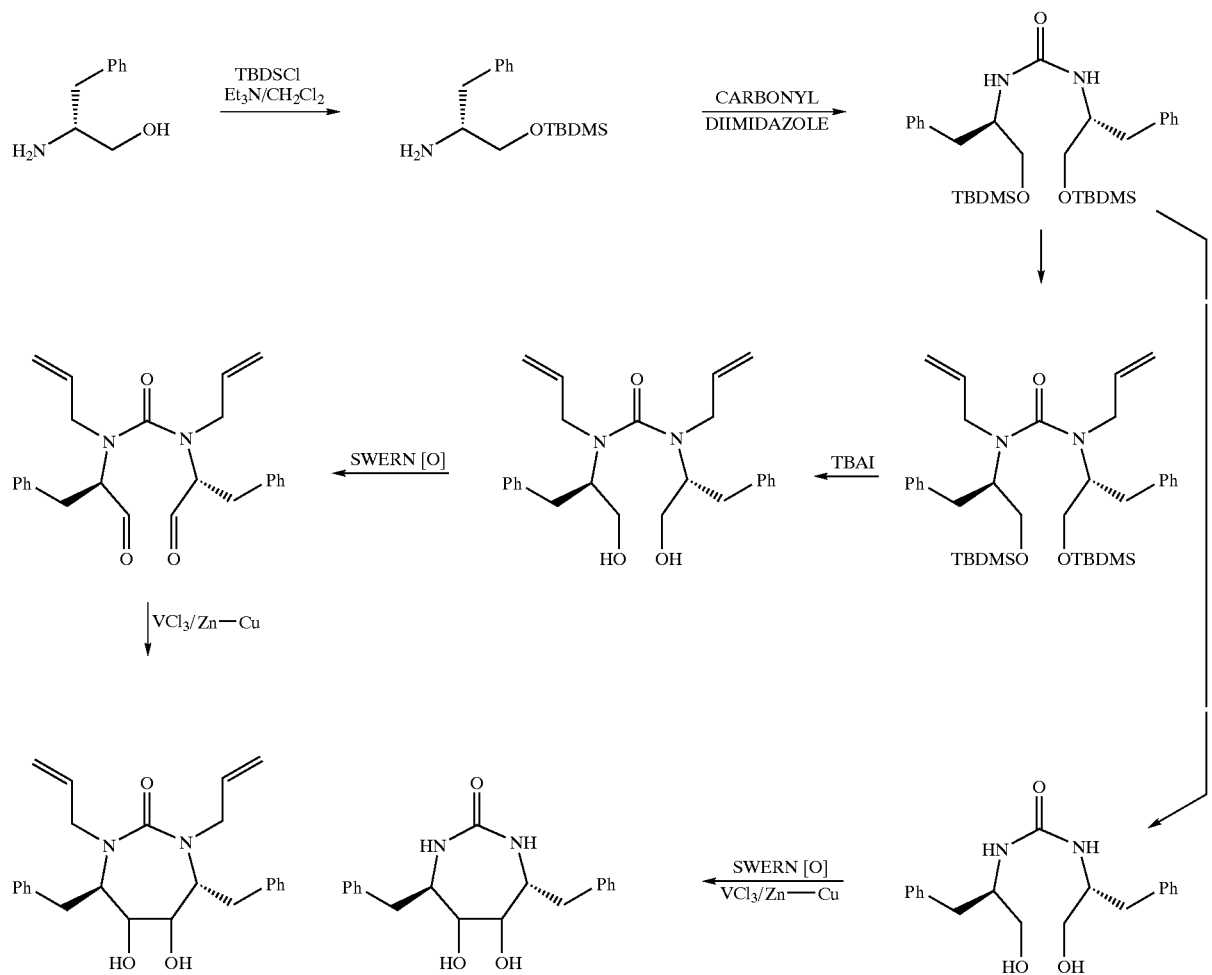
SCHEME 1
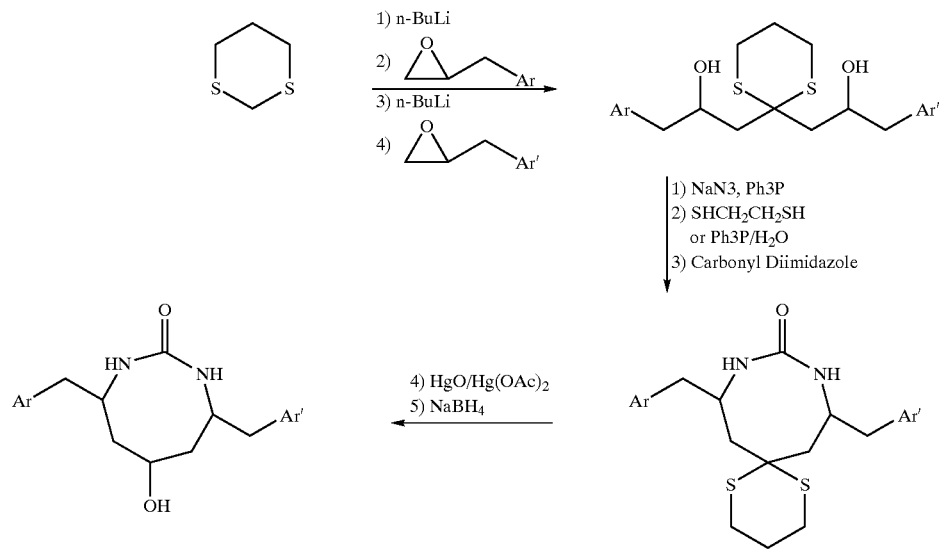
Scheme 2

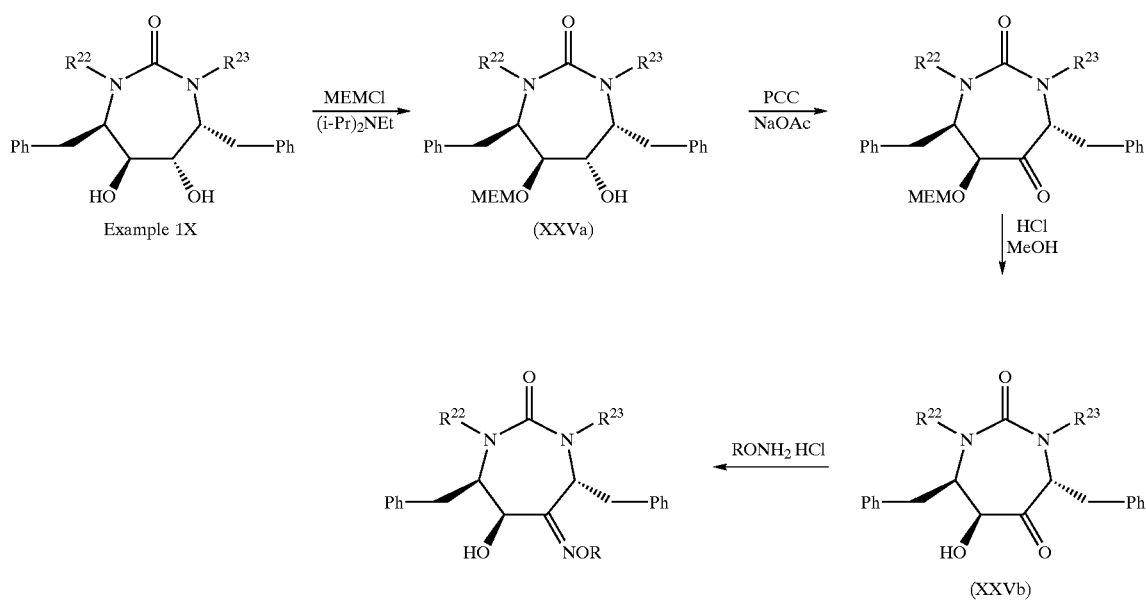
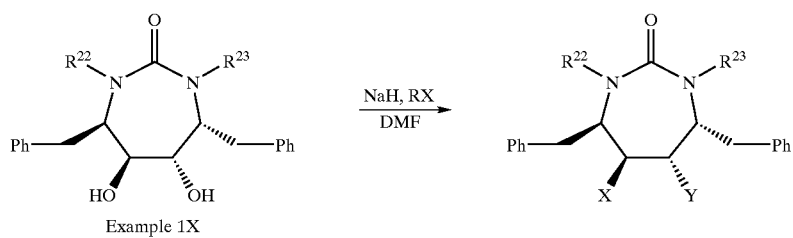
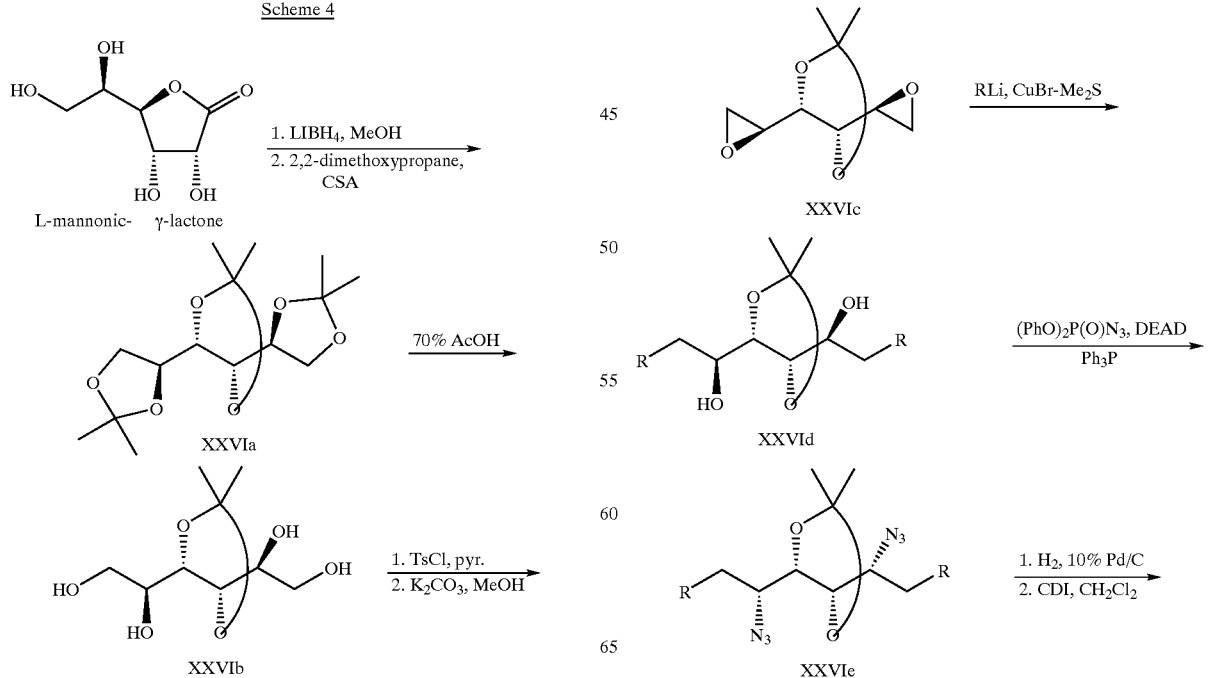

-continued
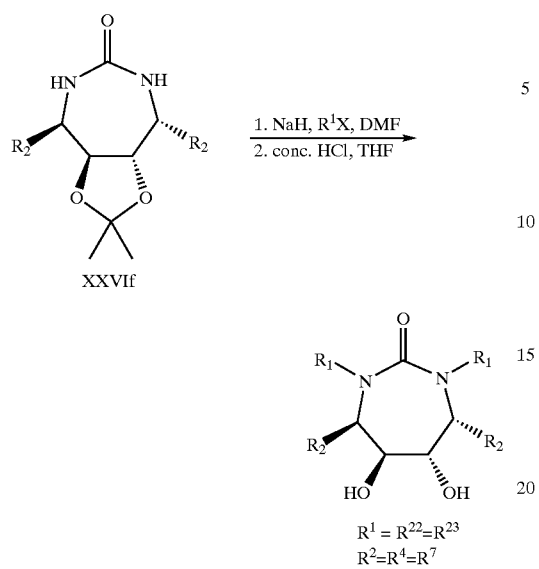
$R^1 = R^{22}=R^{23}$
$R^2=R^4=R^7$
Scheme 5
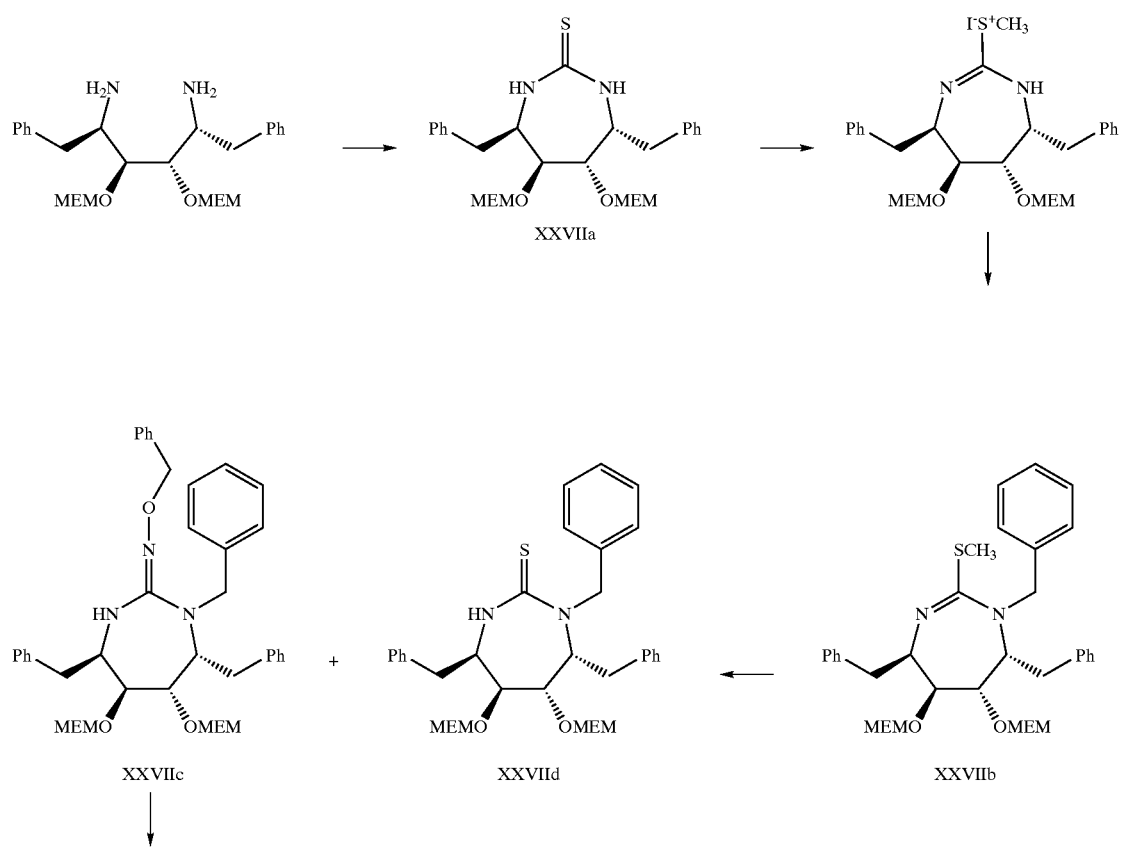

-continued
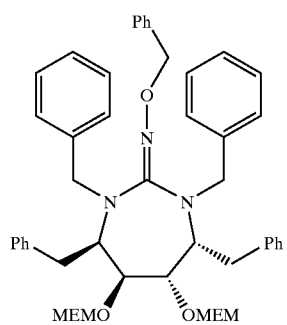
XXVIIe
Scheme 6
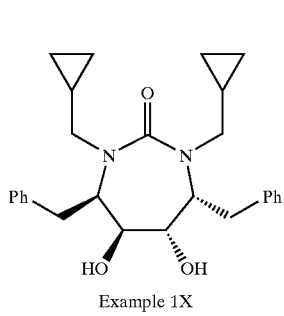 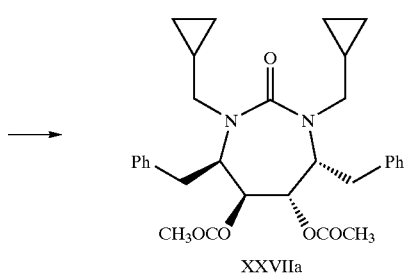
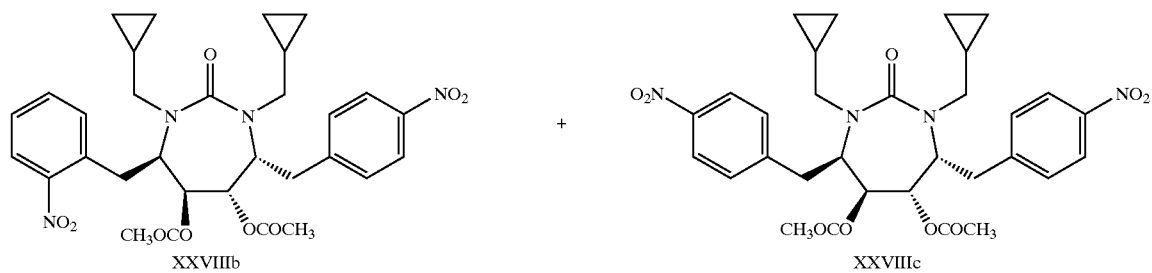
Scheme 7
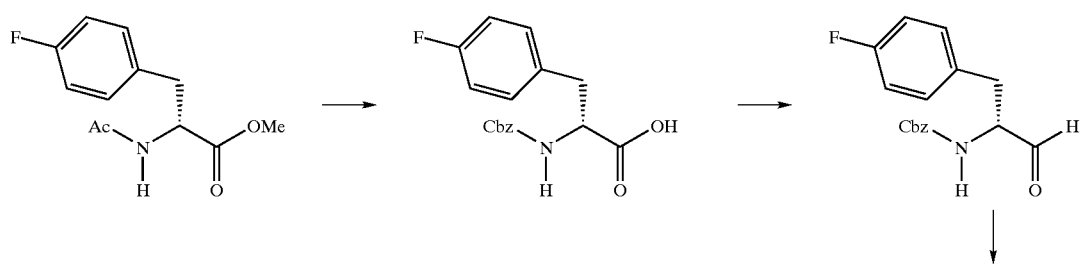

127 128
-continued
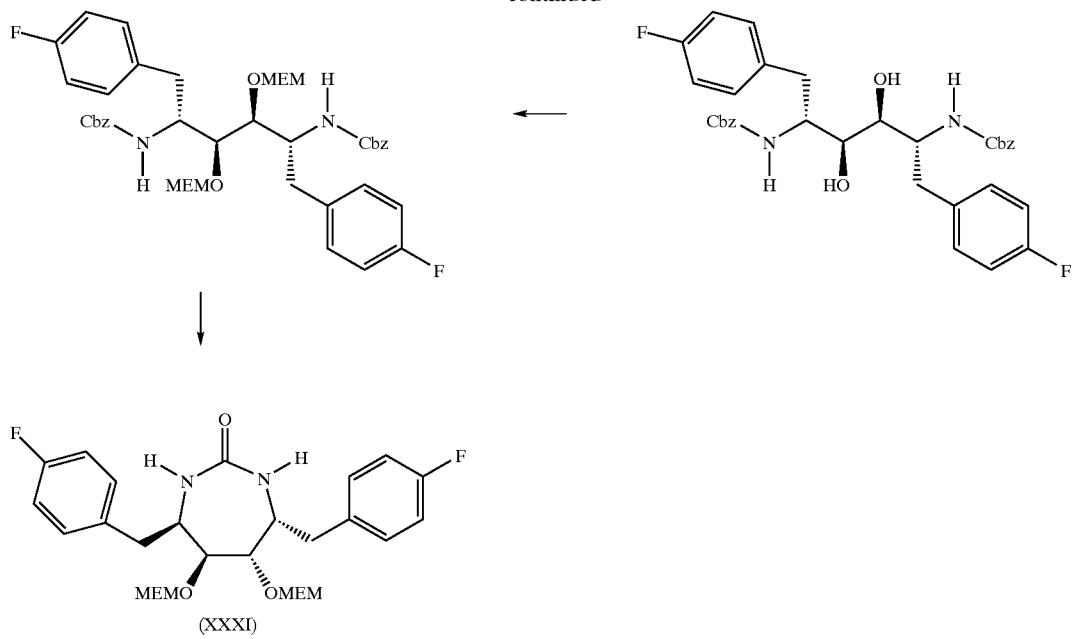
(XXXI)
Scheme 8
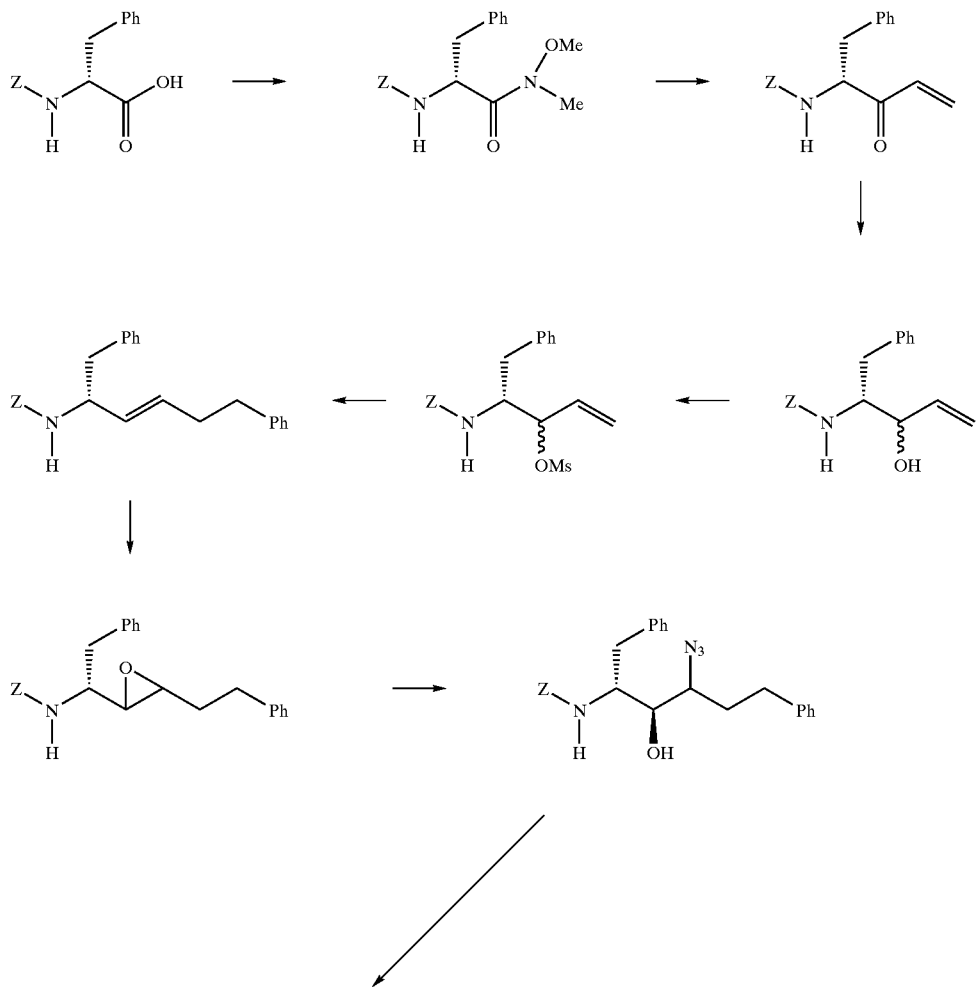

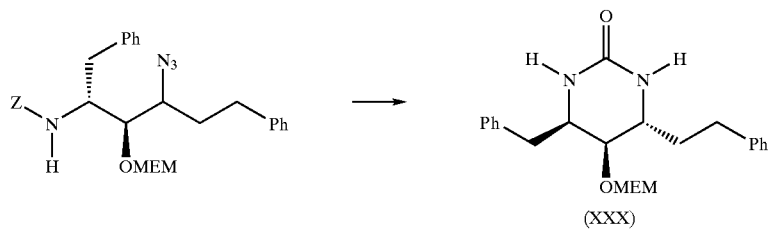
(XXX)
Scheme 9
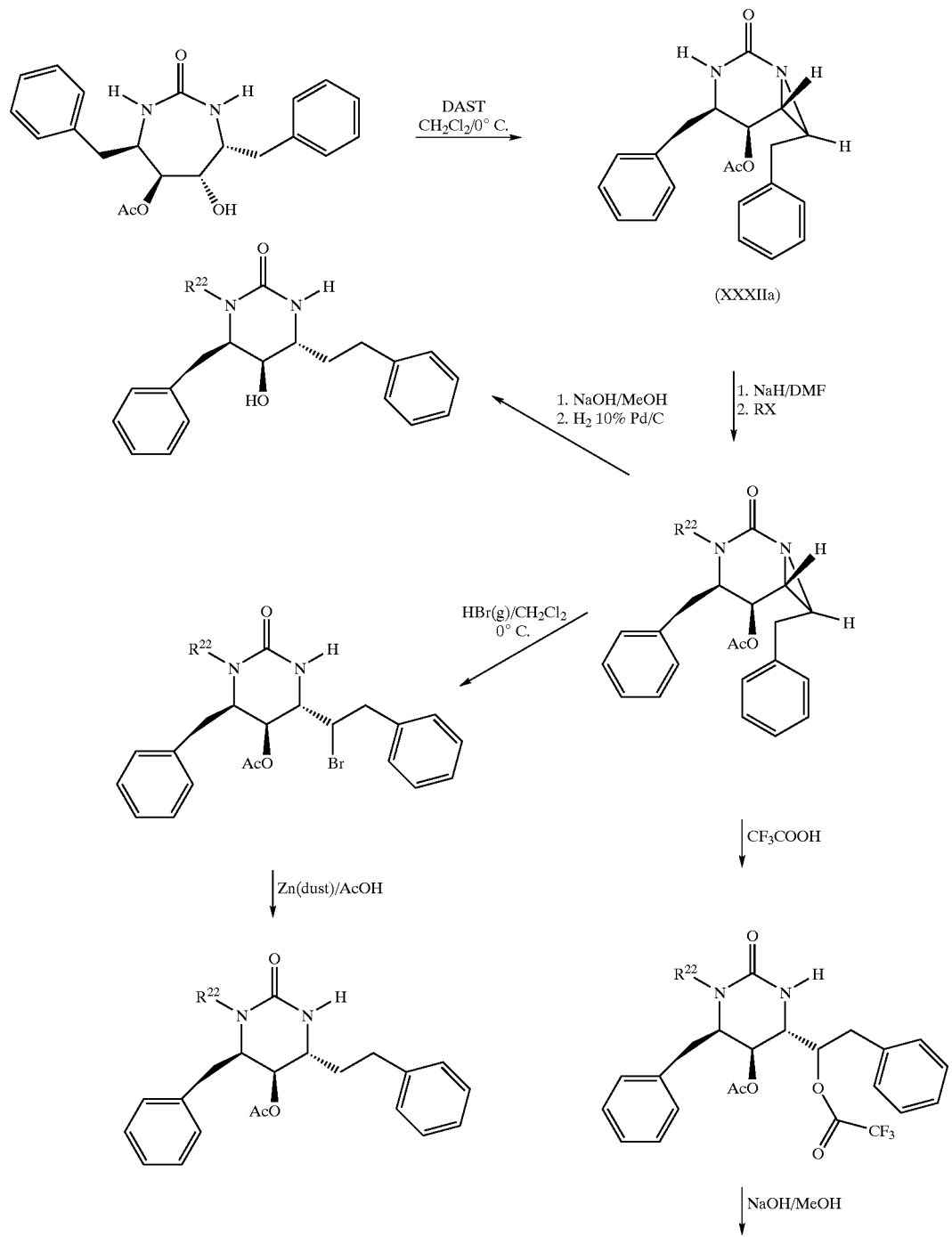

-continued
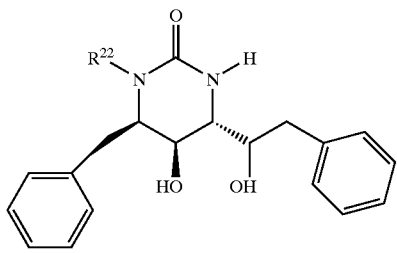
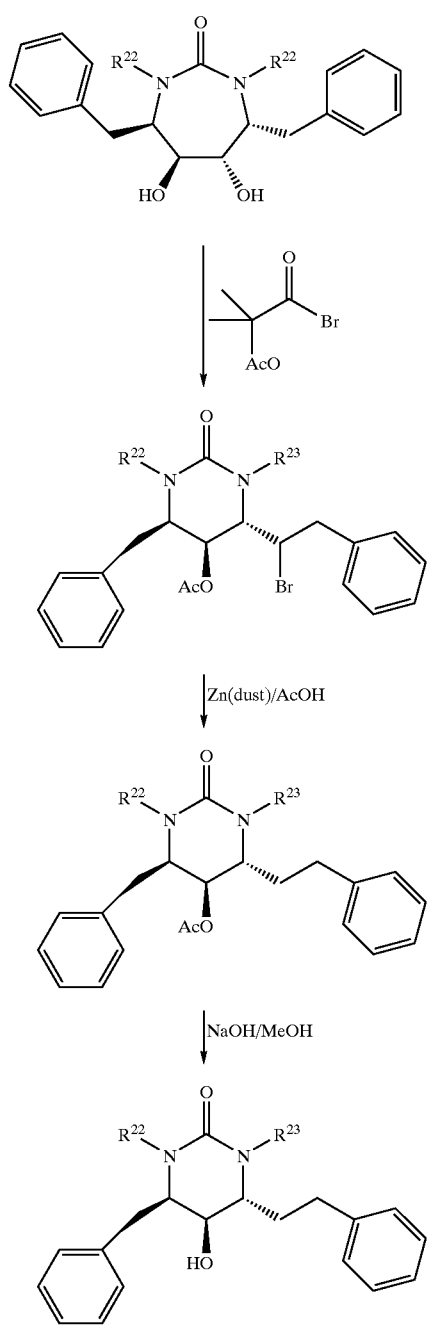
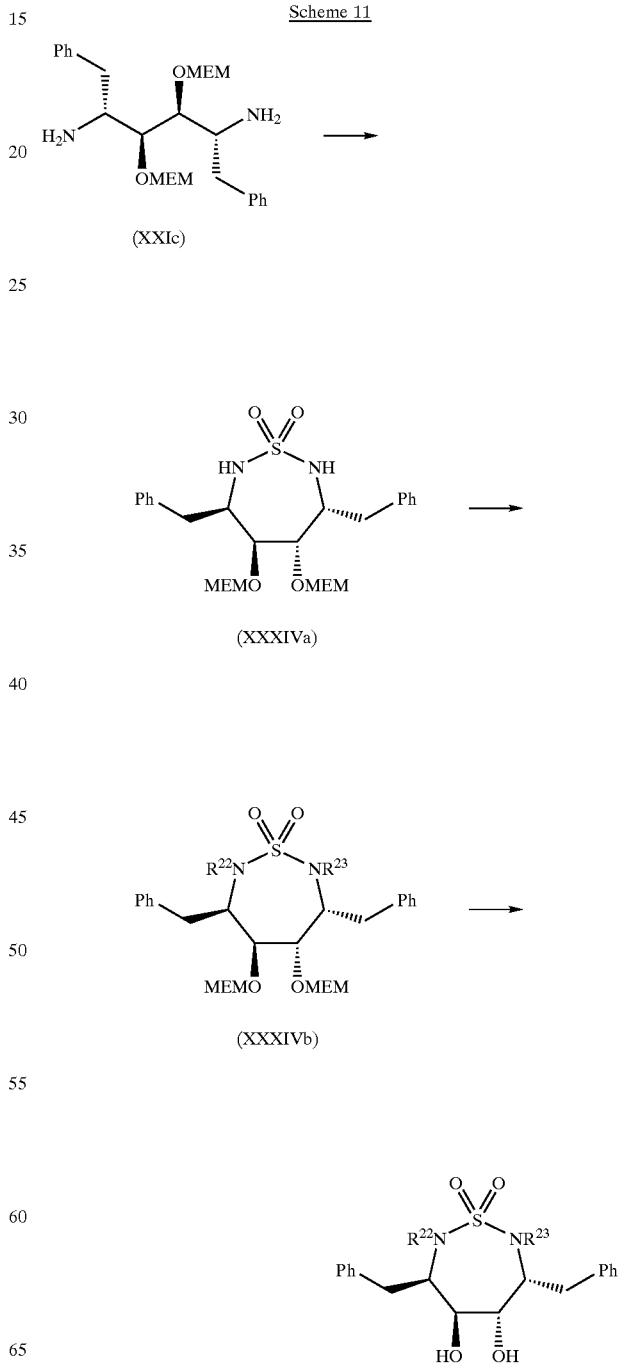

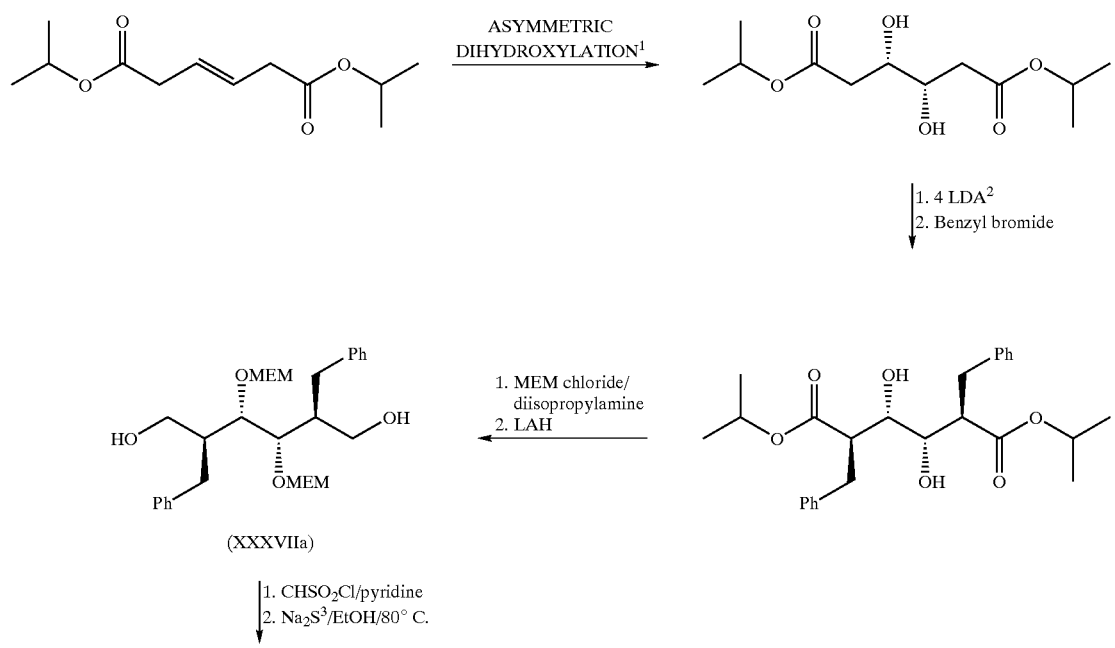
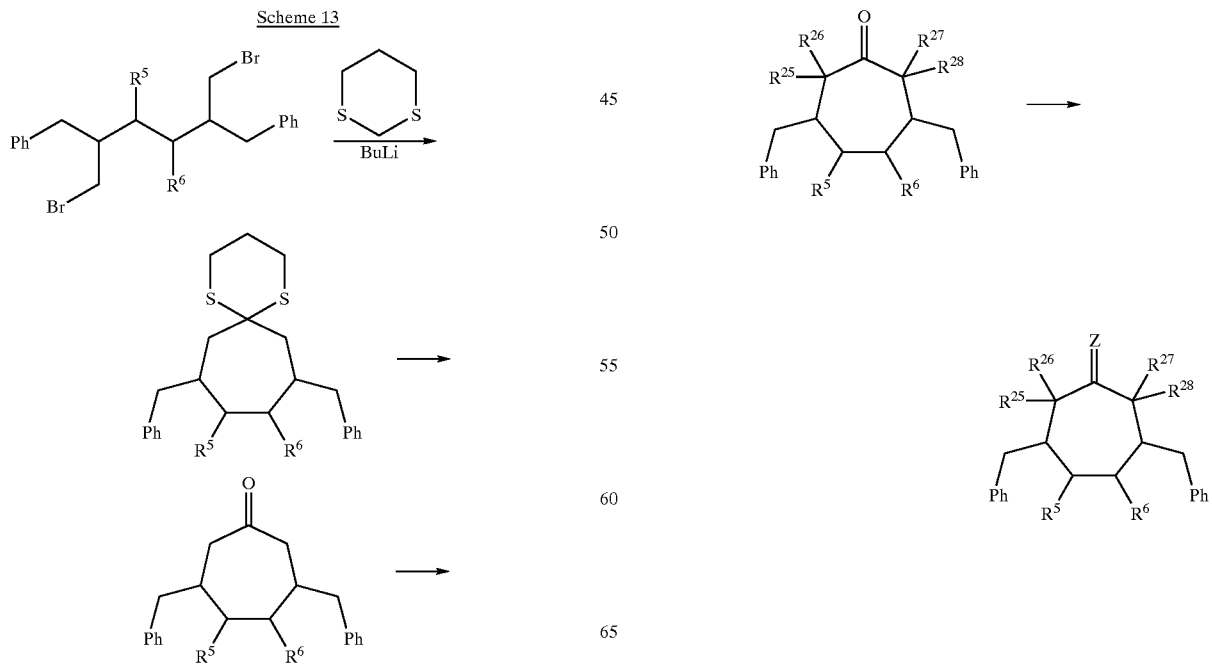

Scheme 14
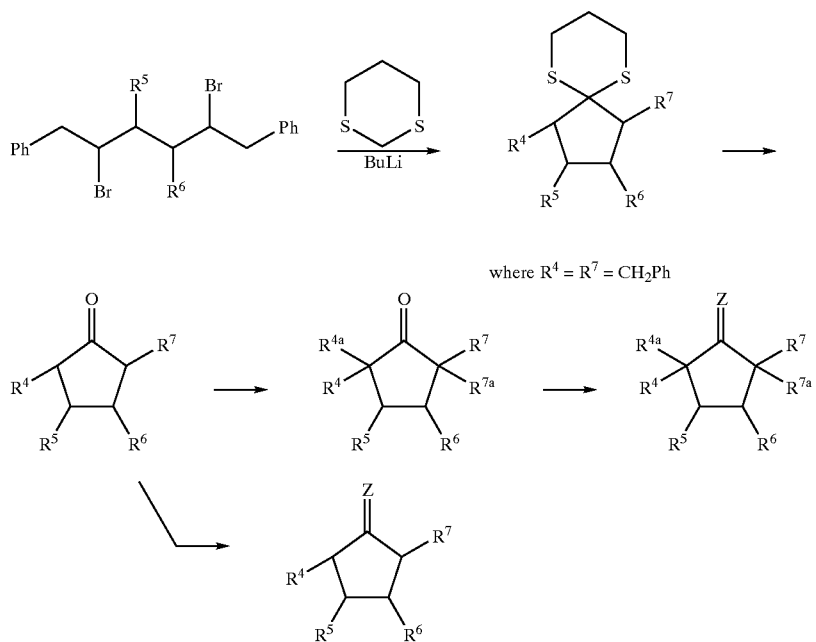
Scheme 15
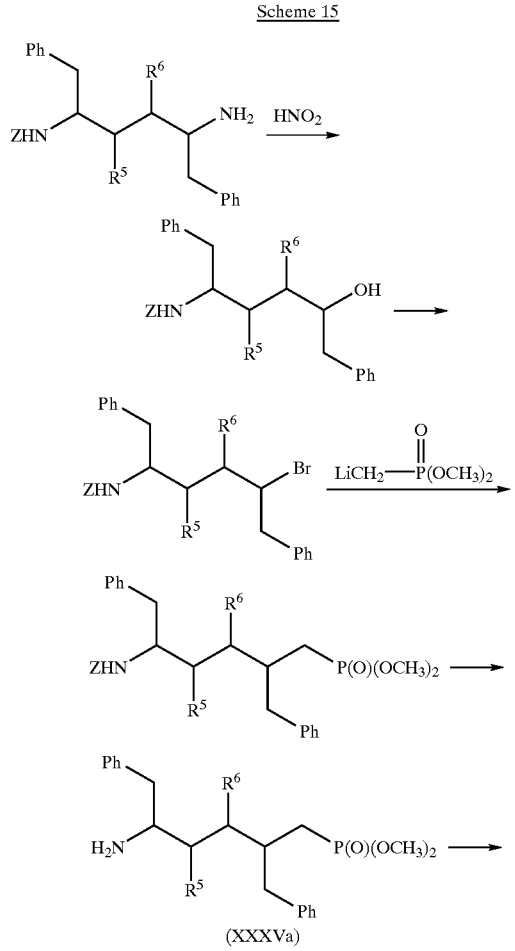
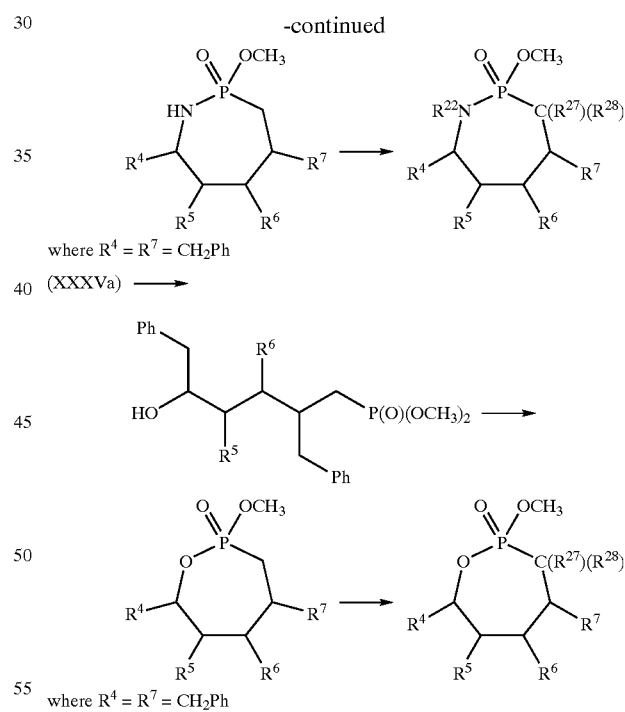
Scheme 16
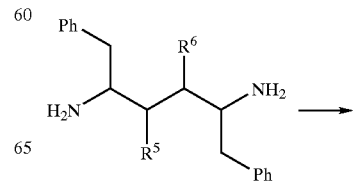

-continued
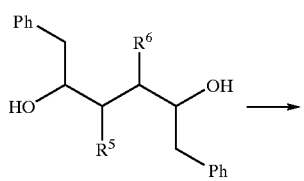
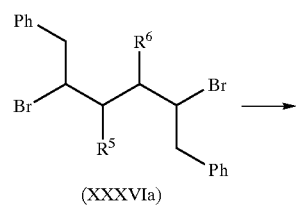
(XXXVIa)
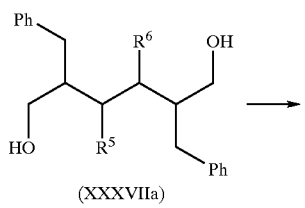
(XXXVIIa)
-continued
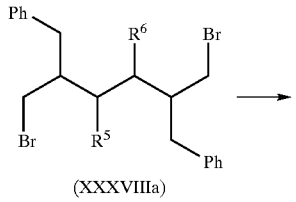
(XXXVIIIa)
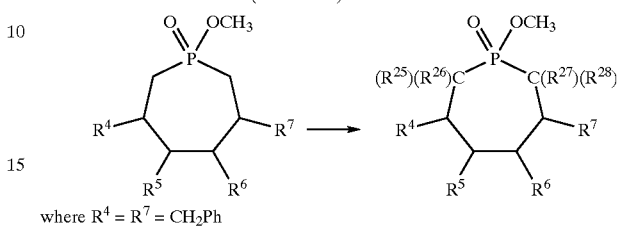
where $R^4 = R^7 = CH_2Ph$
(XXXVIa) ⟶
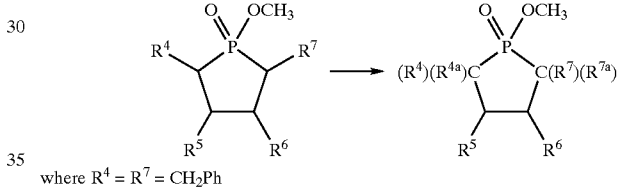
where $R^4 = R^7 = CH_2Ph$
Scheme 17
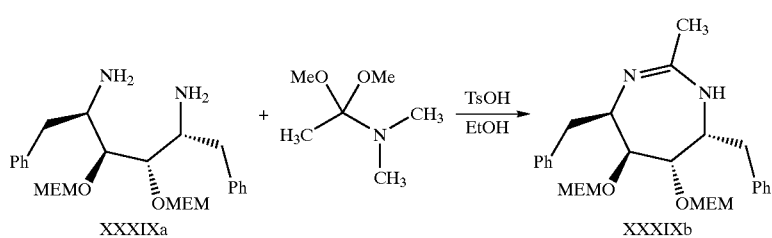
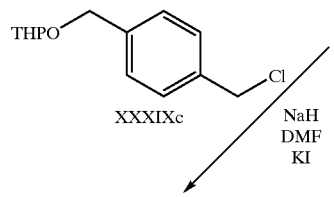

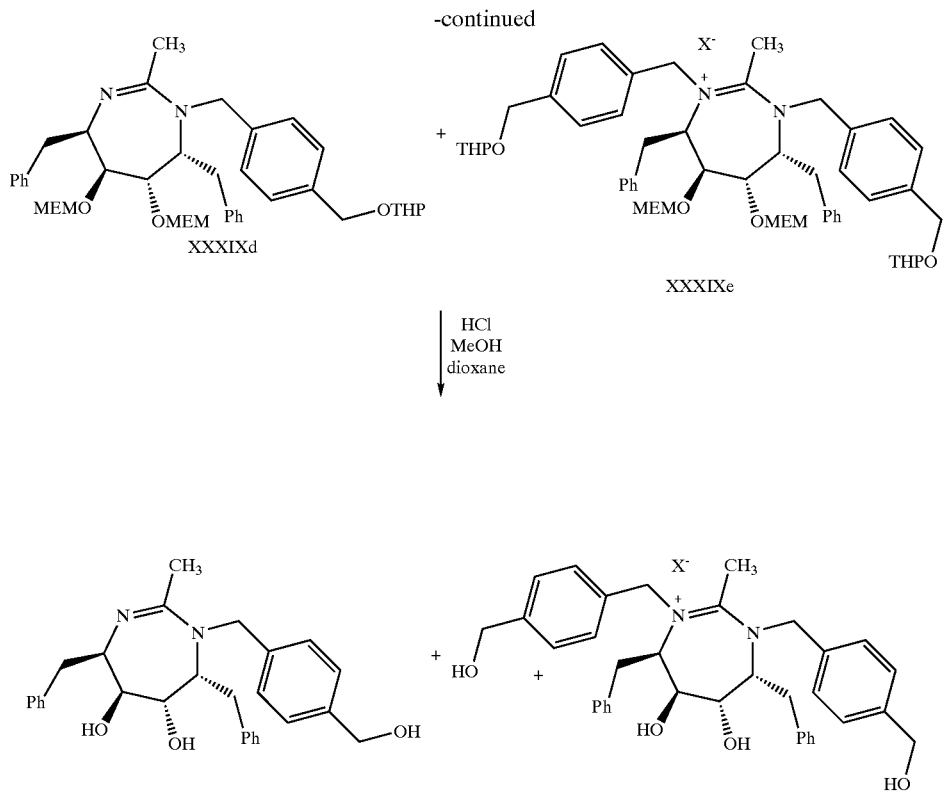
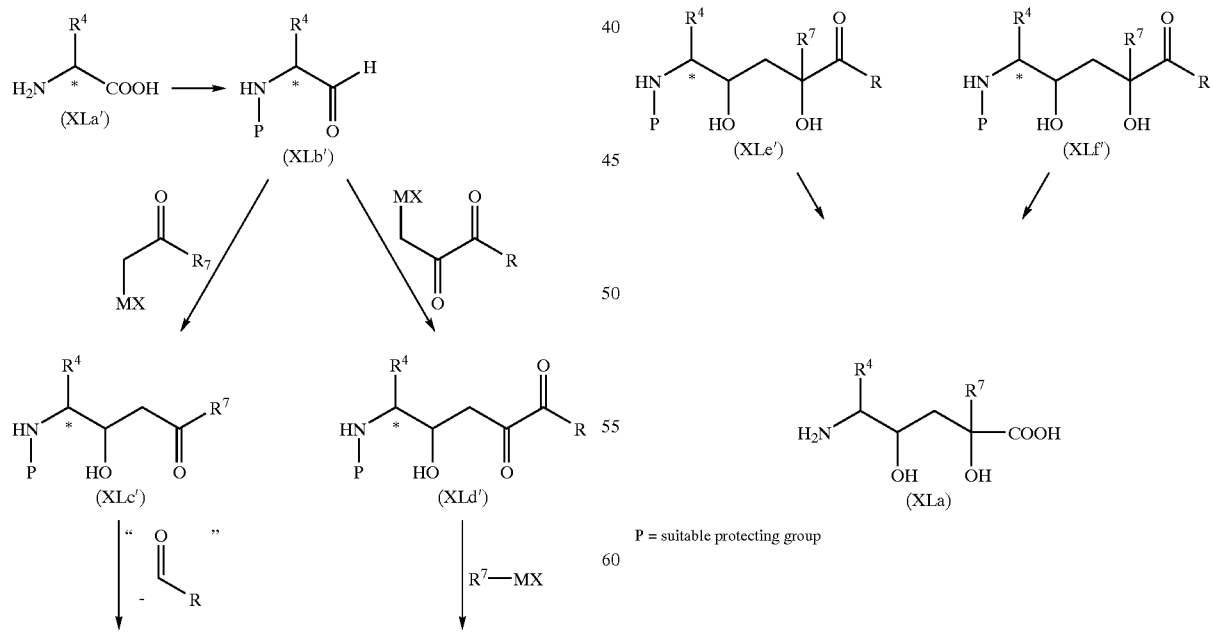
Scheme 18a
General Scheme for preparation of compounds of (XLa)
P = suitable protecting group Scheme 18b
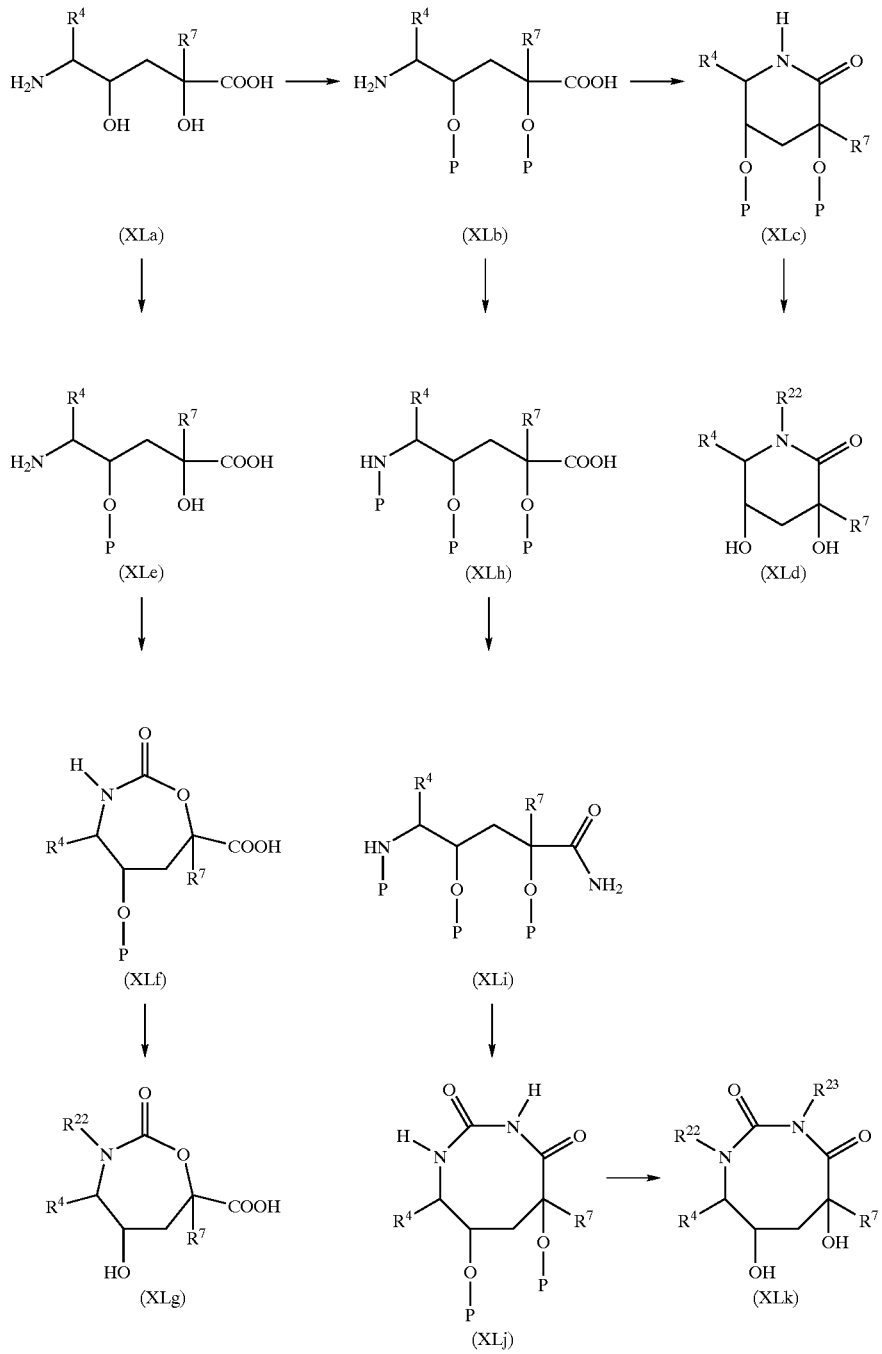
P = suitable protecting group
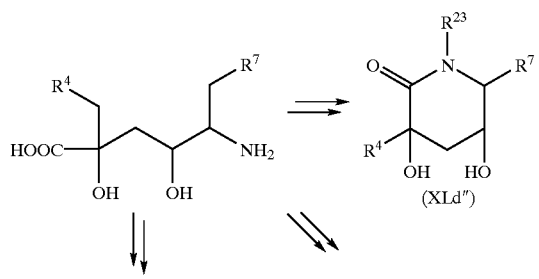

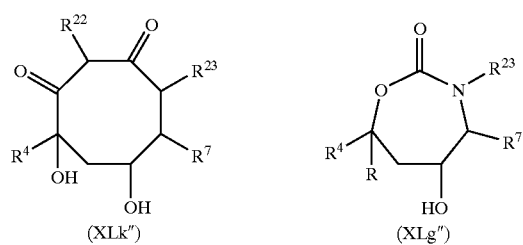
Scheme 18c (detailed)
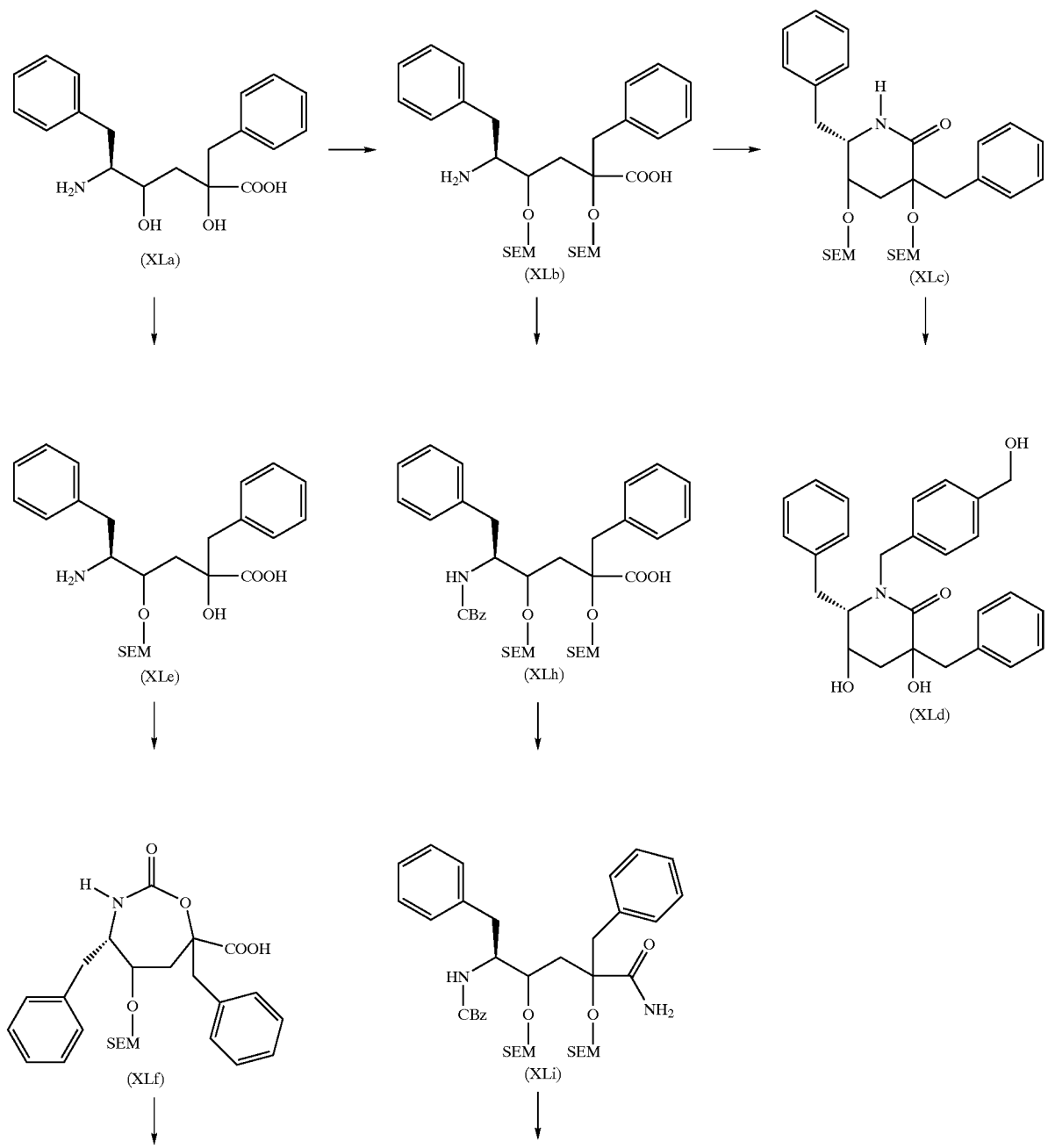

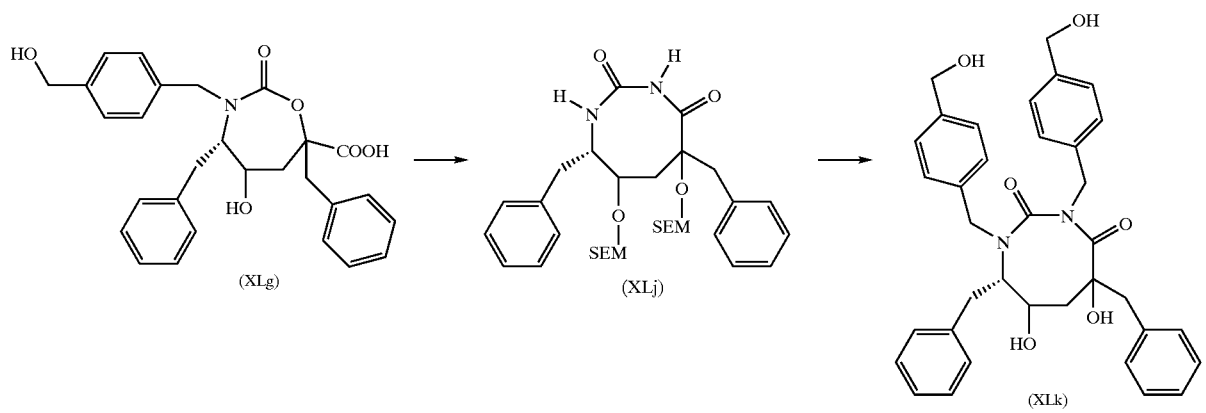
Scheme 19
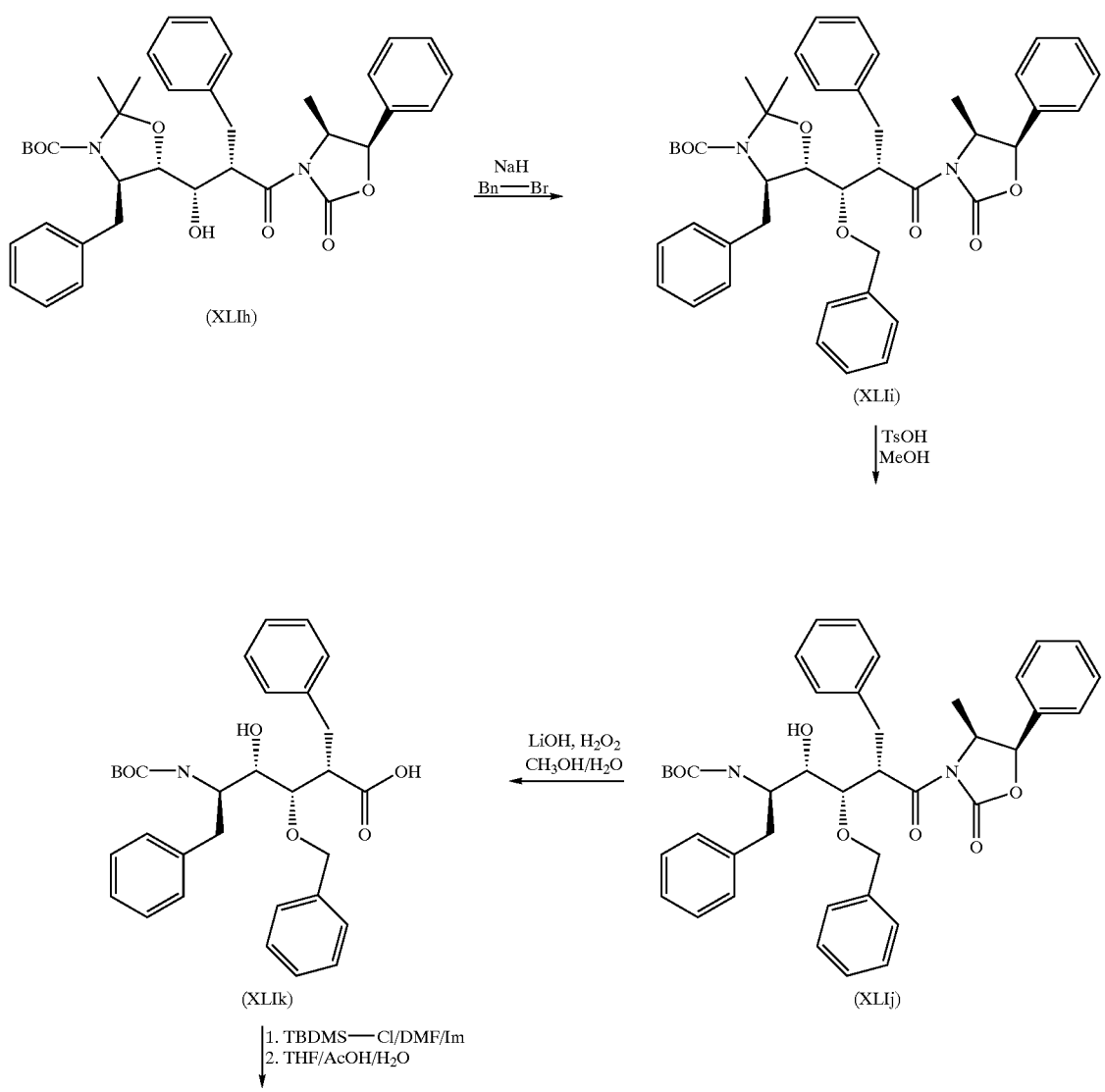

-continued
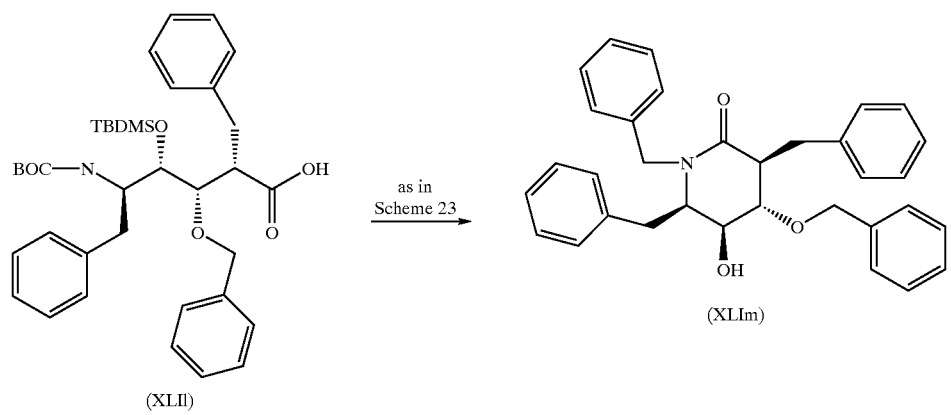
Scheme 20
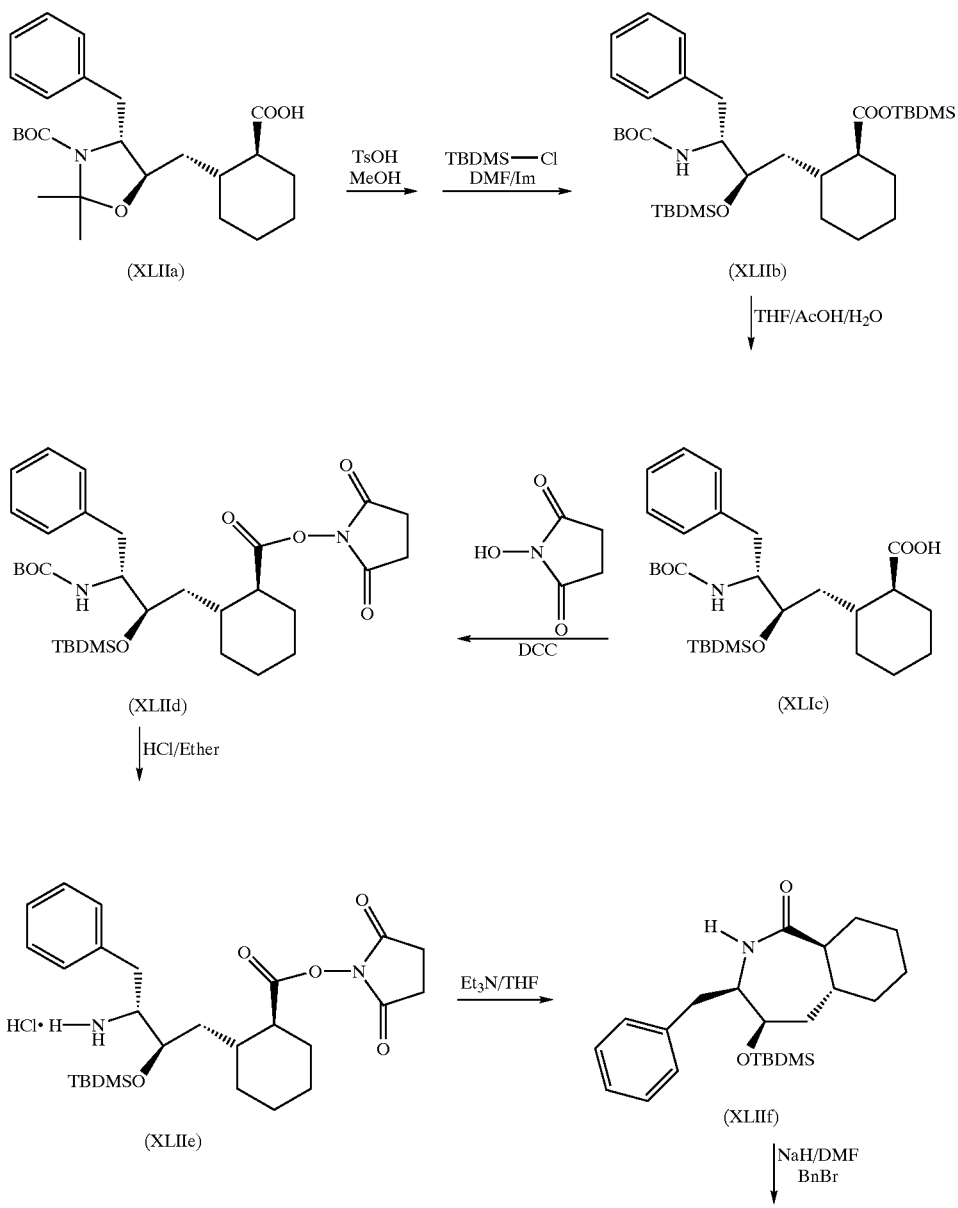

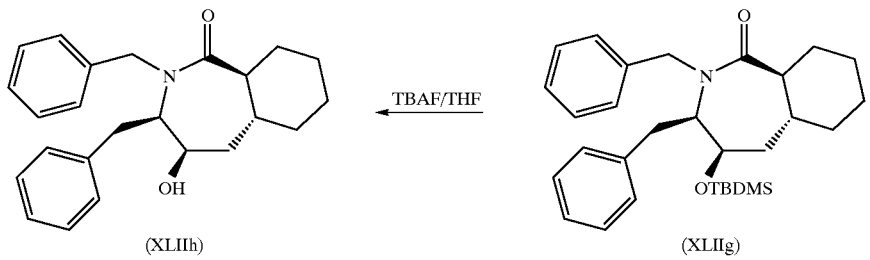
(XLIIh) ← TBAF/THF — (XLIIg)
Scheme 21
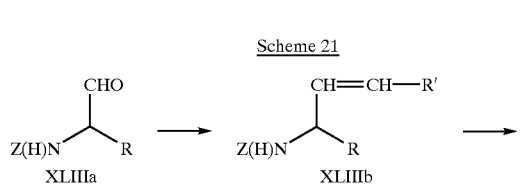
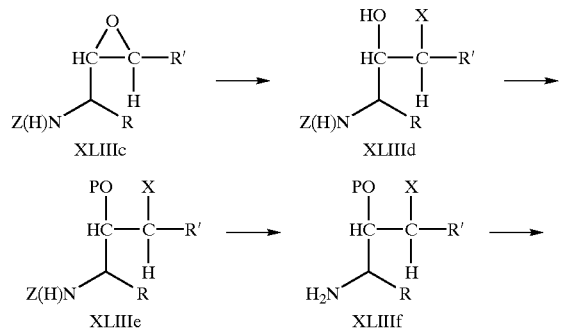
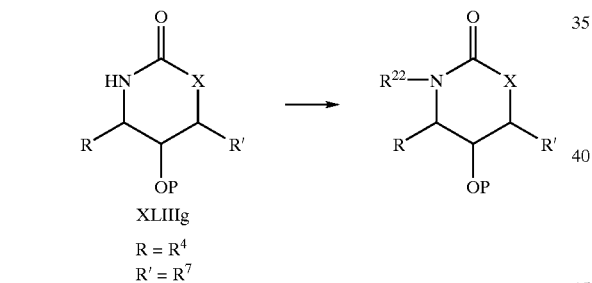
R = R[4]
R' = R[7]
X = O, NR[23]
P = suitable hydroxyl protecting group
Z = CO$_2$CH$_2$C$_6$H$_5$
Scheme 21a
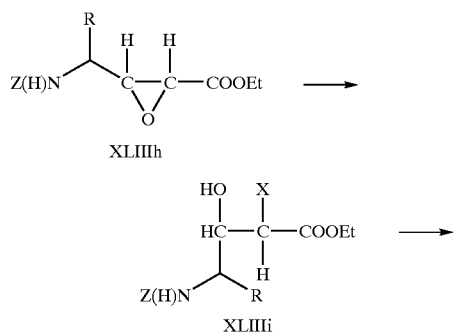
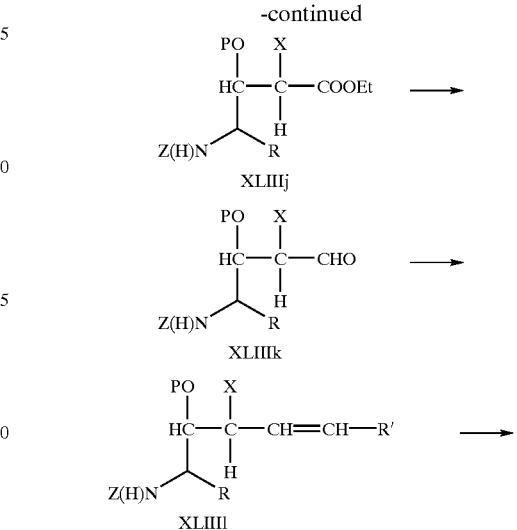
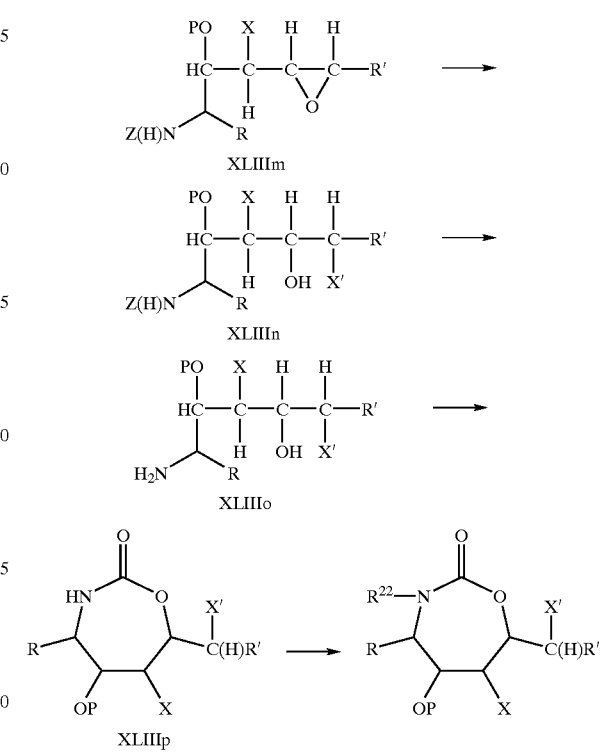
P = hydroxyl protecting group
X and X' can be independently SR, NHR, CR$_3$, OR Scheme 21b
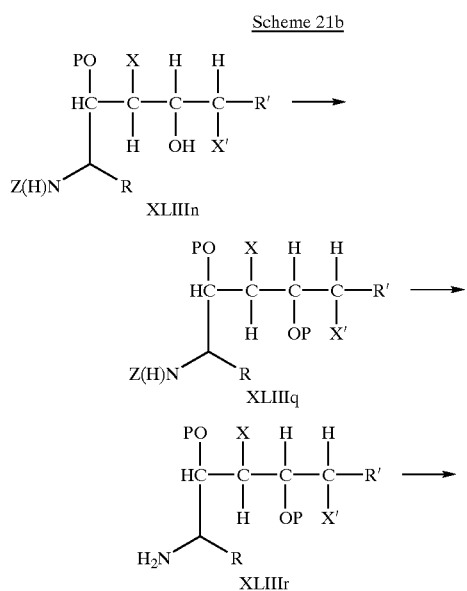
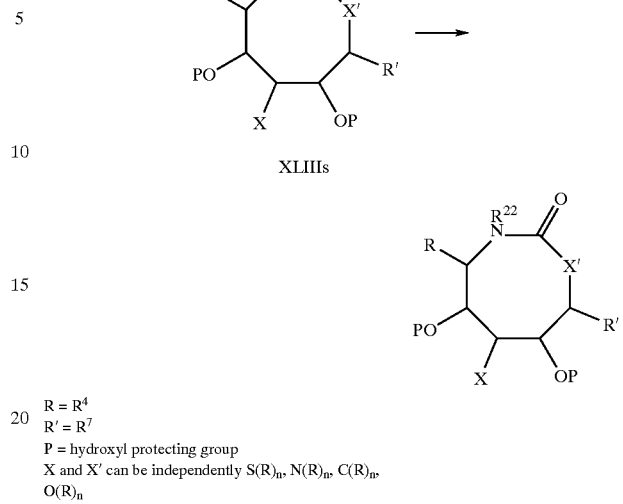
R = R⁴
R' = R⁷
P = hydroxyl protecting group
X and X' can be independently $S(R)_n$, $N(R)_n$, $C(R)_n$, $O(R)_n$
Scheme 22
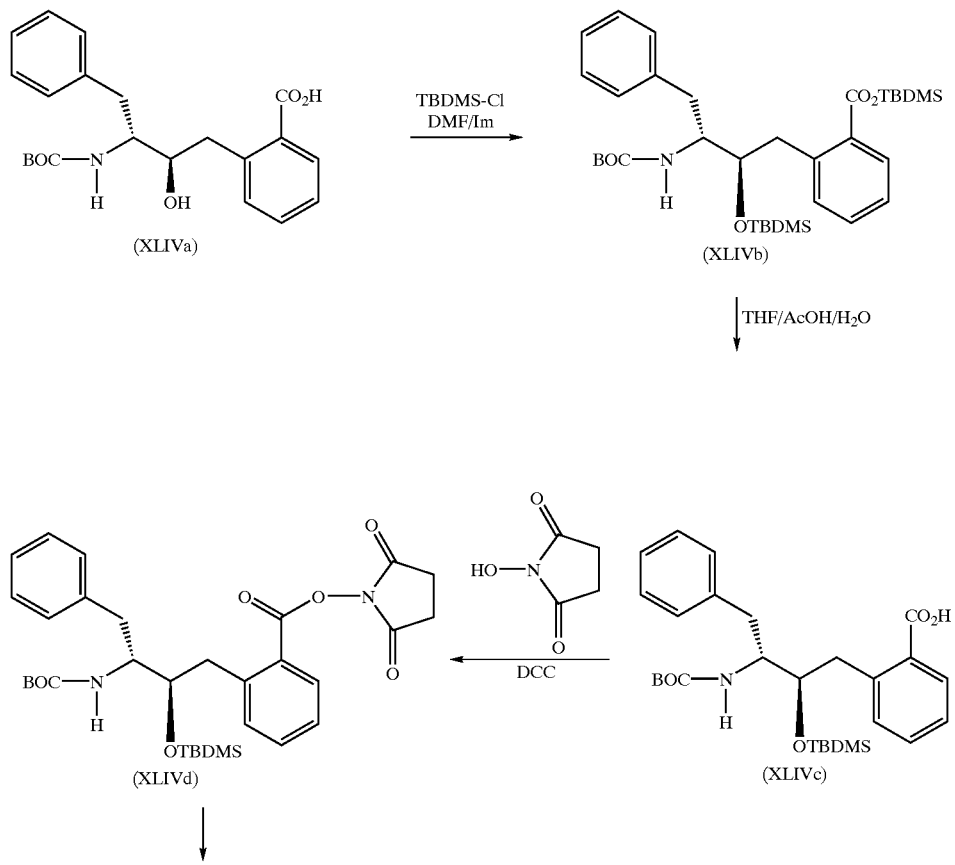

-continued
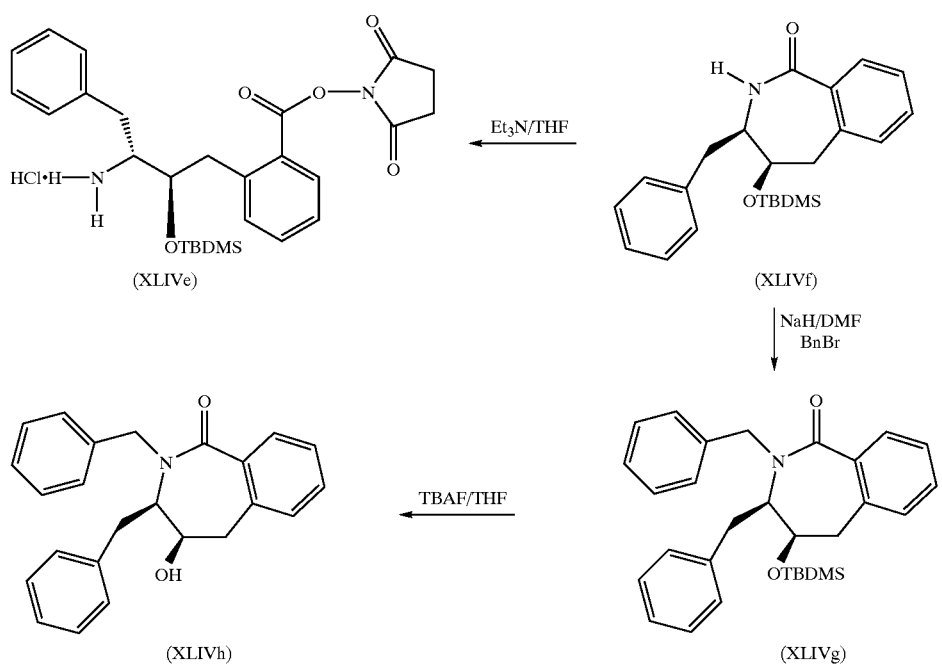
Scheme 23
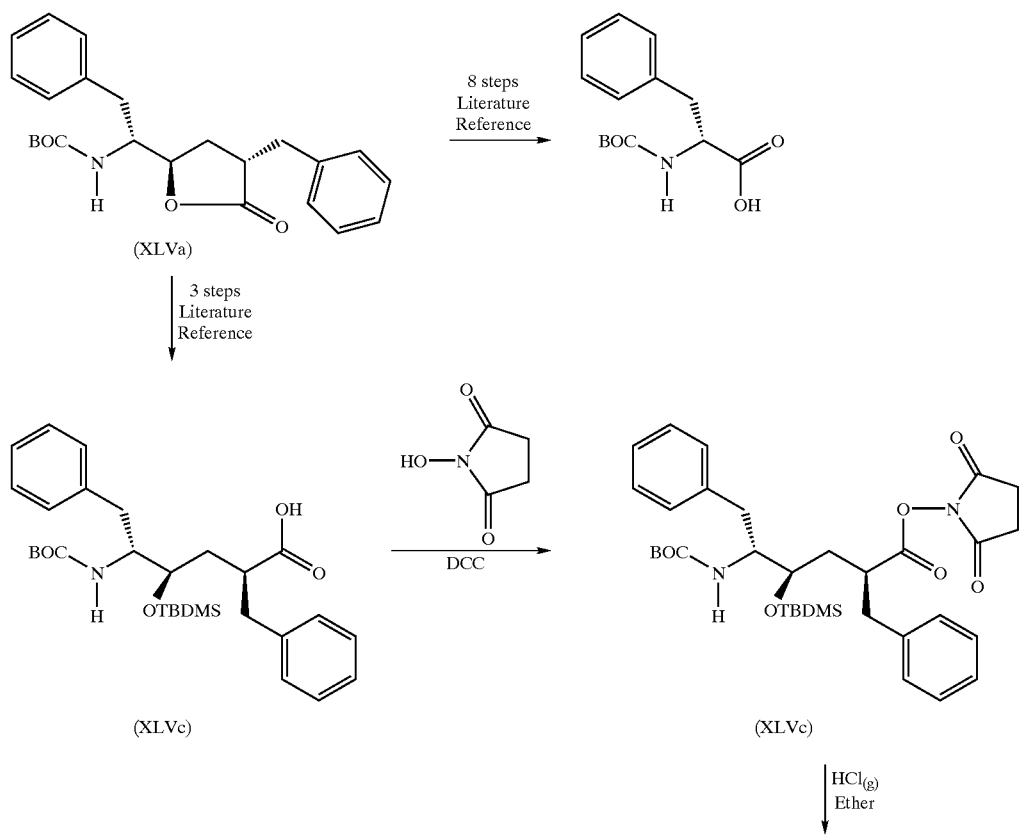

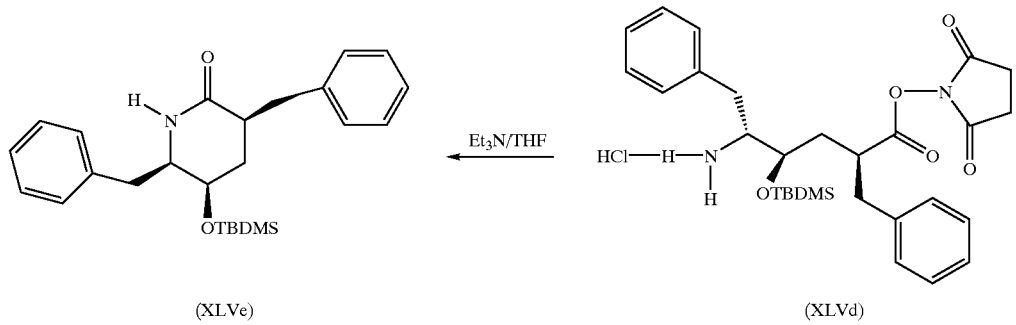
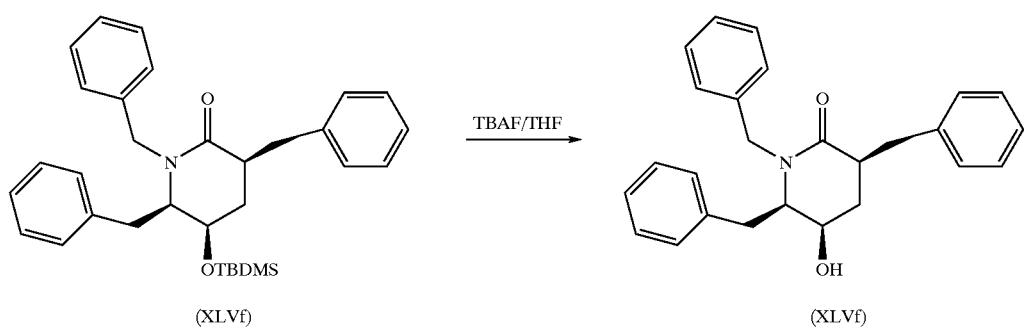
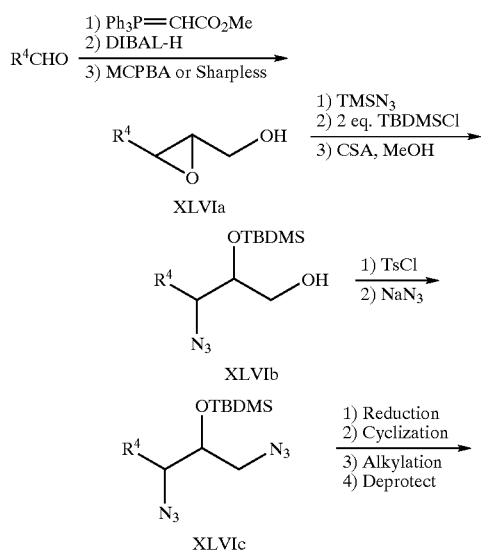
Scheme 24
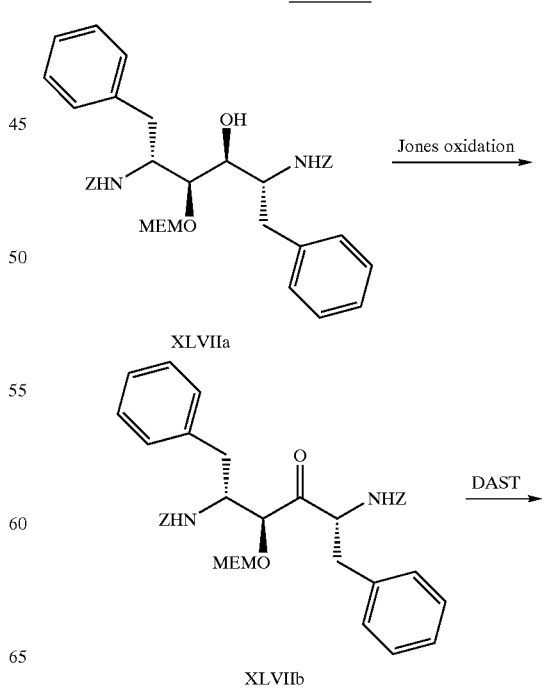
Scheme 25
TBDMS = t-butyldimethylsilyl

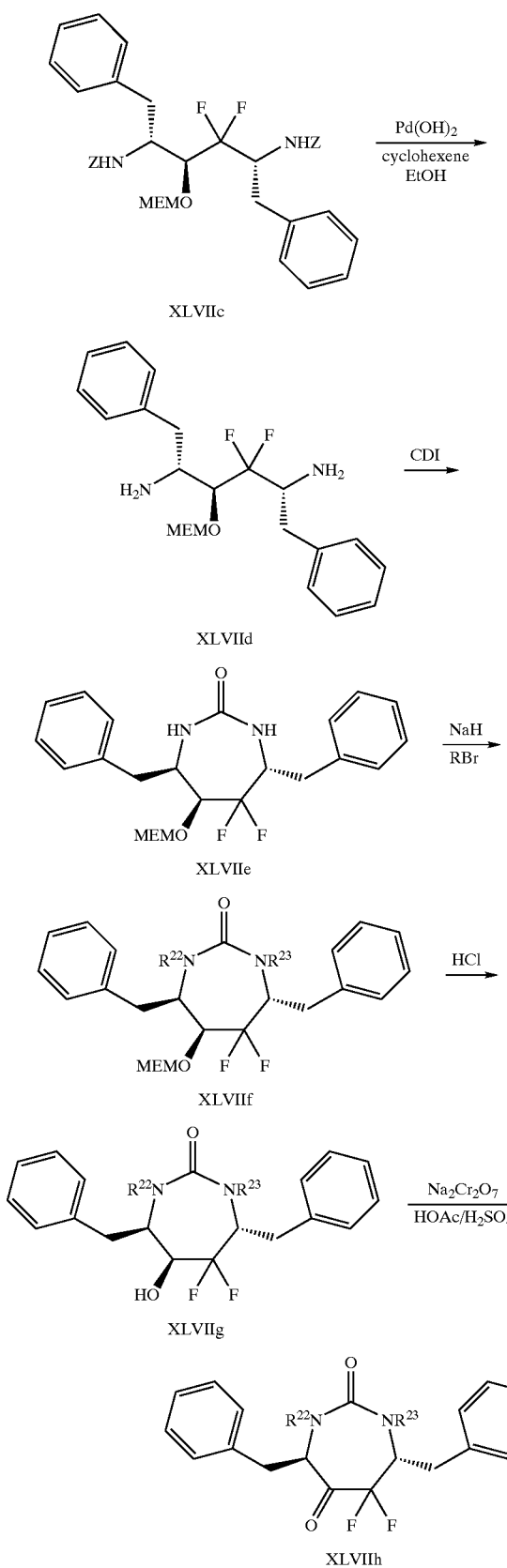
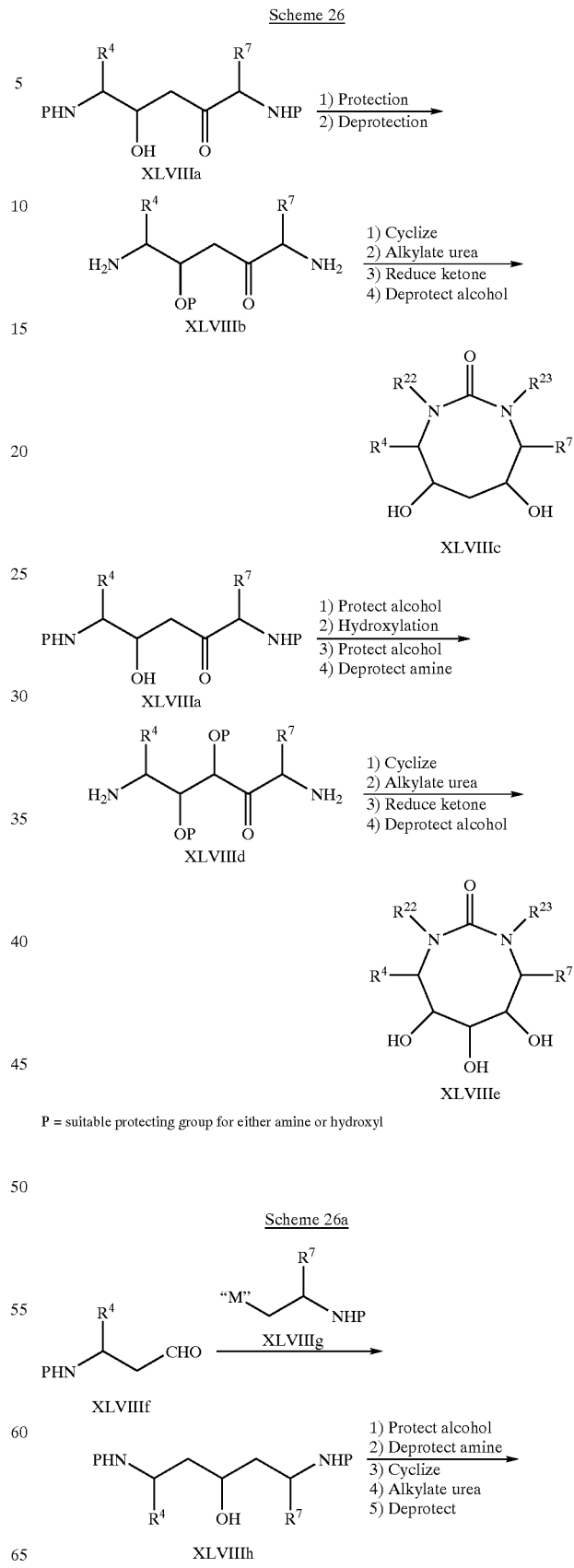
P = suitable protecting group for either amine or hydroxyl -continued
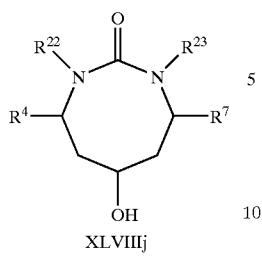
XLVIIIj
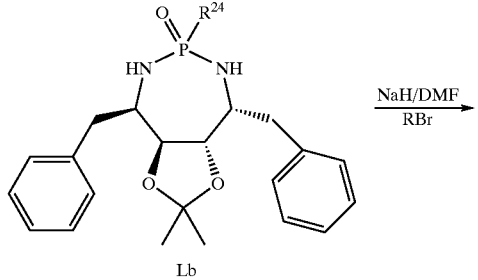
Lb
"M" is an organometallic such as Li, MgX or variant thereof compatable with the functionality present.
P = suitable protecting group
Scheme 27
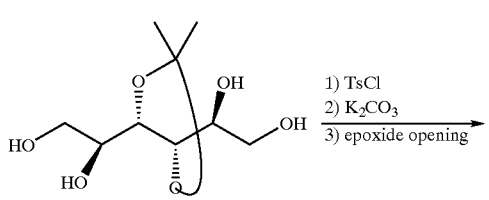
1) TsCl
2) $K_2CO_3$
3) epoxide opening
→
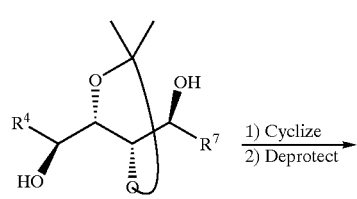
1) Cyclize
2) Deprotect
→
XLIXa
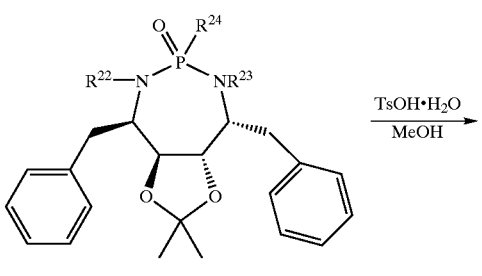
Lc
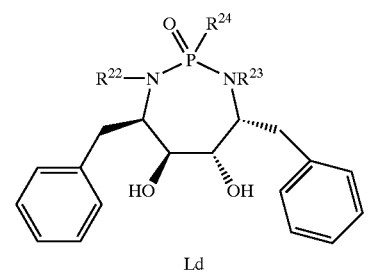
Ld
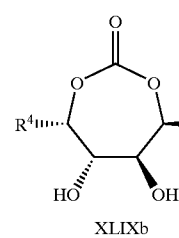
XLIXb
Scheme 29
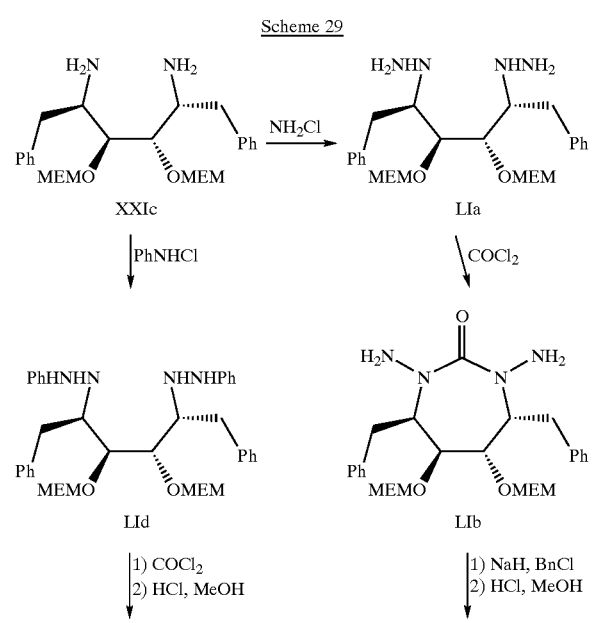
Scheme 28
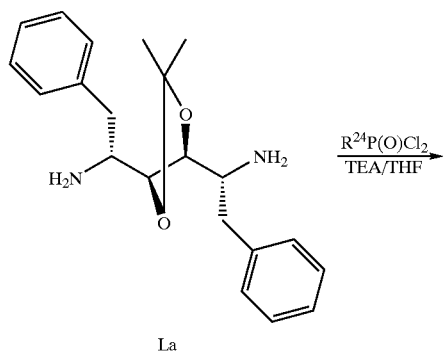
La -continued
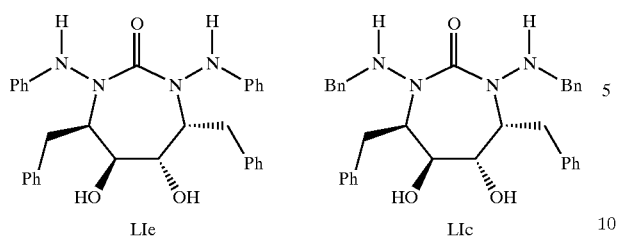
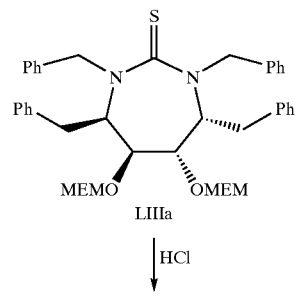
Scheme 30
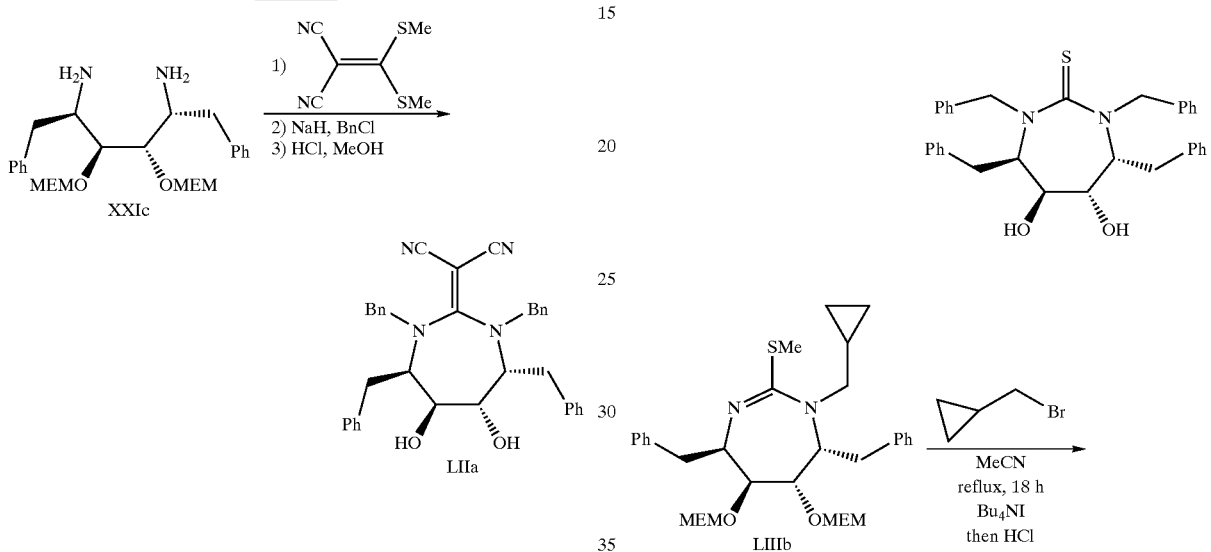
Scheme 31
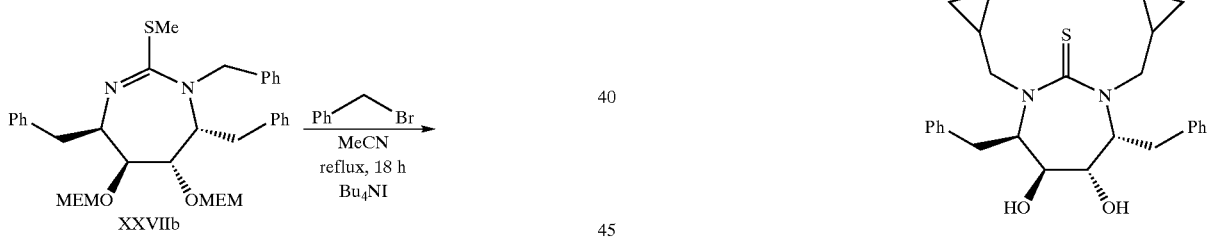
Scheme 32
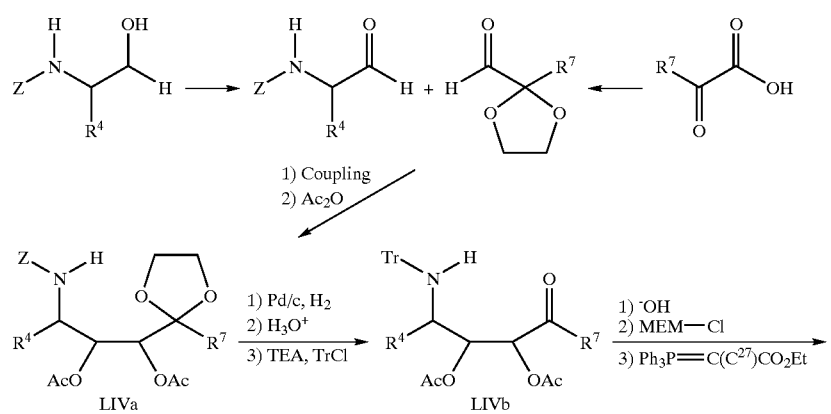

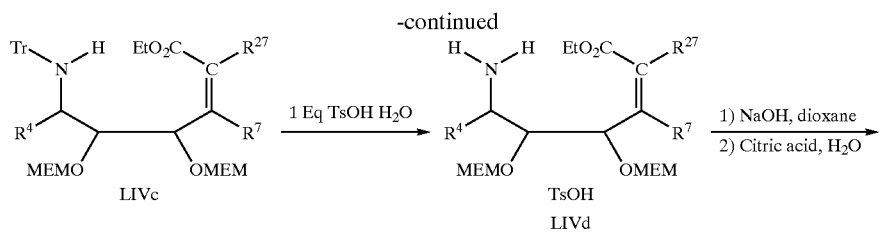
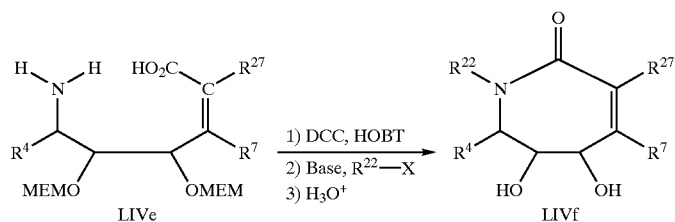
Scheme 33
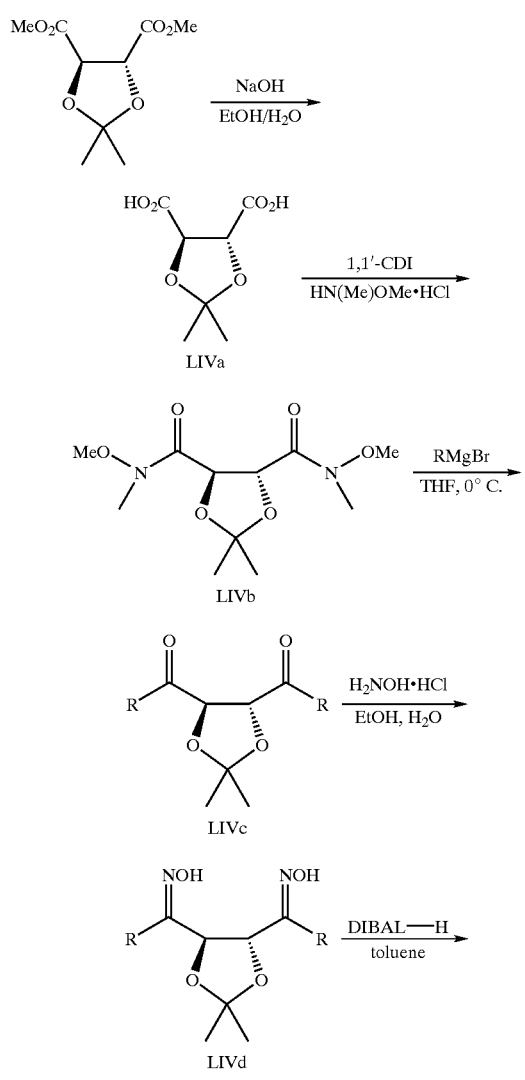
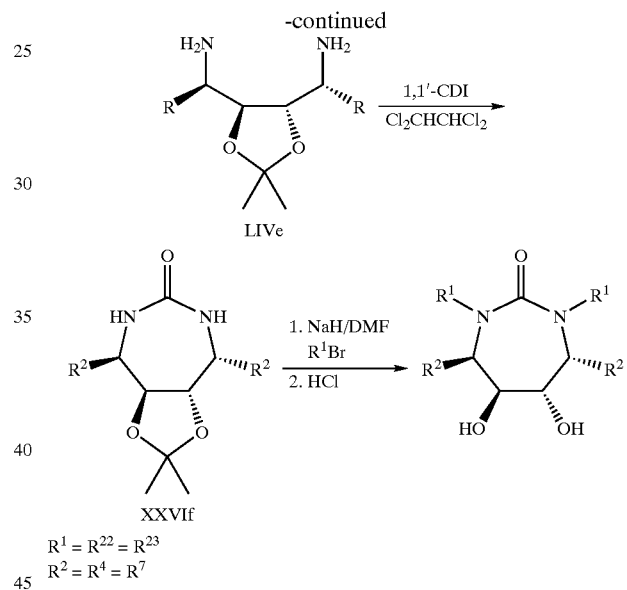
$R^1 = R^{22} = R^{23}$
$R^2 = R^4 = R^7$
Scheme 34a
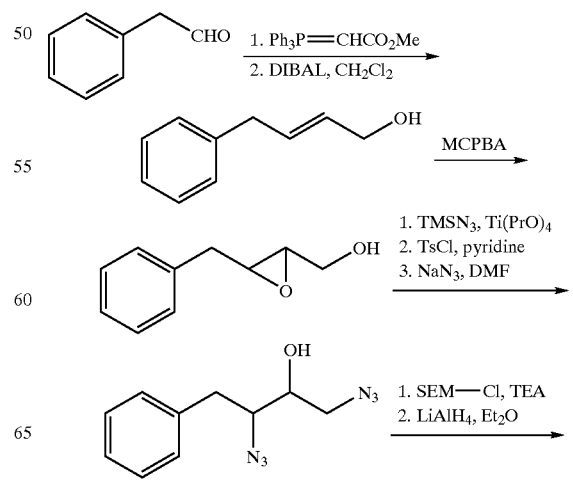

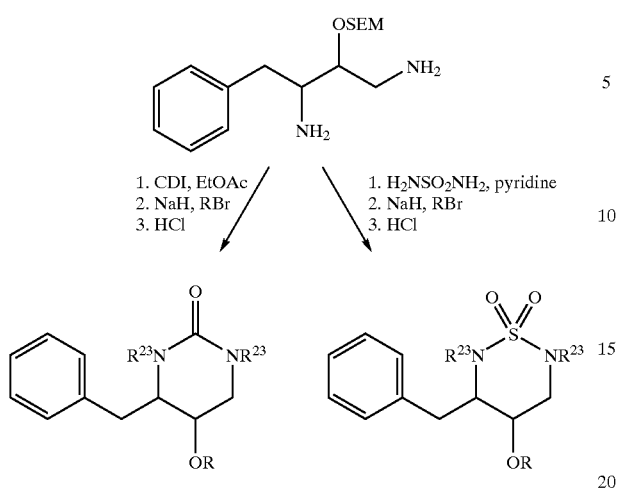

Scheme 34b

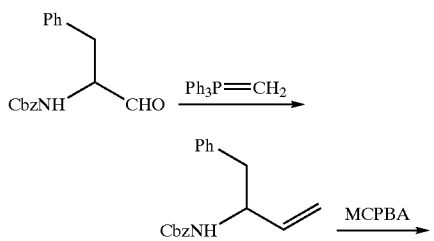

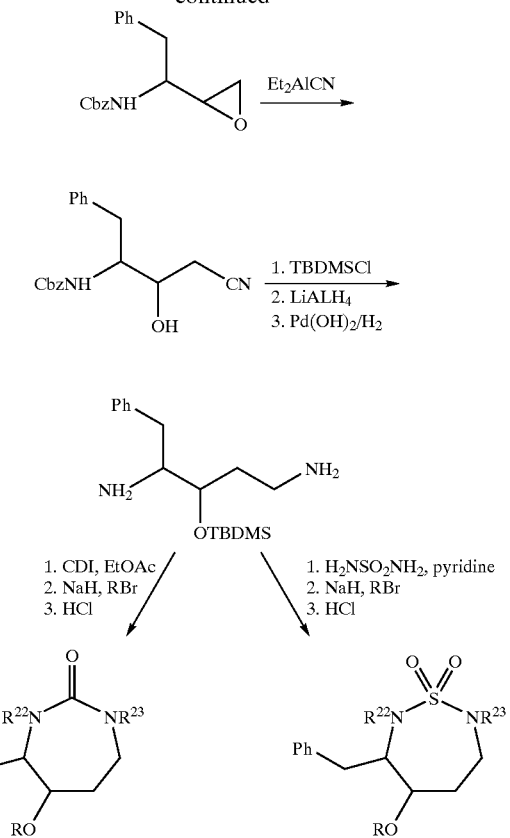

TABLE 2A

| Example Number | $R^{22}$ | $R^{23}$ | MS (M + H) | Ki | $IC_{90}$ | m.p. (° C.) |
|---|---|---|---|---|---|---|
| 2A | $CH_2CHC(CH_3)_2$ | $CH_2CHC(CH_3)_2$ | 463 | +++ | +++ | 165.1 |
| 2B | $CH_2CH_2CH_2C_6H_5$ | $CH_2CH_2CH_2C_6H_5$ | 563 | ++ | +++ | 120.7 |
| 2C | $CH_2CHCH_2$ | $CH_2CHC(CH_3)_2$ | 435 | +++ | +++ | 62 |
| 2D | $CH_2CHC(CH_3)_2$ | $CH_3$ | 409 | ++ | | sin 65 108 |
| 2E | $CH_2C_6H_4$-p-F | $CH_2C_6H_4$-p-F | 543 | +++ | +++ | |
| 2F | cyclopropyl | $CH_2C_6H_5$ | 471 | +++ | +++ | |
| 2G | $CH_2CHCH_2$ | $CH_2C_6H_5$ | 457 | +++ | +++ | 226.5 |
| 2H | $CH_2C_6H_5$ | $CH_3$ | 431 | ++ | +++ | 81 |
| 2I | $CH_2CHC(CH_3)_2$ | cyclopropyl | 440 | +++ | +++ | 76 |
| 2J | $CH_2C_6H_4$-m-$OCF_3$ | $CH_2C_6H_4$-m-$OCF_3$ | 675 | ++ | +++ | 128.3 |
| 2K | $CH_2C_6H_3$-m-$CF_3$-p-F | $CH_2C_6H_3$-m-$CF_3$-p-F | 679 | ++ | +++ | 167.2 |
| 2L | $CH_2C_6H_4$-p-$OCF_3$ | $CH_2C_6H_4$-p-$OCF_3$ | 675 | ++ | +++ | 136.8 |
| 2M | $CH_2C_6H_3$-m-F-m-$CF_3$ | $CH_2C_6H_3$-m-F-m-$CF_3$ | 679 | ++ | | 162.3 |

TABLE 2B

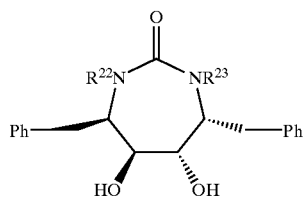

| Example Number | $R^{22}$ | $R^{23}$ | MS (M + H) | Ki | $IC_{90}$ | Notes |
|---|---|---|---|---|---|---|
| 2N | $C_6H_5CH=CHCH_2$ | $C_6H_5CH=CHCH_2$ | 559.30 | +++ | +++ | 1 |
| 2R | -m-F—$C_6H_4CH_2$ | m-F—$C_6H_4CH_2$ | 543.25 | +++ | +++ | 1 |
| 3E | o-$CH_3$—O—$C_6H_4CH_2$ | o-$CH_3$—O—$C_6H_4CH_2$ | 579.23 | ++ | +++ | 1 |
| 3K | m-$NH_2$—$C_6H_4CH_2$ | m-$NH_2$—$C_6H_4CH_2$ | 537.28 | +++ | | 3, 4 |

NOTES:
1. Prepared according to the general alkylation procedure (Procedure 5). Yields of monoalkyl compounds were favored by using one equivalent of alkylating agent.
2. Prepared by alkylating the appropriate monoalkyl compound.
3. Isolated as the dihydrochloride salt.
4. Preparation: a solution of 41.3 mg of Ex. 3B was dissolved in a mixture of 10 ml of ethanol and 1 ml of 1 N hydrochloric acid. Catalyst (20 mg of 10% palladium on carbon) was added, and the mixture was hydrogenated at atm pressure for 16 hours. A quantitative yield of Ex. 3K as isolated as the hydrochloride salt.

TABLE 2C

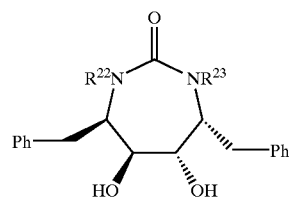

| Example Number | Stereo-isomer | $R^{22}$ | $R^{23}$ | Ki | $IC_{90}$ | MP (° C.) | Mass Spec M + 1 (%) | Notes |
|---|---|---|---|---|---|---|---|---|
| 3L | RSSR | $CH_2C\equiv CH$ | $CH_2C\equiv CH$ | ++ | ++ | 196–197 | 507 | |
| 3M | RSSR | 2-picolinyl | 2-picolinyl | ++ | ++ | 151–153 | 509 | |
| 3N | RSSR | $CH_2CH_2OCH_3$ | $CH_2CH_2OCH_3$ | ++ | + | 183–185 | 443 | |
| 3O | RSSR | $CH_2C_6H_{12}$ | $CH_2C_6H_{12}$ | ++ | + | — | 519 | |
| 3P | RSSR | $CH_2CH_2C(CH_3)_3$ | $CH_2CH_2C(CH_3)_3$ | ++ | + | 242–245 | 495 | |
| 3Q | RSSR | $CH_2C_6H_9$ | $CH_2C_6H_9$ | | | | | |
| 3R | RSSR | $CH_2CH_2OCH_2CH_3$ | $CH_2CH_2OCH_2CH_3$ | + | + | 148–150 | 471 | |
| 3S | RSSR | 3-methyl-5-oxazolinyl-methyl | H | ++ | + | — | 464 | |
| 3T | RSSR | 1-naphthylmethyl | 1-naphthylmethyl | ++ | + | 231–233 | 607 (85%) | |
| 3U | RSSR | 2-naphthylmethyl | 2-naphthylmethyl | +++ | +++ | 202–204 | 607 | |
| 3V | RSSR | n-butyl | benzyl | +++ | +++ | 89–91 | 473 | |
| 3W | RSSR | $CH_2CH=CH_2$ | cyclopropylmethyl | +++ | +++ | 173–175 | 421 | |
| 3X | RSSR | n-butyl | cyclopropylmethyl | +++ | +++ | — | 437 | |
| 3Y | RSSR | $CH_2CH=C(CH_3)_2$ | benzyl | +++ | +++ | 173–174 | 485 | |
| 3Z | RSSR | 3-methyloxy-olinylmethyl | 3-methyloxy-olinylmethyl | + | | — | 527 | |
| 4A | RSSR | benzyl | ethyl | +++ | +++ | 190–193 | 445 | |
| 4B | RSSR | benzyl | 4-picolinyl | +++ | +++ | — | 508 | |
| 4C | RSSR | cyclopropylmethyl | 4-picolinyl | +++ | +++ | — | 472 | |
| 4D | RSSR | $CH_2CH_2OCH=CH_2$ | $CH_2CH_2OCH=CH_2$ | ++ | | — | 467 | |
| 4E | RSSR | benzyl | cyclopentylmethyl | +++ | +++ | 198–200 | 499 | |
| 4F | RSSR | cyclopropylmethyl | cyclopentylmethyl | +++ | +++ | — | 463 | |
| 4G | RSSR | benzyl | n-propyl | +++ | +++ | — | 459 | |
| 4H | RSSR | benzyl-($D_7$) | benzyl-($D_7$) | +++ | +++ | — | 521 | |
| 4I | RSSR | cyclopropylmethyl | cinnamyl | +++ | +++ | — | 497 | |
| 4J | RSSR | 2,3,4,5,6-penta-fluoro-benzyl | 2,3,4,5,6-penta-fluoro-benzyl | + | +++ | 193–195 | 687 | |
| 4K | RSSR | cyclopropylmethyl | 2-naphthylmethyl | +++ | +++ | 175–178 | 521 | |
| 4L | RSSR | cyclopentylmethyl | 2-naphthylmethyl | +++ | +++ | 89–92 | 549 | |
| 4M | RSSR | benzyl | 2-naphthylmethyl | +++ | +++ | 90–92 | 557 | |
| 4N | RSSR | cyclopropylmethyl | 2-picolinyl | +++ | +++ | 220–222 | 472 | |
| 4O | RSSR | benzyl | 2-quinolinylmethyl | ++ | +++ | — | 558 | |

TABLE 2C-continued

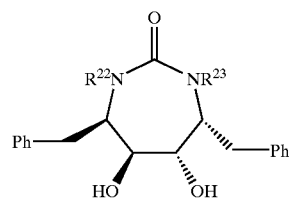

| Example Number | Stereo-isomer | R²² | R²³ | Ki | IC₉₀ | MP (° C.) | Mass Spec M + 1 (%) | Notes |
|---|---|---|---|---|---|---|---|---|
| 4P | RSSR | 3-cyanobenzyl | 3-cyanobenzyl | +++ | +++ | 225~227 | 557 | |
| 4Q | RSSR | 3-benzyloxybenzyl | 3-benzyloxybenzyl | ++ | +++ | 140–141 | 691 | |
| 4R | RSSR | 4-phenylbenzyl | 4-phenylbenzyl | ++ | | 109–110 | 659 | |
| 4S | RSSR | 3-allyl | 2-naphthylmethyl | +++ | +++ | 72–74 | 507 | |
| 4T | RSSR | n-propyl | 2-naphthylmethyl | +++ | +++ | 150~152 | 509 | |
| 4U | RSSR | n-butyl | 2-naphthylmethyl | +++ | +++ | 78–80 | 523 | |
| 4V | RSSR | H | 2-naphthylmethyl | +++ | +++ | 210–213 | 467 | |
| 4W | RSSR | 2-adamantylethyl | 2-adamantylethyl | ++ | | 292~294 | 651 | |
| 4X | RSSR | H | cyclopropylmethyl | ++ | | 189–190 | 381 | |
| 4Y | RSSR | 2-picolinyl | 2-naphthylmethyl | ++ | +++ | 165–166 | 558 | |
| 4Z | RSSR | 4-picolinyl | 2-naphthylmethyl | +++ | +++ | 118–121 | 558 | |
| 5A | RSSR | 3-allyl | H | + | | 180–182 | 367 | |
| 5B | RSSR | 3-allyl | cyclopentylmethyl | +++ | +++ | 190–191 | 449 | |
| 5C | RSSR | 3-allyl | 2-picolinyl | ++ | +++ | 160–162 | 458 | |
| 5D | RSSR | 3-allyl | 2-quinolinylmethyl | +++ | +++ | 145–146 | 507 | |
| 5E | RSSR | 3-allyl | 4-picolinyl | ++ | +++ | | 458 | |
| 5F | RSSR | 3-benzyloxybenzyl | 3-benzyloxybenzyl | ++ | | 165–166 | | |
| 5G | RSSR | 3-picolinyl | cyclopropylmethyl | +++ | +++ | 193~195 | 472 | |
| 5H | RSSR | 3-picolinyl | 2-naphthylmethyl | +++ | +++ | 94–96 | 558 | |
| 5I | RSSR | 3-hydroxybenzyl | 3-hydroxybenzyl | +++ | +++ | 101–103 | 539 | |
| 5J | RSSR | vinylbenzyl | vinylbenzyl | +++ | +++ | 158–160 | 559 | |
| 5K | RSSR | 3-cyclopropyl-methoxy-benzyl | 3-cyclopropyl-methoxy-benzyl | + | | 170–172 | 697 | |
| 5L | RSSR | 3-allyloxybenzyl | 3-allyloxybenzyl | +++ | + | 170–172 | 619 | |
| 5M | RSSR | 3-allyloxybenzyl | 3-hydroxybenzyl | +++ | +++ | 78–79 | 579 | |
| 5N | RSSR | 3-ethoxybenzyl | 3-ethoxybenzyl | ++ | + | 185–186 | 595 | |
| 5O | RSSR | 3-picolinyl | 3-picolinyl | +++ | +++ | — | 509 | |
| 5P | RSSR | 4-benzyoxybenzyl | 4-benzyoxybenzyl | + | + | 80–81 | 719 | |
| 5Q | RSSR | 2-naphthylmethyl- | 4-fluorobenzyl | +++ | +++ | 105–107 | 575 | |
| 5R | RSSR | 4-hydroxybenzyl | 4-hydroxybenzyl | +++ | +++ | 115–117 | 539 (20%) | |
| 5S | RSSR | 3-hydroxymethylbenzyl | 3-hydroxymethylbenzyl | +++ | +++ | 94–95 | 567 (40%) | |
| 5T | RSSR | 3-carbomethoxybenzyl | 3-carbomethoxybenzyl | +++ | +++ | — | 623 (40%) | |
| 5U | RSSR | 4-hydroxymethylbenzyl | 4-hydroxymethylbenzyl | +++ | +++ | 190–195 | 567 | |
| 5V | RSSR | 3-formylbenzyl | 3-formylbenzyl | +++ | +++ | 175–176 | 563 (30%) | |
| 5W | RSSR | 4-cyanobenzyl | 4-cyanobenzyl | +++ | +++ | 140–143 | 557 (15%) | |
| 5X | RSSR | 4-formylbenzyl | 4-formylbenzyl | +++ | +++ | 90–91 | 563 (52%) | |
| 5Y | RSSR | 4-hydroxybenzyl | 2-propyl | +++ | +++ | 246–248 | 475 (80%) | |
| 5Z | RSSR | 3-hydroxybenzyl | 2-propyl | +++ | +++ | 212–213 | 475 (90%) | |
| 6A | RSSR | 3-carboxybenzyl | 3-carboxybenzyl | +++ | +++ | 190–195 | 189 | |
| 6B | RSSR | 4-carboxybenzyl | 4-carboxybenzyl | ++ | ++ | 210–211 | 189 | |
| 6C | RSSR | 3-formaldoximebenzyl | 3-formaldoximebenzyl | +++ | +++ | 185–189 | 593 (2%) | |
| 6D | RSSR | cyclopropylmethyl | 3-hydroxybenzyl | +++ | +++ | 233–234 | 486 | |
| 6E | RSSR | cyclopropylmethyl | 4-hydroxybenzyl | +++ | +++ | 234–236 | 486 | |
| 6F | RSSR | 5-chloro-2-thienyl-methyl | 5-chloro-2-thienyl-methyl | ++ | +++ | | 587 | |
| 6G | RSSR | cyclobutylmethyl | cyclobutylmethyl | +++ | +++ | | 463 | |
| 6H | RSSR | cyclopentylmethyl | cyclopentylmethyl | +++ | +++ | | 491 | |
| 6I | RSSR | n-butyl | $CH_2CH{=}C(CH_3)_2$ | +++ | +++ | | | |
| 6J | RSSR | n-butyl | cyclopentylmethyl | +++ | +++ | | 465 | |
| 6K | RSSR | 2-quinolinyl-methyl | 2-quinolinyl-methyl | ++ | + | | 609 | |
| 6L | RSSR | 2-propyl | 2-picolinyl | ++ | +++ | | 460 | 1 |
| 6M | RSSR | p-CH₃OC₆H₄CH₂— | p-CH₃OC₆H₄CH₂— | ++ | +++ | | 567.29 | 1 |
| 6N | RSSR | (CH₃)₂NCH₂CH₂— | (CH₃)₂NCH₂CH₂— | + | + | | 469.32 | 1 |
| 6O | RSSR | benzyl | H | +++ | +++ | | 417.22 | 1 |
| 6P | RSSR | o-F-C₆H₄CH₂— | o-F-C₆H₄CH₂— | ++ | +++ | | 543.25 | 1 |
| 6Q | RSSR | m-CH₃O—C₆H₄CH₂— | m-CH₃O—C₆H₄CH₂— | +++ | +++ | | 567.29 | 1 |
| 6R | RSSR | (CH₃)₂NCH₂CH₂— | (CH₃)₂NCH₂CH₂— | + | + | | 468.62 | 1 |
| 6S | RSSR | m,p-F₂—C₆H₄CH₂— | m,p-F₂—C₆H₄CH₂— | +++ | +++ | | 579.23 | 1 |
| 6T | RSSR | p-CH₃—C₆H₄CH₂— | p-CH₃—C₆H₄CH₂— | +++ | +++ | | 535.30 | 1 |
| 6U | RSSR | p-Cl—C₆H₄CH₂— | p-Cl—C₆H₄CH₂— | +++ | +++ | | 575.19 ($^{35}$Cl) | 1 |
| 6V | RSSR | p-F-C₆H₄CH₂— | ⌁⊲ | +++ | +++ | 183.4 | 489.26 | 1a |
| 6W | RSSR | p-CF₃—C₆H₄CH₂— | p-CF₃—C₆H₄CH₂— | ++ | + | | 643.24 | 1 |

TABLE 2C-continued

[Structure: 7-membered cyclic urea with R22N-C(=O)-NR23, with Ph and Ph substituents and HO, OH on the ring]

| Example Number | Stereo-isomer | $R^{22}$ | $R^{23}$ | Ki | $IC_{90}$ | MP (° C.) | Mass Spec M + 1 (%) | Notes |
|---|---|---|---|---|---|---|---|---|
| 6X | RSSR | m-Cl—$C_6H_4CH_2$— | m-Cl—$C_6H_4CH_2$— | +++ | +++ | 210.3 | 575.19 ($^{35}$Cl) | 1 |
| 6Y | RSSR | m-$CF_3$—$C_6H_4CH_2$— | m-$CF_3$—$C_6H_4CH_2$— | ++ | + | | 643.24 | 1 |
| 6Z | RSSR | m-$NO_2$—$C_6H_4CH_2$— | m-$NO_2$—$C_6H_4CH_2$— | +++ | +++ | 248.3 | 597.23 | 1 |
| 6ZA | RSSR | m-$CH_3$—$C_6H_4CH_2$— | m-$CH_3$—$C_6H_4CH_2$— | +++ | +++ | | 535.30 | 1 |
| 6ZB | RSSR | o-$CH_3$O—$C_6H_4CH_2$— | o-$CH_3$O—$C_6H_4CH_2$— | + | ++ | | 567.29 | 1 |
| 6ZC | RSSR | m,m-$F_2$—$C_6H_4CH_2$— | m,m-$F_2$—$C_6H_4CH_2$— | ++ | +++ | 167.9 | 579.23 | 1 |
| 6ZD | RSSR | o-Cl—$C_6H_4CH_2$— | o-Cl—$C_6H_4CH_2$— | ++ | +++ | | 575.56 ($^{35}$Cl) | 1 |
| 6ZE | RSSR | m-Br—$C_6H_4CH_2$— | m-Br—$C_6H_4CH_2$— | +++ | +++ | 210.7 | 665.00 | 1 |
| 6ZF | RSSR | p-F—$C_6H_4CH_2$— | H | +++ | +++ | 188.9 | 435.21 | 1 |
| 6ZG | RSSR | p-Br—$C_6H_4CH_2$— | p-Br—$C_6H_4CH_2$— | ++ | +++ | | 663.09 ($^{79}$Br) | 1 |
| 6ZH | RSSR | m-Cl—$C_6H_4CH_2$— | [bicyclopropyl-methyl structure] | +++ | +++ | 126.0 | 505.23 ($^{25}$Cl) | 1 |
| 6ZI | RSSR | m-$NH_2C_6H_4CH_2$—(HCl) | m-$NH_2C_6H_4CH_2$—(HCl) | +++ | +++ | | 537.29 | 2 |
| 6ZJ | RSSR | m,m-$Cl_2$—$C_6H_4CH_2$— | m,m-$Cl_2$—$C_6H_4CH_2$— | ++ | ++ | 231.1 | 642.10 ($^{35}$Cl) | |
| 6ZK | RSSR | m-($NH_2CH_2$)—$C_6H_4CH_2$— | m-($NH_2CH_2$)—$C_6H_4CH_2$— | ++ | ++ | | 565.32 | |
| 6ZL | RSSR | m-$NO_2C_6H_4CH_2$— | H | +++ | +++ | | 462.20 | |
| 6ZM | RSSR | m-(NHCHO)—$C_6H_4CH_2$— | m-(NHCHO)—$C_6H_4CH_2$— | +++ | +++ | | 593.28 | 3 |
| 6ZN | RSSR | m-($NHCOCH_3$)—$C_6H_4CH_2$— | m-($NHCOCH_3$)—$C_6H_4CH_2$— | +++ | +++ | | 621.31 | |
| 6ZO | RSSR | m,p-$(HO)_2$—$C_6H_4CH_2$— | m,p-$(HO)_2$—$C_6H_4CH_2$— | +++ | +++ | | 571.24 | |
| 6ZP | RSSR | [N-benzyl imidazolyl-CH2 group] | [N-benzyl imidazolyl-CH2 group] | + | ++ | | 667.34 | |

All of the compounds of Table 2C were synthesized using procedure 5. In the instance that the alkylation can not be performed using conditions described previously, due to reactivity of a functional groups or groups that may be part of the alkylating agent, then functional group protection may be carried out, based on the methods for functional group protection described in .W. Greene and P. G. M. Wuts, "Protecting Groups in Organic Synthesis", 2nd edition, Wiley (1991). Upon successful alkylation, liberation of the desired functional group would take place based on the aforementioned reference.
1. Prepared according to the general alkylation procedure (Procedure 5). Yields of monoalkyl compounds were favored by using one equivalent of alkylating agent.
1a. Prepared by alkylating the appropriate monoalkyl compound.
2. A mixture of Example 6Z (41.3 mg, 0.069 mmole), ethanol (10 mL), hydrochloric acid (1N, 1 mL), and palladium on carbon (10%, 20 mg) was stirred at atmospheric pressure under an atmosphere of hydrogen for 16 hours. The catalyst was removed by filtration, and the filtrate was evaporated to dryness to give the desired product.
3. The compound from Example 6ZI was converted to the free base by distribution between ethyl acetate and sodium hydroxide (1N). The ethyl acetate solution was evaporated to give a residue of the free base. The free base was refluxed in excess butyl formate for 16 hours, after which the solution was evaporated to dryness to give a residue of the bis-formamide 6ZM.

Synthesis of compounds of the invention in Table 2d is described in further detail below.

EXAMPLE 9A

To a solution of bis m-(HO—N=CH)—$C_6H_4CH_2$ cyclic urea (0.297, 0.502 mmol) in methanol (5 ml) was added boranepyridine complex (0.464 g, 5.02 mmol) at −10° C. and the resultant mixture was stirred for 15 minutes. After treated with 4M HCl in dioxane (5 ml), the reaction mixture was allowed to stir to room temperature for additional 1.5 hours. The solution was neutralized with sat. $NaHCO_3$ to pH=8, washed with water and dried over $MgSO_4$. After removal of solvents, the residue was purified on silica gel plate with ethyl acetate: dichloromethane:methanol (50:50:2) to give 60 mg of a solid, M.P. 214–216° C. $^1$H NMR ($CD_3OD$): δ 8.03 (s, 1H), 7.46–7.06 (m, 18H), 4.74 (d, J=13.9 Hz, 1H), 4.73 (d J=13.9Hz, 1H), 3.92 (s, 2H), 3.62–3.59 (bs, 4H), 3.07–2.91 (m, 6H) $^{13}$C NMR ($CD_3OD$): 163.88, 149.70, 141.26, 141.23, 139.92, 139.39, 138.73, 134.91, 131.50, 131.41, 130.64, 130.00 129.72, 129.64, 129.57, 129.53, 128.47, 127.45 127.42, 127.31, 71.96, 71.92, 67.42, 67.11, 58.65, 57.09, 57.03, 33.62, 33.57, MS: 594 (100%) 595 (M+H, 60%).

EXAMPLE 9C

To a stirred solution of bis m-(HO—N=CH)—$C_6H_4CH_2$ cyclic urea (257 mg, 0.434 mmol), sodium cyanoborohydride (290 mg, 4.6 mmol) and trace amount of methyl orange in methanol (10 ml) at room temperature was added dropwise 2N HCl at a rate sufficient to maintain a pH of 3–4 over 3 hours. The methanol was removed by rotary evaporation. The residue was purified on a reverse phase TLC plate with 90% methanol in water to give the product. $^1$H NMR (CD$_3$OD): δ 7.33–7.09 (m, 18H), 4.75 (d, J=13.9Hz, 2H), 3.93 (s, 4H), 3.61–3.56 (m, 4H), 3.06–2.94 (m, 6H); $^{13}$C NMR (CD$_3$OD): 162.42, 139.72, 137.88, 137.79, 129.92, 129.20, 128.31, 128.14, 128.06, 126.02, 70.36, 65.49, 57.40, 55.59, 32.09.

EXAMPLE 9E

A solution of Example 9C (30 mg) in methanol was treated with 4M HCl in dioxane at room temperature. All solvents were removed under vacuum to give hydroxylamine hydrochloride. $^1$H NMR (CD$_3$OD): δ 7.44–7.23 (m, 14H), 6.99 (d, J=6.2Hz, 4H), 4.65 (d, J=14.3 Hz, 2H), 4.35(s, 4H), 3.70–3.66 (m, 4H), 3.12–3.05 (m, 4H), 2.89–2.85 (m, 2H); $^{13}$C NMR (CD$_3$OD): δ 163.68, 141.13, 140.39, 123.09, 132.03, 131.06, 130.59, 130.50, 129.59, 127.48, 71.82, 68.23, 57.40, 56.12, 33.70.

EXAMPLE 9B

An unpurified sample of example 9C was purified on TLC plate using acetic acid: ethyl acetate: dichloromethane (5:50:45) to give the acetic acid salt. $^1$H NMR (CD$_3$OD): δ 7.35–7.08 (m, 18H), 4.74 (d, J=13.9Hz, 2H), 3.97 (s, 4H), 3.62–3.53 (m, 4H), 3.06–2.88 (m, 6H), 1.97 (s, 6H).

EXAMPLE 9D

A solution of bis (m-CHO—C$_6$H$_4$CH$_2$) cyclic urea (119 mg, 0.212 mml) and O-benzylhydroxylamine hydrochloride (203 mg, 1.27 mmol) in pyridine/ethanol (6 ml 1:1) was refluxed for 3 hours. After removal of solvent, the residue was purified on T.L.C. plate with 15% ethyl acetate in dichloromethane to give the product (164 mg) as a solid, M.P. 170.5–171° C. $^1$H NMR (CDCl$_3$): δ 8.01 (s, 2H), 7.39–7.07 (m, 28H), 5.09 (s, 4H), 4.81 (d, J=14.3Hz, 2H), 3.59 (bs, 2H), 3.52 (d, J=11.0 Hz, 2H), 3.07–2.88 (m, 8H); $^{13}$C NMR (CDCl$_3$): 162.14, 148.55, 139.40, 138.62, 137.39, 132.50, 130.50, 129.43, 128.87, 128.62, 128.35, 128.27, 128.87, 127.57, 126.56, 126.46, 76.34, 71.32, 64.55, 55.57, 32.70; MS 790 (M+NH$_4$, 100%).

EXAMPLE 9F

By the procedure given above Example 9C, a solution of Example 9D (60 mg, 0.078 mmol), sodium cyanoborohydride (70 mg, 1.1 mml), trace amounts of methyl orange in methanol was treated with 2N HCl (approx. 0.5 ml). Purification on T.L.C. plate with 40% ethyl acetate in methylene chloride gave the product (30 mg). $^1$H NMR (CDCl$_3$): δ 8.05 (s, 1H), 7.43–7.06 (m, 28H), 5.13 (s, 2H), 4.90 (d, J=14.3Hz, 1H), 4.87 (d, J=14.3Hz, 1H), 4.61 (s, 2H), 3.98 (s, 2H), 3.59–3.49 (m, 4H), 3.07–2.95 (m, 6H). $^{13}$C NMR (CDCl$_3$): δ 161.98, 148.59, 139.48, 138.86, 138.32, 138.05, 137.74, 137.48, 132.56 130.61, 129.87, 129.51, 128.91, 128.67, 128.65, 128.44, 128.37, 128.11, 127.91, 127.86, 127.66, 126.59, 126.56, 126.40, 77.20, 76.41, 76.15, 71.52, 71.48, 64.33, 64.11, 56.26, 55.58, 55.57, 33.79, 32.47. MS: 792 (M+NH$_4$, 40%) 775 (M+H, 100%).

EXAMPLE 9G

To a suspension solution of bis (m-(HO)—C$_6$H$_4$CH$_2$) cyclic urea (280 mg, 0.52 mmol) and Cs$_2$CO$_3$ (1.5 g, 4.6 mmol) in THF (4 ml) was added methylchloroformate (122.9 mg, 1.3 mm) and the resulting mixture was stirred at room temperature overnight. The mixture was filtered through celite and concentrated to give a residue which was purified on T.L.C. plate with 15% ethyl acetate in methylene chloride to give the product (220 mg) as a solid, M.P. 146–147° C. $^1$H NMR (CD$_3$OD): δ 7.34–6.95 (m, 18m), 4.78 (d. J=14.3 Hz, 2H), 3.78 (s. 6H), 3.68 (bs, 2H), 3.61 (d, J=11.4Hz, 2H), 3.10–2.83 (m, 6H). $^{13}$C NMR (CD$_3$OD): 162.22, 154.08, 151.28 139.74, 129.28, 129.14 128.11, 126.52, 125.99, 121.63, 119.85, 70.44, 66.14, 55.46, 54.51, 32.22; MS: 655 (M+H, 100%).

EXAMPLE 9H

A solution of Example 9P (50 mg, 0.085) in methanol (2 ml) was treated with sodium borohydride (32 mg, 0.85 mmol) at room temperature overnight. After removing the solvent, the mixture is purified on T.L.C. plate with EtOAc/CH$_2$Cl$_2$ (1:1) to give a good yield of the desired product (two stereoisomers):MS=612 (M+NH$_4$+, 100%); HRMS: 595.3177 for C$_{37}$H$_{43}$N$_2$O$_5$ (M+H); $^1$H NMR (CD$_3$OD): δ 7.36–7.06 (M, 18H), 4.82 (d, J=6.3 Hz, 1H) 4.78 (d, J=6.6 Hz, 1H), 4.77 (d, J=13.9 Hz, 2H), 3.64–3.57 (m, 4H), 2.10–2.92 (m, 6 Hz), 1.41 (d, J=6.6Hz, 3H), 1.40 (d, J=6.3Hz, 3H); $^{13}$C NMR (CD$_3$OD): δ 163.93, 148.07, 141.33, 139.36, 130.69, 129.59, 129.55, 127.62, 127.59, 126.01, 125.90, 72.04, 70.60, 70.56, 67.30, 67.05, 57.27, 57.12, 33.66, 25.55.

EXAMPLE 9I

To a solution of Example 9S (100 mg) in tetrahydrofuran (1 ml) was added methyl amine (0.4 ml, 40% in water) and the resulting solution was stirred overnight. After concentration and purification on the plate, the product was obtained in good yield. $^1$H NMR (CD$_3$OD) δ 7.40 (m, 18H) 4.69 (d, J=14.3Hz, 2H) 3.93 (s, 4H) 3.66–3.64 (m, 4H) 3,35–3.02 (m, 4H) 2.90–2.81 (m, 2H) 2.52 (s, 6H); $^{13}$CNMR (CD$_3$OD) δ 163.75, 141.31, 140.86, 139.58, 130.70, 130.64, 129.79, 129.51, 129.33, 128.86, 127.41, 71.91, 67.55, 57.22, 56.21, 35.51, 33.63.

EXAMPLES 9J AND 9K

By the procedure described previously for preparation of Example 9D, and substituting b-ethanolamine and trace amounts of molecular sieves (powder) in ethanol. The reaction mixture was filtered through Celite and concentrated to give a residue, which was purified on reverse phrase T.L.C. plate with 90% methanol in water to the desired compounds.

Example 9J: $^1$H NMR (CD$_3$OD): δ 8.31 (s, 2H), 7.67 (d, J=7.7Hz, 2H), 7.59 (s, 2H), 7.43–7.03 (m, 14H), 4.74 (d, J=14Hz, 2H), 3.81–3.58 (m, 12H), 3.10–2.86 (m, 6H); $^{13}$C NMR (CD$_3$OD): 164.97, 163.73, 141.22, 140.14 137.66, 133.06, 130.65, 130.53, 130.06, 129.56, 128.50, 127.46, 71.93, 67.90, 64.26, 62.29, 57.20, 33.68, MS: 649 (M+H, 100%).

Example 9K: $^1$H NMR (CD$_3$OD): δ 8.31 (s, 1H), 7.68–7.03 (m, 18H), 5.33 (s, 1H), 4.76 (d, J=13.9Hz, 1H), 4.75 (d, J=14.3Hz, 1H), 3.81–3.55 (m, 10H), 3.12–2.7 (m, 8H); $^{13}$C NMR (CD$_3$OD): 164,97, 163.78, 141.29, 141.24, 140.18, 139.39, 137.63, 133.06, 130.67, 130.64, 130.53, 130.48, 130.05, 129.55, 129.50, 128.86, 128.49, 127.47, 127.45, 127.20, 104.35, 71.98, 67.90, 67.40, 64.25 62.39, 57.22, 57.11, 53.23, 33.67; M.S.: 649 (M+H, 100%).

EXAMPLE 9L

To a solution of Example 5I (0.7 g, 1.3 mmol) and triethylamine (0.263 g, 2.6 mmol) in THF (5 ml) was added benzyl isocyanate (0.346 g, 2.6 mmol) and the resulting solution was stirred at room temperature overnight. After removal of all the volatiles, the residue was purified on T.L.C. plate to give 0.7 g of a solid, M.P. 50° C. (decompose). $^1$H NMR (CD$_3$OD): δ 7.33–6.83 (m, 28H), 4.74 (d, J=13.9Hz, 2H), 4.30 (s, 4H), 3.64–3,57 (m, 4H), 3.13–2.91 (m, 6H); $^{13}$C NMR (CD$_3$OD): 162.54, 155.68, 151.33, 139.88, 139.30, 138.64, 129.29, 129.20, 128.24, 128.18, 127.02, 126.90, 126.13, 125.81, 122.44, 120.55, 70.44, 65.28, 55.20, 44.31, 32.28; M.S: 805 (M+H, 100%).

EXAMPLE 9M

To a solution of Example 5I (100 mg, 0.186 mmol) triethylamine (38 mg. 0.39 mmol) in THF (1 ml) was added methyl isocyanate (27 mg. 0.47 mmol) at room temperature and the resulting mixture was stirred overnight. After removal of all volatile reagents, a residue was purified on T.L.C. plate with 40% ethyl acetate in dichloromehane to give 51 mgs of a solid, M.P. 150° C. (decompose). $^1$H NMR (CD$_3$OD) δ 7.44–6.99 (m, 18H), 4.82 (d, J=14.2Hz, 2H), 3.69–3.65 (m, 4H), 3.15–2.95 (m, 6H), 2.84 (s, 6H). $^{13}$C NMR (CD$_3$OD): 163.96, 157.56, 152.92, 141.31 140.83, 130.66, 130.55, 129.58, 127.46, 127.17, 123.70, 121.95, 71.88, 67.02, 56.67, 33.65, 27.57. M.S.: 670 (M+NH, 100%).

EXAMPLE 9N

A solution of bis (m-bromobenzyl) cyclic urea (MEM-protected) (0.84 g, 1 mmol), propargyl alcohol (0.224 g, 4 mmol), tetrakis (triphenylphoshine) palladium (0.116 g, 0.1 mmol), copper iodide (0.019 g, 0.1 mmol) in triethylamine (5 ml) was refluxed under nitrogen overnight. After evaporation of all volatiles, a residue was diluted with ether (20 ml) and filtered through Celite. The filtrate was concentrated and purified on T.L.C. plate to give 400 mg of MEM-protected-mono/coupling product. Deprotection of 170 mg of the coupled product by the standard procedure gave 130 mg of the desired product. $^1$H NMR (CD$_3$OD): δ 7.50–7.09 (m, 18H), 4.72 (d, J=13.9Hz, 1H), 4.69 (d, J=13.4Hz, 1H), 4.46 (s, 2H), 3.75–3.68 (m, 4H), 3.18–2.86 (m, 6H). $^{13}$C NMR (CD$_3$OD): 163.61, 141.99, 141.07, 139.73, 133.64, 133.54, 131.91, 131.76, 131.47, 130.57, 130.50, 129.81, 129.59, 129.19, 127.51, 124.69, 123.46, 89.28, 85.09, 71.93, 71.91, 68.12, 67.75, 57.07, 57.03, 51.15, 33.60, 33.59; M.S.: 639/641 (M+H, 100%), 656/658 (M+NH$_4$, 100%).

EXAMPLES 9O AND 9P

A solution of bis (m-Br-C$_6$H$_4$CH$_2$) cyclic urea (425, mg, 0.64 mmol), 1-ethoxy-1-trimethylstannyl ethylene (833 mg, 3.84 mmol) and Pd(PPh$_3$)$_4$ (37 mg, 0.032 mmol) in THF (5 ml) was refluxed under N$_2$ overnight. After cooling to room temperature, the reaction mixture was diluted with ether (10 ml) and filtered through silica gel to give two products. Further purification on T.L.C. plate with 20% ethyl acetate in methylene chloride gave Example 9O (107 mg, M.P. 190–191° C.) and Example 9P (225 mg, M.P. 158–159° C.).

Example 9O: $^1$H NMR (CDCl$_3$): δ 7.78 (d, J=7.3Hz, 1H), 7.71 (s, 1H), 7.42–7.02 (m, 16H), 4.81 (d, J=13.9Hz, 1H), 4.77 (d, J=13.9H, 1H), 3.71 (bs, 2H), 3.62–3.54 (m, 2H), 3.20–2.85 (m, 8H), 2.50 (s, 3H); $^{13}$C NMR (CDCl$_3$): 198.27, 161.86, 140.38, 139.29, 139.22, 138.81, 137.22, 133.99, 132.36, 130.65, 130.09, 129.36, 129.32, 128.99, 128.86, 128.66, 127.70, 127.55, 126.61, 122.53, 71.38, 65.24, 65.12, 55.83, 55.59, 32.77, 26.58, M.S: 644/646 (M+NH$_4$, 100%).

Example 9P: $^1$H NMR (CDCl$_3$): δ 7.78–7.03 (m, 18H), 4.83 (d, J=14.3Hz, 2H), 3.73–3.62 (m, 4H), 3.17–3.08 (m, 4H), 2.92–2.89 (m, 2H), 2.49 (s, 6H); $^{13}$C NMR (CDCl$_3$): 198.03, 161.83, 139.40, 138.78, 137.12, 133.87, 129.29, 129.04, 128.74, 128.52, 127.36, 126.46, 71.25, 71.15, 65.32, 55.82, 30.73, 26.51; M.S.: 608 (M+NH$_4$, 100%).

EXAMPLE 9Q

A solution of Example 9P (84 mg, 0.142 mmol) and hydroxylamine hydrochloride (59.4 mg, 0.854 mmol) in pyridine/ethanol (6 ml, 1:1) was refluxed overnight. Evaporation of all solvents under vacuum gave a residue which was purified on preparative T.L.C. plates with ethyl acetate: methylene chloride: methanol (50:50:2) to give 71 mg of a solid, M.P. 200–202° C. $^1$H NMR (CD$_3$OD): δ 7.67–7.07 (m, 18H), 4.74 (d, J=13.9Hz, 2H), 3.64–3.62 (m, 4H), 3.09–2.89 (m, 6H), 2.17 (s, 6H); $^{13}$C NMR (CD$_3$OD): 163.94, 155.43, 141.23, 139.46, 138.97, 130.77, 130.65, 129.69, 129.37, 128.10, 127.47, 126.32, 72.02, 67.16, 57.08, 33.62, 11.96; M.S.: 621, (M+H, 100% ).

EXAMPLE 9R

A solution of Example 9Q (50 mg, 0.066 mmol) in methanol (2 ml) was treated with sodium borohydride (25 mg, 0.66 mmol). After the reactions was completed, the mixture was washed with hydrochloric acid(2N), water and dried with magnesium sulfate. Concentration gave a residue which was purified to give a good yield of the desired product: MS 629.2015 for C$_{31}$H$_{38}$N$_2$OrBr; $^1$H NMR (CD$_3$OD); δ 7.42–7.01 (m, 18H), 4.79–4.60 (m, 3H), 3.65–3.58 (m, 4H), 3.08–2.78 (m, 6H), 1.40–1.37 (m, 3H); $^{13}$CNMR (CD$_3$OD): δ 163.73, 148.11, 142.08, 141.19, 139.26, 133.64, 131.75, 131.45, 130.61, 129.62, 129.57, 129.19, 129.15, 127.61, 127.49, 127.17, 126.05, 123.46, 72.06, 71.92, 70.59, 68.20, 6.27, 57.12, 57.04, 53.68, 25.55.

EXAMPLE 9S

Prepared according to the general alkylation and deprotection procedures (see Procedure 5) MS: 603.2163 (M+H$^+$), 100%); HR Mass Spec: 603.2163 for C$_{35}$H$_{37}$N$_2$O$_3$Cl$_2$ (M+H); $^1$HNMR (CD$_3$OD) δ 7.39–7.02 (m, 18H), 4.68 (d, J=14.3 H$_2$, 2H), 4.55 (s, 4H), 3.65–3.59 (m, 4H), 3.09–3.04 (m, 2H), 3.00 (d, J=14.3 H$_2$, 2H), 2.93–2.84 (m, 2H), $^{13}$HNMR (CD$_3$OD, ppm): 162.26, 139.74, 138.47, 138.16, 129.35, 129.16, 128.82, 128.48, 128.09, 127.38, 125.97, 70.47, 66.14, 55.69, 45.19, 32.20.

EXAMPLE 15XC

A solution of Example 9S (100 mg., 0.166 mmol) in tetrahydrofuran (1 ml) was treated with methyl amine (40% in H$_2$O, 1 ml) and the resulting solution was stirred at room temperature overnight. After the solution was concentrated on a rotary evaporator, the residue was obtained and was purified on Prep. T.L.C. to give a good yield of a neutral product which was acidified with 4M HCl in ether to give the desired product. MS: 593 (M+H$^{30}$, 100%); HRMS: 593.2483 for C$_{37}$H$_{45}$N$_4$O$_3$; $^1$H NMR (CD$_3$OD) δ 7.38–7.07 (m, 18H), 4.69 (d, J=14.3 Hz, 2H), 3.93 (s, 4H), 3.66–3.64 (m, 4H), 3.09–3.02 (m, 4H), 2.90–2.81 (m, 2H), 2.52 (s, 6H); $^{13}$CNMR (CD$_3$OD, ppm) 163.75, 141.30, 140.85, 139.58, 130.70, 130.64, 129.79, 129.51, 129.32, 128.85, 127.41, 71.91, 67.55, 57.22, 56.21, 35.50, 33.63.

EXAMPLE 15XE

To a suspension of NaH (240 mg, 60% in mineral oil, 6 mmol) in DMF (4 mL) was added MEM-protected Example 11N (694 mg. 0.98 mmol), and 3-chloromethylpyridine (492 mg., 3 mmol); and the resulting mixture was stirred at room temperature overnight. After the reaction mixture was filtered through Buchner funnel, the filtrate was treated with 4M HCl in dioxane(15 ml) for 16 hours and then was neutralized with sat. NaHCO$_3$, to pH=7. After general workup, the resulting crude was purified on T.L.C. plate using ethyl acetate to give the product in a good yield. MS: 538 (M+H$^+$, 100%); HRMS 538.2693 for C$_{33}$H$_{36}$O$_4$N$_3$ $^{13}$C NMR (CD$_3$OD) ppm 163.67, 151.07, 149.16, 141.11, 139.33, 135.91, 130.59, 130.51, 130.48, 129.62, 128.53, 138.24, 127.51, 127.47, 135.28, 71.96. 71.80, 68.68, 66.98, 64.81, 56.71, 55.10, 33.73, 33.66.

EXAMPLE 15XF

To a solution of Example 9S (100 mg, 0.166 mmol) in DMF (2 ml) was added K$_2$CO$_3$ (138 mg, 1.0 mmol) and diethylamine hydrochloride (80 mg, 1.0 mmol) and the resulting mixture was stirred for 24 hrs. The mixture was diluted with EtOAc and washed with water. After the organic layer was dried over MgSO$_4$, the solution was concentrated under vacuum to give 70 mg. of the product. MS: 677 (M+H, 100%); HRMS: 677.4444 for C$_{43}$H$_{57}$N$_4$O$_3$; $^1$H NMR (CDCl$_3$): δ 7.26–6.96 (m, 18H), 4.84 (d, J=14.3 Hz, 2H), 3.50–3.46 (m, 4H), 3.35 (s, 4H), 2.97–2.78 (m, 6H), 2.36 (q, J=6.9 Hz, 4H), 0.90 (t, J=6.9 Hz, 6H), $^{13}$C NMR (CDCl$_3$,) δ 161.98, 139.52, 138.52, 138.17, 129.99, 129.46, 128.46, 128.25, 128.84, 127.84, 126.30, 71.09, 64.23, 56.98, 55.54, 46.42, 32.62, 11.31.

EXAMPLE 15XG

The experimental procedure is similar as preparation of Example 15XF. MS: 667. (MtH, 100%); HRMS: 667.3394 for C$_{41}$H$_{43}$N$_6$O$_3$; $^{13}$C NMR (CD$_3$OD, ppm): 163.76, 141.27, 141.21, 138.82, 130.62, 130.28, 129.70, 129.56, 127.88, 127.45, 71.93, 67.37, 57.11, 51.36, 33.75; $^1$H NMR (CD$_3$OD): δ 7.69, (s, 2H), 7.35–6.92 (m, 22H), 5.19 (s, 4H), 4.62 (d, J=14.3 Hz, 2H), 3.52–3.50 (m, 4H), 3.03–2.70 (m, 6H).

EXAMPLE 15XH

To a solution of MEM-protected Example 4P (366 mg, 0.5 mmol) in THF (15 mL) at −78° C. was dropwise added $^t$Buli (1.7 M, 2.59 ml, 4.4 mmol), and the resulting solution was allowed to warm to room temperature. The mixture was diluted with ether washed with saturated NH$_4$Cl, water, and dried ever MgSO$_4$. After concentrated on a rotary evaporator, a residue was obtained and was purified on T.L.C. plate with 10% EtOAc in CH$_2$Cl$_2$ to give a good yield of the product; MS: 675.5 (M+H), 100%); HRMS: 675.3805 for C$_{43}$H$_{51}$N$_2$O$_5$; $^1$H NMR (CDCl$_3$): δ 7.56–7.54 (m, 2H), 7.43 (s, 2H), 7.33–7.25 (s, 10H), 7.08–7.06 (m, 4H), 4.88 (d, J=14.3 Hz, 2H, 3.64–3.53 (m, 4H), 3.09–2.87 (m, 6H), 1.29 (s, 18H); $^{13}$C NMR (CDCl$_3$): δ 209.24, 161.87, 139.35, 139.05, 138.23, 131.66, 129.43, 128.70, 128.36, 126.96, 126.62, 71.58, 64.76, 55.80, 44.21, 32.89, 27.94.

EXAMPLE 15XI

To a solution of trifluoromethyl trimethylsilane (312 mg. 2.2 mmol), in THF (3 ml) in an ice-water bath was added a solution of MEM-protected Example 5V (400 mg, 0.55 mmol) in THF (2 mL); and then to the resulting solution was added tetrabutylammonium fluoride catalyst (TBAF, 3 mg, 0.011 mmol. After the reaction mixture was stirred at 0° C. for 40 min., the cooling bath was removed and the reaction mixture was brought to room temperature and was continued for an additional hour. The reaction mixture was then treated with 4M HCl in dioxane (5 mL) overnight. General workup and purification on TLC plate with 20% EtOAc in CH$_2$Cl$_2$ to furnish a quantitative yield of Example 15XI: MS: 703 (M+H, 100%); HRMS: 703.2611 for C$_{37}$H$_{37}$N$_2$O$_5$F$_6$; $^{13}$C NMR (CDCl$_3$, ppm) 162.40, 139.70, 138.02, 135.76, 129.61, 129.18, 128.30, 128.14, 126.74, 126.58, 126.03, 71.39 (q, J=32.4 Hz), 70.55, 65.88 (d, J=6.2 Hz), 55.66, 32.12; $^{19}$F NMR (CDCl$_3$) 79.72 (q.J =6.0 H$_2$); $^1$H NMR (CDCl$_3$): δ 7.83–7.04 (m, 18H), 5.01–4.98 (m, 2H), 4.72 (d, J=14.2 Hz, 2H), 3.67–3.58 (m, 4H), 3.09–2.92 (m, 6H).

EXAMPLE 15XJ

To a solution of N-SEM protected imidazole (552 mg., 2.78 mmol) in THF (10 ml) at −78° C. was added n-Buli (1.6M, 2.5 mL, 4 mmol) dropwise and the resulting solution was allowed to warm to −20° C. over one hour. After a solution of MEM-protected 5V(510 mg., 0.697 mmol) in THF (10 mL) was added, the reaction mixture was allowed to warm to room temperature and was stirred for an additional hour. Workup by general procedure and purification on T.L.C. plate with 50% ether in CH$_2$Cl$_2$ gave an oily intermediate (160 mg., 21.3% of yield), which was deprotected with 4M HCl in dioxane to give the product in good yield: MS: 695 (M+H, 100%); HRMS: 695.2977 for C$_{41}$H$_{39}$N$_6$O$_5$, $^{13}$C NMR (CD$_3$OD, ppm): 183.16, 164.07, 146.27, 141.34, 139.59, 137.92, 135.08, 133.06, 130.70, 130.53, 120.74, 120.57, 127.45, 71.92, 66.93, 56.72, 33.72; $^1$H NMR (CD$_3$OD): δ 8.50 (s, 2H), 8.29–8.27 (m, 2H), 7.61–7.21 (m, 18H), 4.94 (d, J=14.3 Hz, 2H), 3.77–3.72 (m, 4H), 3.20–3.09 (m, 6H).

EXAMPLE 15XK

A solution of Example 15XE in MeOH was acidified with 4M HCl in dioxane to give the product: $^1$H NMR (CD$_3$OD): δ 8.58 (d, J=1.1 Hz, 2H), 8.42 (dd, J,=1.1 Hz, J=4.0 Hz, 1H), 7.78 (bs, 1H), 7.30–7.00 (m, 12H), 6.78 (d, J=6.4 Hz, 2H), 4.61 (d, J=14.2 Hz, 1H), 4.32 (dd, J=39.8 Hz, J=14.2 Hz, 2H), 4.03–3.99 (m, 1H), 3.71–3.62 (m, 4H), 3.21 (d, J=13.2 Hz, 1H), 3.02–2.90 (m, 4H), 2.72–2.66 (m, 1H), $^{13}$C NMR (CD$_3$OD, ppm) 163.80, 148.66, 143.75, 142.32, 141.38, 140.85, 140.44, 137.59, 130.46, 129.60, 129.54, 128.43, 128.20, 127.66, 127.53, 71.54, 70.84, 68.41, 67.56, 64.67, 56.67, 54.02, 34.36, 33.05.

EXAMPLE 15XL

The experimental procedures is similar as preparations Example 9N: MS: 632 (M+N14, 100%); HRMS: 615.2853 for C$_{39}$H$_{39}$N$_2$O$_5$; $^1$H NMR (CD$_3$OD): δ 7.32–6.99 (M, 18H), 4.82 (d, J=1.3 Hz, 2H), 4.65 (d, J=13.9 Hz, 2H), 4.37 (s, 2H), 3.31–3.30 (m, 4H); 3.08–3.04 (m, 2H), 3.98 (d, J=13.9 Hz, 2H), 2.89–2.84 (m, 2H).

EXAMPLE 15XM

To a solution of MEM-protected-m-iodobenzyl cyclic urea (980 mg., 1.07 mmol) in THF (10 ml) at −78° C. was added t-BuLi (1.7M in hexane, 2.64 mL, 4.5 mmol) and the resulting solution was stirred for another 30 mins. The N,N-dimethyl trifluoroacetamide (560 mg., 4 mmol) was added and the mixture was stirred for 2.5 hours. The mixture was diluted with ether and acidified with 2N HCl to pH=1. The ether layer was neutralized and washed with water, brine, and dried over MgSO$_4$. The solution was concentrated to give a residue which was purified on silica gel column with gradient solvents (0–20% ethyl acetate in CH$_2$Cl$_2$) to give an oily intermediate (350 mg).

The oil was dissolved in CH$_2$Cl$_2$ (5 ml) and was treated with 4M HCl in dioxane overnight. General workup and purification on Prep. T.L.C. plate with 40% EtOAc in $CH_2Cl_2$ gave the the product (300 mg) in 40.2% yield. MS: 699.4 (M+H, 100%); HRMS: 699.2286 for $C_{37}H_{33}N_2O_5F_6$; $^1$H NMR ($CD_3COCD_3$): δ 7.97 (bs, 4H), 7.73–7.59 (m, 4H), 7.14–6.96 (m, 10H), 4.75 (d, J=13.9 Hz, 2H), 3.72–3.63 (m, 4H), 3.32 (d, J=14.3 Hz, 2H), 3.18–3.13 (m, 2H), 2.95–2.79 (m, 4H); $^{19}$FNMR ($CD_3COCD_3$): δ 72.54; $^{13}$C NMR ($CD_3COCD_3$) 180.83 (q, J=34.3 Hz), 162.39, 141.27, 141.06, 137.90, 131.60, 130.43, 130.35, 130.23, 129.73, 129.16, 127.05, 117.62 (q, J=291.4 Hz), 71.83, 67.40, 56.55, 33.59.

EXAMPLE 15XN

To a solution of MEM-protected 4P (750 mg, 1.02 mmol) in THF (20 mL) was added ethyl magnesium bromide (2M in $Et_2O$, 4 mL) and the resulting mixture was allowed to reflux for 2 hours. After removing all solvents on rotary evaporator, the resulting residue was dissolved in MeOH (15 mL) and was treated with 4M HCl in dioxane overnight. After general workup and purification on T.L.C. plate with 40% EtOAc in $CH_2Cl_2$. Example 15XN was obtained (600 mg) in 95.2% yield. MS: 636 (M+N $H_4$, 100%); HRMS: 619.3181 for $C_{39}H_{43}N_2O_5$; $^1$H NMR ($CDCl_3$): δ 7.77–7.71 (m, 4H), 7.39–7.22 (m, 10H), 7.06–7.03 (m, 4H), 4.83 (d, J=14.3 Hz, 2H), 3.75 (bs,2H) 3.64–3.60 (m, 2H), 3.53 (s, 2H), 3.14 (d, J=14.31 Hz, 2H), 3.10 (d, J=11.6 Hz, 2H), 2.95–2.86 (m, 2H), 2.87 (q, J=7.3 Hz, 4H), 1.12 (t, J=7.3 Hz, 6H); $^{13}$C NMR ($CDCl_3$, ppm) 200.85. 161.88, 139.36, 138.72, 136.92, 133.70, 129.31, 128.75, 128.66, 128.54, 127.09, 126.50, 71.28, 65.28, 55.84, 32.70, 31.70, 8.04.

EXAMPLE 15XP

The experimental procedure of Note 5, Table 2D was followed: MS: 649 (M+H$^+$, 100%); $^1$H NMR ($CD_3OD$): δ 7.62–7.08 (m, 18H), 4.76 (d, J=13.9 Hz, 2H), 3.63–3.60 (m, 4H), 3.10–2.91 (m, 4H), 2.97 (d, J=13.9 Hz, 2H), 2.78 (q, J=7.7 Hz, 4H), 1.06 (t, J=7.7 Hz, 6H); $^{13}$C NMR($CD_3OD$, ppm) 162.46, 158.95, 139.71, 138.00, 136.45, 129.31, 129.17, 128.29, 128.11, 126.81, 126.02, 125.09, 70.53, 65.63, 55.57, 32.17, 18.67, 9.88.

EXAMPLE 15XO

To a solution of MEM-protected-m-iodobenzyl cyclic urea (1 g, 1.07 mmol) in THF (15 mL) at −78° C. was dropwise added t-Buli (1.7M in hexane, 2.5 mL) and the resulting solution was stirred for another 30 minutes. Sulfur dioxide gas was introduced into the basic solution at the same temperature for 15 mins. The mixture was allowed to warm to R.T. over 2 hours and then was cooled to −78° C. again. Sulfuryl chloride (0.72g., 5.35 mmol) was added and the resulting mixture was allowed to warm to R.T. and stirred overnight. After all volatile reagents and solvents were removed under vacuum, the residue was dissolved in THF (10 mL) at −60° C. and was treated with excess ammonia gas for 10 minutes. The final mixture was diluted with EtOAc and washed with water, brine and dried over anhydrous $MgSO_4$ followed by filtration. The solvents were removed on a rotary evaporator and the residue was deprotected by general procedure. Finally, the crude was purified on T.L.C. plate and further purified on HPLC to give the desired product in moderated yield. MS: 682 (M+$NH_4$, 10%); HRMS: 665.2103 for $C_{33}H_{37}N_4O_7S_2$; $^{13}$C NMR ($CD_3CCD_3$, ppm) 162.33, 145.25, 141.16, 140.81, 133.59, 130.38, 129.86, 129.21, 127.77, 126.95, 125.85, 71.87, 67.52, 56.78, 33.56; $^1$H NMR ($CD_3OD$): δ 8.19–7.32 (m, 18H), 5.06 (d,=14.3 Hz, 2H), 4.08–3.95 (m, 4H), 3.49–3.16 (m, 6H).

EXAMPLE 15XR

The experimental procedure in Note 5 of Table 2d was followed. MS: 745 (M+18, 100%); HRMS: 729.2500 for $C_{37}H_{35}N_4O_5N_6$; $^1$H NMR ($CD_3OD$): δ 7.47–7.39 (m, 6H), 7.29–7.24 (m, 8H), 7.06–7.03 (m, 4H), 4.71 (d, J=13.9 Hz, 2H), 3.66 (s, 2H), 3.62 (d, J=11.7 Hz, 2H), 3.08 (d, J=12.5 Hz, 2H), 2.98 (d, J=14.2 Hz, 2H), 2.95–2.89 (m, 2H), $^{13}$C NMR ($CD_3OD$, ppm) 163.87, 141.26, 139.71, 132.08, 131.04, 130.64, 129.75, 129.56, 128.95, 128.92, 127.45, 122.57 (q, J=273.1 Hz), 72.02, 67.42, 57.02, 33.67; $^{19}$F NMR ($CD_3OD$) 67.75.

EXAMPLE 15XS

The experimental procedure of Note 5, Table 2D was followed. The obtained product was further purified on chiral-HPLC to give the product: MS: 621 (M+H$^+$, 100%); $^1$H NMR [$CDCl_3$+$CD_3OD$ (1:1)]: δ 7.26–6.76 (m, 18H), 4.47 (d, J=14.3 Hz, 2H), 3.24–3.03 (m, 4H), 2.76–2.56 (m, 6H,) 1.86 (s, 6H); $^{13}$C NMR [$CDCl_3$+$CD_3OD$ (1:1), ppm] 163.28, 155.56, 140.48, 138.78, 138.18, 130.34, 130.09, 129.22, 129.12, 127.62, 127.04, 125.84, 71.45, 66.00, 56.42, 33.15, 12.25;

EXAMPLE 15YG

To a stirred mixture of cyclic urea Example 5I (Table 2c) (300 mg, 0.56 mmol) and anhydrous cesium carbonate (912 mg, 2.8 mmol) in dioxane, free base of N-(2-chloroethyl) morpholine (2.5 g, 16.8 mmol) was added (prepared by dissolving 3.1 g of the hydrochloride in 5 mL of water and 5 mL of sat'd $NaHCO_3$, extracting with 100 mL of Hexane, drying over $MgSO_4$, and concentrating) (Thompson; et al. *J. Med. Chem.* 1992, 35, 1698) and heated up to 80° C. for 2 days. The mixture was filtered, rinsed with chloroform and purified on silica gel (1:5 Methanol:Chloroform) to give 339 mg (79%) pure product. M. P. 110–112° C. M. S. 765 (M+1, 100%).

EXAMPLE 15YH

The intermediate was prepared by alkylating the appropriate monoalkylated compound with m-cyanobenzyl chloride. Lithium aluminum hydride (158 mg, 4.18 mmol) was added to $AlCl_3$ (180 mg, 1.39 mmol) in ether at 0° C. The mixture was warmed up to RT and stirred for 15 min. Then a solution of the above intermediate (950 mg, 1.16 mmol) in ether was added dropwise. The mixture was stirred at RT for 1 h, quenched with 1 mL of $H_2O$, 1 mL of 5% NaOH and washed with $H_2O$, sat'd NaCl and dried over $MgSO_4$. Following the same hydrolysis procedure, the product was isolated (70 mg) in 10% yield. M. P. 132–134° C. M.S. 566 (M+1, 100%).

EXAMPLE 15YT

To the mixture of 1 mL of DMF and 4 mL $CH_2Cl_2$, oxalyl chloride (0.72 mL, 2M in $CH_2Cl_2$) was added dropwise at −20° C. under $N_2$. After 20 min, 500 mg (0.65 mmol) of bis(N-m-benzoic acid) cyclic urea Example 6A (Table 2c) and 0.14 mL (2 mmol) of N-methyl-morpholine were added. The mixture was stirred at −20° C. for 20 min. N-methylhydroxylamine hydrochloride (217 mg, 4 mmol) and an additional 0.56 mL (8 mmol) of N-methylmorpholine were added. The reaction mixture was diluted with ethyl acetate, washed with cold 5% HCl, sat'd $NaHCO_3$, $H_2O$, brine and purified on silica gel (1:95 Methanol:chloroform). Following the same hydrolysis procedure, the product (80 mg) was isolated in 20% yield. M. P. 223–224° C.

EXAMPLE 15YJ

Using an analogous procedure to that reported by Paul Unangst, et al. (in *J. Med. Chem.* 1992, 35, 3691–3698) the title compound can be prepared from the hydroxyamidine. To a stirred solution of hydroxyamidine analog (150 mg, 0.19 mmol) containing triethylamine (0.13 mL, 0.95 mmol), ethyl chloroformate in 10 mL chloroform was added dropwise at 0° C. The mixture was stirred at RT for 2 h and washed with water, brine and dried over $MgSO_4$. The residue was purified on silica gel (1:1 ethyl acetate:methylene chloride). The product (137 mg, 76% yield) was isolated as ester intermediate.

To the above ester intermediate, toluene was added and the solution was heated up to 110° C. for 48 h. The solvent was removed on rotary evaporator. Following the same hydrolysis procedure. The product (45 mg) was isolated in 35% yield. M. P. 223–224° C. (decomp.).

EXAMPLE 15YF

A solution of bis(N-m-benzaldehyde) cyclic urea Example 5V (Table 2c) (120 mg, 0.21 mmol) containing small amount of 3A molecular sieves was treated with toluenesulfonylhydrazide dropwise at 0° C. under $N_2$. The mixture was stirred at RT for overnight. The solvent was removed on rotary evaporator and purified on silica gel (1:4 ethyl acetate:methylene chloride) to give 92 mg (52%) pure product. M. P. 169–171° C.

EXAMPLE 15YK

To a solution of N-SEM-imidazole (396 mg, 2 mmol) in THF (10 mL) at −78° C. was added n-BuLi (5 mmol, 3.1 mL) dropwise and the resultant mixture was stirred for 30 minutes, and to this was added a solution of zinc chloride (410 mg, 3 mmol) in THF (5 mL). After the resulting solution was allowed to warm to room temperature, a solution of m-iodobenzyl cyclic urea (466 mg, 0.5 mmol) in THF (2 mL) and $Pd(PPh_3)_4$ (77 mg, 0.07 mmol) were added under nitrogen and resultant mixture was allowed to reflux overnight. Work-up and deprotection by general procedure, followed by purification on TLC plate with 50% EtOAc in $CH_2Cl_2$ gave Example 15YK as a solid. $^1H$ NMR ($CD_3OD$) δ 7.74–7.09 (m, 22H), 5.34 (s, 2H), 4.84 (d, J=13.3 Hz, 1H), 4.68 (d, J=14.3 Hz, 1H), 3.76–3.69 (m, 4H), 3.60 (t, J=8.0 Hz, 2H), 3.18–3.03 (m, 4H), 2.96–2.88 (m, 2H), 0.90 (t, J=8.0 Hz, 2H), 0 00 (s, 9H); $^{13}C$ NMR ($CD_3OD$): ppm 164.91, 150.71, 143.28, 142.52, 142.43, 141.37, 141.11, 139.14, 135.08, 135.06, 134.43, 134.33, 133.13, 132.84, 132.72, 132.34, 131.96, 131.38, 131.35, 131.22, 131.03, 130.94, 130.91, 130.84, 129.79, 128.84, 128.80, 124.79, 96.36, 77.82, 73.27, 73.24, 69.49, 68.97, 68.84, 58.54, 58.32, 35.16, 34.91, 19.94, 0.00.

EXAMPLE 15YL

To a solution of N-SEM protected pyrazole (1.98 g., 10 mmol) in THF (40 mL) at −78° C. was added n-BuLi (1.6 M, 7.5 mL, 12 mmol) dropwise and the resulting solution was stirred for an additional half hour, and then triisopropylborate (9.4 g, 50 mmol) was added. After being allowed to warm to room temperature over 2 hours, the reaction mixture was acidified with 2 N HCl, extracted with ether, washed with water and brine, and dried over $MgSO_4$. Filtration and concentration gave N-SEM-3-hydroxyboricpyrazole (2.4 g, 100%) as a solid. $^1H$ NMR ($CD_3OD$) δ 7.57 (s, 1H), 6.80 (s, 1H), 5.70 (s, 2H), 3.57 (t, J=7.8 Hz, 2H), 0.89 (t, J=8.0 Hz, 2H), 0.00 (s, 9H); $^{13}C$ NMR ($CD_3OD$): ppm 138.54, 115.65, 78.98, 65.98, 17.31, −2.30.

To a solution of m-iodobenzyl cyclic urea (932 mg, 1 mmol) in THF (5 mL) was added N-SEM-3-hydroxyboricpyrazole (968 mg, 4 mmol), $Pd(PPh_3)_4$ (57.8 mg, 5%) and $Na_2CO_3$ (1.7 g in $H_2O$ (4 mL) under nitrogen and the resultant mixture was allowed to reflux over 48 hours. The organic layer was concentrated on rotary evaporatior to give a residue, which was deprotected by the general procedure, followed by purification on TLC plate with 20% EtOH in hexane to give Example 15YL (560 mg, 87.8%) as a solid. MS 639 (M+H⁺, 100%); HRMS calcd for $C_{39}H_{39}N_6O_3$ 639.3084, Found 639.3081; $^1H$ NMR ($CD_3OD$) δ 7.76–7.69 (m, 6H), 7.45–7.15 (m, 14H), 6.66 (s, 2H), 4.87 (d, J=14.3 Hz, 2H), 3.77 (b, 4H), 3.19–2.98 (m, 6H); $^{13}C$ NMR ($CD_3OD$) ppm 162.82, 140.19, 139.01, 129.67, 129.22, 128.96, 128.59, 127.06, 126.49, 125.03, 102.41, 71.02, 66.69, 56.37, 32.65.

EXAMPLE 15YM

A solution of Example 15YL (200 mg) in methanol (5 mL) was treated with HCl gas for 2 seconds and the solvent was removed under full vacuum to give Example 15YM as a solid. $^1H$ NMR ($CD_3OD$) δ 8.34–8.32 (m, 2H), 7.76–7.74 (m, 2H), 7.73–7.66 (m, 2H), 7.55–7.50 (m, 4H), 7.15–7.09 (m, 8H), 6.89–6.86 (m, 4H), 4.58 (d, J=13.9 Hz, 2H), 3.88–3.78 (m, 4H), 3.32 (d, J=13.9 Hz, 2H), 3.08–3.04 (m, 2H), 2.78–2.69 (m, 2H); $^{13}C$ NMR ($CD_3OD$) ppm 161.86, 147.23, 139.72, 139.50, 135.07, 132.00, 129.53, 129.04, 128.00, 127.92, 126.03, 125.97, 125.74, 104.78, 70.21, 67.75, 56.28, 32.27.

EXAMPLE 15YN

To a solution of N-SEM protected pyrazole (780 mg., 3.9 mmol) in THF (40 mL) at −78° C. was added t-BuLi (1.7 M, 2.8 mL, 4.7 mmol) dropwise and the resulting solution was stirred for an additional 30 minutes. The solution was transferred to another solution of MEM-protected m-cyanobenzyl cyclic urea (732 mg., 1 mmol) in THF (10 mL) at −78° C. and the resulting reaction mixture was allowed to warm to room temperature and was stirred overnight. After evaporation of all volatiles, the residue was diluted with methanol (20 mL) and then treated with 4M HCl in dioxane (20 mL) overnight. Workup by general procedure and purification on reverse phase T.L.C. plate with 70% MeOH in $H_2O$ gave Example 15YN in good yield: MS: 695 (M+H, 100%); HRMS calcd for $C_{41}H_{39}N_6O_5$ 695.2983, Found 695.2967; $^{13}C$ NMR ($CD_3OD$): ppm 183.16, 164.07, 146.27, 141.34, 139.59, 137.92, 135.08, 133.06, 130.70, 130.53, 120.74, 120.57, 127.45, 71.92, 66.93, 56.72, 33.72; $^1H$ NMR ($CD_3OD$) δ 8.50 (s, 2H), 8.29–8.27 (m, 2H), 7.61–7.21 (m, 18H), 4.94 (d, J=14.3 Hz, 2H), 3.77–3.72 (m, 4H), 3.20–3.09 (m, 6H).

EXAMPLE 15BI

A solution of MEM-protected compound 12J (0.94 g, 1.0 mmol) was treated with n-BuLi (1.6 M, 1.6 mL) at −78° C. for 20 minutes, followed by quenching with N-methoxy-N-methyl benzyloxyacetamide (1.35 g, 6 mmol), prepared by a reaction of benzyloxyacetyl chloride with N-methoxy-N-methylamine in pyridine and $CH_2Cl_2$ at room temperature. Removal of MEM-groups by general hydrolysis procedure followed by purification by preparative T.L.C. gave compound 15BI in moderate yield. $^1H$ NMR ($CDCl_3$) δ 7.72–7.66 (m, 4H), 7.42–7.00 (m, 24H), 4.79 (d, J=14.6 Hz, 2H), 4.64 (s, 2H), 4.57 (d, J=2.5 Hz, 2H), 3.71–2.82 (m, 14H); $^{13}C$ NMR ($CDCl_3$) δ 196.08, 161.84, 139.30, 138.95, 136.89, 134.40, 129.45, 129.40, 129.29, 128.92, 128.58, 128.48, 128.02, 127.96, 126.97, 126.54, 73.26, 72.29, 71.12, 65.40, 55.82, 32.72; HRMS: calcd. for $C_{51}H_{51}N_2O_7$: 803.3696; found 803.3693.

EXAMPLE 15BJ

To a solution of SEM protected imidazole (2 g) in THF (20 mL) was added t-BuLi (1.7 M, 6.9 mL) at −78° C. and the mixture was stirred for 20 minutes. After addition of TMSCl (1.25 g), the resulting mixture was allowed to warm to 0° C. over 2 hours, and then cooled to −78° C. again. The mixture was treated with t-BuLi (1.7 M, 6.9 mL), stirred for 20 minutes, followed by addition of B(OMe)$_3$ (10.4 g). The reaction mixture was warmed to room temperature and stirred overnight. The reaction was poured into EtOAc/H$_2$O and the organic layer was washed to PH 7, dried with NaSO$_4$, and purified on column with MeOH to give pure N-SEM-5-borono-imidazole (2.3 g 95%) as a solid. $^1$H NMR (CD$_3$OD) δ 7.63 (d, J=0.74 Hz, 1H), 6.87 (d, J=1.1 Hz, 1H), 5.47 (s, 2H), 3.55 (t, J=8.4 Hz, 2H), 0.93 (t, J=8.4 Hz, 2H), 0.00 (s, 9H); $^{13}$C NMR (CD$_3$OD) δ 138.97, 134.54, 77.89, 68.00, 20.19, 0.00.

A solution of the borono-imidazole prepared above (1.3 g, 5.37 mmol), MEM-protected cpd 12J (0.937 g, 1.01 mmol), Pd(Ph$_3$P)$_4$ (0.18 g, 0.16 mmol) and K$_2$CO$_3$ (7.5 g) in THF (20 mL) and H$_2$O (20 mL) was degassed, and then was heated to reflux under N$_2$ overnight. The reaction mixture was cooled to room temperature and partitioned between EtOAc/H$_2$O. The organic layer was dried over MgSO$_4$ and concentrated to give a residue, which was deprotected by general hydrolysis procedures and purified on T.L.C. plate with 5% MeOH in EtOAc to give the coupling product, 15BJ (0.4 g, 37.2%). $^1$H NMR (CD$_3$OD) δ 7.97 (s, 2H), 7.61–7.11 (m, 20H), 5.37 (s, 4H), 4.83 (d, J=13.9 Hz, 2H), 3.78–3.73 (m, 4H), 3.59 (t, J=8.0 Hz, 4H), 3.18–2.97 (m, 6H), 0.90 (t. J=8.0 Hz, 4H), 0.00 (s, 18H).

EXAMPLE 15BK

Compound 15BJ was treated with 4M HCl in dioxane under reflux overnight. After the solvent was removed under full vacuum, the residue was purified on reverse phase T.L.C. plate to give the desired compound as a solid in moderate yield. $^1$H NMR (CD$_3$OD) δ 7.71 (sb, 2H), 7.61 (d, J=7.7 Hz, 2H), 7.52 (s, 2H), 7.35–7.19 (m, 10H), 7.10–7.08 (m, 6H), 4.78 (d, J=13.9 Hz, 2H), 3.71–3.65 (m, 4H), 3.32–3.00 (m, 4H), 2.96–2.87 (m, 2H); $^{13}$C NMR (CD$_3$OD) δ 163.80, 141.26, 139.94, 137.20, 134.78, 130.67, 130.11, 129.52, 128.88, 127.40, 127.08, 125.22, 72.00, 67.72, 57.38, 33.60; HRMS: calcd. for $C_{39}H_{39}N_6O_3$: 639.3084; found 639.3089.

EXAMPLE 15BL

Compound 15BK in MeOH was treated with 4M HCl in dioxane and the resulting solvents ware evaporated under full vacuum to give the hydrochloride salt. $^1$H NMR (CD$_3$OD) δ 9.02 (d, J=1.1 Hz, 2H), 7.87 (d, J=1.1 Hz, 2H), 7.65–7.38 (m, 8H), 7.19–7.17 (m, 6H), 6.93–6.90 (m, 4H), 4.65 (d, J=14.3 Hz, 2H), 3.78–3.72 (m, 4H), 3.25 (d, J=14.3, 2H), 3.06–3.02 (m, 2H), 2.81–2.7 (m, 2H); $^{13}$C NMR (CD$_3$OD) δ 163.41, 141.11, 141.04, 135.91, 134.97, 131.95, 130.89, 130.51, 129.47, 128.16, 128.10, 127.43, 126.09, 116.38, 71.80, 69.21, 57.87, 33.73.

EXAMPLE 15BM

2-Trimethyltin-N-dimethylsulfamoyl-imidazole was prepared in situ by lithiation of N-dimethylsulfamoyl-imidazole (1.75 g, 10 mmol) in THF (30 mL) at −78° C. with n-BuLi (1.6M, 7.5 mL), followed by quenching with trimethyltin chloride (2.19 g, 11 mmol). A coupling reaction of the tin reagent (1.2 g, crude) and MEM-protected compound 12J (0.8 g, 0.86 mmol) in the presence of Pd(Ph$_3$P)$_4$ (0.18 g, 0.16 mmol) was carried out under reflux overnight. After being cooled to room temperature, the reaction mixture was poured into EtOAc/H$_2$O. The organic layer was dried over MgSO$_4$ and concentrated on a rotary evaporator. The residue was dissolved in MeOH, saturated with HCl (gas) at 0° C. for 5 minutes and then stirred at that temperature for 1 hour. The resulting mixture was worked up and purified on column with EtOAc to give compound 15BM as a solid (450 mg, 61%). $^1$H NMR (CD$_3$OD) δ 7.61–7.11 (m, 22H), 4.86 (d, J=14.3 Hz, 2H), 3.61–3.59 (m, 4H), 3.10–2.92 (m, 6H), 2.54 (s, 6H); $^{13}$C NMR (CD$_3$OD) δ 163.98, 148.97, 141.21, 139.37, 132.57, 132.17, 131.55, 130.98, 130.69, 129.63, 129.50, 128.30, 127.53, 123.61, 71.92, 66.99, 56.66, 38.23, 33.74. HRMS: calcd. for $C_{43}H_{49}N_8O_7S_2$: 853.3166; found 853.3163.

EXAMPLE 15BN

A solution of 4-iodopyrazole (1.54 g, 8 mmol) in THF (20 mL), was treated with NaH (4.3 g, 10.6 mmol), followed by quenching with dimethylsulfamoyl chloride (1.38 g, 9.6 mmol) to form the N-protected pyrazole (2.4 g, 92%). This intermediate (1.5 g, 5 mmol) was reacted with hexamethylditin (1.8 g, 5.5 mmol) in the presence of Pd(Ph$_3$P)$_4$ (0.055 g, 0.01 mmol) in THF (25 mL) at 78° C. overnight to give crude 4-trimethyltin-N-dimethylsulfamoyl-pyrazole.

The crude tin compound was reacted with MEM-protected cpd 12J (0.932 g, 1.0 mmol) in the presence of Pd(Ph$_3$P)$_4$ (0.18 g, 0.16 mmol) under reflux to form the coupled product, which was deprotected by general hydrolysis procedure, followed by purification on reverse phase TLC plate with 85% MeOH in water to give compound 15BN as a solid. $^1$H NMR (CD$_3$OD) δ 7.77–7.12 (m, 4H), 7.38–6.95 (m, 18H), 4.72 (d, J=14.3 Hz, 2H), 3.59–3.55 (m, 4H), 3.02–2.88 (m, 6H); $^{13}$C NMR (CD$_3$OD) δ 163.36, 140.63, 139.40, 133.75, 130.19, 129.83, 129.18, 127.87, 127.38, 127.12, 125.47, 122.79, 71.64, 66.46, 56.76, 33.23;

EXAMPLE 15BP

MEM-protected mono-m-bromobenzyl cyclic urea was made by general procedure for preparation of monoalkylated cyclic ureas. The monoalkyated intermediate (2.4 g, 3.56 mmol) was dissolved in DMF (15 mL) and treated with NaH (0.43 g, 10.75 mmol), followed by addition of methyl m-bromomethylbenzoate (1.63 g, 7.1 mmol) to give pure desired asymmetric cyclic urea (1.6 g, 55%).

This asymmetric urea (1.6 g, 2 mmol) was coupled with 5-borono-N-SEM-pyrazole (0.48 g, 2 mmol) by the same procedure described for example 15BJ above to provide pure coupled product, which was further deprotected by general hydrolysis procedure to form compound 15BP (0.9 g, 73.2% for the two steps). $^1$H NMR (CD$_3$OD) δ 7.85–7.82 (m, 2H), 7.66–7.57 (m, 4H), 7.35–7.01 (m, 13H), 6.56 (s, 1H), 4.76 (d, J=14.3 Hz, 1H), 4.69 (d, J=14.3 Hz, 1H), 3.77 (s, 3H), 3.72–3.58 (m, 4H), 3.11–3.02 (m, 4H), 2.94–2.84 (m, 2H); $^{13}$C NMR (CD$_3$OD) δ 166.79, 162.24, 139.69. 139.59, 138.56, 138.50, 133.63, 130.09, 129.16, 128.78, 128.61, 128.46, 128.29, 128.16, 126.59, 126.08, 124.60, 102.00, 70.50, 66.36, 66.31, 55.99, 55.63, 51.32, 32.23, 32.15; LRMS: 631.4 (M+1, 100%); HRMS: calcd. for $C_{38}H_{39}N_4O_5$: 631.2920; found 631.2916.

EXAMPLE 15BQ

To a solution of compound 15BP (63 mg, 0.1 mmol) in THF (1 mL) was added LiBH$_4$ (2M in THF, 0.3 mL) and MeOH (57.6 mg, 1.8 mmol) and the resulting mixture was stirred at room temperature overnight. The mixture was acidified to pH 1 with 2N HCl and extracted with EtOAc. The organic layer was washed with $H_2O$, brine, dried over $MgSO_4$, and concentrated. The residue was purified on TLC plate with EtOAc to give the desired compound (46 mg, 76.3%). $^1$H NMR ($CD_3OD$) δ 7.78–7.60 (m, 4H), 7.50–7.07 (m, 15H), 6.68 (d, J=2.2 Hz, 1H), 4.90–4.81 (m, 2H), 4.66 (bs, 2H), 3.79–3.63 (m, 4H), 3.18–3.00 (m, 6H); $^{13}$C NMR ($CD_3OD$) δ 163.92, 143.24, 141.32, 141.23, 139.41, 130.67, 130.17, 129.93, 129.69, 129.57, 129.53, 129.30, 129.04, 128.04, 127.45, 127.41, 127.25, 126.01, 103.33, 72.02, 71.96, 67.04, 64.97, 57.30, 57.07, 33.63, 33.57; LRMS: 603.2 (M+1, 100%); HRMS: calcd. for $C_{37}H_{39}N_4O_4$: 603.291; found 603.2968.

EXAMPLE 15BR

N-dimethylsulfamoyl-imidaz-2-yl zinc chloride was prepared in situ by lithiation of N-dimethylsulfamoylimidazole (0.97 g, 5.5 mmol) in THF (20 mL) with t-BuLi (1.7M, 6.7 mL), followed by quenching with zinc chloride (1.87 g, 13.75 mmol).

A coupling reaction of the zinc reagent (crude) and MEM-protected cpd 12J (0.932 g, 1.0 mmol) in the presence of $Pd(Ph_3P)_4$ (0.12 g, 0.1 mmol) was carried out under reflux overnight. After cooling to room temperature, the reaction mixture was poured into $EtOAc/H_2O$. The organic layer was dried over $MgSO_4$ and concentrated on a rotary evaporator. The residue was dissolved in MeOH, and treated with 4M HCl in dioxane under reflux for 2 hours. The resulting mixture was worked up and purified on a reverse phase TLC plate with 75% MeOH in water to give compound 15BR as a solid. $^1$H NMR ($CD_3OD$) δ 7.75–7.70 (m, 4H), 7.42–7.33 (m, 2H), 7.28–7.12 (m, 12H), 7.00–6.94 (m, 4H), 4.73 (d, J=14.3 Hz, 2H), 3.71 (bs, 4H), 3.14 (d, J=13.9 Hz, 2H), 3.04–2.99 (m, 2H), 2.85–2.77 (m, 2H); $^{13}$C NMR ($CD_3OD$) δ 162.00, 146.27, 139.58, 138.87, 130.23, 129.36, 129.11, 128.80, 128.00, 126.20, 125.89, 124.36, 122.64, 70.39, 67.14, 56.29, 32.22; HRMS: calcd. for $C_{39}H_{39}N_6O_3$: 639.3084; found 639.3069.

EXAMPLE 15BS

Compound 15BR was dissolved in MeOH, and treated with 4M HCl in dioxane at r.t. for 1 minute. The resulting mixture was concentrated in vacuo to give the solid dihydrochloride salt. $^1$H NMR ($CD_3OD$) δ 7.81–7.79 (m, 2H), 7.73 (s, 2H), 7.65 (s, 4H), 7.61–7.57 (m, 4H), 7.13–7.11 (m, 6H), 6.86–6.84 (m, 4H), 4.59 (d, J=13.9 Hz, 2H), 3.84 (s, 2H), 3.76 (d, J=11.7 Hz, 2H), 3.45 (d, J=14.1 Hz, 2H), 3.06 (d, J=12.2 Hz, 2H), 2.75–2.68 (m, 2H); $^{13}$C NMR ($CD_3OD$) δ 163.39, 145.94, 141.63, 140.94, 134.79, 131.28, 130,46, 129.44, 129.13, 127.38, 127.14, 124.31, 121.37, 71.58, 69.54, 57.82, 33.84.

EXAMPLE 15BT

To compound 15BP (63 mg, 0.1 mmol) was added 4-(2-aminoethyl)morpholine (0.13 g, 1 mmol) and the resulting mixture was stirred at 110° C. overnight. The mixture was evaporated in vacuo to remove the excess 4-(2-aminoethyl) morpholine, and the residue was purified on TLC plate with 10% MeOH in EtOAc to give pure product (44 mg, 60.4%). $^1$H NMR ($CD_3OD$) δ 8.04 (s, 1H), 7.73–6.99 (m, 18H), 6.59 (d, J=2.2 Hz, 1H), 4.72 (d, J=14.4 Hz, 2H), 3.69–3.64 (m, 8H), 3.36 (t, J=6.6 Hz, 2H), 3.14 (J=14.2 Hz, 2H), 3.08–2.85 (m, 4H), 2.54 (t, J=6.6 Hz, 2H), 2.51–2.45 (m, 4H); $^{13}$C NMR ($CD_3OD$) δ 169.84, 163.68, 141.25, 141.12, 140.09, 136.07, 133.65, 130.63, 129.87, 129.56, 129.51, 128.02, 127.44, 103.31, 71.98, 71,91, 68.26, 67.75, 58.62, 58.37, 58.45, 54.68, 37.76, 35.76, 33.69, 33.62; HRMS: calcd. for $C_{43}H_{49}N_6O_5$: 729.3764; found 729.3753.

EXAMPLE 15BU

MEM-protected mono-m-bromobenzyl cyclic urea was made by general procedure for preparation of monoalkylated cyclic ureas. The mono cyclic urea (2.4 g, 3.56 mmol) in DMF (15 mL) was coupled with 5-borono-N-SEM-pyrazole by the same procedure used to make compound 20AX to provide pure coupled product, MEM-protected mono m-(N-SEM-pyraz-5-yl)benzyl cyclic urea.

This intermediate (0.2 g, 0.25 mmol) in DMF (5 mL) was treated with NaH (0.04 g, 1.0 mmol), followed by quenching with m-picolyl chloride hydrochloride (0.123 g, 0.75 mmol) to give desired asymmetric cyclic urea, which was further deprotected by general hydrolysis procedure to form compound 15BU. $^1$H NMR ($CD_3OD$) δ 8.51–8.46 (m, 2H), 7.83–7.63 (m, 4H), 7.48–7.03 (m, 13H), 6.68 (d, J=2.2 Hz, 1H), 4.84 (d, J=14.3 Hz, 1H), 4.66 (d, J=14.3 Hz, 1H), 3.85–3.76 (m, 4H), 3.20–2.83 (m, 6H); $^{13}$C NMR ($CD_3OD$) δ 163.63, 151.12, 149.22, 141.12, 141.07, 139.41, 135.98, 130.60, 130.55, 130.24, 129.63, 129.60, 128.04, 127.54, 126.08, 125.34, 103.35, 71.94, 71.81, 68.72, 55.13, 33.75, 33.61; HRMS: calcd. for $C_{35}H_{36}N_5O_3$: 574.2818; found 574.2811.

EXAMPLE 15BV

The MEM-protected mono m-(N-SEM-pyraz-5-yl)-benzyl cyclic urea (788 mg, 1 mmol), described in procedure of example 15U was dissolved in DMF (8 mL) and treated with NaH (0.16 g, 4.0 mmol, 60% in mineral oil), followed by quenching with α-bromo-m-tolunitrile (0.392 g, 2.0 mmol) to give desired asymmetric cyclic urea, which was further deprotected by general hydrolysis procedure to form compound 15BV. $^1$H NMR ($CD_3OD$) δ 7.99–7.07 (m, 19H), 6.68 (bs, 1H), 4.70 (d, J=13.9 Hz, 1H), 4.64 (d, J=13.9 Hz, 1H), 3.93–3.70 (m, 4H), 3.21–2.83 (m, 6H); $^{13}$C NMR ($CD_3OD$) δ 163.82, 141.40, 141.24, 141.14, 135.42, 134.42, 133.90, 132.52, 130.85, 130.67, 130.15, 130.03, 129.82, 129.71, 128.16, 127.66, 119.67, 113.62, 103.40, 71.92, 71.87, 68.67, 57.14, 33.79, 33.62; HRMS: calcd. for $C_{37}H_{36}N_5O_3$: 598.2818; found 598.2813.

EXAMPLE 15BW

To a solution of compound 15BV (50 mg, 0.084 mmol) in pyridine (3 mL) was added hydroxylamine hydrochloride (36 mg, 5.2 mmol) and the resulting mixture was refluxed overnight. After being cooled to room temperature, the mixture was evaporated in vacuo to remove pyridine. The resulting residue was worked up and purified on TLC plate with EtOAc to give pure amidoxime (32 mg, 60.6%). $^1$H NMR ($CD_3OD$) δ 7.96–7.05 (m, 19H), 6.59 (d, J=2.2 Hz, 1H), 4.78 (d, J=14.3 Hz, 1H), 4.75 (d, J=14.3 Hz, 1H), 3.70–3.59 (m, 4H), 3.11–3.03 (m, 4H), 2.96–2.88 (m, 2H); $^{13}$C NMR ($CD_3OD$) δ 163.82, 141.25, 141.14, 140.02, 139.77, 134.52, 134.00, 131.68, 130.62, 130.18, 129.93, 129.69, 129.56, 129.54, 128.04, 127.44, 126.01, 103.32, 71.97, 67.65, 67.58, 57.31, 56.97, 33.67, 33.56.

EXAMPLE 15BX

Mono-m-(N-SEM-pyraz-5-yl)-benzyl cyclic urea prepared above in procdure of Example 15BU was deprotected by general hydrolysis procedure to give compound XS618.

¹H NMR (CD₃OD) δ 7.67–7.05 (M, 15H), 6.58 (d, J=4.0 Hz, 1H), 4.80 (d, J=14.7 Hz, 1H), 3.86–3.82 (m, 1H), 3.71–3.62 (m, 2H), 3.51–3.48 (m, 1H), 3.18–2.99 (m, 4H), 2.80–2.72 (m, 1H); ¹³C NMR (CD₃OD) δ 163.90, 141.47, 140.89, 130.63, 130.49, 130.09, 130.01, 129.64, 129.49, 129.27, 127.52, 127.25, 125.85, 103.33, 72.99, 72.55, 66.50, 66.47, 55.27, 35.13, 34.32; HRMS: calcd. for C₂₉H₃₁N₄O₃: 483.2400; found 483.2401.

EXAMPLE 15BY

MEM-protected mono m-(N-SEM-pyraz-5-yl)benzyl cyclic urea described above (220 mg, 0.28 mmol) was dissolved in DMF (3 mL) and treated with NaH (0.045 g, 1.12 mmol, 60% in mineral oil), followed by quenching with p-benzyloxybenzyl chloride (0.13 g, 0.56 mmol) to give the desired asymmetric cyclic urea, which was deprotected by general hydrolysis procedure to give compound 15BY. ¹H NMR (CD₃OD) δ 7.68–6.91 (m, 24H), 6.58 (d, J=2.2 Hz, 1H), 5.02 (s, 2H), 4.78 (d, J=13.9 Hz, 1H), 4.66 (d, J=13.9 Hz, 1H), 3.67–3.54 (m, 4H), 3.08–2.88 (m, 6H); ¹³C NMR (CD₃OD) 163.88, 159.84, 141.29, 138.63, 131.73, 131.58, 130.69, 130.64, 130.15, 129.56, 129.49, 129.46, 128.82, 128.50, 128.03, 127.46, 127.37, 125.99, 116.07, 103.32, 72.05, 72.02, 66.81, 56.45, 33.62, 33.59; HRMS: calcd. for C₄₃H₄₃N₄O₄: 6779.3284; found 679.3284.

EXAMPLE 15BZ

To compound 15BP (45 mg, 0.071 mmol) was added 3-(aminomethyl)pyridine (0.077 g, 0.71 mmol) and the resulting mixture was stirred at 110° C. overnight. The mixture was evaporated in vacuo to remove the excess 3-(aminomethyl)-pyridine. The residue was purified on TLC plate with 15% MeOH in EtOAc to give pure product (37 mg, 73.8%). ¹H NMR (CD₃OD) δ 7.80–6.95 (m, 23H), 6.59 (d, J=2.2 Hz, 1H), 4.77–4.72 (m, 1H), 4.68 (d, J=14.3 Hz, 1H), 4.58 (d, J=2.2 Hz, 2H), 3.66–3.64 (m, 4H), 3.15 (d, J=14.3 Hz, 1H), 3.06–2.82 (m, 5H); ¹³C NMR (CD₃OD) δ 170.09, 163.83, 152.96, 149.63, 141.32, 141.23, 140.30, 137.40, 136.94, 135.80, 134.04, 130.71, 130.29, 130.09, 129.75, 129.66, 128.12, 127.67, 127.54, 126.14, 125.34, 125.19, 103.38, 72.00, 71.93, 68.47, 57.56, 42.02, 33.62.

EXAMPLE 15AC

Hydrogenation of compound 15BY in MeOH in the presence of catalytic amount of 10% Pd/C produced the hydroxymethyl compound in good yield. ¹H NMR (CD₃OD) δ 7.68–7.58 (m, 3H), 7.39–7.05 (m, 12H), 6.98 (d, J=8.4 Hz, 2H), 6.73 (d, J=8.4 Hz, 2H), 6.58 (d, J=2.2 Hz, 1H), 4.78 (d, J=14.3 Hz, 1H), 4.66 (d, J=13.9 Hz, 1H), 3.68–3.50 (m, 4H), 3.08–2.83 (m, 6H); ¹³C NMR (CD₃OD) δ 163.94, 158.15, 141.31, 140.11, 131.73, 130.69, 130.65, 130.16, 129.96, 129.56, 129.48, 128.04, 127.46, 127.35, 125.98, 116.39, 103.32, 72.10, 72.02, 66.42, 57.22, 56.37, 33.56; HRMS: calcd. for C₃₆H₃₇N₄O₄: 589.2815; found 589.2811.

EXAMPLE 15BC

To compound 15BP (44 mg, 0.07 mmol) was added 2-(aminomethyl)pyridine (0.077 g, 0.71 mmol) and the resulting mixture was stirred at 110° C. overnight. The mixture was evaporated in vacuo to remove the excess 2-(aminomethyl)pyridine. The residue was purified on a TLC plate with 20% MeOH in EtOAc to give pure product (35 mg, 71%). ¹H NMR (CD₃OD) δ 8.45 (d, J=4.8 Hz, 1H), 7.80–6.98 (m, 22H), 6.58 (d, J=1.5 Hz, 1H), 4.77 (d, J=14.3 Hz, 1H), 4.71 (d, J=14.3 Hz, 1H), 4.66 (d, J=4.8 Hz, 2H), 3.68–3.65 (m, 4H), 3.17–2.82 (m, 6H); ¹³C NMR (CD₃OD) δ 169.99, 163.71, 159.28, 149.75, 141.25, 141.14, 140.17, 139.98, 138.80, 135.79, 133.94, 130.63, 130.18, 129.96, 129.92, 129.57, 128.03, 127.64, 127.45, 126.03, 123.72, 122.76, 103.32, 71.99, 71.92, 68.32, 67.72, 57.50, 57.30, 45.92, 33.69, 33.65; HRMS: calcd. for C₄₃H₄₃N₆O₄: 707.3346; found 707.3344.

EXAMPLE 15CC

MEM-protected mono m-(N-SEM-pyraz-5-yl)benzyl cyclic urea (200 mg, 0.254 mmol) was dissolved in DMF (5 mL) and treated with NaH (0.041 g, 1.02 mmol, 60% in mineral oil), followed by quenching with m,p-dibenzyloxybenzyl chloride (0.172 g, 0.51 mmol) to give the desired asymmetric cyclic urea. After deprotection by general hydrolysis procedure, the urea was hydrogenated to give the dihydroxy compound. ¹H NMR (CD₃OD) δ 7.83–7.07 (m, 15H), 6.81–6.71 (m, 3H), 6.53 (s, 1H), 4.86 (d, J=13.9 Hz, 1H), 4.72 (d, J=13.6 Hz, 1H), 3.80–3.66 (m, 4H), 3.19–2.82 (m, 6H); ¹³C NMR (CD₃OD) δ 164.10, 149.97, 146.56, 146.12, 141.43, 141.32, 140.29, 134.53, 133.55, 130.82, 130.71, 130.67, 130.29, 129.64, 129.53, 128.23, 127.51, 127.42, 126.14, 122.22, 117.49, 116.39, 103.59, 72.13, 72.01, 67.77, 65.89, 57.28, 56.35, 33.61, 33.45; HRMS: calcd. for C₃₆H₃₇N₄O₅: 605.2764; found 605.2750.

EXAMPLE 15CD

MEM-protected mono m-(N-SEM-pyraz-5-yl)-benzyl cyclic urea (560 mg, 0.71 mmol) was dissolved in DMF (10 mL) was treated with NaH (0.114 g, 2.84 mmol, 60% in mineral oil), followed by quenching of m-nitrobenzyl chloride (0.360 g, 2.13 mmol) to give desired asymmetric cyclic urea. After deprotection by general de-MEM procedure, the urea was purified on TLC plate with EtOAc to give pure product. ¹H NMR (CD₃OD) δ 8.11–8.06 (m, 2H), 7.69–7.15 (m, 13H), 7.06–6.95 (m, 4H), 6.59 (d, J=2.2 Hz, 1H), 4.76 (d, J=13.9 Hz, 1H), 4.61 (d, J=14.3 Hz, 1H), 3.78–3.56 (m, 4H), 3.15–2.79 (m, 6H); ¹³C NMR (CD₃OD) δ 163.75, 149.67, 141.75, 141.12, 140.97, 136.71, 130.78, 130.53, 130.21, 129.93, 129.73, 129.57, 128.04, 127.53, 127.43, 126.07, 125.37, 123.51, 103.33, 71.84, 68.28, 57.31, 56.86, 33.85, 33.58; HRMS: calcd. for C₃₆H₃₆N₅O₅: 618.2716; found 618.2703.

EXAMPLE 15CE

Hydrogenation of compound 15CD (210 mg, 0.34 mmol) in MeOH (5 mL) and 1N HCl (1 mL) in the presence of 10% Pd/C was carried out at room temperature overnight. The catalyst was removed by filtration, and the filtrate was concentrated. The residue was purified on TLC plate with EtOAc to give the amino compound (140 mg, 61%). ¹H NMR (CD₃OD) δ 8.31 (s, 1H), 7.81–6.88 (m, 19H), 4.60 (d, J=13.6 Hz, 2H), 3.80–3.57 (m, 4H), 3.16–2.68 (m, 6H); ¹³CNMR (CD₃OD) δ 163.99, 149.09, 141.38, 141.23, 140.01, 130.73, 130.65, 130.35, 130.15, 129.93, 129.55, 129.46, 128.04, 127.42, 127.35, 125.97, 120.06, 117.33, 115.81, 103.32, 72.11, 71.99, 66.39, 57.28, 56.97, 33.66, 33.53; HRMS: calcd. for C₃₆H₃₈N₅O₃: 588.2975; found 588.2983.

EXAMPLE 15CF

MEM-protected mono m-(N-SEM-pyraz-5-yl)-benzyl cyclic urea (240 mg, 0.3 mmol) was dissolved in DMF (5 mL) and treated with NaH (0.049 g, 1.2 mmol, 60% in mineral oil), followed by addition of m-cyano-p-fluorobenzyl bromide (0.128 g, 0.6 mmol) to give desired asymmetric cyclic urea. After deprotection by general hydrolysis procedure, the urea was purified on TLC plate with EtOAc to give pure compound 15CF (72 mg, 39%). $^1$H NMR (CD$_3$OD) δ 7.68–6.86 (m, 18H), 6.57 (d, J=0.7 Hz, 1H), 4.72 (d, J=14.1 Hz, 1H), 4.36 (d, J=13.8 Hz, 1H), 3.82–3.55 (m, 4H), 3.16–2.69 (m, 6H); HRMS: calcd. for C$_{37}$H$_{35}$N$_5$O$_3$F: 616.2713; found 616.2710.

EXAMPLE 15CG

A solution of compound 15BX in MeOH was treated with 4M HCl in dioxane, and the resulting solution was evaporated to dryness in vacuo to give the hydrochloride salt. $^1$H NMR (CD$_3$OD) δ 58.31 (d, J=2.6 Hz, 1H), 7.72–7.06 (m, 15H), 4.68 (d, J=15 Hz, 1H), 3.83–3.75 (m, 3H), 3.73–3.60 (m, 1H), 3.59–3.41 (m, 1H), 3.23–3.03 (m, 3H), 2.69–2.65 (m, 1H); $^{13}$C NMR (CD$_3$OD) δ 163.52, 148.75, 141.15, 140.30, 136.47. 132.50, 130.88, 130.49, 130.35, 129.62, 129.46, 128.32, 127.53, 127.35, 127.04, 106.27, 73.14, 72.49, 67.06, 58.97, 55.16, 35.61, 34.93.

EXAMPLE 15GH

A solution of the compound of Example 9P (0.11 g, 0.2 mmol) and hydroxylamine hydrochloride (0.014 mg, 0.2 mmol) in pyridine (2 mL) was refluxed overnight. Workup and purification using HPLC with a solvent gradient from 10% hexane in EtOH to 100% of EtOH provided compound 15GH (28 mg). $^1$H NMR (CD$_3$OD) δ 7.89–7.86 (m, 1H), 7.81 (s, 1H), 7.54 (d, J=4.0 Hz, 1H), 7.45–7.00 (m, 15H), 4.73 (d, J=14.1 Hz, 1H), 4.71 (d, J=14.2 Hz, 1H), 3.62–3.55 (m, 4H), 3.17 (d, J=14.2 Hz, 1H), 3.08–3.05 (m, 2H), 2.98 (d, J=14.1 Hz, 1H), 2.96–2.83 (m, 2H), 2.54 (s, 3H), 2.16 (s, 3H); $^{13}$C NMR (CD$_3$OD) δ 200.03, 163.85, 155.42, 141.19, 141.16, 140.19, 139.40, 139.00, 138.63, 135.31, 130.77, 130.62, 130.59, 130.48, 130.07, 129.71, 129.60, 129.57, 128.71, 128.11, 127.50, 126.35, 71.99, 71.93, 67.81, 67.24, 57.15, 57.09, 33.65, 26.72, 11.94; HRMS: calcd. for C$_{37}$H$_{40}$N$_3$O$_5$: 606.2968; found 606.2971.

EXAMPLE 15CI and 15CJ

Bis-m-cyano-p-fluorobenzyl cyclic urea was prepared using general alkylation and deprotection procedures. The urea (0.47 g, 0.79 mmol) in THF (20 mL) was treated with MeMgBr (3M, 2.5 mL, 0.5 mmol) under reflux for 3 hours. General workup and purification on TLC plate with 40% EtOAc in CH$_2$Cl$_2$, followed by further purification on HPLC with 85% hexane in EtOH gave compound 15CI (40 mg) and compound 15CJ (80 mg).

EXAMPLE 15CI: $^1$H NMR (CDCl$_3$) δ 7.64 (dd, J=7.0 Hz, J=2.2 Hz, 2H), 7.40–7.00 (m, 14H), 4.72 (dd, J=14.6 Hz, 2H), 3.75 (s, 2H), 3.55 (d, J=11.4 Hz, 2H), 3.22 (d, J=14.6 Hz, 2H), 3.08 (dd, J=13,6 Hz, J=2.6 Hz, 2H), 2.83 (dd, J=13.2 Hz, J=11.0 Hz, 2H), 2.59 (d, J=4.8 Hz, 6H), 2.51 (b, 2H); $^{13}$C NMR (CDCl$_3$) δ 196.31 (d, J=3.1 Hz), 161.71, 161.46 (d, J=255.6 Hz), 139.39, 135.78 (d, J=9.2 Hz), 134.74, 130.82 (d, J=2.3 Hz), 129.31, 128.60, 126.48, 125.38 (d, J=13.0 Hz), 116.97 (d, J=14.4 Hz), 70.89, 65.58, 55.08, 32.78, 31.26 (d, J=7.6 Hz); HRMS: calcd. for C$_{37}$H$_{37}$N$_2$O$_5$F$_2$: 627.2671; found 62.2670.

Example 15CJ: $^1$H NMR (CDCl$_3$) 7.74 (dd, J=7.0 Hz, J=2.2 Hz, 2H), 7.57–7.00 (m, 14H), 4.80 (d, J=14.3 Hz, 1H), 4.62 (d, J=14.3 Hz, 1H), 3.90 (bs, 2H), 3.71–3.61 (m, 2H), 3.53 (d, J=14.6 Hz, 1H), 3.29 (d, J=14.3 Hz, 1H), 3.25–3.17 (m, 4H), 2.93–2.82 (m, 2H), 2.68 (s, 3H), 2.66 (s, 3H); $^{13}$C NMR (CDCl$_3$) δ 196.48 (d, J=2.3 Hz), 162.37 (d, J=259.4 Hz), 161.75, 161.58 (d, J=255.6 Hz), 139.21, 139.15, 136.02 (d, J=8.4 Hz), 135.85 (d, J=8.4 Hz), 135.34 (d, J=3.8 Hz), 134.62 (d, J=3.0 Hz), 134.31, 130.76, 129.24, 128.68, 128.62, 126.63, 126.59, 125.42 (d, J=13.0 Hz), 117.03 (d, J=14.4 Hz), 116.41 (d, J=19.9 Hz), 113.67, 101.28 (d, J=15.3 Hz), 70.85, 65.96, 65.75, 55.09, 54.95, 32.96, 32.79, 31.25 (d, J=6.9 Hz); HRMS: calcd. for C$_{36}$H$_{34}$N$_3$O$_4$F$_2$: 610.2517; found 610.2534.

EXAMPLE 15CK

In the synthesis of compound 9Q, compound 15CK was a minor stereoisomer and was isolated on HPLC with 80% hexane in EtOH. $^1$H NMR (CD$_3$OD) δ 7.55–7.53 (m, 2H), 7.48 (s, 2H), 7.33–7.14 (m, 10H), 7.10–7.07 (m, 4H), 4.75 (d, J=14.6 Hz, 2H), 3.61–3.58 (m, 4H), 3.08–3.04 (m, 2H), 2.99 (d, J=14.3 Hz, 2H), 2.96–2.90 (m, 2H), 2.17 (s, 6H); $^{13}$C NMR (CD$_3$OD) δ 163.94, 155.44, 141.22, 139.43, 138.96, 130.76, 130.63, 129.68, 129.56, 128.09, 127.46, 126.30, 72.00, 67.09, 57.03, 33.59, 11.97; HRMS: calcd. for C$_{37}$H$_{41}$N$_4$O$_5$: 621.3077; found 620.3091.

EXAMPLE 15CL

By the same procedure used to make Example 9Q, compound 15CL was obtained from compound 15CI in good yield. $^1$H NMR (CD$_3$OD) δ 7.31–7.02 (m, 16H), 4.63 (d, J=13.9 Hz, 2H), 3.62–3.56 (m, 4H), 3.09–2.99 (m, 4H), 2.90–2.82 (m, 2H), 2.16 (d, J=2.2 Hz, 6H); $^{13}$C NMR (CD$_3$OD) δ 163.76, 161.28 (d, J=248.7 Hz), 153.70, 141.18, 135.44 (d, J=3.8 Hz), 132.57 (d, J=8.4 Hz), 131.86 (d, J=3.8 Hz), 130.60, 129.59, 127.49, 127.13 (d, J=13.7 Hz), 117.21 (d, J=22.9 Hz), 71.90, 67.41, 56.34, 33.66, 14.8 (d, J=4.6 Hz); HRMS: calcd. for C$_{37}$H$_{39}$N$_4$O$_5$F$_2$: 657.2889; found 657.2874.

EXAMPLE 15CM

Compound 15CM was obtained from compound XS534 by the same procedure used to make Example 9Q. $^1$H NMR (CD$_3$OD) δ 7.34–7.02 (m, 16H), 4.66 (d, J=14.2 Hz, 1H), 4.64 (d, J=14.2 Hz, 1H), 3.64–3.54 (m, 4H), 3.09–2.83 (m, 6H), 2.15 (d, J=2.4 Hz, 3H); $^{13}$C NMR (CD$_3$OD) δ 163.83, 161.29 (d, J=248.0 Hz), 161.08 (d, J=250.3 Hz), 153.67, 151.69, 141.21, 141.16, 135.44, 133.40 (d, J=9.2 Hz), 132.58 (d, J=8.4 Hz), 132.20, 131.98 (d, J=3.8 Hz), 130.61, 129.63, 127.49, 127.14 (d, J=13.7 Hz), 122.37 (d, J=13.77 Hz), 117.43 (d, J=22.9 Hz), 117.20 (d, J=22.9 Hz), 71.84, 67.41, 66.99, 56.38, 56.98, 33.74, 33.58, 14.78 (d, J=5.3 Hz); HRMS: calcd. for C$_{36}$H$_{38}$N$_5$O$_5$F$_2$: 658.2841; found 658.2838.

EXAMPLE 15FN

To a stirred solution of 3.66 g (10 mmol) of compound XXVIIIf in 15 mL of DMF and 7 mL of THF, cooled to 0° C., was added 1.2 g (40 mmol) of an 80% dispersion of sodium hydride in mineral oil. The mixture was stirred 5 min., and 4.66 g (40 mmol) of 3-furylmethylchloride was added. The mixture was warmed to ambient temperature over 30 min. and then recooled to 0° C. The reaction was quenched by the addition of 0.4 N HCl, and the resulting mixture was extracted with Et$_2$O. The organic extract was washed with sat'd aq. NaHCO$_3$, then brine, dried (MgSO$_4$), and concentrated under reduced pressure to afford 4.92 g (93%) of alkylated intermediate. $^1$H NMR (CDCl$_3$) δ 7.11–7.42 (m, 7H); 6.32 (s, 1H); 4.72 (d, 1H); 3.88 (s, 1H); 3.82 (m, 1H); 3.03 (d, 1H); 2.79–2.97 (m, 2H); 1.40 (s, 6H).

To 0.20 g (0.38 mmol) of acetonide protected bis(N-3-furylmethyl cyclic urea above was added 8 mL of MeOH and 1 mL of conc. aq. HCl. The solution was stirred 1 h at ambient temperature and poured into water. The white colloidal suspension was extracted with 1:1 Et$_2$O-EtOAc, and the organic extract was washed with sat'd aq. NaHCO$_3$, brine, dried (MgSO$_4$), and concentrated under reduced pressure to afford an off-white solid. This material was dissolved in 7 mL of EtOAc and warmed to boiling. Hexane, 20 mL, was introduced, and the solution was concentrated to ~6 mL. The product was triturated with 3 mL of hexanes and allowed to cool. Solvent was removed by pipette, and the white crystalline solid was washed with 9:1 hexanes-EtOAc. The diol 15FN, following removal of residual solvent at vacuum pump pressure, weighed 111 mg (60% of theoretical).

EXAMPLE 15FO

To 0.22 mL (2.3 mmol) of stirred, cooled POCl$_3$ was added 0.20 mL (2.5 mmol) of DMF. The solution was stirred 5 min., and a solution of 530 mg (1.0 mmol) of acetonide protected bis(N-3-furylmethyl)cyclic urea, described in example 15FN above, in 0.5 mL of THF and 0.5 mL of DMF was introduced. The solution was warmed to ambient temperature with stirring over 25 min., whereupon an additional 0.10 mL of POCl$_3$ was introduced. The reaction was heated to reflux for 30 min., cooled, and poured into water. The resulting colloidal solid was extracted with 1:1 Et$_2$O-EtOAc, and the organic extract was washed with sat'd aq. NaHCO$_3$, water, then brine. Drying (MgSO$_4$), and concentration under reduced pressure afforded a brown oil. Chromatography on silica gel (gradient elution with 3:1 to 1:1 hexanes-EtOAc) afforded 120 mg (22%) of monoaldehyde intermediate as an oil. $^1$H NMR (CDCl$_3$) δ 9.41 (s, 1H, CHO); 7.52 (s, 1H, furyl); 7.00–7.38 (m, 12H, aryl); 6.59 (s, 1H, furyl); 6.31 (s, 1H, furyl); 4.80 (d, 1H, J=14.6 Hz, one of NCH$_2$); 4.69 (d, 1H, J=14.6 Hz, NCH$_2$); 3.77–4.03 (m, 5H, 2×Hα, one of NCH$_2$, CHOC (CH$_3$)$_2$OCH); 2.68–302 (m, 5H, one of NCH$_2$, 4×Hβ); 1.44 (s, 3H, CH$_3$); 1.42 (s, 3H, CH$_3$).

To a stirred solution of 100 mg (0.18 mmol) of the monoaldehyde intermediate in 10 mL of MeOH and 1 mL of water was added 0.5 mL of conc. aq. HCl. The solution was stirred for 1 h at ambient temperature, poured into water, and extracted with 1:1 Et$_2$O-EtOAc. The organic extract was washed with brine, dried (MgSO$_4$), and concentrated under reduced pressure to afford diol 15FO as an oil. $^1$H NMR (CDCl$_3$) δ 9.43 (s, 1H); 7.51 (s, 1H); 6.98–7.36 (m, 12H); 6.64 (s, 1H); 6.32 (s, 1H); 4.73 (d, 1H, J=15 Hz); 4.64 (d, 1H, J=15 Hz); 3.55–3.78 (m, 5H); 2.62–3.14 (m, 6H).

EXAMPLE 15FP

To a stirred solution of 530 mg (1.00 mmol) of acetonide protected bis(N-3-furylmethyl cyclic urea, described in example 15FN above, in 8 mL of THF, cooled to −78° C., was added 1.6 mL (2.5 mmol) of a 1.6 M solution of n-BuLi in THF. The solution was stirred 20 min. at −78° C., and DMF was added. The reaction was stirred 1 h at −78° C., whereupon it was quenched with 1N HCl. The mixture was extracted with Et$_2$O, and the organic extract was washed with brine, dried (MgSO$_4$), and concentrated under reduced pressure. Chromatography on silica gel (elution with 1:1 EtOAc-hexanes) afforded, after removal of solvent, 310 mg (53%) of dialdehyde intermediate as an oil. $^1$H NMR (CDCl$_3$) δ 9.42 (s, 1H); 7.52 (d, 1H, J=2 Hz); 7.20–7.36 (m, 5H); 6.58 (d, 1H, J=2H); 4.18 (ABq, 2H, J$_{AB}$=13 Hz, Δν=330 Hz); 4.00 (br. s, 1H); 3.90 (d, 1H, J=11 Hz); 2.84 (ABx, 2H, J$_{AB}$=13.5 Hz, J$_{AX}$=1.7 Hz, J$_{BX}$=11.3 Hz, Δν=78 Hz); 1.45 (s, 6H).

To a stirred, cooled (−78° C.) solution of 120 mg (0.21 mmol) of the dialdehyde intermediate in 4 mL of Et$_2$O was added 2 mL (2 mmol) of 1 M diisobutylaluminum hydride in CH$_2$Cl$_2$. The solution was stirred 15 min at −78° C., the dry ice bath was removed, and the reaction was quenched with saturated aqueous sodium potassium tartrate. The mixture was diluted with Et$_2$O, and the two phases were stirred together for 30 min. The phases were separated, and the organic phase was dried (MgSO$_4$), concentrated, and chromatographed on silica gel. The product was eluted with EtOAc, concentrated, and redissolved in 8 mL of MeOH. This solution was treated with 0.4 mL of con. aq. HCl, stirred 1 h, and poured into water. The colloidal suspension was extracted with EtOAc, and the organic extract was washed with brine, dried (MgSO$_4$), and concentrated under reduced pressure. Chromatography on silica gel (elution with EtOAc) afforded a glass which was lyophilized from benzeneacetonitrile to give 62 mg (57%) of tetraol 15FP as a powder. $^1$H NMR (CD$_3$OD) δ 7.43 (d, 1H, J=2 Hz); 7.20–7.37 (m, 3H); 7.11 (dd, 2H, J=8.1, 1.1 Hz); 6.37 (d, 1H, J=2H); 4.22 (ABq, 2H, J$_{AB}$=13.3 Hz, Δν=33 Hz); 3.76 (ABq, 2H, J=14.6 Hz, Δν=460 Hz); 3.65 (br. s, 1H); 3.56 (br. d, 1H, J=11 Hz); 2.98 (ABx, 2H, J$_{AB}$=13.3 Hz, J$_{AX}$=1.8 Hz, J$_{BX}$=12.1 Hz, Δν=54 Hz). Mass spec.(NH$_3$—CI/DDIP): 529 ((M+H–H$_2$O)$^+$, 100%).

EXAMPLE 15FQ

To a stirred solution of 55 mg (0.1 mmol) of monoaldehyde intermediate prepared in example 15FO in 2 mL of EtOH and 1 mL of water was added 35 mg (0.5 mmol) of hydroxylamine hydrochloride. The solution was stirred 25 h at ambient temperature, poured into water, and extracted with EtOAc. The organic extract was washed with brine, dried (MgSO$_4$), and concentrated under reduced pressure to afford 33 mg (58%) of oxime 15FQ as an amorphous solid. Mass Spec. (NH$_3$—CI/DDIP): 530 ((M+H)$^+$, 8%); 512 ((M+H–H$_2$O)$^+$, 100%). $^1$H NMR (CDCl$_3$) δ 7.76 (s, 1H); 7.01–7.38 (m, 13H); 6.47 (s, 1H); 6.32 (s, 1H); 4.59–4.76 (m, 2H); 3.55–3.84 (m, 4H); 3.25 (d, 1H, J=15 Hz); 2.75–3.09 (m, 5H).

EXAMPLE 15FR c.) To a stirred solution of 50 mg (0.097 mmol) of compound of example 15FO in 6 mL of EtOH was added 20 mg (excess) sodium borohydride. The solution was stirred 3 h at ambient temperature, kept at −23° C. for 15 h, and rewarmed to ambient temperature with stirring over 6 h. The reaction was quenched with 10% aq. HOAc, stirred for 30 min., and extracted with EtOAc. The organic extract was washed with brine, dried (MgSO4), and concentrated under reduced pressure. Chromatography on silica gel (elution with EtOAc) followed by lyophilization afforded 45 mg (90%) of triol 15FR as a white powder. $^1$H NMR (CDCl$_3$) δ 7.05–7.38 (m, 11H); 6.85 (s, 1H); 6.82 (s, 1H); 6.30 (s, 2H); 4.51–4.61 (m, 2H); 4.31 (d, 1H, J=13 Hz); 3.93 (dd, J=14, 5 Hz); 3.65–3.77 (m, 2H) 3.51–3.60 (m, 1H); 2.74–3.12 (m, 6H). Mass Spec. (NH$_3$—CI/DDIP): 517 ((M+NH$_4$–H$_2$O)$^+$, 7%); 499 ((M+H–H$_2$O)$^+$, 100%).

EXAMPLE 15FS and 15FT

A flask was charged with lithium chloride (1.02 g, 24.0 mmol, 1.2 equiv.) and flame dried in vacuo. A nitrogen atmosphere was introduced and dry dimethylformamide (12.0 ml) was added. The flask was cooled to 0° C. and the starting alcohol, 2-furylmethanol (1.7 ml, 20.0 mmol) was added via syringe. The reagents, 2,6-lutidine (3.5 ml, 30.0 mmol, 1.5 equiv., distilled from calcium hydride) and methanesulfonyl chloride (1.7 ml, 22.0 mmol, 1.1 equiv.), were added and stirring continued for one hour. The reaction was poured onto ice and extracted with ether. The ethereal layer was washed with a saturated aqueous solution of sodium carbonate, whereupon a precipitate formed. The precipitate was removed by filtration and the layers separated. The organic layer was dried with anhydrous sodium carbonate. The product was isolated by filtration and removal of solvent on an ice cooled rotary evaporator. When the volume neared 20 ml, the flask was removed from the rotary evaporator, flushed with nitrogen and diluted with dry dimethylformamide (20.0 ml). This solution containing 2-chloromethylfuran was used without characterization in the next reaction.

The cyclic urea acetonide XXVIIIf (1.02 g, 2.79 mmol) was added to the solution of 2-chloromethylfuran. Sodium hydride (490 mg, 16.3 mmol, 5.9 equiv., 80% oil dispersion) was added and stirring continued for one hour. The reaction was then quenched by the addition of water and extracted with ethyl acetate-hexanes (1:1). The organic phase was washed twice with water, once with brine, and dried over anhydrous magnesium sulfate. Filtration and evaporation gave the crude product which was purified by flash column chromatography (30% ethyl acetate-70% hexanes). The column provided two major fractions: a nonpolar fraction containing the significantly contaminated bis-alkylated product and a polar fraction containing adequately pure mono-alkylated cyclic urea intermediate (343 mg). $^1$H-NMR (300 Hz, CDCl$_3$) δ 7.28 (11H, m), 6.27 (1H, t), 6.05 (1H, d), 5.07 (1H, d), 4.83 (1H, d), 4.22 (1H, dd), 3.88 (2H, m), 3.48 (1H, m), 3.15–2.88 (4H, m), 2.70 (1H, t), 1.48 (3H, s), 1.46 (3H, s). HRMS (NH$_3$ CI) Calculated for C$_{27}$H$_{31}$N$_2$O$_4$ (M+H): 447.2284; observed: 447.2277. The nonpolar fraction was further purified by flash column chromatography (15% ethyl acetate-85% hexanes) to give pure bis-alkylated intermediate (73.4 mg, 5%). $^1$H-NMR (300 Hz, CDCl$_3$) δ 7.37–7.09 (11H, m), 6.27 (2H, dd), 6.08 (2H, d), 4.94 (2H, d), 3.90 (2H, s), 3.82 (2H, b), 3.03 (2H, d), 2.90 (4H, m), 1.41 (6H, s). $^{13}$C NMR (75.4 Hz, CDCl$_3$) δ 160.74, 151.93, 142.19, 138.86, 129.45, 128.57, 126.46, 110.21, 108.71, 75.26, 61.49, 48.45, 32.87, 26.71. MS (NH$_3$ CI) m/e 527 (M+H).

The monoalkylated cyclic urea acetonide above (33.5 mg, 0.075 mmol) was dissolved in methanol (3.0 ml). p-Toluenesulfonic acid monohydrate (2.9 mg) was added and stirring continued for four hours. The reaction was quenched by the addition of saturated aqueous sodium carbonate. The solvent was removed on a rotary evaporator and the residue applied to a flash silica gel column. The column was eluted with initially 50% ethyl acetate-50% hexanes and finally 100% ethyl acetate. This provided 15FS (27.8 mg, 91%) in excellent yield. $^1$H-NMR (300 Hz, CD$_3$OD) δ 7.43 (1H, s), 7.34–7.12 (10H, m), 6.31 (1H, m), 6.10 (1H, d), 4.75 (1H, d), 3.86 (1H, dd), 3.65 (2H, m), 3.39 (1H, m), 3.11 (2H, m), 3.01 (1H, dd), 2.88 (1H, d), 2.77 (1H, dd). $^{13}$C NMR (75.4 Hz, CD$_3$OD) δ 162.17, 151.45, 142.30, 139.79, 139.74, 129.10, 129.06, 128.08, 127.91, 125.96, 125.64, 109.80, 108.15, 70.90, 70.53, 65.28, 58.73, 32.70, 31.94. HRMS (NH$_3$ CI) Calculated for C$_{24}$H$_{27}$N$_2$O$_4$ (M+H): 407.1971; Observed: 407.1961.

The bisalkylated acetonide was deprotected using the same procedure. Flash silica gel chromatography using 50% ethyl acetate-50% hexanes gave 15FT in 83% yield. $^1$H-NMR (400 Hz, CD$_3$OD) δ 7.44 (2H, dd), 7.32–7.13 (10H, m), 6.33 (2H, dd), 6.15 (2H, d), 4.75 (2H, d), 3.64 (2H, bd), 3.60 (2H, s), 3.05–2.89 (6H, m). $^{13}$C NMR (100.6 Hz, CD$_3$OD) δ 163.11, 153.01, 143.93, 130.63, 129.47, 127.38, 111.36, 110.01, 71.75, 67.24, 48.88, 32.99. HRMS (NH$_3$ CI): Calculated for C$_{29}$H$_{31}$N$_2$O$_5$ (M+H): 487.2233; Observed: 487.2226.

EXAMPLE 15FU

The starting 3-carbomethoxy-2,5-dihydrothiophene was prepared from 1,4-dithiane-2,5-diol, trimethylphosphonoacrylate and triethylamine as described in the literature [*J. Org. Chem.* 43 (23) 4431 (1978)]. The resulting ester (1.03 g, 7.15 mmol) was dissolved in dry methylene chloride (16.0 ml) and cooled to –78° C. under a nitrogen atmosphere. A solution of diisobutylaluminum hydride (11.9 ml, 17.88 mmol, 2.5 equiv., 1.5 M in toluene) was added and stirring continued for two hours. The reaction was then briefly warmed to room temperature then recooled to –78° C. Excess reagent was then quenched with methanol (5.0 ml) and the reaction was allowed to warm to room temperature. The reaction was diluted with ether and treated with a saturated solution of sodium potassium tartrate. The clarified aqueous phase was extracted with two additional portions of ether. The combined organic layers were dried with magnesium sulfate, filtered and evaporated. Purification was accomplished by flash silica gel chromatography (5% methanol 95% methylene chloride). The resulting 3-hydroxymethyl-2,5-dihydrothiophene was isolated in 91% yield (753.7 mg). $^1$H-NMR (300 Hz, CDCl$_3$) δ 5.77 (1H, bs), 4.22 (2H, d), 3.74 (4H, m), 2.09 (1H, t). $^{13}$C NMR (75.4 Hz, CDCl$_3$) δ 142.77, 124.13, 61.39, 38.45, 38.21. MS (CH$_4$ CI) m/e 117 (M+H).

The alcohol (663.0 mg, 5.72 mmol) was dissolved in dry methylene chloride (20 ml) under a nitrogen atmosphere. Dry triethylamine (1.2 ml, 8.57 mmol, 1.5 equiv.) was added and the reaction cooled to 0° C. Methanesulfonic anhydride (1.2 g, 6.86 mmol, 1.2 equiv.) was added and reaction continued for 0.5 hours. The reaction was diluted with methylene chloride and washed with dilute hydrochloric acid and brine. Drying over magnesium sulfate, filtration and evaporation gave the crude mesylate which was used without purification.

The residue was dissolved in dry dimethylformamide (5.0 ml) and the cyclic urea acetonide XXVIIIf (524.5 mg, 1.43 mmol) was added. Sodium hydride (172 mg, 5.72 mmol, circa 4 equiv., 80% oil dispersion) was added and stirring continued overnight. The reaction was quenched by the careful addition of water and extracted with 50% ethyl acetate-50% hexanes. The organic phase was washed twice with water, once with brine, and dried over magnesium sulfate. Filtration and evaporation gave the crude product which was purified by flash silica gel chromatography (15% ethyl acetate-85% hexanes). The desired bisalkylated product was obtained in excellent yield (720.1 mg, 90%). $^1$H-NMR (300 Hz, CDCl$_3$) δ 7.29 (6H, m), 7.14 (4H, d), 5.40 (2H, s), 4.32 (2H, d), 4.08 (2H, s), 3.83 (2H, d), 3.78–3.49 (8H, m), 3.06 (2H, dd), 2.87 (2H, d), 2.83 (2H, dd), 1.31 (6H, s). HRMS (NH$_3$ CI) Calculated for C$_{32}$H$_{39}$N$_2$O$_3$S$_2$ (M+H)$^+$: 563.2402; Observed: 563.2394.

Removal of the acetonide protecting group using the hydrolysis procedure described in the procedure of example 15FS gave compound 15FU. (34.1 mg, 78%). $^1$H-NMR (300 Hz, CDCl$_3$) δ 7.36–7.11 (10H, m), 5.45 (2H, bs), 4.27 (2H, d), 3.93 (2H, bs), 3.82–3.49 (10H, m), 3.16 (2H, dd), 2.87 (2H, dd), 2.84 (2H, d), 2.62 (2H, bs). $^{13}$C-NMR (75.43 Hz, CDCl$_3$) δ 162.14, 139.66, 139.10, 129.36, 128.66, 128.51, 126.70, 71.81, 63.01, 50.97, 39.70, 38.31, 32.91. HRMS (NH$_3$ CI) Calculated for C$_{29}$H$_{35}$N$_2$O$_3$S$_2$ (M+H): 523.2089; Observed: 523.2071.

EXAMPLE FW

Compound 15FU, protected as the acetonide, (53.2 mg, 0.0947 mmol) was dissolved in dry methylene chloride (2.0 ml) under a nitrogen atmosphere. The reaction was cooled to 0° C. and solid m-chloroperoxybenzoic acid (83.7 mg, 0.388 mmol, 4.1 equiv., circa 80% active) was added and stirring continued for three hours with gradual warming to room temperature. The reaction was then diluted with methylene chloride and washed successively with saturated sodium bisulfite, saturated sodium carbonate, and brine. The organic phase was dried with magnesium sulfate, filtered and evaporated. The crude product was purified by flash silica gel chromatography (50% ethyl acetate-50% hexanes) to give the bis-sulfone acetonide (61.5 mg, slightly more than theoretical). This material was of sufficient purity for the subsequent transformations. $^1$H-NMR (300 Hz, CDCl$_3$) δ 7.39–6.95 (10H, m), 5.60 (2H, bs), 4.22 (2H, d), 4.06 (2H, s), 3.83–3.47 (10H, m), 3.13 (2H, d), 2.99 (2H, d), 2.73 (2H, dd), 1.31 (6H, s). MS (NH$_3$ CI) m/e 563 (M+H–SO$_2$), 499 (M+H–2SO$_2$).

Removal of the acetonide protecting group using the hydrolysis procedure described in the procedure of example 15FS gave compound 15FV (17.4 mg, 65%). $^1$H-NMR (300 Hz, CDCl$_3$) δ 7.28 (6H, m), 7.11 (4H, d), 5.57 (2H, bs), 4.16 (2H, d), 3.92 (2H, s), 3.83–3.45 (10H, m), 3.23 (2H, d), 2.92 (2H, d), 2.74 (2H, t). $^{13}$C-NMR (100.6 Hz, CDCl$_3$) δ 161.99, 139.00, 135.52, 129.32, 128.84, 127.04, 123.28, 71.04, 63.84, 56.53, 53.07, 33.14. HRMS (FAB (glycerol/TFA)): Calculated for C$_{29}$H$_{35}$N$_2$O$_7$S$_2$ (M+H): 587.1886; Observed: 587.1889.

EXAMPLE 15FW

Compound 15FU, protected as the acetonide, (46.6 mg, 0.0829 mmol) was dissolved in dry 1,2-dichloroethane (2.0 ml). Addition of 2,3-dichloro-5,6-dicyanobenzoquinone (41.4 mg, 0.182 mmol, 2.2 equiv.) resulted in an instantaneous conversion to product. The reaction was applied to a flash silica gel column and eluted with first methylene chloride then 5% methanol-95% methylene chloride. The desired bis-thiophene intermediate was isolated in 92% yield (42.4 mg). $^1$H-NMR (300 Hz, CDCl$_3$) δ 7.37–7.20 (8H, m), 7.10 (4H, d), 6.98 (2H, d), 6.95 (2H, b), 4.88 (2H, d), 3.83 (2H, bs), 3.80 (2H, bd (obscured)), 3.16 (2H, d), 2.92 (2H, dd), 2.82 (2H, dd), 1.37 (6H, s). $^{13}$C-NMR (75.4 Hz, CDCl$_3$) δ 161.29, 139.01, 138.84, 129.43, 128.71, 127.74, 126.53, 126.37, 123.87, 110.19, 75.59, 60.89, 51.00, 33.58, 26.79. MS (NH$_3$ CI) m/e 559 (M+H).

After deprotection of the acetonide as described for example 15FS, the resulting residue was applied to a preparative silica gel plate (0.25 mm) and eluted with 50% ethyl acetate-50% hexanes. Isolation of the appropriate fractions gave compound 15FW (12.9 mg, 61%). $^1$H-NMR (300 Hz, CDCl$_3$) δ 7.38 (8H, m), 7.12 (4H, d), 7.00 (2H, dd), 6.97 (2H, bd), 4.82 (2H, d), 3.64 (2H, s), 3.58 (2H, bd), 3.16 (2H, d), 3.04 (2H, dd), 2.89 (2H, dd), 2.34 (2H, bs). $^{13}$C-NMR (75.4 Hz, CDCl$_3$) δ 161.69, 139.4, 138.92, 129.46, 128.68, 127.98, 126.58, 126.43, 124.07, 71.77, 64.04, 50.20, 32.81. MS (NH$_3$ CI) m/e 519 (M+H).

EXAMPLE 15FX

Compound 15FV, protected as the acetonide, (15.5 mg, 0.024 mmol) was dissolved in dry toluene (5.0 ml) under nitrogen. The reaction was heated at reflux for seven hours then allow to cool overnight. The solvent was removed under reduced pressure and the residue applied to a preparative silica gel plate (0.25 mm) and eluted with 25% ethyl acetate-75% hexanes. The bis-diene intermediate was isolated in 61% yield (7.5 mg). $^1$H-NMR (300 Hz, CDCl$_3$) δ 7.37–7.17 (10H, m), 6.31 (2H, dd), 5.35 (2H, d), 5.14 (2H, s), 5.13 (2H, d), 4.83 (2H, d), 4.70 (2H, d), 3.88 (2H, s), 3.85 (2H, m), 2.89 (4H, m), 2.64 (2H, d), 1.44 (6H, s) $^{13}$C-NMR (100.6 Hz, CDCl$_3$) δ 161.68, 142.93, 139.49, 136.85, 129.39, 128.64, 126.49, 120.23, 115.46, 110.22, 75.76, 59.19, 52.81, 33.40, 26.90. MS (NH$_3$ CI) m/e 499 (M+H).

After deprotection of the acetonide as described for example 15FS, the resulting residue was applied to a preparative silica gel plate (0.25 mm) and eluted with 50% ethyl acetate-50% hexanes. Isolation of the appropriate fractions gave compound 15FX (2.9 mg, 42%). $^1$H-NMR (400 Hz, CDCl$_3$) δ 7.37–7.16 (10H, m), 6.31 (2H, dd), 5.34 (2H, d), 5.17 (2H, s), 5.12 (2H, d), 4.79 (2H, s), 4.74 (2H, d), 3.76 (2H, s), 3.64 (2H, d), 3.06–2.88 (4H, m), 2.67 (2H, d), 2.28 (2H, s). $^{13}$C-NMR (100.6 Hz, CDCl$_3$) δ 162.02, 143.05, 139.93, 136.88, 129.48, 128.68, 126.47, 120.08, 115.61, 71.89, 63.06, 52.42, 32.68. HRMS (NH$_3$ CI): Calculated for C$_{29}$H$_{35}$N$_2$O$_3$ (M+H): 459.2648; Observed: 459.2653.

TABLE 2d

[Structure: 7-membered ring with NR²³, C=O, R²²N, two Ph-CH₂ substituents, and two OH groups]

| Ex. No. | Stereo 2:3:4:5 | R²² | R²³ | HPLC K₁ | IC₉₀ | mp, °C. | MS M+H (M+NH₄) | Notes |
|---|---|---|---|---|---|---|---|---|
| 9A | RSSR | m-(HO—N=CH)C₆H₄CH₂— | n-(HONHCH₂)—C₆H₄CH₂— | +++ | +++ | 214–216 | 595 | |
| 9B | RSSR | m-(HONHCH₂)—C₆H₄CH₂—·HOAC | m-(HONHCH₂)—C₆H₄CH₂—·HOAc | +++ | +++ | | 610 | |
| 9C | RSSR | m-(HONHCH₂)—C₆H₄CH₂— | m-(HONHCH₂)—C₆H₄CH₂— | ++ | ++ | 170.5–171 | 790 | |
| 9D | RSSR | m-(C₆H₅CH₂ON=CH)—C₆H₄CH₂— | m-(C₆H₅CH₂ON=CH)—C₆H₄CH₂— | ++ | +++ | | | |
| 9E | RSSR | m-(HONHCH₂)—C₆H₄CH₂—·HCl | m-(HONHCH₂)—C₆H₄CH₂—·HCl | +++ | + | | | |
| 9F | RSSR | m-(C₆H₅CH₂ONHCH₂)—C₆H₄CH₂— | m-(C₆H₅CH₂ONHCH₂)—C₆H₄CH₂— | +++ | +++ | 775 (792) | 655 | |
| 9G | RSSR | m-(CH₃OC(=O)—O)—C₆H₄CH₂— | m-(CH₃OC(=O)—O)—C₆H₄CH₂— | +++ | +++ | 146–147 | 612 | |
| 9H | RSSR | m-(CH₃CH(OH))C₆H₄CH₂ | m-(CH₃CH(OH))C₆H₄CH₂ | | | | 593 | |
| 9I | RSSR | m-(CH₃NHCH₂)—C₆H₄CH₂— | m-(CH₃NHCH₂)—C₆H₄CH₂— | +++ | +++ | | 649 | |
| 9J | RSSR | m-(HOCH₂CH₂N=CH)—C₆H₄CH₂— | m-(HOCH₂CH₂N=CH)—C₆H₄CH₂— | | | | | |
| 9K | RSSR | m-(HOCH₂CH₂N=CH)—C₆H₄CH₂— | [structure: tetrahydrofuran with NH, ethyl, phenyl] | +++ | +++ | | 649 | |
| 9L | RSSR | m-(C₆H₅CH₂NHC(=O)—O)—C₆H₄CH₂— | m-(C₆H₅CH₂NHC(=O)—O)—C₆H₄CH₂— | +++ | +++ | 150 (dec) | 805 | |
| 9M | RSSR | m-(CH₃NHC(=O)—O)—C₆H₄CH₂— | m-(CH₃NHC(=O)—O)—C₆H₄CH₂— | +++ | +++ | 150 (dec) | 670 | |
| 9N | RSSR | m-(HOCH₂CO)—C₆H₄CH₂— | m-Br—C₆H₄CH₂— | +++ | +++ | | 639/641 (656/658) | |
| 9o | RSSR | m-(CH₃C(=O))—C₆H₄CH₂— | m-Br—C₆H₄CH₂— | +++ | +++ | 190 | 644/646 | |
| 9P | RSSR | m-(CH₃C(=O))—C₆H₄CH₂— | m-(CH₃C(=O))—C₆H₄CH₂— | +++ | +++ | 158–159 | 608 | |
| 9Q | RSSR | m-(CH₃C(=NOH))—C₆H₄CH₂— | m-(CH₃C(=NOH))—C₆H₄CH₂— | +++ | +++ | 200–202 | 621 | |
| 9R | RSSR | m-(CH₃CH(OH))—C₆H₄CH₂— | m-Br—C₆H₄CH₂— | +++ | +++ | | 629/631 | |
| 9S | RSSR | m-(ClCH₂)—C₆H₄CH₂— | m-(ClCH₂)—C₆H₄CH₂— | +++ | +++ | 156 | 603 | |
| 9T | RSSR | m-(5-tetrazolyl)·C₆H₄CH₂— | m-(5-tetrazolyl)C₆H₄CH₂— | +++ | + | 159.4 | 643.2893 | |
| 9U | RSSR | m-(5-tetrazolyl)·C₆H₄CH₂— | cyclopropyl-methyl | +++ | +++ | 171.6 | 539.2771 | |
| 10A | RSSR | m-(CO₂H)—C₆H₄CH₂— | H | +++ | + | 141–143 | 560 (577) | 2 |
| 10C | RSSR | m-(NO₂)—C₆H₄CH₂— | n-(OHC)—C₆H₄CH₂— | ++ | + | 189–191 | (638) | 4 |
| 10D | RSSR | m-(CH₃ON=CH)—C₆H₄CH₂— | m-(CH₃ON=CH)—C₆H₄CH₂— | ++ | + | 183–185 | 623 | 5 |
| 10E | RSSR | p-(CH₃C(=O)O)—C₆H₄CH₂— | p-(HO)—C₆H₄CH₂— | ++ | +++ | 110–112 | 623 | 6 |
| 10F | RSSR | m-(CH₃C(=O)O)—C₆H₄CH₂— | m-(CH₃C(=O)O)—C₆H₄CH₂— | +++ | +++ | | | 8 |
| 10G | RSSR | m-(NH₂C(=O))—C₆H₄CH₂— | m-(NH₂C(=O))—C₆H₄CH₂— | +++ | +++ | | (610) | 7 |
| 10H | RSSR | m-(HO)—C₆H₄CH₂— | m-(NH₂C(=O)—CH₂O)—C₆H₄CH₂— | +++ | +++ | | NMR Only | |
| 10I | RSSR | | H | +++ | +++ | 193–194 | 433 | 2 |

TABLE 2d-continued

[Structure: 7-membered ring with NR²³ and C=O, R²²N, two Ph-CH₂ substituents, and HO, OH groups]

| Ex. No. | Stereo 2,3,4,5 | R²² | R²³ | HPLC K₁ | IC₉₀ | mp, °C. | MS M + H (M + NH₄) | Notes |
|---|---|---|---|---|---|---|---|---|
| 10J | RSSR | m-(CH₃)—C₆H₄CH₂— | m-(HO)—C₆H₄CH₂— | +++ | +++ | | 537 | 3 |
| 10K | RSSR | 2-Naphthylmethyl | m-(HO)—C₆H₄CH₂— | ++ | +++ | 137–138 | 573 | 3 |
| 10L | RSSR | p-CH₃C(=O)—O—C₆H₄CH₂— | p-CH₃C(=O)—O—C₆H₄CH₂— | +++ | +++ | | 623 | 8 |
| 10M | RSSR | m-(NH₂NHC(=O))—C₆H₄CH₂— | m-(NH₂NHC(=O))—C₆H₄CH₂— | +++ | +++ | 205 | 623 | 7 |
| 10N | RSSR | p-(NH₂NHC(=O))—C₆H₄CH₂— | p-(NH₂NHC(=O))—C₆H₄CH₂— | +++ | +++ | 215–217 | 623 | 7 |
| 10o | RSSR | p-(HOCH₂)—C₆H₄CH₂— | p-(HOCH₂)—C₆H₄CH₂— | +++ | +++ | 141–144 | 553 | 3 |
| 10P | RSSR | m-(NH₂C(=O)—NHN=CH)—C₆H₄CH₂— | m-(NH₂C(=O)—NHN=CH)—C₆H₄CH₂— | +++ | +++ | 301–303 | | 5 |
| 10Q | RSSR | 2-picolinyl- | m-(HO)—C₆H₄CH₂— | ++ | +++ | | 524 | 3 |
| 10R | RSSR | m-(CH₃ONHC(=O))—C₆H₄CH₂— | m-(CH₃ONHC(=O))—C₆H₄CH₂— | +++ | +++ | 150–158 | (670) | 7 |
| 10S | RSSR | p-(CH₃ONHC(=O))—C₆H₄CH₂— | p-(CH₃ONHC(=O))—C₆H₄CH₂— | +++ | +++ | 186–189 | 653 | 7 |
| 10T | RSSR | m-(HOCH₂CH(OH)—CH₂O)—C₆H₄CH₂— | m-(HOCH₂CH(OH)—CH₂O)—C₆H₄CH₂— | +++ | +++ | 113–115 | | 9 |
| 10U | RSSR | m-(adamantamido)—C₆H₄CH₂— | m-(adamantamido)—C₆H₄CH₂— | + | +++ | 183–184 | 893 | 8 |
| 10V | RSSR | m-(HO)—C₆H₄CH₂— | m-(adamantamido)—C₆H₄CH₂— | +++ | +++ | 196–198 | 716 | 6 |
| 10W | RSSR | m-(CH₃CH₂OC(=O))—C₆H₄CH₂— | m-(CH₃CH₂OC(=O))—C₆H₄CH₂— | ++++ | + | 178–180 | 651 | 10 |
| 10X | RSSR | m-(HONHC(=O))—C₆H₄CH₂— | m-(HONHC(=O))—C₆H₄CH₂— | + | +++ | 139–143 | | 11 |
| 10Y | RSSR | m-(HOCH₂O)—C₆H₄CH₂— | m-(HOCH₂O)—C₆H₄CH₂— | +++ | +++ | 245–247 | 627 | 12 |
| 10Z | RSSR | p-(HOCH₂)C₆H₄CH₂ | p-(HOCH₂)C₆H₄CH₂ | + | + | 198–199 | 567 | 1 |
| 11A | RSSR | m-(NH₂C(=NH)—C₆H₄CH₂—HOAc | m-(NH₂C(=NH)—C₆H₄CH₂—HOAc | ++ | ++ | 224–226 | 591 | 13 |
| 11B | RSSR | (HOCH₂—CH(OH)—C₆H₄CH₂— m, p, positions mixture | (HOCH₂—CH(OH))—C₆H₄CH₂— m, p, positions mixture | +++ | +++ | 135–137 | 627 | 9 |
| 11C | RSSR | m-(NH₂C(=NH))—C₆H₄CH₂—HOAC | m-(NH₂C(=NH))—C₆H₄CH₂—HOAC | +++ | +++ | 229–231 | | 4 |
| 11D | RSSR | p-(HO)-m-(HOCH₃)—C₆H₄CH₂— | p-(HO)-m-(HOCH₃)—C₆H₄CH₂— | ++ | ++ | 178–180 | | 14 |
| 11E | RSSR | p-(HO)-m-(OCH₃)—C₆H₄CH₂— | p-(HO)-m-(OCH₃)—C₆H₄CH₂— | + | + | 174–178 | 567 | 14 |
| 11F | RSSR | p-CH₃OC(=O)—C₆H₄CH₂— | p-CH₃OC(=O)—C₆H₄CH₂— | ++ | +++ | 158–161 | 651 | 10 |
| 11G | RSSR | m-(CH₃OC(=O))—C₆H₄CH₂— | m-(CH₃OC(=O))—C₆H₄CH₂— | +++ | +++ | 160–163 | 622 (639) | 4 |
| 11H | RSSR | m-(CH₃NHC(=O))—C₆H₄CH₂— | m-(CH₃NHC(=O))—C₆H₄CH₂— | +++ | +++ | 189–193 | 621 | 7 |
| 11I | RSSR | m-(HO)—C₆H₄CH₂— | m-(HO)—C₆H₄CH₂— | +++ | +++ | 199–201 | 523 | 3 |
| 11J | RSSR | benzyl | p-(HOCH₂)—C₆H₄CH₂— | +++ | +++ | | 587 | 3 |
| 11K | RSSR | 2-Naphthylmethyl | m-(HOCH₂—CH(OH))—C₆H₄CH₂— | +++ | +++ | | 627 | 9 |
| 11L | RSSR | m-(HOCH₂—CH(OH))—C₆H₄CH₂— | m-(HOCH₂—CH(OH))—C₆H₄CH₂— | +++ | +++ | | 627 | 9 |
| 11M | RSSR | m-(HOCH₂)—C₆H₄CH₂— | m-(CH₃NHC(=O))—C₆H₄CH₂— | +++ | +++ | 107–109 | (611) 594 | 4 |
| 11N | RSSR | p-(HOCH₂)—C₆H₄CH₂— | H | +++ | +++ | 112–114 | 447 | 2 |
| 11o | RSSR | m-((HO)₂B)—C₆H₄CH₂— | m-((HO)₂B)—C₆H₄CH₂— | +++ | +++ | 263–267 | (675) | 15 |
| 11P | RSSR | m-(NO₂)—C₆H₄CH₂— | m-(HO)—C₆H₄CH₂— | +++ | +++ | 173–176 | 538 | 3 |
| 11Q | RSSR | m-(NH₂)—C₆H₄CH₂— | m-(HO)—C₆H₄CH₂— | +++ | +++ | 116–120 | 649 | 3 |
| 11R | RSSR | m-((CH₃)₂NC(=O))—C₆H₄CH₂— | m-((CH₃)₂NC(=O))—C₆H₄CH₂— | ++ | +++ | 135–138 | 649 | 7 |
| 11S | RSSR | m-(CH₃CH₂NHC(=O))—C₆H₄CH₂— | m-(CH₃CH₂NHC(=O))—C₆H₄CH₂— | +++ | +++ | 132–134 | 649 | 7 |
| 11T | RSSR | m-(CH₃O₂C)—C₆H₄CH₂— | m-((CH₃)₂NC(=O))—C₆H₄CH₂— | +++ | +++ | | (681) | 4 |

TABLE 2d-continued

[Structure: 7-membered ring lactam with R22N-C(=O)-...-NR23, with Ph and OH substituents, and benzyl/HO groups]

| Ex. No. | Stereo 2:3:4:5 | R22 | R23 | HPLC K$_i$ | IC$_{90}$ | mp, °C. | MS M+H (M+NH$_4$) | Notes |
|---|---|---|---|---|---|---|---|---|
| 11U | RSSR | m-(CH$_3$O$_2$C)—C$_6$H$_4$CH$_2$— | m-((CH$_3$CH$_2$)$_2$NHC(=O))—C$_6$H$_4$CH$_2$— | +++ | +++ | | (653) | 4 |
| 12A | RSSR | 6-amino-1-hexyl | 6-amino-1-hexyl | + | + | | 525 | |
| 12B | RSSR | 6-amino-1-hexyl | benzyl | ++ | + | | 516 | |
| 12C | RSSR | 6-hydroxy-1-hexyl | H | +++ | +++ | | 427 | |
| 12D | RSSR | 6-hydroxy-1-hexyl | 6-hydroxy-1-hexyl | +++ | +++ | | 527 | |
| 12E | RSSR | cyclopropyl methyl | 6-hydroxy-1-hexyl | ++ | ++ | | 481 | |
| 12F | RSSR | 4-hydroxy-1-butyl | 4-hydroxy-1-butyl | +++ | +++ | | 471 | |
| 12G | RSSR | 5-carboxy-1-pentyl | 5-carboxy-1-pentyl | ++ | ++ | | 555 | |
| 12H | RSSR | 5-carbomethoxy-1-pentyl | 5-carbomethoxy-1-pentyl | +++ | + | | 583 | |
| 12I | RSSR | 5-carbomethoxy-1-pentyl | 5-carboxy-1-pentyl | | | | | |
| 12J | RSSR | 3-iodobenzyl | 3-iodobenzyl | +++ | +++ | | 759 | |
| 12K | RSSR | 8-hydroxy-1-octyl | 8-hydroxy-1-octyl | ++ | +++ | | 583 | |
| 12L | RSSR | 2-(hydroxymethyl)-cyclopropyl-methyl | 2-(hydroxymethyl)-cyclopropyl-methyl | +++ | | | 495 | |
| 12M | RSSR | benzyl | 2-(hydroxymethyl)-cyclopropyl-methyl | ++ | +++ | | 501 | |
| 12N | RSSR | H | H | +++ | + | | 411 | |
| 12o | RSSR | 7-hydroxy-1-heptyl | H | ++ | ++ | | 411 | |
| 12P | RSSR | 7-hydroxy-1-heptyl | 7-hydroxy-1-heptyl | +++ | +++ | | 555 | |
| 12Q | RSSR | 3-(carbamoylthio)benzyl | 3-(carbamoylthio)benzyl | ++ | + | 185 | 655 | |
| 12R | RSSR | 3-(methylthio)benzyl | 3-(methylthio)benzyl | +++ | +++ | 169 | 599 | |
| 12S | RSSR | 3-(methylsulfonyl)benzyl | 3-(methylsulfonyl)benzyl | +++ | +++ | | 633 | |
| 12T | RSSR | H | 2-[(2-hydroxyethyl)oxy]ethyl | ++ | + | | 415 | |
| 12U | RSSR | 2-[(2-hydroxyethyl)oxy]ethyl | 2-[(2-hydroxyethyl)oxy]ethyl | + | ++ | | 503 | |
| 12V | RSSR | 6-acetoxy-1-hexyl | 6-acetoxy-1-hexyl | ++ | +++ | | 569 | |
| 12W | RSSR | 6-(N-methylaminocarboxy)-1-hexyl | 6-(N-methylaminocarboxy)-1-hexyl | ++ | + | | 641 | |
| 12X | RSSR | 6-(N-methylaminocarboxy)-1-hexyl | 6-acetoxy-1-hexyl | ++ | +++ | | 626 | |
| 12Y | RSSR | 6-(N-methylaminocarboxy)-1-hexyl | 6-acetoxy-1-hexyl | +++ | +++ | | 584 | |
| 12Z | RSSR | 2-(2-hydroxyethyl)cyclopropyl-methyl | H | ++ | | | 425 | |
| 13A | RSSR | 2-(2-hydroxyethyl)cyclopropyl-methyl | H | ++ | | | 439 | 16 |
| 13B | RSSR | [2-(2-hydroxypropyl)-3,3-dimethyl] cyclopropyl methyl | H | ++ | | | 481 | 16 |
| 13C | RSSR | [2-(2-hydroxypropyl)-3,3-dimethyl] cyclopropyl methyl | | + | | | 635 (652) | 16 |
| 13D | RSSR | 6-hexenyl | 6-hexenyl | +++ | +++ | | 491 | |
| 13E | RSSR | 5,6-epoxy-1-hexyl | 5,6-epoxy-1-hexyl | ++ | ++ | | 523 | |
| 13F | RSSR | 5,6-dibromo-1-hexyl | 5,6-dibromo-1-hexyl | ++ | + | | 811 | |
| 13G | RSSR | 6-bromo-5-hydroxy-1-hexyl | 6-bromo-5-hydroxy-1-hexyl | +++ | +++ | | 685 | |
| 13H | RSSR | 5-hydroxy-1-pentyl | 5-hydroxy-1-pentyl | +++ | ++ | | 499 | |
| 13I | RSSR | 5-dihydroxy-1-hexyl | 5-dihydroxy-1-hexyl | +++ | + | | 559 | |

TABLE 2d-continued

| Ex. No. | Stereo 2;3;4;5 | R$^{22}$ | R$^{23}$ | HPLC K$_I$ | IC$_{90}$ | mp, °C. | MS M + H (M + NH$_4$) | Notes |
|---|---|---|---|---|---|---|---|---|
| 13J | RRSR | cyclopropyl-methyl | cyclopropyl-methyl | +++ | +++ | | 435 | |
| 13K | RRSR | allyl | allyl | +++ | +++ | | 407 | |
| 13L | RRSR | benzyl | benzyl | +++ | +++ | | 507 | |
| 13M | RRSR | 4-(hydroxymethyl)benzyl | 4-(hydroxymethyl)benzyl | + | ++ | | 567 | |
| 13N | RRRR | allyl | allyl | + | ++ | | 407 | |
| 13o | RRRR | cyclopropyl-methyl | cyclopropyl-methyl | + | + | | 435 | |
| 13P | RRRR | H | H | + | +++ | | 327 | |
| 13Q | RRRR | benzyl | benzyl | ++ | +++ | | 507 | |
| 13R | RRRR | n-butyl | n-butyl | + | ++ | | 439 | |
| 13S | RRRR | 4-(hydroxymethyl)benzyl | 4-(hydroxymethyl)benzyl | ++ | ++ | | 567 | |
| 13T | RRRR | (1,2,3,4-tetrahydro)-6-isoquinolyl-methyl | (1,2,3,4-tetrahydro)-6-isoquinolyl-methyl | ++ | + | 264–6 | 617 | |
| 13U | RSSR | 6-isoquinolyl-methyl | 6-isoquinolyl-methyl | + | + | | 609 | |
| 13V | RSSR | 2-thiazolyl-methyl | 2-thiazolyl-methyl | ++ | ++ | | 521 | |
| 13W | RSSR | (5-t-butoxycarbonyl)-2-furanylmethyl | (5-t-butoxycarbonyl)-2-furanylmethyl | +++ | +++ | 182–4 | 687 | |
| 13X | RRRS | (5-hydroxymethyl)-2-furanylmethyl | (5-hydroxymethyl)-2-furanylmethyl | + | + | | 547 | |
| 13Y | RSSR | benzyl | benzyl | +++ | +++ | | 507 | |
| 13Z | RSSR | 4-chloro-3-pyridylmethyl | 4-chloro-3-pyridylmethyl | ++ | ++ | | 577 (594) | |
| 14A | RSSR | 2-chloro-3-pyridylmethyl | 2-chloro-3-pyridylmethyl | ++ | ++ | | 685 | |
| 14B | RSSR | 2-(t-butylthio)-3-pyridylmethyl | 2-(t-butylthio)-3-pyridylmethyl | ++ | + | | 541 | |
| 14C | RSSR | 4-hydroxy-3-pyridylmethyl | 4-hydroxy-3-pyridylmethyl | ++ | ++ | | 458 | |
| 14D | RSSR | 2-pyridyl | 2-pyridyl | ++ | +++ | | 543 | |
| 14E | RSSR | oct-2-yn-1-yl | oct-2-yn-1-yl | ++ | | | 739 | 16 |
| 14F | RSSR | 3,3-diphenyl-2(R)-cylpropylmethl | 3,3-diphenyl-2(R)-cylpropylmethl | ++ | | | 479 | |
| 14G | RSSR | phenyl | phenyl | ++ | + | | 587 | 16 |
| 14H | RSSR | 3(S)-phenyl-2(R)-cyclopropyl-methyl | 3(S)-phenyl-2(R)-cyclopropyl-methyl | +++ | ++ | 141.8 | 457 | 16 |
| 14I | RSSR | 3(S)-phenyl-2(R)-cyclopropyl-methyl | H | ++ | +++ | | | |
| 14J | RSSR | 3-benzyloxy-5-methyl-4-pyridylmethyl | 3-benzyloxy-5-methyl-4-pyridylmethyl | +++ | +++ | | | |
| 14K | RSSR | 3-hydroxy-5-methyl-4-pyridylmethyl | 3-hydroxy-5-methyl-4-pyridylmethyl | ++ | + | | | |
| 15A | RSSR | p-(HOCH$_2$)—C$_6$H$_4$CH$_2$— | p-(HOCH$_2$)—C$_6$H$_4$CH$_2$— | +++ | +++ | 180.3 | 552.29 | 17 |
| 15B | RSSR | m-(CF$_3$O$_2$SNH)—C$_6$H$_4$CH$_2$— | m-(CF$_3$O$_2$SNH)—C$_6$H$_4$CH$_2$— | +++ | ++ | 190.7 | 801.19 | 18 |
| 15C | RSSR | m-(H$_2$NCONH)—C$_6$H$_4$CH$_2$— | m-(H$_2$NCONH)—C$_6$H$_4$CH$_2$— | +++ | +++ | | | 19 |
| 15D | RSSR | m-(CH$_3$NH)—C$_6$H$_4$CH$_2$— | m-(CH$_3$NH)—C$_6$H$_4$CH$_2$— | +++ | +++ | 82.0 | 565.32 | 20 |
| 15E | RSSR | m-(C$_6$H$_5$CH$_2$OCONH)—C$_6$H$_4$CH$_2$— | m-(C$_6$H$_5$CH$_2$OCONH)—C$_6$H$_4$CH$_2$— | ++ | + | 108.9 | 822.39 | 21 |
| 15F | RSSR | m-(CH$_3$(OHC)N)—C$_6$H$_4$CH$_2$— | m-(CH$_3$(OHC)N)—C$_6$H$_4$CH$_2$— | +++ | +++ | | 621.31 | 22 |
| 15G | RSSR | m-(H$_2$N)—C$_6$H$_4$CH$_2$—HCl | m-(H$_2$N)—C$_6$H$_4$CH$_2$—HCl | +++ | +++ | | 486.27 | 23 |
| 15H | RSSR | cyclopropyl-methyl | cyclopropyl-methyl | +++ | +++ | | 516.25 | |
| 15I | RSSR | m-((CH$_3$)$_2$N)—C$_6$H$_4$CH$_2$— | m-((CH$_3$)$_2$N)—C$_6$H$_4$CH$_2$— | +++ | +++ | 199.9 | 593.35 | 24 |
| 15J | RSSR | p-(HOCH$_2$)—C$_6$H$_4$CH$_2$— | p-(HOCH$_2$)—C$_6$H$_4$CH$_2$— | +++ | +++ | 92.0 | (599) | |

TABLE 2d-continued

[Structure: seven-membered ring with O=C-NR²³, bearing Ph, OH, OH, Ph substituents; R²²N on nitrogen]

| Ex. No. | Stereo 2;3;4;5 | R²² | R²³ | HPLC K$_i$ | IC$_{90}$ | mp, °C | MS M+H (M+NH$_4$) | Notes |
|---|---|---|---|---|---|---|---|---|
| 15K | RSSR | m-(H$_2$N)—C$_6$H$_4$CH$_2$— | m-(CH$_3$NHCONH)—C$_6$H$_4$CH$_2$— | +++ | | 153.3 | 594.5 | 25 |
| 15L | RSSR | m-(CH$_3$NHCONH)—C$_6$H$_4$CH$_2$— | m-(CH$_3$NHCONH)—C$_6$H$_4$CH$_2$— | +++ | | 173.7 | (651.4) | 25 |
| 15M | RSSR | m-(NHCH$_3$)—C$_6$H$_4$CH$_2$— | p-(HOCH$_2$)—C$_6$H$_4$CH$_2$— | +++ | +++ | 107.6 | 566.03 | 26 |
| 15N | RSSR | m-((CH$_3$)$_2$NCH$_2$—C(O)NH—C$_6$H$_4$CH$_2$—...HCl | m-((CH$_3$)$_2$NCH$_2$—C(O)NH—C$_6$H$_4$CH$_2$— | +++ | +++ | 92.8 | 707.39 | 27 |
| 15O | RSSR | m-((CH$_3$)$_2$NCH$_2$—C(O)NH—C$_6$H$_4$CH$_2$—...HCl | p-(HOCH$_2$)—C$_6$H$_4$CH$_2$— | +++ | +++ | 202.6 | 679.36 | 27 |
| 15P | RSSR | m-((CH$_3$)$_2$NCH$_2$—C(O)NH—C$_6$H$_4$CH$_2$—...HCl | p-(HOCH$_2$)—C$_6$H$_4$CH$_2$— | +++ | +++ | 108.1 | 637.34 | 27 |
| 15Q | RSSR | m-((CH$_3$)$_2$NCH$_2$—C(O)NH—C$_6$H$_4$CH$_2$— | m-(H$_2$NCH$_2$C(O)NH)—C$_6$H$_4$CH$_2$—...HCl | +++ | +++ | 114.6 | 651.33 | 27 |
| 15R | RSSR | m-(H$_2$NCH$_2$C(O)NH)—C$_6$H$_4$CH$_2$— | m-(L-C$_6$H$_5$CH$_2$OC(O)NH—CH(CH$_3$)C(O)NH)—C$_6$H$_4$CH$_2$— | +++ | +++ | 233.7 | 947.43 | 27 |
| 15S | RSSR | m-(L-C$_6$H$_5$CH$_2$OC(O)NH—CH(CH$_3$)C(O)NH)—C$_6$H$_4$CH$_2$— | m-(L-C$_6$H$_5$CH$_2$OC(O)NHCH(CH$_2$C$_6$H$_5$)C(O)NH)—C$_6$H$_4$CH$_2$— | +++ | | 100.6 | 1099.50 | 27 |
| 15T | RSSR | m-(L-C$_6$H$_5$CH$_2$OC(O)NHCH(CH$_2$C$_6$H$_5$)C(O)NH)—C$_6$H$_4$CH$_2$— | m-(L-H$_2$NCH(CH$_3$)C(O)NH)—C$_6$H$_4$CH$_2$—...HCl | +++ | +++ | 107.9 | 679.36 | 27 |
| 15U | RSSR | m-(L-H$_2$NCH(CH$_3$)C(O)NH)—C$_6$H$_4$CH$_2$—...HCl | m-(L-H$_2$NCH(CH$_2$C$_6$H$_5$)—C(O)NH)—C$_6$H$_4$CH$_2$—...HCl | +++ | +++ | 112.3 | 831.42 | 27 |
| 15V | RSSR | m-(L-H$_2$NCH(CH$_2$C$_6$H$_5$)—C(O)NH)—C$_6$H$_4$CH$_2$—...HCl | 4-oxocyclohexyl-methyl | +++ | +/+ | 210.6 | 437 | |
| 15VA | RSSR | H | 4,4-dimethoxy-cyclohexylmethyl | ++ | ++/+ | | 452 (469) | |
| 15VB | RSSR | H | 4-(oxime)-cyclohexylmethyl | ++ | ++/+ | | 451 | |
| 15VC | RSSR | H | | | | | (M+ H—OCH$_3$) 437 | |
| 15VD | RSSR | CH$_3$NHC(=O)—(CH$_2$)$_5$— | CH$_3$NHC(=O)—(CH$_2$)$_5$— | ++ | ++ | | 581 (598) | |
| 15VE | RSSR | HO(CH$_2$)$_6$— | Cl(CH$_2$)$_6$— | ++ | +++ | | 545 | 28 |
| 15VF | RSSR | HO(CH$_2$)$_5$— | CH$_3$NHSO$_3$(CH$_2$)$_6$— | +++ | +++ | | 620 | 28 |
| 15VG | RSSR | H | HO(CH$_2$)$_5$— | ++ | +++ | | 413 | 29 |
| 15VH | RSSR | HO(CH$_2$)$_5$— | b-Naphthyl—CH$_2$— | +++ | +++ | 84.6 | 553 | 28 |
| 15VI | RSSR | HO(CH$_2$)$_5$— | C$_6$H$_5$CH$_2$— | ++ | +++ | | 503 | 28 |
| 15VJ | RSSR | HO(CH$_2$)$_5$— | CH$_3$S(CH$_2$)$_5$— | +++ | +++ | | 529 | 28 |
| 15VK | RSSR | H | p-(HOCH$_2$)—C$_6$H$_4$CH$_2$— | ++ | +++ | | 533 | 28 |
| 15VL | RSSR | H | CH$_3$CH$_2$CH(OH)CH$_2$— | ++/+ | ++/+ | | 399 | 30 |
| 15VM | RSSR | H | CH$_3$(CH$_2$)3CH(OH)—CH$_2$— | + | ++/+ | | 427 | 31 |
| 15VN | RSSR | CH$_3$CH$_2$CH(OH)—CH$_2$— | CH$_3$CH$_2$CH(OH)—CH$_2$— | + | ++/+ | 99.2 | 471 | 30 |
| 15VO | RSSR | CH$_3$CH$_2$C(=O)CH$_2$— | CH$_3$CH$_2$C(=O)CH$_2$— | ++ | ++ | | 467 | 32 |
| 15VP | RSSR | CH$_3$CH$_2$C(=NOH)—CH$_2$— | CH$_3$CH$_2$C(=NOH)—CH$_2$— | ++ | +/+ | | 497 | 33 |
| 15VQ | RSSR | HO(CH$_2$)$_5$— | b-Naphthyl—CH$_2$— | +++ | +++ | | 567 | |
| 15VR | RSSR | HO(CH$_2$)$_5$— | m-HOC$_6$H$_4$CH$_2$— | +++ | +++ | | 519 | |
| 15VS | RSSR | HO(CH$_2$)$_5$— | CH$_3$SO$_2$(CH$_2$)$_5$— | +++ | +++ | | 561 (578) | |
| 15VT | RSSR | HO(CH$_2$)$_5$— | CH$_3$SO(CH$_2$)$_5$— | +++ | +++ | | 545 (562) | |
| 15VU | RSSR | HO(CH$_2$)$_5$— | C$_3$H$_5$CH$_2$— | ++ | +/+ | | 467 | |
| 15VV | RSSR | CH$_3$O(CH$_2$)$_5$— | CH$_3$O(CH$_2$)$_5$— | ++ | ++ | | 527 (544) | 34 |
| 15VW | RSSR | HO(CH$_2$)$_5$— | CH$_3$O(CH$_2$)$_5$— | +++ | +++ | | 513 | |
| 15VX | RSSR | HO(CH$_2$)$_5$— | m-CN—C$_6$H$_4$CH$_2$— | +++ | +++ | | 528 (545) | 35 |

TABLE 2d-continued

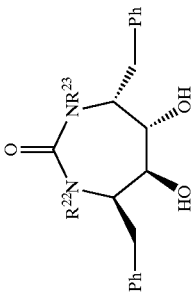

| Ex. No. | Stereo 2,3,4,5 | R22 | R23 | HPLC K1 | IC90 | mp, °C. | MS M+H (M+NH4) | Notes |
|---|---|---|---|---|---|---|---|---|
| 15VY | RSSR | HO(CH2)5— | m-(C2H5OC(=O))—C6H4CH2— | +++ | +++ | | 575 (592) | 36 |
| 15VZ | RSSR | CH3CH(OH)(CH2)4— | CH3CH(OH)(CH2)4— | +++ | +++ | | 527 (544) | 36 |
| 15WA | RSSR | CH3CH(OH)(CH2)4— | b-Naphthyl-CH2— | ++ | ++ | 80.7 | 567 (584) | 36 |
| 15WB | RSSR | CH3C(=O)(CH2)4— | CH3C(=O)(CH2)4— | ++ | ++ | | 523 | 32 |
| 15WC | RSSR | CH3C(=NOH)(CH2)4— | CH3C(=NOH)(CH2)4— | ++ | ++ | | 553 | |
| 15WD | RSSR | H2N(CH2)6— | p-(HOCH2)—C6H4CH2— | +++ | +++ | | 546 | 37 |
| 15WE | RSSR | HO(CH2)5— | m-(HOCH2)—C6H4CH2— | +++ | +++ | | 533 (550) | |
| 15WF | RSSR | m-(Et2NC(O))—C6H4CH2— | m-(Et2NC(O))—C6H4CH2— | +++ | +++ | 89–91 | (722) | 38 |
| 15WG | RSSR | m-(MeO2C)—C6H4CH2— | m-(Et2NC(O))—C6H4CH2— | +++ | +++ | | (681) | 39 |
| 15WH | RSSR | m-(MeO2C)—C6H4CH2— | m-(Et2NHC(O))—C6H4CH2— | +++ | +++ | | (653) | 39 |
| 15WI | RSSR | H | m-(HOCH2)—C6H4CH2— | +++ | +++ | 176–177 | 447 | 40 |
| 15WJ | RSSR | m-(HOCH2)—C6H4CH2— | m-(Et2NHC(O))—C6H4CH2— | +++ | +++ | 88.9–90.0 | 636 (20%) | 39 |
| 15WK | RSSR | m-(HOCH2)—C6H4CH2— | m-iPrNHC(O)—C6H4CH2— | + | + | | 608 | 39 |
| 15WL | RSSR | m-iPrNHC(O)—C6H4CH2— | m-iPrNC(O)—C6H4CH2— | +++ | +++ | 165–167 | 678 | 39 |
| 15WM | RSSR | m-(iPr-NHC(O))—C6H4CH2— | m-(iPr-NHC(O))—C6H4CH2— | +++ | +++ | 164–167 | 677 | 39 |
| 15WN | RSSR | m-(HO2C)C6H4CH2— | m-(H2NC(O))C6H4CH2— | +++ | +++ | 151–153 | 636 | 39 |
| 15WO | RSSR | m-(HO2C)C6H4CH2— | m-(iPr-NHC(O))—C6H4CH2— | +++ | +++ | 122–124 | 636 (32%) | 39 |
| 15WP | RSSR | m-(HO2C)C6H4CH2— | Benzyl | +++ | +++ | 135–137 | (568) | 39 |
| 15WQ | RSSR | m-(HO2C)C6H4CH2— | Cyclopropyl-methyl | +++ | +++ | 130–132 | (532) | 39 |
| 15WR | RSSR | p-(HOCH2)—C6H4CH2— | 3-picolinyl | +++ | +++ | | (598) | 39 |
| 15WS | RSSR | p-(HOCH2)—C6H4CH2— | m-(H2NC(O))C6H4CH2— | +++ | +++ | | 538 | 39 |
| 15WT | RSSR | p-(HOCH2)—C6H4CH2— | 2-naphthyl | +++ | +++ | 123–124 | 580 | 39 |
| 15WU | RSSR | m-(H2NC6H4CH2— | m-(H2NC(O))C6H4CH2— | +++ | +++ | | 572 | 39 |
| 15WV | RSSR | Cyclopropyl-methyl | m-(H2NC(O))C6H4CH2— | +++ | +++ | 128–130 | 514 | 39 |
| 15WW | RSSR | H | m-(EtHNC(O))—C6H4CH2— | +++ | +++ | 114–116 | 460 | 39 |
| 15WX | RSSR | m-(HOCH2)—C6H4CH2— | m-(EtHNC(O))—C6H4CH2— | +++ | +++ | 88–89 | 580 | 39 |
| 15WY | RSSR | m-(HOCH2)—C6H4CH2— | m-(MeNHC(O))—C6H4CH2— | +++ | +++ | 111–113 | 552 | 39 |
| 15WZ | RSSR | m-(MeNH)C6H4CH2— | 2-Naphthylmethyl | +++ | +++ | 98–100 | 586 | 39 |
| 15XA | RSSR | p-(HO2C)C6H4CH2— | p-(HOCH2)—C6H4CH2— | +++ | ++ | | (598) | 41 |
| 15XB | RSSR | p-(HC(O))—C6H4CH2— | p-(HOCH2)—C6H4CH2— | +++ | +++ | | 565 | 42 |
| 15XC | RSSR | m-(MeNHCH2)—C6H4CH2— | m-(MeNHCH2)—C6H4CH2—·HCl | ++ | ++ | | 593.3483 | |
| 15XD | RSSR | m-(CH3CHOH)—C6H4CH2— | m-(CH3CHOH)—C6H4CH2— | +++ | +++ | | 595.3177 (612) | |
| 15XE | RSSR | 3-picolinyl | p-(HOCH2)—C6H4CH2— | +++ | +++ | | 538.2693 | |
| 15XF | RSSR | m-(Et2NCH2)—C6H4CH2— | m-(EtNCH2)—C6H4CH2— | ++ | ++ | | 677.444 | |
| 15XG | RSSR | m-(N-imidazol-methyl)C6H4CH2— | m-(N-imidazol-methyl)C6H4CH2— | +++ | +++ | | 667.3394 | |
| 15XH | RSSR | m-(tBuC(O))—C6H4CH2— | m-(tBuC(O))—C6H4CH2— | +++ | +++ | | 675.3805 | |
| 15XI | RSSR | m-(CF3CHOH)—C6H4CH2— | m-(CF3CHOH)—C6H4CH2— | +++ | +++ | | 703.2611 | |

TABLE 2d-continued

| Ex. No. | Stereo 2;3;4;5 | R22 | R23 | HPLC K₁ | IC₉₀ | mp, °C. | MS M + H (M + NH₄) | Notes |
|---|---|---|---|---|---|---|---|---|
| 15XJ | RSSR | m-(2-imidazolyl-C(O)C₆H₄CH₂— | m-(2-imidazolyl-C(O)C₆H₄CH₂— | +++ | +++ | | 695.2977 (538) | |
| 15XK | RSSR | 3-picolinyl.HCl | p-(HOCH₂)—C₆H₄CH₂— | +++ | +++ | | 615.2853 (632) | |
| 15XL | RSSR | m-(HOCH₂C)—C₆H₄CH₂— | m-(HOCH₂)—C₆H₄CH₂— | +++ | +++ | | | |
| 15XM | RSSR | m-(CF₃C(O))—C₆H₄CH₂— | m-(CF₃C(O))—C₆H₄CH₂— | +++ | +++ | | 699.2286 (636) | |
| 15XN | RSSR | m-(CH₃CH₂C(O))—C₆H₄CH₂— | m-(CH₃CH₂C(O))—C₆H₄CH₂— | +++ | +++ | | 639.3181 | |
| 15Xo | RSSR | m-(3-pyrazolyl-C₆H₄CH₂— | m-(3-pyrazolyl)-C₆H₄CH₂— | +++ | +++ | | 639.3100 (656) | |
| 15XP | RSSR | m-[Et—C(=N—OH)]—C₆H₄CH₂— | m-[Et—C(=N—OH)]—C₆H₄CH₂— | +++ | +++ | | (649) | |
| 15XQ | RSSR | m-(NH₂SO₂)—C₆H₄CH₂— | m-(NH₂SO₂)—C₆H₄CH₂— | +++ | +++ | | 665.2103 (682) | |
| 15XR | RSSR | m-[CF₃—C(=N—OH)]C₆H₄CH₂— | m-[CF₃—C(=N—OH)]C₆H₄CH₂— | +++ | +++ | | 729.2500 (746) | |
| 15XS | RSSR | m-Me—C(=N—OH)]C₆H₄CH₂— | m-Me—C(=N—OH)C₆H₄CH₂— | +++ | +++ | | 621.3070 | |
| 15XT | RSSR | m-(H₂NCH₂C(=O)NH]—C₆H₄CH₂—...HCl | p-(HOCH₂)—C₆H₄CH₂— | +++ | +++ | | 645.20 | |
| 15XU | RSSR | m-(2-4-morpholinoethylNHC(=O)C₆H₄CH₂— | m-(2-4-morpholinoethylNHC(=O))C₆H₄CH₂— | +++ | +++ | 102–105 | 819.4435 | |
| 15XV | RSSR | m-(2-N,N-dimethylamino)ethylNHC(=O)—C₆H₄CH₂— | m-(2-N,N-dimethylamino)ethylNHC(=O))—C₆H₄CH₂— | +++ | ++ | 100–103 | 735.4226 | |
| 15XW | RSSR | m-(2-N,N-dimethylamino)ethylNHC(=O)—C₆H₄CH₂— | m-(2-N,N-dimethylamino)ethylNHC(=O))—C₆H₄CH₂— | +++ | ++ | 101–103 | 735.422676 | |
| 15XX | RSSR | CH3 | m-(2-N,N-dimethylamino)ethylNHC(=O))—C₆H₄CH₂— | ++ | +/++ | 118–120 | 587.323422 | |
| 15XY | RSSR | CH3 | benzyl(3-(pyrrolidinoethyl)benzamido)methyl | ++ | +/++ | 134–136 | 571.327642 | |
| 15XZ | RSSR | cyclopropylmethyl | m-(2-(N,N-dimethylamino)ethylNHC(=O)—C₆H₄CH₂— | +++ | +++ | 97–99 | 585.343057 | |
| 15YA | RSSR | cyclopropylmethyl | m-(2-4-morpholinoethylNHC(=O)C₆H₄CH₂— | +++ | +++ | 103–105 | 627.354642 | |
| 15YB | RSSR | cyclopropylmethyl | benzyl(3-(pyrrolidinoethyl)benzamido)methyl | +++ | +++ | 110–112 | 611.359872 | |
| 15YC | RSSR | cyclopropylmethyl | m-((3-pyridyl)-methylNHC(=O)—C₆H₄CH₂— | ++ | +++ | 115–117 | 605.311364 | |
| 15YD | RSSR | cyclopropylmethyl | m-((2-pyridyl)-methylNHC(=O)—C₆H₄CH₂— | ++ | +++ | | | |
| 15YE | RSSR | m-(p-toluylsulfonylhydrazone)C₆H₄CH₂— | m-(p-toluylsulfonylhydrazone-)C₆H₄CH₂— | +++ | +++ | 169–171 | | |
| 15YF | RSSR | m-(N-morpholinoethoxy)C₆H₄CH₂— | m-(N-morpholinoethoxy)-C₆H₄CH₂— | ++ | ++ | 110–112 | | |
| 15YG | RSSR | p-H₂NCH6H₄CH₂— | p-H₂NC₆H₄CH₂— | ++ | ++ | 132–134 | 566 | |
| 15YH | RSSR | p-HOCH₂C₆H₄CH₂— | m-(CH₃NHOC—O)—C₆H₄CH₂— | +++ | +++ | 223–224 | | |
| 15YI | RSSR | m-(CH₃NHOC=O)—C₆H₄CH₂— | m-(1,2,4-oxadiazolidinon-3-yl)-C₆H₄CH₂— | ++ | ++ | 202 (dec) | | |
| 15YJ | RSSR | m-(1,2,4-oxadiazolidinon-3-yl)-C₆H₄CH₂— | m-(N—SEM-2-imidazole)-C₆H₄CH₂— | +++ | +++ | | 769 | |
| 15YK | RSSR | m-(2-imidazole)-C₆H₄CH₂— | m-(2-imidazole)-C₆H₄CH₂— | +++ | +++ | 208–210 | 639.4 | |
| 15YL | RSSR | m-(3-pyrazole)-C₆H₄CH₂— | m-(3-pyrazole)-C₆H₄CH₂— | +++ | +++ | 195–197 | | |
| 15YM | RSSR | m-(3-pyrazole)-C₆H₄CH₂—.HCl | m-(3-pyrazole-CO)-C₆H₄CH₂— | +++ | +++ | | 695 | |
| 15YN | RSSR | m-(3-pyrazole-CO)-C₆H₄CH₂— | m-(ClCH₂C(O)NHC(O)NH—C₆H₄CH₂— | +++ | +++ | | | 51 |
| 15AA | RSSR | m-(ClCH₂C(O)NHC(O)NH—C₆H₄CH₂— | m-isonicotinamido-C₆H₄CH₂— | +++ | +++ | 208 (dec) | 642 | 4 |
| 15AB | RSSR | m-H₂NC₆H₄CH₂.HCl | | | | | | |

TABLE 2d-continued

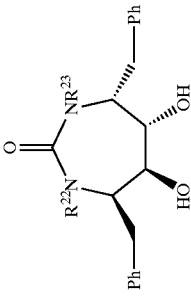

| Ex. No. | Stereo 2;3;4;5 | $R^{22}$ | $R^{23}$ | HPLC $K_i$ | $IC_{90}$ | mp, °C. | MS M + H (M + NH$_4$) | Notes |
|---|---|---|---|---|---|---|---|---|
| 15AC | RSSR | m-isonicotinamido-C$_6$H$_4$CH$_2$·HCl | m-isonicotinamido-C$_6$H$_4$CH$_2$·HCl | +++ | +++ | 205 (dec) | 747 | 47 |
| 15AD | RSSR | m-((CH$_3$)$_2$NHC$_2$CH$_2$C(O))—C$_6$H$_4$CH$_2$ | m-CH$_3$C(O)C$_6$H$_4$CH$_2$ | +++ | +++ | 170 (dec) | 646 | 4 |
| 15AE | RSSR | m-((CH$_3$)$_2$NHC$_2$CH$_2$C(O))—C$_6$H$_4$CH$_2$ | m-((CH$_3$)$_2$NHC$_2$CH$_2$C(O))—C$_6$H$_4$CH$_2$ | +++ | +++ | 164 (dec) | 701 | 43 |
| 15AF | RSSR | m-H$_2$NC(=NOH)—C$_6$H$_4$CH$_2$ | cyclopropylmethyl | +++ | +++ | 183–186 | 529 | 44 |
| 15AG | RSSR | m,p-dihydroxy-C$_6$H$_3$CH$_2$ | cyclopropylmethyl | +++ | +++ | 141 | 503 | 2 |
| 15AH | RSSR | m-(H$_2$NC(=NOH)C$_6$H$_4$CH$_2$ | p-hydroxymethyl—C$_6$H$_4$CH$_2$ | +++ | +++ | 198–199 | 595 | 44 |
| 15AI | RSSR | m-(H$_2$NC(=NOH)C$_6$H$_4$CH$_2$ | p-hydroxymethylC$_6$H$_4$CH$_2$ | +++ | +++ | 215 | 595 | 44 |
| 15AJ | RSSR | m-(5-amino-1,3,4-oxadiazo-2-yl)-C$_6$H$_4$CH$_2$ | m-(5-amino-1,3,4-oxadiazo-2-yl)-C$_6$H$_4$CH$_2$ | +++ | +++ | 208–209 | 690 | 49 |
| 15AK | RSSR | m-hydrazide-C$_6$H$_4$CH$_2$ | cyclopropylmethyl | +++ | +++ | 176–177 | 529 | 48 |
| 15AL | RSSR | m-((CH$_3$)$_2$COC(O))—C$_6$H$_4$CH$_2$ | m-(5-amino-1,3,4-oxadiazo-2-yl)-C$_6$H$_4$CH$_2$ | +++ | +++ | 227–228 | 808 | 50 |
| 15AM | RSSR | m-(C$_2$H$_5$OC(O))—C$_6$H$_4$CH$_2$ | 2-naphthylmethyl | ++ | +++ | 192–193 | 661 | 53 |
| 15AN | RSSR | m-(H$_2$NC(=NOH))—C$_6$H$_4$CH$_2$ | 3-((5-(CH$_3$)$_2$NCH$_2$)-1,2,4-oxadiazolyl)-C$_6$H$_4$CH$_2$·HCl | +++ | +++ | 165 (dec) | 615 | 44 |
| 15AO | RSSR | 3-((5-(CH$_3$)$_2$NCH$_2$)-1,2,4-oxadiazolyl)-C$_6$H$_4$CH$_2$ | H | + | | 147–149 | 467 | 56 |
| 15AP | RSSR | m-(N-methyl-N'-piperazinyl)propyl·HCl | p-hydroxyC$_6$H$_4$CH$_2$ | +++ | +++ | | 548 | 2 |
| 15AQ | RSSR | m-cyanoC$_6$H$_4$CH$_2$ | m-3-pyridylmethyl | +++ | +++ | | 533 | 54 |
| 15AR | RSSR | m-cyanoC$_6$H$_4$CH$_2$ | H | + | +/++ | 150 | 467 | 55 |
| 15AS | RSSR | m-(N-methyl-N'-piperazinyl)propyl)propyl·HCl | H | +++ | +++ | 172–179 | 475 | 2 |
| 15AT | RSSR | m-(H$_2$NC(=NOH))—C$_6$H$_4$CH$_2$ | p-hydroxyC$_6$H$_4$CH$_2$ | +++ | +++ | 195–197 | 581 | 44 |
| 15AU | RSSR | m-(H$_2$NC(=NOH))—C$_6$H$_4$CH$_2$ | p-benzyloxy-C$_6$H$_4$CH$_2$ | ++ | | 180–182 | 671 | 44 |
| 15AV | RSSR | m-(H$_2$NC(=NOH))—C$_6$H$_4$CH$_2$ | 4-pyridylmethyl | +++ | +++ | 178–192 | 566 | 44 |
| 15AX | RSSR | m-(2-benzimidazolyl)-C$_6$H$_4$CH$_2$ | m-(2-benzimidazolyl)-C$_6$H$_4$CH$_2$ | ++ | | 205 | 739 | 46 |
| 15AY | RSSR | m-(2-benzimidazolyl)-C$_6$H$_4$CH$_2$ | m-(2-benzimidazolyl)-C$_6$H$_4$CH$_2$·HCl | +++ | +++ | 217–219 (dec) | 739 | 46 |
| 15AZ | RSSR | m-CH$_3$NHC(=NOH))—C$_6$H$_4$CH$_2$ | m-(CH$_3$N=HC(=NOH))—C$_6$H$_4$CH$_2$ | ++ | | 192 (dec) | 651 | 46 |
| 15BA | RSSR | m-(C3H7NHC(=NOH))—C$_6$H$_4$CH$_2$ | m-(C3H7/NHC(=NOH))—CC$_6$H$_4$CH$_2$ | +++ | +++ | 177 | 707 | 46 |
| 15BB | RSSR | m-(2-amino-pyrimidin-4-yl)-CC$_6$H$_4$CH$_2$ | m-(2-amino-pyrimidin-4-yl)-CC$_6$H$_4$CH$_2$ | ++ | | 226–227 | 693 | 45 |
| 15BC | RSSR | cyclopropylmethyl | 4-fluoro-3-cyano-C$_6$H$_4$CH$_2$ | ++ | | | 514 | 44 |
| 15BD | RSSR | m-(2-amino-4-thienyl)-C$_6$H$_4$CH$_2$ | m-(2-amino-4-thienyl)-C$_6$H$_4$CH$_2$ | +++ | +++ | 151–160 | 703 | |
| 15BE | RSSR | m-(2-chloromethyl-2-propenyl)-C$_6$H$_4$CH$_2$ | m-(2-chloromethyl-2-propenyl)-C$_6$H$_4$CH$_2$ | ++ | ++ | 118–127 | 569 | |
| 15BF | RSSR | m-(2-hydroxymethyl-2-propenyl)-C$_6$H$_4$CH$_2$ | m-(2-hydroxymethyl-2-propenyl)-C$_6$H$_4$CH$_2$ | + | | 178–181 | 503 | |
| 15BG | RSSR | cyclopropylmethyl | ((2-benzimidazolyl)-C$_6$H$_4$CH$_2$— | +++ | +++ | 73–80 | 467 | |
| 15BH | RSSR | cyclopropylmethyl | cyclopropylmethyl | +++ | +++ | 155–164 | 643 | |
| 15BI | RSSR | m-(benzyloxymethylcarbonyl)-C$_6$H$_4$CH$_2$ | m-(benzyloxymethylcarbonyl)-C$_6$H$_4$CH$_2$ | +++ | +++ | | 803.5 | |
| 15BJ | RSSR | m-(1-SEM-5-imidazoyl)-C$_6$H$_4$CH$_2$ | m-(1-SEM-5-imidazoyl)-C$_6$H$_4$CH$_2$ | ++ | +++ | | 899.5 | |
| 15BK | RSSR | m-(5-imidazoyl)-C$_6$H$_4$CH$_2$ | m-(5-imidazoyl)-C$_6$H$_4$CH$_2$ | +++ | +++ | 171–175 | 639 | |
| 15BL | RSSR | m-(5-imidazoyl)-C$_6$H$_4$CH$_2$—·HCl | m-(5-imidazoyl)-C$_6$H$_4$CH$_2$—·HCl | +++ | +++ | | | |
| 15BM | RSSR | m-(1-(N,N-dimethylsulfamoyl)-2-imidazoyl)-C$_6$H$_4$CH$_2$— | m-(1-(N,N-dimethylsulfamoyl)-2-imidazoyl)-C$_6$H$_4$CH$_2$— | ++ | +++ | | | |
| 15BN | RSSR | m-(4-pyrazole)-C$_6$H$_4$CH$_2$— | m-(4-pyrazole)-C$_6$H$_4$CH$_2$—·HCl | +++ | +++ | | 853 | |

TABLE 2d-continued

| Ex. No. | Stereo 2,3,4,5 | R22 | R23 | HPLC K_i | IC90 | mp, °C. | MS M+H (M+NH4) | Notes |
|---|---|---|---|---|---|---|---|---|
| 15BP | RSSR | m-carbomethoxy-C6H4CH2— | m-(3-pyrazole)-C6H4CH2— | +++ | +++ | 127–130 | 631.4 | |
| 15BQ | RSSR | m-hydroxymethyl-C6H4CH2— | m-(3-pyrazole)-C6H4CH2— | +++ | +++ | | 603.2 | |
| 15BR | RSSR | m-(2-imidazoyul-C6H4CH2— | m-(3-pyrazole)-C6H4CH2— | +++ | +++ | 178–180 | 639.4 | |
| 15BS | RSSR | m-(2-imidazoyul-C6H4CH2— | m-(2-imidazoyul-C6H4CH2— | +++ | +++ | 191–194 | | |
| 15BT | RSSR | m-((morpholinoethyl)aminocarbonyl-C6H4CH2— | m-(2-imidazoyul-C6H4CH2— | +++ | +++ | | 729.5 | |
| 15BU | RSSR | 3-pyridinylmethyl | m-(2-pyrazole)-C6H4CH2— | +++ | +++ | 133–136 | 574.2 | |
| 15BV | RSSR | m-cyano-C6H4CH2— | m-(3-pyrazole)-C6H4CH2— | +++ | +++ | | 598.2 | |
| 15BW | RSSR | m-(H2NC(=NOH))—C6H4CH2— | m-(3-pyrazole)-C6H4CH2— | +++ | +++ | | | |
| 15BX | RSSR | H | m-(3-pyrazole)-C6H4CH2— | +++ | +++ | | 483.2 | |
| 15BY | RSSR | p-(benzyloxy)-C6H4CH2— | m-(3-pyrazole)-C6H4CH2— | +++ | +++ | | 679.3 | |
| 15BZ | RSSR | m-((3-pyridinylmethyl)aminocarbonyl)-C6H4CH2— | m-(3-pyrazole)-C6H4CH2— | +++ | +++ | | 707.5 | |
| 15CA | RSSR | p-hydroxy-C6H4CH2— | m-(3-pyrazole)-C6H4CH2— | +++ | +++ | 150–153 | 589.3 | |
| 15CB | RSSR | m-((2-pyridinylmethyl)aminocarbonyl)-C6H4CH2— | m-(3-pyrazole)-C6H4CH2— | +++ | +++ | | 707 | |
| 15CC | RSSR | m,p-dihydroxy-C6H4CH2— | m-(3-pyrazole)-C6H4CH2— | +++ | +++ | 177–180 | 622 | |
| 15CD | RSSR | m-nitro-C6H4CH2— | m-(3-pyrazole)-C6H4CH2— | +++ | +++ | | (635) | |
| 15CE | RSSR | m-amino-C6H4CH2— | m-(3-pyrazole)-C6H4CH2— | +++ | +++ | 136–138 | 605 | |
| 15CF | RSSR | m-cyanop-fluoro-C6H4CH2— | m-(3-pyrazole)-C6H4CH2— | +++ | +++ | 118–120 | 616 | |
| 15CG | RSSR | H | m-(3-pyrazole)-C6H4CH2—·HCl | +++ | +++ | 152–154 | | |
| 15CH | RSSR | m-acetyl-C6H4CH2— | m-(CH3C(=NOH)-C6H4CH2— | +++ | +++ | 186–188 | 606.4 | |
| 15CI | RSSR | m-acetyl-p-fluoro-C6H4CH2— | m-acetyl-p-fluoroC6H4CH2— | +++ | +++ | 203–204 | 649.3 (M+Na) | |
| 15CJ | RSSR | m-cyanop-fluoro-C6H4CH2— | m-acetyl-p-fluoroC6H4CH2— | | | | | |
| 15CK | RSSR | m-(CH3C(=NOH))—C6H4CH2— | m-(CH3C(=NOH))—C6H4CH2— | +++ | +++ | 192–193 | 621.4 | |
| 15CL | RSSR | m-(CH3C(=NOH))-p-fluoro-C6H4CH2— | m-(CH3C(=NOH))-p-fluoro-C6H4CH2— | ++ | ++ | | 657.3 | |
| 15CM | RSSR | m-(H2NC(=NOH))-p-fluoro-C6H4CH2— | m-(H2NC(=NOH))-p-fluoro-C6H4CH2— | ++ | ++ | | 658.4 | |
| 15CN | RSSR | 2-naphthylmethyl | 5-methyl-5-carbomethoxyhexyl | +++ | +++ | | 627 | |
| 15CO | RSSR | 2-naphthylmethyl | 5-methyl-5-carboxyhexyl | +++ | +++ | | 595 | |
| 15CP | RSSR | 5,5-dimethyl-6-hydroxyhexyl | 5,5-dimethyl-6-hydroxyhexyl | ++ | ++ | | 583 | |
| 15CQ | RSSR | p-aminobenzyl | p-aminobenzyl | ++ | ++ | 114–116 | | |
| 15CR | RSSR | 5-benzimidazolyl | 5-benzimidazolyl | ++ | ++ | 209–212 | | |
| 15CS | RSSR | 5-benzotriazolylmethyl | 5-benzotriazolylmethyl | +++ | +++ | >310 | | |
| 15CT | RSSR | 3-hydroxy-5-benzotriazolylmethyl | 3-hydroxy-5-benzotriazolylmethyl | ++ | ++ | 185–192 | | |
| 15CV | RSSR | 2-oxo-5-benzimidazolyl-methyl | 2-oxo-5-benzimidazolyl-methyl | ++ | ++ | 240–245 | | |
| 15CW | RSSR | 5-(2,2-dioxo-benz-2,1,3-thiadiazolyl)-methyl | 5-(2,2-dioxo-benz-2,1,3-thiadiazolyl)-methyl | +++ | +++ | 210(dec) | | |
| 15CX | RSSR | 5-indazolylmethyl | 5-indazolylmethyl | +++ | +++ | 165–170 | | |
| 15CY | RSSR | 6-indazolylmethyl | 6-indazolylmethyl | +++ | +++ | 170–175 | | |
| 15CZ | RSSR | (3-methyl-2-oxo-5-benzimidazolyl)-methyl | (3-methyl-2-oxo-5-benzimidazolyl)-methyl | +++ | +++ | 192–200 | | |
| 15DA | RSSR | 5-isatinylmethyl | 5-isatinylmethyl | +++ | +++ | 196–200 | | |

TABLE 2d-continued

| Ex. No. | Stereo 2;3;4;5 | R²² | R²³ | HPLC K₁ | IC₉₀ | mp, °C. | MS M + H (M + NH₄) | Notes |
|---|---|---|---|---|---|---|---|---|
| 15DB | RSSR | (3-hydroxyimino-5-oxindolyl)methyl | (3-hydroxyimino-5-oxindolyl)methyl | +++ | +++ | 242–245 | | |
| 15DC | RSSR | (2-oxo-5-benzoxazolin-2-yl)-methyl | (2-oxo-5-benzoxazolin-2-yl)-methyl | +++ | +++ | 181–185 | | |
| 15DD | RSSR | 5-oxindolylmethyl | 5-oxindolylmethyl | +++ | +++ | 170–175 | | |
| 15DE | RSSR | 5-indolylmethyl | 5-indolylmethyl | +++ | +++ | 170(dec) | | |
| 15DF | RSSR | (3-amino-5-indazolyl)methyl | (3-amino-5-indazolyl)methyl | +++ | +++ | 180–184 | | |
| 15DG | RSSR | (3-amino-5-benzisoxazolyl)methyl | (3-amino-5-benzisoxazolyl)methyl | +++ | +++ | 153–158 | | |
| 15DH | RSSR | (3-methylamino-5-indazolyl)methyl | (3-methylamino-5-indazolyl)methyl | +++ | +++ | 174–177 | | |
| 15DI | RSSR | (3-chloro-5-indazolyl)methyl | (3-chloro-5-indazolyl)methyl | +++ | +++ | 290(dec) | | |
| 15DJ | RSSR | (3-ethylamino-5-indazolyl)methyl | (3-ethylamino-5-indazolyl)methyl | +++ | +++ | 158–162 | | |
| 15DK | RSSR | (3-methylamino-5-benzisoxazolyl)methyl | (3-methylamino-5-benzisoxazolyl)methyl | +++ | +++ | 150–153 | | |
| 15DL | RSSR | (3-isopropylamino-5-indazolyl)methyl | (3-isopropylamino-5-indazolyl)methyl | +++ | +++ | 147–152 | | |
| 15DM | RSSR | H | 5-benzotriazolylmethyl | +++ | +++ | 188–190 | | |
| 15DN | RSSR | benzyl | 5-benzotriazolylmethyl | +++ | +++ | 268–270 | | |
| 15DO | RSSR | 2-naphthlmethyl | 5-benzotriazolylmethyl | +++ | +++ | 155–159 | | |
| 15DP | RSSR | cyclopropylmethyl | 5-benzotriazolylmethyl | +++ | +++ | 146–150 | | |
| 15DQ | RSSR | p-hydroxymethyl-C₆H₄CH₂— | 5-benzotriazolylmethyl | +++ | +++ | 151–153 | | |
| 15DR | RSSR | m-hydroxymethylC₆H₄CH₂— | 5-benzotriazolylmethyl | +++ | +++ | 296–298 | | |
| 15DS | RSSR | m-(3-pyrazolyl)C₆H₄CH₂— | 5-benzotriazolylmethyl | +++ | +++ | 183–186 | | |
| 15DT | RSSR | m-iodoC₆H₄CH₂— | 5-benzotriazolylmethyl | +++ | +++ | 153–156 | | |
| 15DU | RSSR | m-cyanomethylC₆H₄CH₂— | m-cyanomethylC₆H₄CH₂— | ++ | ++ | | 585.2 | |
| 15DV | RSSR | m-(H₂NC(O)CH₂)—C₆H₄CH₂— | m-(H₂NC(O)CH₂)—C₆H₄CH₂— | +++ | +++ | | 621.4 | |
| 15DW | RSSR | m-(carbomethoxymethyl)-C₆H₄CH₂— | m-(carbomethoxymethyl)-C₆H₄CH₂— | +++ | +++ | | 651.4 | |
| 15DX | RSSR | m-(2-hydroxyethyl)-C₆H₄CH₂— | m-(2-hydroxyethyl)-C₆H₄CH₂— | +++ | +++ | | 595.4 | |
| 15DY | RSSR | o-hydroxy-C₆H₄CH₂— | o-hydroxy-C₆H₄CH₂— | +++ | +++ | | 539.3 | |
| 15DZ | RSSR | m-(methylamino)p-fluoro-C₆H₄CH₂— | m-(methylamino)p-fluoro-C₆H₄CH₂— | +++ | +++ | | 500.2 | |
| 15EA | RSSR | H | p-hydroxymethyl-C₆H₄CH₂— | +++ | +++ | | 553.3 | |
| 15EB | RSSR | o-hydroxy-C₆H₄CH₂— | m-hydroxymethyl-C₆H₄CH₂— | ++ | ++ | | 553.3 | |
| 15EC | RSSR | o-hydroxy-C₆H₄CH₂— | m-cyano-p-fluoro-C₆H₄CH₂— | ++ | ++ | | (610.2) | |
| 15ED | RSSR | m-cyano-p-fluoro-C₆H₄CH₂— | m-(H₂NC(O))-p-fluoro-C₆H₄CH₂— | +++ | +++ | | (646.4) | |
| 15EE | RSSR | m-carbomethoxy-p-fluoro-C₆H₄CH₂— | m-carbomethoxy-p-fluoro-C₆H₄CH₂— | + | + | | (676.3) | |
| 15EF | RSSR | m-(H₂NC(=NOH))-p-fluoro-C₆H₄CH₂— | m-(H₂NC(=NOH))-p-fluoro-C₆H₄CH₂— | +++ | +++ | | 659.1 | |
| 15EG | RSSR | m-(hydroxymethyl)-p-fluoro-C₆H₄CH₂— | m-(hydroxymethyl)-p-fluoro-C₆H₄CH₂— | +++ | +++ | | 603.3 | |
| 15EH | RSSR | m-(hydroxymethyl)-p-fluoro-C₆H₄CH₂— | m-(H₂NC(=NOH))-p-fluoro-C₆H₄CH₂— | +++ | +++ | | 644.0 | |
| 15EI | RSSR | p-methylC₆H₄CH₂— | p-hydroxymethyl-C₆H₄CH₂— | ++ | ++ | 174–175 | 551 | |
| 15EJ | RSSR | 5-hydroxy-5-methylhexyl | 5-hydroxy-5-methylhexyl | ++ | ++ | | 555 | |
| 15EK | RSSR | 5-(methylaminocarbonyloxy)pentyl | 5-(methylaminocarbonyloxy)pentyl | + | + | | 613 | |
| 15EL | RSSR | 7-(1,1,4,4-tetramethyl-1,2,3,4-tetrahydronaphthyl)methyl | 7-(1,1,4,4-tetramethyl-1,2,3,4-tetrahydronaphthyl)methyl | + | ++/+ | | 727 | |

TABLE 2d-continued

| Ex. No. | Stereo 2,3,4,5 | R$^{22}$ | R$^{23}$ | HPLC K$_I$ | IC$_{90}$ | mp, °C. | MS M + H (M + NH$_4$) | Notes |
|---|---|---|---|---|---|---|---|---|
| 15EM | RSSR | 5-azidopentyl | 5-azidopentyl | ++ | +++ | | 549 (566) | |
| 15EN | RSSR | 5-(methylsulfonylamino)-pentyl | 5-(methylsulfonylamino)-pentyl | ++ | ++/+ | | (670) | |
| 15EO | RSSR | 5-(p-methylphenylsulfonyl)pentyl | 5-(p-methylphenylsulfonyl)pentyl | + | ++/+ | | (822) | |
| 15EP | RSSR | 5-aminopentyl | 5-aminopentyl | ++ | ++/+ | | 497 | |
| 15EQ | RSSR | 5-methoxycarbonylaminopentyl | 5-methoxycarbonylaminopentyl | ++ | ++/+ | | (630) | |
| 15ER | RSSR | 5-(phenylaminocarbonylamino)pentyl | 5-(phenylaminocarbonylamino)pentyl | ++ | ++/+ | | 611 (628) | |
| 15ES | RSSR | 5-(phenylaminocarbonylamino)pentyl | 5-(phenylaminocarbonylamino)pentyl | ++ | ++/+ | | (598) | |
| 15ET | RSSR | 5-(acetylamino)pentyl | 5-(acetylamino)pentyl | ++ | ++/+ | | 767 | |
| 15EU | RSSR | 5-((3-pyridinyl)methoxy)carbonylamino)pentyl.HCl | 5-((3-pyridinyl)methoxy)carbonylamino)pentyl.HCl | +++ | ++/+ | | 643 | |
| 15EV | RSSR | 5-((methylamino)thiocarbonylamino)-pentyl | 5-((methylamino)thiocarbonylamino)-pentyl | ++ | ++/+ | | 767 | |
| 15EW | RSSR | 5-(phenylamino)thiocarbonylamino)-pentyl | 5-(phenylamino)thiocarbonylamino)-pentyl | ++ | ++/+ | | (722) | |
| 15EX | RSSR | 5-(benzoylamino)-pentyl | 5-(benzoylamino)-pentyl | ++ | +++ | | 741 | |
| 15EY | RSSR | 5-((3-fluorobenzoyl)amino)-pentyl | 5-((3-fluorobenzoyl)amino)-pentyl | ++ | ++/+ | | 639 | |
| 15EZ | RSSR | 5-(N-methylglycylamino)-pentyl.HCl | 5-(N-methylglycylamino)-pentyl.HCl | ++ | +++ | | 707 | |
| 15FA | RSSR | 5-(4-pyridinylcarbonylamino)-pentyl.HCl | 5-(4-pyridinylcarbonylamino)-pentyl.HCl | ++ | ++/+ | | 741 (758) | |
| 15FB | RSSR | 5-((2-fluorobenzoyl)amino)-pentyl | 5-((2-fluorobenzoyl)amino)-pentyl | ++ | ++/+ | | 741 (758) | |
| 15FC | RSSR | 5-((4-fluorobenzoyl)amino)-pentyl | 5-((4-fluorobenzoyl)amino)-pentyl | ++ | ++/+ | | 489 (506) | |
| 15FD | RSSR | 4-cyanobutyl | 4-cyanobutyl | ++ | ++ | | 751 | |
| 15FE | RSSR | 5-(4-morpholinylmethylcarbonyl-amino)-pentyl.HCl | 5-(4-morpholinylmethylcarbonyl-amino)-pentyl.HCl | ++ | ++/+ | | | |
| 15FF | RSSR | 5-(2-pyrazinylcarbonylamino)-pentyl | 5-(2-pyrazinylcarbonylamino)-pentyl | + | ++/+ | | (726) | |
| 15FG | RSSR | 5-(3,5-difluorobenzoyl)amino)-pentyl | 5-(3,5-difluorobenzoyl)amino)-pentyl | ++ | ++/+ | | (794) | |
| 15FH | RSSR | 4-(dimethylamino)butyl.HCl | 4-(dimethylamino)butyl.HCl | ++ | ++/+ | | 525 | |
| 15FI | RSSR | 4-aminobutyl.HCl | 4-aminobutyl.HCl | + | ++/+ | | 469 | |

TABLE 2d-continued

| Ex. No. | Stereo 2:3:4:5 | $R^{22}$ | $R^{23}$ | HPLC $K_i$ | $IC_{90}$ | mp, °C. | MS M + H ($M + NH_4$) | Notes |
|---|---|---|---|---|---|---|---|---|
| 15FJ | RSSR | 5-((3-trifluoromethylbenzoyl)amino-pentyl | 5-((3-trifluoromethylbenzoyl)amino-pentyl | ++ | ++/+ | | 841 | |
| 15FK | RSSR | 4-(1-imidazolyl)-pentyl.HCl | 4-(1-imidazolyl)-pentyl.HCl | + | | | 599 | |
| 15FL | RSSR | 5-(1-pyrazolyl)-pentyl | 5-(1-pyrazolyl)-pentyl | + | | | 599 | |
| 15FM | RSSR | 5-(4-morpholinyl)pentyl.HCl | 5-(4-morpholinyl)pentyl.HCl | + | | | 637 | |
| 15FN | RSSR | 3-furylmethyl | 3-furylmethyl | +++ | +++ | 152.5–153 | | |
| 15FO | RSSR | 3-furylmethyl (5-carbonyl-3-furyl)-methyl | 3-furylmethyl (5-carbonyl-3-furyl)-methyl | | | oil | | |
| 15FP | RSSR | (5-hydroxymethyl-3-furyl)-methyl | (5-hydroxymethyl-3-furyl)-methyl | +++ | | | | |
| 15FQ | RSSR | (5-hydroxyiminomethyl-3-furyl)-methyl | (5-hydroxyiminomethyl-3-furyl)-methyl | +++ | +++ | | | |
| 15FR | RSSR | 3-furylmethyl | (5-hydroxymethyl-3-furyl)-methyl | +++ | +++ | | | |
| 15FS | RSSR | (2,5-dihydro)-3-thienylmethyl | (2,5-dihydro)-3-thienylmethyl | ++ | | | | |
| 15FT | RSSR | 3-thienylmethyl | 3-thienylmethyl | +++ | | | 519 | |
| 15FU | RSSR | (1,1-dioxo-2,5-dihydro-3-thienyl)-methyl | (1,1-dioxo-2,5-dihydro-3-thienyl)-methyl | + | | | | |
| 15FV | RSSR | 2-furylmethyl | H | +++ | | | | |
| 15FW | RSSR | 2-furylmethyl | 2-furylmethyl | +++ | | | | |
| 15FX | RSSR | 2-methylene-3-butenyl | 2-methylene-3-butenyl | ++ | | | | |
| 15FY | RSSR | 5-hydroxymethyl-2-furylmethyl | 5-hydroxymethyl-2-furylmethyl | ++ | | | | |

Notes (for Table 2d):
(1) Prepared according to the general alkylation procedure.
(2) Monoalkylated compounds were prepared by following the procedure 5 under the title of synthesis of monoalkyl cyclic urea. Further functional group elaboration is similar to the corresponding dialkylated cyclic ureas described herein.
(3) Prepared by the alkylating the appropriate monoalkylated compound. Further functional group elaboration is similar to the corresponding dialkylated compounds described herein.
(4) Isolated as the side product due to incomplete reaction.
(5) Methoxylamine hydrochloride (92 mg, 1.08 mmol) was added to bis(N-m-benzaldehyde) cyclic urea (100 mg, 0.18 mmol) in a mixture of 2 mL pyridine and 2 mL ethanol. The mixture was heated to reflux for 4 hr and the solvent was removed on a rotary evaporator. The residue was purified on silica gel (0.2:3:7 methanol:ethyl acetate:methylene chloride) to provide the product (93 mg) in 83% yield. Other amines such as, but not limited to, hydrazine and semicarbazides, can be used instead of methoxylamine. E.g. hydroxylamine was used to make formaldoxime as in 6C in Table 2C.
(6) Preparation of monoacyl compounds were favored by using one equivalent of acylating agent.
(7) A solution of bis(N-m-benzoic acid) cyclic urea (1.2 g, 1.56 mmol) in 1:1 benzene:methylene chloride containing 1 drop of DMF and pyridine (0.75 mL, 9.36 mmol) was treated with oxalyl chloride (2M in methylene chloride, 4.87 mL, 9.36 mmol) at zero degree and stirred at room temperature for overnight. The solvent removed on a rotary evaporator and the resulting residue was dried under pump for 2 hr. To the residue 20 mL methylene chloride was added followed by pyridine (0.75 mL, 9.36 mmol) and methylamine (8.03M in ethanol, 1.17 mL, 9.36 mmol). Stirred at room temperature for overnight. The mixture was extracted with EtOAc, dried over $MgSO_4$ and purified on silica gel (1:9 methanol chloroform). Following the same hydrolysis procedure, the product (66 mg) was isolated in 68% yield. Other alkylamines or ammonia can be used instead of methylamine.
(8) A solution of bis(N-m-hydroxy-benzyl)cyclic urea (500 mg, 0.93 mmol) in methylene chloride was treated with triethylamine (0.23 mL, 1.67 mmol) at −20° C. Then a solution of 1-adamantyl isocyanate (252 mg, 1.4 mmol) in 5 mL methylene chloride was added dropwise. The mixture was stirred at −20° C. for 10 min, 0° C. for 1 hr, room temperature for overnight and washed with cooled 5% HCl, sat'd $NaHCO_3$, water, and dried over $MgSO_4$. The residue was purified on silica gel (2:8 ethyl acetate:methylene chloride). The product was isolated (150 mg) in 18% yield. Other acylating agents besides isocyanates can be used.
(9) 2 drops of $OsO_4$ (25% in t-BuOH) was added into the mixture of bis(N-m-allyloxy-benzyl) cyclic urea (120 mg, 0.19 mmol) and N-methyl-morpholine N-oxide (77 mg, 0.57 mmol) in 5 mL acetone. The mixture was stirred at RT for overnight. The solvent was removed on a totary evaporator and the residue was purified on silica gel (2:8 methanol:chloroform). The product was isolated (145 mg) in 100% yeild.
(10) The ethyl ester was prepared by refluxing the appropriate acid with 4M HCl (in dioxane) in ethanol.
(11) To the appropriate ethyl ester (139 mg, 0.21 mmol) and hydroxylamine hydrochloride (118 mg, 1.71 mmol) mixture (10 mL methanol was used as the solvent), a 5M (2.4 mL, 2.1 mmol) solution of potassium hydroxide in methanol was added dropwisely at room temperature. After stirring for 24 hr, methanol was evaporated and the solid residue acidified with acetic acid and extracted with ethyl acetate which was purified on silica gel (0.1:3:7 acetic acid:methanol:ethyl acetate). The product was isolated (90 mg) in 69% yield
(12) To the bis(N-m-allyloxy-benzyl) cyclic urea (100 mg, 0.16 mmol) in 10 mL methanol, ozone was bubbled through for 10 min at -78° C. After warmed up to RT, sodium borohydride (60.5 mg, 1.6 mmol) was added and stirred at RT for overnight. The reaction was worked up by quenching with acetic acid, the solvent was removed on rotary evaporator and purified on silica gel (0.3:9.7 methanol:ethyl acetate). The product was isolated (88 mg) in 88% yield.
(13) A solution of the bis-cyano compound (400 mg, 0.55 mmol) in absolute methanol was saturated with hydrochloric acid and left at zero degree for 3 hr followed by TLC until completed. After evaporation of the solvent, the resulting was solubilized in 2M ammonia in methanol. After one week stirring at room temperature, the solvent was removed under reduced pressure and the residue was purified on silica gel (by 0.2:1:9 acetic acid:methanol:ethyl acetate) to give a solid. The overall yield was 53% (171 mg).
(14) To the bis(N-p-hydroxy-benzyl) cyclic urea (600 mg, 1.11 mmol) in ethanol, NaOH (622 mg, 15.54 mmol) in 2 mL water was added dropwise. The mixture was heated up to 80° C for 1 hr, then 2 mL chloroform was added following additional heating at 80° C for overnight. The reaction was worked up by neutralizing with 5% cooled HCl, washed with sat'd sodium bicarbonate, water and dried over $MgSO_4$. The residue was purified on silica gel (1.5:8.5 methanol:chloroform) to give 11E as a solid (59 mg, 11%). To this solid, ethanol was added followed by excess sodium borohydride (10 equiv). The mixture was heated up to reflux for 2 hr. The reaction was worked up by quenching with acetic acid, the solvent was removed on rotary evaporator and the purified on silica gel (2:8 methanol:chloroform). The product was isolated (36 mg) in 63% yield.
(15) n-Butyllithium (1.6M in hexane, 1.6 mL, 2.5 mmol) was added dropwise to bis(N-m-bromo-benzyl) cyclic urea (840 mg, 1 mmol) in THF at −78° C. After stirring for 0.5 hr, trimethyl borate (0.58 mL, 5 mmol) was added. The mixture slowly warmed up to room temperature and remained stirring for 4 hr. The reaction mixture was decomposed by the addition of 5% HCl, diluted with ethyl acetate, washed 2 time with water and dried over $MgSO_4$. The residue was purified on silica gel (0.1: 0.5:9.5 acetic acid:methanol:chloroform). Following the same hydrolysis procedure, the product was isolated (176 mg) in 53% yield.
(16) Required alkylating agents were prepared in a three step sequence: 1.) Asymmetric cyclopropanation [D. A. Evans et al. , J. Amer. Chem. Soc. 1991, 113, 726-728]. 2.) Reduction with lithium aluminum hydride. 3.) Conversion to the bromide with $CBr_4$, $Ph_3P$, and imidazole.
(17) Prepared from Example 15J using the conditions described for Example 6ZI in Table 2C.
(18) Prepared from the compound of Table 2C, Example 6ZI using methanesulfonic anhydride.
(19) Prepared from Example 6ZI using isocyanic acid.
(20) A solution (60ml) of borane in tetrahydrofuran (THF, 2M) was added dropwise into a cooled solution (0° C) of bis-formamide 6ZM (9.18g, 15.5 mmoles) in anhydrous THF (200ml). The mixture was stirred for 16 hours at room temperature, followed by dropwise addition of methanol (50ml). When the effervescence had subsided, hydrochloric acid (conc., 35ml) was added. The residue was stirred for 30 minutes, evaporated to dryness, and partitioned between ethyl acetate and sodium hydroxide (1 N). The organic layer was washed with brine, dried over magnesium sulfate, filtered and evaporated to give 8.65g of the product.

(21) Prepared from Example 6ZI using benzyl chloroformate.

(22) Prepared from Example 15D using the conditions described of 6ZM.

(23) Prepared from Example 15H using the conditions described for Example 6ZI.

(24) Prepared from Example 15F using the procedure described for Example 15D.

(25) Prepared form Example 6ZI using methyl isocyanate.

(26) The formamide of Example 15A was prepared by the procedure Example 6ZM, followed by reduction described for Example 15D.

(27) The amide bond is formed between an amino acid and aminobenzyl cyclic urea using dicyclohexylcarbodiimide/ catalytic 1-hydroxybenzotriazole in N,N- dimethylformamide in the proper proportions. When the desired product is to be a primary or secondary amine, the N-terminus of the amino acid was first suitably protected, based on the compatability with later reactions (see T.W. Greene and P.G.M. Wuts, "Protecting Groups in Organic Synthesis", 2nd edition, Wiley (1991)) and then later removed.

(28) Cyclic urea XXIIc was alkylated with sodium hydride (2.5 equiv) and THPO($CH_2$)$_5$Br (prepared in 2 steps from HO($CH_2$)$_5$OH) (4 equiv) in DMF to give the monoalkylated product. Where upon further treatment with sodium hydride and a second bromo-alkylating agent provided an intermediate which was deprotected using methanolic HCl in dioxane to provide the product.

(29) Prepared by acidic deprotection of the monoalkyated intermediate.

(30) Prepared from intermediate (XXII) by treatment with phenyllithium, boron trifluoride and 1,2-epoxybutane, followed by acidic deprotection.

(31) Prepared from intermediate (XXII) by treatment with phenyllithium, boron trifluoride and 1,2-epoxyhexane, followed by acidic deprotection.

(32) Prepared by pyridinium chlorochromate oxidation of the corresponding alcohol.

(33) Prepared from Example 15VQ using hydroxylamine hydrochloride.

(34) See preparation of Example 15VW using excess reagents.

(35) Prepared by selective monoalkylation of the dialkylated diol using sodium hydride/methyl iodide.

(36) Prepared by substituting $CH_3CH(OTHP)(CH_2)_4Br$ in the procedure described for Example 15VE. Bromide is prepared from $CH_3CH(OH)(CH_2)_4OH$ by the following sequence: (1) $Ac_2O$; (2) THP, H+; (3) NaOH; (4) $CBr_4$, $Ph_3P$.

(37) Prepared by substituting $Ph_2C=N(CH_2)_2Br$ in the procedure described for Example 15VE. Bromide is prepared from $H_2N(CH_2)_2OH$ by the following sequence: (1) $Ph_2CO$; (2) $CBr_4$, $Ph_3P$.

(38) See note 7, Table 2d.

(39) See note 3, Table 2d.

(40) See note 2, Table 2d.

(41) The intermediate was prepared by following Procedure 5 under the title of synthesis of monoalkyl cyclic urea. This was followed by alkylation with Bromo-m-tolunitrile. This intermediate (670 mg, 0.82 mmol) was treated with potassium hydroxide (0.4g, 7.13 mmol) in ethylene glycol at 140° C overnight. The solution was acidified with pre-cooled hydrochloric acid (1N) and extracted with ethyl acetate. The organic phase was concentrated to give 415 mg (61%) of MEM-protected diol. Procedure for hydrolysis of this product is covered under procedure 5.

(42) The intermediate was prepared by following Procedure 5 under the title of synthesis of monoalkyl cyclic urea followed by alkylation with Bromo-m- tolunitrile. This intermediate (210 mg, 0.26 mmol) was treated with DIBAL-H (0.19 mL, 1.5M in toluene, 0.286 mmol) at −78° C under nitrogen, stirred at −78° C for 1 hour and RT for 3 hours. The reaction was quenched with cooled hydrochloric acid (1N) and worked up in the usual manner to give 180 mg (87%) of the MEM-protected product. Hydrolysis of this product is covered under procedure 5.

(43) N,N-dimethylformamide dimethyl acetal (2.1 ml, 15.9 mmol) was added to a solution of ketone 9P (940 mg, 1.59 mmol) in ethanol. The mixture was heated at reflux overnight, and the solvent was removed on a rotary evaporator. The residue was purified on silica gel ( 15% methanol/chloroform) to provide the product (940 mg, 84%).

(44) The intermediate was prepared by following procedure 5 under the title of synthesis of monoalkyl cyclic urea. The monoalkylation product was further alkylated with bromo-m-tolunitrile. This intermediate (185mg, 0.24 mmol) was treated with hydroxylamine•HCl (25 mg, 0.37 mmol), and triethylamine (0.05 ml, 0.37 mml) in refluxing ethanol for 16 h. The resulting solution was partitioned between ethyl acetate/water. The organic layer was washed twice with water and concentrated to give MEM-protected product which can be further hydrolyzed as described above to yield 90 mg (58%) product 9C.

(45) Guanidine carbonate (7.2g, 40.23 mmol) was added to Ex 15AE in xylene. The mixture was heated at 130° C until no starting material was left. The solution was partitioned between ethyl acetate/water and the organic layer washed with water twice. The organic residue was purified on silica gel (10% methanol/ ethyl acetate) to provide the pure product (347 mg, 37%).

(46) To a solution of MEM-protected formaldoxime 6C 0.5 g, 0.65 mol) in DMF was added 1/3 of N- chlorosuccinimide (173 mg, 1.3 mmol) . The mixture was stirred for 10 min followed by 2 min of heating at 40- 50° C. After stirring for another 10 min, the rest of NCS was added. The mixture was stirred at room temperature for overnight. The solution was then partitioned between ethyl acetate/water. The organic layer was washed with water and dried over $MgSO_4$. Treatment of the hydroximoyl chloride with 3 equivalents of o-phenylenediamine in ethanol gave a single product which can be further hydrolyzed to the product (126 mg, 43%).

(47) To a solution of aniline 3K (146 mg, 0.27 mmol) in methylene chloride, was added isonicotinoyl chloride hydrochloride (110 mg, 0.59 mmol) followed by potassium carbonate ( 187 mg, 1.35 mmol) at 0° C. The mixture was stirred for 2 h and then slowly warmed up to room temperature overnight. The mixture was partitioned between ethyl acetate/water. The organic layer was washed twice with water and dried over $MgSO_4$. The residue was purified on silica gel (5% methanol/ethyl acetate) to gave the product (52 mg, 26%).

(48) The benzoyl chloride intermediate (0.51g, 0.72 mmol) was prepared by following procedure (41) & (7) without removing MEM-protecting group. To the residue, 20 ml methylene chloride was added, followed by pyridine (0.11 ml, 1.44 mmol) and tert-butyl carbazate (190 mg, 1.44 mmol). The mixture was stirred at room temperature overnight. The mixture was washed with water & dried over $MgSO_4$. The residue was purified on silica gel (10% ethyl acetate/methylene chloride). Following the hydrolysis procedure dexcribed above, the product (182 mg) was isolated in 47% yield.

(49) To the MEM-protected hydrazide 10M (450 mg, 0.72 mmol) in dioxane was added 165 mg (1.5 mmol) of CNBr followed by a solution of 125 mg (1.5 mmol) of sodium bicarbonate in 10 ml water. The resulting mixture was stirred 2 h at room temperature. The solution was concentrated to 1/2 volume in vacuo. The mixture was diluted with 10 ml of water and the resulting solid isolated by filtration and purified on silica gel (15% methanol/chloroform) to provide (38.4 mg, 8%).

(50) t-Butyl carbazate (264 mg, 2 mmol) was added to aldehyde 5V(450 mg, 0.8 mmol) in ethanol. The mixture was stirred at room temperature for 2 h and heated at reflux overnight. The residue was purified on silica gel (20% ethyl acetate/methylene chloride) to provide the product (179 mg, 28%).

(51) To a solution of aniline 3K(160 mg, 0.3 mmol) in THF, chloroacetyl isocyanate was added dropwise at 0° C. The mixture was stirred for 0.5 h and then slowly warmed up to room temperature overnight. The solution was partitioned between ethyl acetate/water. The organic phase was washed with water and dried over $MgSO_4$. The residue was purified on silica gel (5% methanol/chloroform) to gave 217 mg in 93% yield.

(53) To a solution of 333 mg (6.16 mmol) of anhydrous $NaOCH_3$ in 20 ml of anhydrous methanol at 0° C was added 855 mg (6.16 mmol) of aminoguanidine carbonate followed by 2 ml methanol. The resulting mixture was treated dropwise with 500 mg (0.77 mmol) of ethyl ester 11F which was made by following procedure (10) in 5 ml of methanol. The mixture was heated at reflux overnight, then poured into ice water, brought to PH 7 with 5% aqueous HCl, filtered, and purified on silica gel (10% methanol.chloroform) to give 20 mg (4%) product.

(54) A solution of MEM-protected cyclic urea wherein $R^{22}$ and $R^{23}$ are (H2NC(=NOH))benzyl (210 mg, 0.26 mmol) and $Et_3N$ (0.18 ml, 1.3 mmol) was treated dropwise with a solution of chloroacetyl chloride (0.046 ml, 0.57 mmol) in $CHCl_3$. The mixture was stirred at room temperature for 2 days and then evaporated, and the residue was redissolved in ethyl acetate. The solution was washed with water, brine, dried over $Na_2SO_4$. The residue was purified on silica gel (10% ethyl acetate/methylene chloride) to provide 140 mg (59%) intermediate. The intermediate was dissolved in DMF and treated with excess dimethylamine gas. The mixture was stirred overnight, then poured into ice water, and extracted with ethyl acetate. The extracts were washed with water, dried over $MgSO_4$. Following the usual hydrolysis procedure, the product (15.6 mg) was isolated in 10% yield.

Listed below are a representative list of data for compounds listed in Table 2d:

Example 12A: MS: 525 (M+1). NMR ($CD_3OD$): δ 7.30–7.10 (m, 10H), 3.96–3.88 (m, 2H), 3.58–3.42 (m, 4H), 3.37–3.28 (m, 4H), 3.17–3.10 (m, 2H), 2.94–2.78 (m, 6H), 2.20–2.08 (m, 2H), 1.72–1.10 (br m, 14H).

Example 12B: MS: 516 (M+1, 100). NMR ($CD_3OD$): δ 6.96–7.72 (br m, 15H), 4.68 (d, 1H), 3.78–3.89 (m, 1H), 3.43–3.64 (m, 3H), 3.28–3.34 (m, 2H), 3.10–3.19 (m, 1H), 2.81–3.02 (m, 6H), 2.12–2.26 (m, 1H), 1.10–1.84 (br m, 9H).

Example 12C: MS: 427 (M+1, 100). NMR ($CDCl_3$): δ 7.16–7.36 (m, 10H), 4.82 (d, 1H), 3.88–3.98 (m, 2H), 3.37–3.69 (m, 8H), 3.04–3.19 (m, 3H), 2.63–2.77 (m, 1H), 2.08–2.22 (m, 1H), 1.74–1.88 (m, 2H), 1.10–1.64 (br m, 6H).

Example 12D: MS: 527 (M+1, 100). NMR ($CDCl_3$): δ 7.17–7.38 (m, 10H), 3.99 (s, 2H), 3.45–3.75 (m, 8H), 3.03–3.14 (m, 2H), 2.89–3.01 (m, 2H), 2.60–2.68 (m, 2H), 2.12–2.24 (m, 2H), 1.12–1.62 (br m, 18H).

Example 12E: MS: 481 (M+1, 100). NMR ($CDCl_3$): δ 7.17–7.37 (m, 10H), 3.94–4.13 (m, 2H), 3.61–3.75 (m, 2H), 3.43–3.61 (m, 4H), 3.05–3.20 (m, 3H), 2.73–3.03 (m, 3H), 2.10–2.23 (m, 1H), 1.98–2.08 (m, 1H), 1.02–1.75 (br m, 9H), 0.82–0.97 (m, 1H), 0.30–0.47 (m, 2H), 0.02–0.13 (m, 2H).

Example 12F: MS: 471 (M+1, 100). NMR (DMSO-$d_6$): δ 7.06–7.33 (m, 10H), 5.25 (s, 2H), 4.34 (t, 2H), 3.71 (s, 2H), 3.44–3.58 (m, 2H), 3.20–3.42 (m, 6H), 2.96–3.06 (m, 2H), 2.79–2.91 (m, 2H), 1.83–1.97 (m, 2H), 1.08–1.42 (br m, 8H).

Example 12G: FABMS: 555 (M+1, 100). NMR (DMSO-$d_6$): δ 8.41 (s, 4H), 7.06–7.33 (m, 10H), 3.71 (s, 2H), 3.33–3.50 (m, 5H), 3.00–3.09 (m, 2H), 2.75–2.88 (m, 2H), 2.11–2.21 (m, 2H), 2.03–2.11 (m, 3H), 1.90–2.03 (m, 2H), 1.02–1.54 (br m, 10 H).

Example 12H: MS: 583 (M+1, 100). NMR ($CDCl_3$): δ 7.12–7.35 (m, 10H), 3.98 (s, 2H), 3.61 (s, 6H), 3.60–3.74 (m, 2H), 3.45–3.58 (m, 2H), 3.03–3.13 (m, 2H), 2.84–3.03 (m, 4H), 2.07–2.28 (m, 6H), 1.08–1.81 (br m, 12H).

Example 12I: MS: 555 (M–$CH_2$+1, 100). NMR ($CDCl_3$): δ 7.12–7.34 (m, 10H), 3.98 (s, 2H), 3.62 (s, 3H), 3.45–3.76 (m, 6H), 3.04–3.13 (m, 2H), 2.85–2.99 (m, 3H), 2.79 (s, 1H), 2.10–2.28 (m, 4H), 1.08–1.64 (br m, 12H).

Example 12J: MS: 759 (M+1, 100), 633 (M–I+1, 33), 507 (M–2I+1, 17). NMR ($CDCl_3$): δ 7.00–7.64 (br m, 18H), 4.77 (d, 2H), 3.70 (s, 2H), 3.49–3.57 (m, 2H), 2.99–3.12 (m, 4H), 2.81–2.93 (m, 2H), 2.29 (s, 2H).

Example 12K: MS: 583 (M+1, 100). NMR ($CDCl_3$): δ 7.15–7.35 (m, 10H), 3.98 (s, 2H), 3.44–3.74 (m, 8H), 3.02–3.22 (m, 2H), 2.88–3.02 (m, 2H), 2.02–2.20 (m, 2H), 0.94–1.92 (br m, 28H).

Example 12L: MS: 495 (M+1, 100) NMR ($CDCl_3$): δ 7.31 (m, 10H) 4.22 (m. 4H) 3.76–4.05 (m. 6H) 3.60 (m, 2H) 3.03–3.37 (m, 6H) 1.89 (m, 2H) 0.95 (m, 2H) 0.80 (m, 2H) 0.45 (m, 2H) 0.30 (m, 2H).

Example 12M: MS: 501 (M+1, 100) NMR ($CDCl_3$): δ 7.05–7.38 (m, 15H) 4.84 (dd, 1H) 4.04 (m, 1H) 3.93 (m, 1H) 3.49–3.75 (m. 3H) 3.05 (m, 6H) 1.74 (m, 2H) 0.70–0.98 (m, 2H) 0.40 (m, 1H) 0.28 (m, 1H).

Example 12N: MS: 411 (M+1, 100) NMR ($CDCl_3$): δ 7.25 (m, 10H) 4.72 (bs, 1H) 3.95 (m, 5H) 3.53 (m. 2H) 3.11 (m. 6H) 2.94 (t, 1H) 2.76 (m. 1H) 0.84 (m. 2H) 0.39 (m, 1H) 0.24 (m. 1H).

Example 12o: MS: 441 (M+1, 100). NMR ($CDCl_3$): δ 7.17–7.36 (m, 10H), 4.70 (d, 1H), 3.90–4.01 (m, 2H), 3.53–3.68 (m, 4H), 3.37–3.45 (m, 1H), 3.04–3.20 (m, 3H), 2.78–3.03 (m, 1H), 2.68–2.77 (m, 1H), 2.09–2.24 (m, 1H), 1.10–1.95 (br m, 12H).

Example 12P: MS: 555 (M+1, 100). NMR ($CDCl_3$): δ 7.13–7.37 (m, 10H), 3.98 (s, 2H), 3.44–3.77 (m, 10H), 3.03–3.14 (m, 2H), 2.80–3.01 (m, 4H), 2.06–2.21 (m, 2H), 1.00–1.75 (br m, 20H).

Example 12Q: m. p. 185.7° C. FABMS: 655 (M+1, 100), 613 (M–HNCNH+1, 80). NMR (DMSO-$d_6$): δ 8.99 (br s, 8H), 6.87–7.62 (br m, 18H), 5.08–5.35 (m, 2H), 4.44–4.62 (m, 2H), 3.41–3.61 (m, 4H), 2.96–3.18 (m, 4H), 2.64–2.81 (m, 2H). Reference: K. Takagi, Chemistry Letters (1985), pp. 1307–1308.

Example 12R: m. p. 169.3° C. MS: 599 (M+1, 100). NMR (CDCl$_3$): δ 6.90–7.40 (m, 18H), 4.88 (d, 2H), 3.63 (s, 2H), 3.49–3.58 (m, 2H), 2.91–3.12 (m, 6H), 2.42 (s, 6H), 2.22 (s, 2H).

Example 12S: MS: 663 (M+1), 680 (M+NH$_3$+1). NMR (CDCl$_3$): δ 6.93–7.83 (br m, 18H), 4.78 (d, 2H), 3.71 (s, 2H), 3.53–3.59 (m, 2H), 3.19 (d, 2H), 3.00–3.14 (m, 4H), 2.98 (s, 6H), 2.75–2.83 (m, 2H).

Example 12T: MS: 415 (M+1). NMR (Acetone-d$_6$): δ 7.15–7.30 (m, 10H), 5.29 (s, 1H), 4.41 (s, 1H), 4.25 (s, 1H), 3.81–4.05 (m, 3H), 3.63–3.78 (m, 2H), 3.56–3.63 (m, 2H), 3.37–3.47 (m, 5H), 3.05–3.25 (m, 3H), 2.79–2.94 (m, 1H), 2.20 (br s, 1H).

Example 12U: MS: 503 (M+1). NMR (Acetone-d$_6$): δ 7.15–7.28 (m, 10H), 4.29 (s, 1H), 3.95–4.07 (m, 4H), 3.49–3.66 (m, 8H), 3.35–3.49 (m, 8H), 3.14–3.22 (m, 2H), 3.02–3.09 (m, 2H), 2.08–2.21 (m, 3H).

Example 12V: MS: 569 (M+1). NMR (CDCl$_3$): δ 7.14–7.34 (m, 10H), 3.90–4.03 (m, 4H), 3.42–3.74 (m, 8H), 3.03–3.14 (m, 2H), 2.86–3.01 (m, 2H), 2.68–2.86 (m, 2H), 2.05–2.23 (m, 2H), 2.01 (s, 3H), 0.98–1.75 (br m, 15 H).

Example 12W: MS: 641 (M+1), 584 (M–CONHCH$_2$+1), 527 (M–2CONHCH$_2$+1). NMR (CDCl$_3$): δ 7.10–7.35 (m, 10H), 4.77 (br s, 2H), 3.89–4.12 (m, 6H), 3.60–3.80 (m, 2H), 3.35–3.47 (m, 2H), 3.04–3.16 (m, 2H), 2.87–3.01 (m, 2H), 2.78 (d, 6H), 2.01–2.16 (m, 2H), 0.98–1.80 (br m, 18H).

Example 12X: MS: 626 (M+1), 569 (M–CONHCH$_2$+1). NMR (CDCl$_3$): δ 7.09–7.35 (m, 10H), 4.79 (br s, 1H), 3.82–4.14 (m, 6H), 3.38–3.81 (m, 4H), 3.01–3.22 (m, 2H), 2.83–3.01 (m, 2H), 2.79 (d, 3H), 2.04–2.20 (m, 2H), 2.01 (s, 3H), 0.96–1.84 (br m, 18 H).

Example 12Y: MS: 584 (M+1), 527 (M–CONHCH$_2$+1). NMR (CDCl$_3$): δ 7.11–7.41 (m, 10H), 4.81 (br s, 1H), 3.87–4.10 (m, 4H), 3.41–3.76 (m, 6H), 3.02–3.16 (m, 2H), 2.81–3.02 (m, 2H), 2.78 (d, 3H), 2.00–2.21 (m, 2H), 1.79 (br s, 1H), 0.95–1.63 (br m, 18H).

Example 12Z: MS: 425 (M+1, 100).

Example 13A: MS: 439 (M+1, 100).

Example 13B: MS: 481 (M+1, 100).

Example 13C: MS: 635 (M+1, 100) 652 (M+NH$_4$).

Example 13D: MS: 491 (M+1, 100); NMR (CDCl$_3$): δ 7.24 (m, 10H), 5.68 (m, 2H), 4.90 (m, 4H), 3.98 (s, 2H), 3.66 (m, 2H), 3.50 (m, 2H), 3.04 (m, 4H), 2.19 (m, 2H), 1.95 (m, 4H), 1.22 (m, 8H).

Example 13E: MS: 523 (M+1, 100); NMR (CDCl$_3$): δ 7.19 (m, 10H), 3.98 (s, 2H), 3.66 (m, 2H), 3.53 (m, 2H), 3.23 (s, 2H), 3.14–2.66 (m, 8H), 2.40 (m, 2H), 2.21 (m, 2H), 1.55–1.23 (m, 12H).

Example 13F: MS: 811 (M+1, 100); NMR (CDCl$_3$): δ 7.22 (m, 10H), 4.00 (m, 4H), 3.77 (dd, 2H), 3.56 (m, 6H), 3.13 (m, 4H), 2.93 (m, 2H), 2.23 (m, 2H), 2.00 (m, 2H), 1.65 (m, 2H), 1.50–1.23 (m, 8H).

Example 13G: MS: 685 (M+1, 100); NMR (CDCl$_3$): δ 7.22 (m, 10H), 4.01 (m, 2H), 3.72–3.26 (m, 12H), 3.14 (d, 2H), 2.96–2.70 (m, 6H), 2.26 (m, 2H), 1.43–1.18 (m, 8H).

Example 13H: MS: 499 (M+1, 100); NMR (CDCl$_3$): δ 7.23 (m, 10H), 3.99 (s, 2H), 3.54 (m, 8H), 3.12 (m, 2H), 2.94 (m, 4H), 2.22 (m, 2H), 1.47–1.20 (m, 12H).

Example 13I: MS: 559 (M+1, 100); NMR (CDCl$_3$/CD$_3$OD): δ 7.02 (m, 10H), 3.79 (s, 2H), 3.69 (s, 2H), 3.28 (m, 6H), 3.13 (m, 4H), 2.86 (m, 2H), 2.67 (m, 2H), 1.95 (m, 2H), 1.09–0.90 (m, 12H).

Example 13J: MS: 435 (M+, 1100); NMR (CDCl$_3$): δ 7.26 (m, 10H), 4.15 (m, 1H), 3.86 (m, 1H), 3.76 (m, 1H), 3.64 (m, 1H), 3.53 (m, 2H), 3.23–2.97 (m, 4H), 2.78 (m, 2H), 2.16 (d, 1H), 1.92 (m, 1H), 1.18 (m, 1H), 0.88 (m, 1H), 0.58 (m, 2H), 0.46 (m, 2H), 0.29 (d, 1H), 0.07 (d, 1H).

Example 13K: MS: 407 (M+1, 100); NMR (CDCl$_3$): δ 7.23 (m, 10H), 6.05 (m, 1H), 5.67 (m, 1H), 5.25 (m, 2H), 5.05 (dd, 2H), 4.17 (m, 2H), 3.96 (m, 1H), 3.83 (m, 1H), 3.65 (m, 1H), 3.55 (m, 1H), 3.12–2.79 (m, 5H), 2.59 (br s, 1H), 2.35 (d, 1H).

Example 13L: MS: 507 (M+1, 100); NMR (CDCl$_3$): δ 7.28 (m, 18H), 6.91 (d, 2H), 4.10 (d, 2H), 3.92 (d, 1H), 3.58 (m, 4H), 3.18–2.63 (m, 5H).

Example 13M: MS: 567 (M+1, 100); NMR (CDCl$_3$): δ 7.46–6.95 (m, 18H), 4.90 (dd, 2H), 4.67 (br d, 4H), 3.84 (d, 1H), 3.53 (m, 4H), 3.09–2.75 (m, 5H), 2.44 (d, 1H).

Example 13N: MS: 407 (M+1, 100); NMR (CDCl$_3$): δ 7.24 (m, 10H), 5.55 (m, 2H), 5.14 (m, 4H), 4.07 (dd, 2H), 3.74 (m, 2H), 3.27 (m, 2H), 3.12–2.84 (m, 6H), 2.09 (s, 2H).

Example 13o: MS: 435 (M+1, 100); NMR (CDCl$_3$): δ 7.26 (m,10H), 3.85 (s, 2H), 3.41 (m, 4H), 3.01 (ddd, 4H), 2.28 (dd, 2H), 2.19 (s, 2H), 0.93 (m, 2H), 0.50 (m, 2H), 0.16 (m, 2H).

Example 13P: MS:327 (M+1, 100); NMR (CDCl$_3$): δ 7.28 (m, 10H), 4.25 (m, 2H), 3.35 (m, 6H), 2.81 (m, 2H), 2.65 (m, 2H).

Example 13Q: MS: 507 (M+1, 100); NMR (CDCl$_3$): δ 7.24 (m, 20H), 4.74 (d, 2H), 3.55 (m, 4H), 3.20 (m, 2H), 2.96 (m, 2H), 2.77 (m, 2H).

Example 13R: MS: 439 (M+1, 100); NMR (CDCl$_3$): δ 7.26 (m, 10H), 3.75 (s, 2H), 3.62 (m, 2H), 3.20 (m, 2H), 3.08 (m, 2H), 2.84 (m, 2H), 2.38 (m, 2H), 1.38–1.23 (m, 8H), 0.90 (m, 6H).

Example 13S: MS: 567 (M+1, 100); NMR (CDCl$_3$): δ 7.34–7.07 (m, 18H), 4.68 (m, 6H), 3.57 (m, 4H), 3.17 (m, 2H), 2.96 (m, 2H), 2.79 (m, 2H).

Example 13T: MS: 617 (M+H, 100%); NMR (CDCl$_3$, 300 Hz): δ 7.3 (m, 10H), 6.7 (m, 4H), 6.35 (m, 2H), 4.75 (d, 2H), 3.5 (s, 4H), 3.3 (m, 4H), 3.0 (m, 6H), 2.7 (m, 4H), 1.9 (m, 4H).

Example 13U: m.p. 264–266° C.; MS: 609 (M+H, 100%); NMR (CDCl$_3$, 300 Hz): δ 8.6 (d, 2H), 7.95 (d, 2H), 7.8 (d, 2H), 7.6 (d, 2H), 7.3 (m, 14H), 5.1 (d, 2H), 3.7 (m, 4H), 3.2 (m, 6H).

Example 13V: MS: 521 (M+H, 100%); NMR (CDCl$_3$, 300 Hz): δ 8.8 (s, 2H), 7.2 (m, 12H), 4.15 (s, 2H), 3.8 (t, 2H), 3.6 (m, 4H), 2.9 (m, 4H).

Example 13W: m.p. 182–184° C.; MS: 687 (M+H, 100%); NMR (CDCl$_3$, 300 Hz): δ 7.2 (m, 10H), 6.95 (d, 2H), 6.2 (d, 2H), 4.9 (d, 2H), 4.15 (d, 2H), 3.9 (bs, 2H), 3.7 (d, 2H), 3.0 (m, 6H), 1.45 (s, 18H).

Example 13X: MS: 547 (M+H, 100%); NMR (CDCl$_3$, 300 Hz): δ 7.2 (m, 10H), 6.2 (d, 2H), 6.0 (d, 2H), 4.8 (d, 2H), 4.5 (bs, 2H), 3.8 (s, 2H), 3.5 (d, 2H), 3.1 (m, 6H).

Example 13Y: MS: 507 (M+1, 100%); NMR (CDCl$_3$, 300 Hz): δ 7.0–7.4 (m, 20H), 4.7–4.8 (d, 2H), 4.5 (m, 2H), 3.45 (m, 4H), 3.1 (m, 4H), 2.9 (m, 2H).

Example 13Z: MS: 577 ((M+H)$^+$, 100%); 594 ((M+NH$_4$)$^+$, 80%). NMR (CDCl$_3$): δ 8.08 (s 1H), 7.48 (dd, 1H, J=8.4, 1.9 Hz), 7.25–7.38 (m, 3H); 7.19 (d, 1H, J=8.4 Hz), 7.00–7.03 (m, 2H), 3.96 (ABq, 2H), 3.73 (d, 1H, J=1.1 Hz), 3.50 (dd, 1H, J=11.4, 1.1 Hz), 3.23 (br.s., 1H), 2.98 (ABx, 2H).

Example 14A: NMR (CDCl$_3$): δ 8.27 (dd, 1H, J=4.9, 2.0 Hz), 7.66 (dd, 1H, J=7.5, 2.0 Hz), 7.14–7.27 (m, 4H), 6.68 (dd, 2H, J=7.5, 3.6 Hz), 4.16 (d, 1H, J=0.8 Hz), 3.90 (ABq, 2H), 3.72 (dd, 1H, J=11.3, 1.1 Hz), 3.14 (br.s., 1H), 2.87 (ABx, 2H).

Example 14B: MS: 685 ((M+H)$^+$, 100%). NMR (CDCl$_3$): δ 8.34 (dd, 1H, J=4.8, 1.9 Hz), 7.16–7.37 (m, 4H), 6.93 (dd, 1H, J=7.6, 4.8 Hz), 6.87 (dd, 2H, J=7.5, 1.7 Hz), 4.14 (s, 1H), 3.90 (ABq, 2H), 3.68 (td, 1H, J=6.3, 0.7 Hz), 2.99 (d, 2H, J=6.3 Hz), 2.43 (br.s., 1H).

Example 14C: MS: 541 ((M+H)+, 100%). NMR (CD$_3$OD): δ 7.53 (dd, 1H, J=9.5, 2.6 Hz), 7.15–7.26 (m, 3H), 7.06 (d, 1H, J=2.6 Hz), 6.96–6.99 (m, 2H), 6.42 (d, 1H, J=9.5 Hz), 3.80 (s, 1H), 3.71 (ABq, 2H), 3.62 (dd, 1H, J=11.7, 0.7 Hz), 2.92 (ABx, 2H)

Example 14D: MS: 458 (M+H+, 100%).

Example 14E: MS: 543 (M+H+, 100%) NMR (CDCl$_3$): δ 7.4–7.1 (m, 5H), 4.42 (d, J=17.5 Hz, 1H), 4.10 (s, 1H), 3.83 (d, J=10.6 Hz), 3.2–3.0 (m, 2H), 2.82 (d, J=17.6 Hz, 1H), 2.36 (s, 1H), 2.14 (m, 2H), 1.5–1.2 (m, 6H), 0.85 (t, J=7.0 Hz, 3H).

Example 14F: MS: 739.5 (M+H+) NMR (CDCl$_3$): δ 7.4–7.0 (m, 15H), 3.90 (s, 1H), 3.3–3.1 (m, 2H), 3.04 (m, 2H), 2.43 (dd, J=14.7, 5.7 Hz, 1H), 2.17 (s, 1H), 1.824 (m, 1H), 1.26 (t, J=6.0 Hz, 1H), 1.02 (dd, J=9.0, 5.1 Hz, 1H).

Example 14G: MS: 479 (M+H+, 100%) NMR (CDCl$_3$): δ 7.24 (bs, 5H), 7.15–6.9 (m, 3H), 6.72 (d, J=7.5 Hz, 2H), 4.15 (s, 1H), 4.06 (d, J=10.5 Hz, 1H), 3.5–3.2 (m, 2H), 2.98 (s, 1H).

Example 14H: MS: 587 (M+H+, 100%) NMR (CDCl$_3$): δ 7.4–6.9 (m, 10H), 3.92 (s, 1H), 3.8–3.6 (m, 2H), 3.03 (m, 2H), 2.50 (bs, 1H), 2.19 (dd, J=14.3, 7.0 Hz, 1H), 1.57 (m, 1H), 1.0–0.7 (m, 2H).

Example 14I: MS: 457 (M+H+, 100%), 474 (M+NH$_4$+, 15%) NMR (CDCl$_3$): δ 7.4–6.9 (m, 15H), 4.69 (d, J=6.2 Hz, 1H), 3.95 (m, 2H), 3.77 (m, 2H), 3.37 (m, 1H), 3.25–3.0 (m, 3H), 2.15 (b, 1H), 1.61 (m, 2H), 1.24 (m, 1H), 1.0–0.7 (m, 2H).

Example 14J: NMR (CDCl$_3$): δ 7.42 (d, 2H, J=7.3 Hz), 7.22–7.38 (m, 6H), 7.11 (d, 2H, J=6.6 Hz), 6.54 (s, 1H), 6.35 (s, 1H), 5.31 (s, 2H), 3.84 (ABq, 2H), 3.72 (s, 1H), 3.49 (d, 1H, J=10.4 Hz), 2.90–3.01 (m, 2H), 2.39 (s, 3H).

Example 14K: NMR ((CD$_3$)$_2$SO): δ 7.00–7.33 (m, 7H), 3.61 (s, 1H), 3.55 (ABq, 2H), 3.45 (d, 1H, J=11.0 Hz), 2.95 (ABx, 2H), 2.09 (s, 3H,).

Example 15VA: NMR (CDCl$_3$): δ 7.19–7.40 (m, 10H) 4.66 (d, 1H) 3.99–4.12 (m, 2H) 3.59–3.69 (m, 2H) 3.37–3.49 (m, 2H) 3.10–3.21 (m, 2H) 2.25–2.38 (m, 3H) 1.90–2.00 (m, 2H) 0.85–0.92 (m, 8H).

Example 15VB: NMR (CD$_3$OD): δ 7.50–7.70 (m, 1H) 7.10–7.35 (m, 9H) 3.95 (m, 2H) 3.53–3.70 (m, 2H) 3.40–3.50 (m, 2H) 3.00–3.20 (m, 3H) 2.75 (t, 1H) 2.30 (m, 1H) 1.60–2.10 (m, 7H) 1.28 (m, 2H) 0.81–1.10 (m, 2H).

Example 15VC: NMR (CDCl$_3$): δ 7.15–7.40 (m, 10H) 4.70 (d, 1H) 4.05 (m, 2H) 3.50–3.70 (m, 3H) 3.57 (m, 1H) 3.20 (m, 1H) 3.07 (s, 3H) 3.05 (s, 3H) 2.75 (t, 1H) 2.59 (s, 2H) 2.93 (m, 2H) 1.40–1.55 (m, 5H) 1.17–1.32 (m, 2H) 1.00–1.15 (m, 2H).

Example 15VD: NMR (CDCl$_3$): δ 7.05–7.30 (m, 10H), 5.55 (br s, 2H), 3.93 (s, 2H), 3.66–3.80 (m, 4H), 3.53 (d, 2H), 3.09 (d, 2H), 2.85–2.92 (m, 2H), 2.81 (d, 6H), 1.98–2.26 (m, 6H), 0.96–1.52 (br m, 12H).

Example 15VE: NMR (CDCl$_3$): δ 7.17–7.34 (m, 10H), 3.99 (s, 2H), 3.55–3.73 (m, 4H), 3.43–3.53 (m, 4H), 3.05–3.13 (m, 2H), 2.90–3.00 (m, 2H), 2.58 (br d, 2H), 2.15–2.28 (m, 2H), 1.12–1.80 (br m, 17H).

Example 15VF: NMR (CDCl$_3$): δ 7.17–7.34 (m, 10H), 4.57 (br s, 1H), 4.08 (t, 2H), 3.99 (s, 2H), 3.60–3.72 (m, 2H), 3.59 (t, 2H), 3.46–3.54 (m, 2H), 3.05–3.13 (m, 2H), 2.89–3.00 (m, 2H), 2.78 (d, 3H), 2.70 (br s, 2H), 2.14–2.24 (m, 2H), 1.12–1.80 (br m, 17H).

Example 15VG: NMR (CDCl$_3$): δ 7.10–7.37 (m, 10H), 4.80 (d, 1H), 3.92 (s, 2H), 3.20–3.70 (br m, 6H), 3.00–3.19 (m, 4H), 3.61–3.77 (m, 1H), 2.21 (m, 1H), 1.10–1.50 (br m, 7H).

Example 15VH: NMR (CDCl$_3$): δ 7.64–7.84 (m, 3H), 7.05–7.57 (m, 14H), 4.96 (d, 1H), 3.92 (m, 1H), 3.38–3.80 (m, 6H), 3.21 (d, 1H), 2.99–3.18 (m, 3H), 2.75–2.98 (m, 2H), 2.43 (br s, 1H), 2.20–2.35 (m, 2H), 1.10–1.88 (br m, 7H).

Example 15VI: NMR (CDCl$_3$): δ 7.04–7.40 (m, 15H), 4.80 (d, 1H), 3.94 (m, 1H), 3.42–3.80 (m, 7H), 2.83–3.17 (m, 6H), 2.64 (br s, 1H), 2.19–2.31 (m, 1H), 1.16–1.50 (br m, 6H).

Example 15VJ: NMR (CDCl$_3$): δ 7.11–7.35 (m, 10H), 3.99 (s, 2H), 3.43–3.69 (m, 6H), 3.10 (m, 2H), 2.95 (m, 3H), 2.80 (s, 1H), 2.38 (t, 2H), 2.20 (m, 2H), 2.02 (s, 3H), 1.18–1.56 (br m, 13H).

Example 15VK: NMR (CDCl$_3$): δ 7.05–7.40 (m, 14H), 4.79 (d, 1H), 4.58–4.70 (m, 2H), 4.50 (d, 1H), 3.91 (m, 1H), 3.40–3.75 (m, 6H), 2.98–3.14 (m, 4H), 2.81–2.95 (m, 2H), 2.72 (s, 1H), 2.25 (m, 1H), 2.07 (br s, 1H), 1.16–1.50 (br m, 6H).

Example 15VL: NMR (CDCl$_3$): δ 7.18–7.36 (10H, m) 4.53 (1H, s) 3.95 (2H, s) 3.79 (1H, m) 3.51 (1H, m) 3.33 (2H, m) 3.13 (6H, m) 2.72 (1H, t) 2.60 (1H, s) 1.33 (2H, m) 0.84 (3H, t).

Example 15VM: NMR (CDCl$_3$): δ 7.20–7.34 (10H, m) 4.57 (1H, s) 3.94 (2H, s) 3.79 (1H, m) 3.52 (1H, m) 3.38 (1H, m) 3.33 (1H, d) 3.13 (5H, m) 2.94 (2H, bs) 2.72 (1H, t) 1.26 (6H, m) 0.86 (3H, t).

Example 15VO: NMR (CDCl$_3$): δ 7.14–7.35 (10H, m) 4.63 (2H, d) 4.41 (2H, s) 3.49 (2H, d) 3.34 (2H, m) 3.14 (2H, m) 2.85 (2H, d) 2.45 (2H, s) 2.10–2.32 (4H, m) 0.99 (6H, t).

Example 15VP: NMR(CDCl$_3$): δ 8.81 (2H, s) 7.23 (10H, m) 4.80 (2H, d) 4.14 (4H, m) 3.68 (2H, m) 3.14 (2H, m) 2.60 (2H,d) 2.44 (2H, m) 2.03 (2H, m) 0.98 (6H, t).

Example 15VQ: NMR (CDCl$_3$): δ 7.64–7.82 (m, 3H), 7.07–7.53 (m, 14H), 4.96 (d, 1H), 3.88–3.96 (m, 1H), 3.44–3.80 (m, 7H), 3.21 (d, 1H), 2.99–3.16 (m, 3H), 2.84–2.98 (m, 1H), 2.70 (s, 1H), 2.19–2.33 (m, 2H), 1.08–1.56 (br m, 8H).

Example 15VR: NMR (Acetone-d$_6$): δ 8.38 (s, 1H), 7.02–7.40 (m, 11H), 6.70 (m, 2H), 6.52 (d, 1H), 4.73 (d, 1H), 4.34 (s, 2H), 3.84–3.96 (m, 1H), 3.38–3.76 (br m, 7H), 2.80–3.21 (br m, 5H), 2.07–2.19 (m, 1H), 1.16–1.52 (br m, 6H).

Example 15VS: NMR (CDCl$_3$): δ 7.15–7.33 (m, 10H), 4.00 (s, 2H), 3.44–3.69 (m, 5H), 3.10 (d, 2H), 2.88–2.98 (m, 3H), 2.85 (s, 3H), 2.56–2.76 (m, 2H), 2.17–2.35 (m, 2H), 1.18–1.80 (m, 15H).

Example 15VU: NMR (CDCl$_3$): δ 7.10–7.36 (m, 10H), 4.04 (m, 2H), 3.39–3.79 (br m, 7H), 2.78–3.22 (br m, 6H), 2.17–2.29 (m, 1H), 2.03 (m, 1H), 1.15–1.52 (br m, 6H), 0.91 (m, 1H), 0.41 (m, 2H), 0.06 (m, 2H).

Example 15VV: NMR (CDCl$_3$): δ 7.15–7.33 (m, 10H), 3.99 (s, 2H), 3.65 (m, 2H), 3.49 (d, 2H), 3.25 (s, 6H), 3.21–3.33 (m, 4H), 3.04–3.14 (m, 2H), 2.89–3.00 (m, 2H), 2.63 (s, 2H), 2.18 (m, 2H), 1.72 (br s, 2H), 1.15–1.52 (br m, 10H).

Example 15VW: NMR (CDCl$_3$): δ 7.13–7.33 (m, 10H), 3.99 (s, 2H), 3.45–3.71 (br m, 6H), 3.24 (s, 3H), 3.20–3.33 (m, 3H), 3.10 (d, 3H), 2.89–3.00 (m, 2H), 2.10–2.28 (m, 2H), 1.85 (br d, 2H), 1.15–1.53 (br m, 11H).

Example 15VX: NMR (CDCl$_3$): δ 7.13–7.57 (br m, 11H), 6.98 (d, 1H), 4.68 (d, 1H), 3.98 (m, 1H), 3.74–3.83 (m, 2H), 3.46–3.69 (m, 3H), 3.22 (d, 1H), 3.01–3.18 (m, 3H), 2.81–2.93 (m, 3H), 2.66 (br d, 2H), 2.23 (m, 1H), 1.18–1.56 (br m, 6H).

Example 15VY: NMR (CDCl$_3$): δ 7.91 (m, 1H), 7.83 (s, 1H), 7.17–7.39 (m, 10H), 7.09 (d, 2H), 4.84 (d, 1H), 4.31 (q, 2H), 3.95 (dd, 1H), 3.62–3.72 (m, 2H), 3.48–3.60 (m, 4H), 2.86–3.16 (br m, 5H), 2.57 (br s, 1H), 2.39 (br s, 1H), 2.29 (m, 1H), 1.05–1.52 (br m, 10H).

Example 15VZ: NMR (CDCl$_3$): δ 7.17–7.32 (10H, m) 3.99 (2H, s) 3.68 (4H, m) 3.50 (2H, d) 3.09 (2H, dd) 2.94 (2H, t) 2.62 (2H, s) 2.23 (2H, m) 1.33 (14H, m) 1.12 (6H, d).

Example 15WB: NMR (CDCl$_3$): δ 7.13–7.33 (m, 10H), 4.02 (s, 2H), 3.61 (m, 2H), 3.50 (d, 2H), 3.10 (dd, 2H), 2.85–2.97 (m, 2H), 2.82 (s, 2H), 2.33 (t, 4H), 2.18 (m, 2H), 2.06 (s, 6H), 1.18–1.50 (br m, 8H).

Example 15WC: NMR (DMSO-d$_6$): δ 10.17, 10.09 (2 singlets, 2H, 3:1 mixture of isomers), 7.08–7.32 (m, 10H), 5.21 (s, 2H), 3.70 (s, 2H), 3.48 (m, 2H), 3.38 (d, 2H), 3.03 (d, 2H), 2.81 (m, 2H), 1.91–2.19 (br m, 6H), 1.61–1.71 (m, 6H), 1.15–1.39 (m, 8H).

Example 15WD: NMR (DMSO-d$_6$): δ 6.91–7.40 (br m, 14H), 5.01–5.22 (m, 1H), 4.61 (m, 1H), 4.42–4.50 (m, 1H), 3.66 (m, 1H), 3.12–3.54 (br m, 7H), 3.06 (d, 1H), 2.75–2.99 (m, 4H), 2.32–2.57 (m, 4H), 1.94–2.07 (m, 1H), 1.05–1.38 (br m, 8H).

Example 15WE: NMR (CDCl$_3$): δ 7.18–7.38 (m, 10H), 7.33 (s, 1H), 7.06 (m, 3H), 4.80 (d, 1H), 4.60 (d, 2H), 3.94 (m, 1H), 3.46–3.75 (m, 7H), 2.80–3.15 (m, 7H), 2.23–2.42 (m, 2H), 1.18–1.50 (br m, 6H).

15BC; MS (DCI): 514 (M+H$^+$, 100%). $^1$H NMR (CD$_3$OD, 300 Hz) δ 0.1 (m, 2H), 0.4 (m, 2H), 0.8 (m, 1H), 1.9 (m, 1H), 3.0 (m, 4H), 3.3 (d, 1H), 3.4 (m, 2H), 3.6 (m, 1H), 3.75 (m, 1H), 4.0 (m, 1H), 4.4 (d, 1H), 6.8–7.4 (m, 13H).

15AA $^1$H NMR (CD$_3$OD, 300 Hz) δ 3.00 (m, 6H), 3.6 (m, 4H), 4.4 (s, 4H), 4.7 (d, 2H), 6.9–7.5 (m, 18H).

15AM MS (DCI): 661 (M+H, 100%). $^1$H NMR (CD$_3$OD, 300 Hz) δ 1.2 (t, 3H), 3.0 (m, 6H), 3.6 (m, 4H), 4.3 (q, 2H), 4.8 (d, 2H), 7.0–7.4 (m, 18), 7.8–8.0 (m, 3H).

15AQ: MS (DCI): 548 (M+H, 100%). $^1$H MNR (CD3OD, 300 Hz) δ 3.0 (m, 6H), 3.6 (m, 4H), 4.8 (m, 2H), 6.8–7.8 (m, 18H).

15AR: MS (DCI): 533 (M+H, 100%). $^1$H NMR (CD$_3$OD, 300 Hz) δ 3.0 (m, 6H), 3.7 (m, 4H), 4.7 (d, 2H), 4.8 (d, 1H), 7.0–8.4 (m, 18H).

15AO: $^1$H NMR (CD$_3$OD, 300 Hz) δ 2.4 (s, 12H), 3.0 (m, 6H), 3.6 (s, 4H), 3.9 (s, 4H), 4.8 (d, J=15 Hz, 2H), 7.05–7.50 (m, 14H) 7.96 (d, J=7.5 Hz, 2H), 8.0 (s, 2H).

The structures of the Examples below are shown in Table 2e.

Ketal Formation: Preparation of Triacetonide (XXVIa):

Lithium borohydride (1.2 gr, 56.2 mmol) was added in four portions to a suspension of L-mannonic-g-lactone (5 gr, 28.1 mmol) in methanol (250 mL) at 0° C. over 10 min. Ice bath was removed and reaction stirred at room temperature for 30 min. Reaction was quenched at 0° C. with 2N HCl. Solvent was evaporated and residue taken up in acetone (75 mL) to which 2,2-dimethoxypropane (20 mL, 168.6 mmol) and camphorsulphonic acid (20 gr, 84.3 mmol) were added in four portions. Reaction becomes clear for a few minutes and then a precipitate forms. Reaction stirred at room temperature for 14 h. Solvent volume then reduced by ⅔ at reduced pressure and then poured into EtOAc, washed with saturated NaHCO$_3$, dried (MgSO$_4$) and concentrated. Solid residue taken up in hexane and filtered thru a pad of silica gel. Filtrate concentrated to give triacetonide (XXVIa) as a yellowish solid (7.1 gr, 80%). m.p. 72–74° C.; MS: 303 (M+H, 100%); NMR (CDCl$_3$, 300 Hz): δ 4.25 (m, 2H), 4.15 (m, 2H), 4.05 (m, 4H), 1.5 (s, 6H), 1.45 (s, 6H), 1.4 (s, 6H).

Selective Acetonide Deprotection: Preparation of Tetraol (XXVIb):

Compound (XXVIa) (14 gr) in 70% AcOH (200 mL) was stirred at 45° C. for 2 h. Solvent removed at reduced pressure with a bath temperature of 45° C. Residue recrystalized from ether. Mother liquors concentrated and chromatographed (silica, 10% methanol in methylene chloride) to give the desired product as a white solid (8.2 gr, 80%). m.p. 91–93° C.; [a]$_D$=−26.40 (c=3, H2O); MS: 240 (M+NH$_4$, 100%); NMR (CDCl$_3$, 300 Hz): δ 3.95 (m, 6H), 3.75 (m, 4H), 2.5 (bs, 2H), 1.4 (s, 6H).

Epoxide Formation: Preparation of Diepoxide (XXVIc):

A solution of Compound (XXVIb) (1 g, 4.5 mmol) in pyridine (5 mL) was cooled to −20° C. and treated with p-toluenesulfonyl chloride (1.89 g, 10 mmol). Stirring continued at −20° C. for 20 min, 0° C. for 20 min, and 23° C. for 20 min. The reaction was then diluted with methylene chloride and washed with 2N HCl and NaHCO$_3$. The organic extract was dried over MgSO$_4$ and concentrated. The crude product was then taken up in methanol (14 mL) and cooled to 0° C. Next, K$_2$CO$_3$ (3.11 g, 22 mmol) was added and the reaction stirred at room temperature for 30 min. The methanol was then stripped off (do not evaporate to dryness, epoxide is volatile) and the crude was washed with water, extracted with ether, dried over MgSO$_4$, filtered, and concentrated. The compound was purified on SiO$_2$ and eluted with 30–60% ether/petroleum ether to afford the diepoxide (0.63 g, 75%) as an oil. NMR (CDCl$_3$, 300 Hz): δ 3.81 (m, 2H), 3.10 (m, 2H), 2.80 (t, 2H), 2.68 (m, 2H), 1.40 (s, 6H, CH$_3$).

Opening of Epoxide: Prepepartion of Diol (XXVId):

To a suspension of cuprous bromide-dimethyl sulfide complex (1.8 g, 8.7 mmol) in anhydrous THF (5 mL) at −20° C. was added 8.5 ml benzylmagnesium chloride (2M in THF, 17 mmol). Reaction stirred at −20° C. for 30 min and at 0° C. for 1 h. Next, Compound (XXVIc) (0.54 g, 3 mmol) in THF (5 mL) was added, and the reaction stirred at 0° C. for 1 h. The excess reagent was quenched with saturated NH$_4$Cl solution and allowed to warm to room temperature. The contents were then washed with water and brine, extracted with ether, dried over MgSO$_4$, filtered, and concentrated. Crude material was then purified by flash chromatography (30–60% ether/petroleum ether) to yield 0.84 g (78%) of an oil. MS: 371 (M+H, 66%); NMR (CDCl$_3$, 300 Hz): δ 7.2–7.4 (m, 10H), 4.65 (s, 2H), 3.6–3.8 (m, 4H), 2.6–3.0 (m, 4H), 1.8–2.2 (m, 4H), 1.4 (s, 6H).

Hydroxyl Displacement: Preparation of Diazide (XXVIe):

To a solution of Compound (XXVId) (0.48 g, 1.3 mmol) and triphenyl phosphine (1.0 g, 3.9 mmol) in THF (5 mL) at 0° C. was added diethylazodicarboxylate (0.61 mL, 3.9 mmol) and dipheylphosphorylazide (0.84 mL, 3.9 mmol). Contents were allowed to warm to room temperature in the ice bath for 1 h. The excess reagents were quenched by the addition of methanol (0.2 mL, 5 mmol) at 0° C. The mixture was then stirred at room temperature for 30 min and then concentrated to a small volume. Crude was then purified on SiO$_2$ using 1:40 ethyl acetate/hexane giving 0.245 g (45%) of an oil. MS: 438 (M+NH$_4$, 8%); NMR (CDCl$_3$, 300 Hz): δ 7.2–7.4 (m, 10H), 4.18 (s, 2H), 2.7–3.0 (m, 6H), 2.0–2.3 (m, 4H), 1.58 (s, 6H).

Reduction of Diazide (XXVIe):

To Compound (XXVIe) (0.245 g, 0.58 mmol) in ethanol (6 mL) under N$_2$ was added 10% Pd/C (73.5 mg, 30%/weight). Reaction stirred under H$_2$ atmosphere at room temperature overnite. Crude was then filtered through celite and concentrated. 0.21 g (98%) of the diamine was collected as an oil and taken onto next step without further purification. MS: 369 (M+H, 100%); NMR (CDCl$_3$, 300 Hz): δ 7.05–7.3 (m, 10H), 3.9 (bs, 2H), 3.05 (bs. 4H), 2.8 (m, 2H), 2.6 (m, 4H), 1.7 (bs, 4H), 1.35 (s, 6H).

Cyclization of the Diamine: Formation of Cyclic Urea (XXVIf):

The diamine (0.21 g, 0.57 mmol) was dissolved in methylene chloride (50 mL) and carbonyldiimidazole (0.102 g, 0.63 mmol) was added and the reaction stirred at 23° C. overnite. The solution was then concentrated and purified on $SiO_2$ using 75% ethyl acetate/hexane as elutent which gave 85 mg (38%) of (XXVIf) as a foam. MS: 395 (M+H, 100%); NMR ($CDCl_3$, 300 Hz): δ 7.0–7.2 (m, 10H), 3.6–4.0 (m, 4H), 3.6–2.7 (m, 4H), 1.8–1.9 (m, 4H), 1.3 (s, 6H).

Alkylation of the Cyclic Urea (XXVIf):

To Compound (XXVIf) (85 mg, 0.22 mmol) in dry DMF (3 mL) was added 60% NaH (0.07 g, 1.7 mmol). The solution was stirred for 5 min at room temperature. Next, benzyl bromide (0.1 mL, 0.86 mmol) was added and the reaction stirred at 23° C. overnite. Reaction was then quenched with methanol (several drops), washed with $H_2O$, extracted with ether, dried ($MgSO_4$), and concentrated. Crude was then purified on silica gel using 1:1 hexane/ethyl acetate affording 0.03 g (25%) of the bis-alkylated urea as a foam. MS: 575 (M+H, 100%); NMR ($CDCl_3$, 300 Hz): δ 7.1–7.4 (m, 20H), 5.1 (d, 2H), 4.0 (d, 2H), 3.75 (bs, 2H), 3.6 (m, 2H), 2.7 (m, 2H), 2.6 (m, 2H), 1.9–2.0 (m, 4H), 1.25 (s, 6H).

Deprotection of Acetonide: Preparation of Example 16A:

To above prepared bis-alkylated cyclic urea (0.03 g, 0.05 mmol) in THF (2 mL) at room temperature was added several drops of concentrated HCl. Reaction stirred at room temperature for 2 h. Reaction was then washed with 1 N NaOH, extracted with ethyl acetate, dried ($MgSO_4$), and concentrated. Chromatography (silica, 1–5% methanol in methylenechloride) gave 0.024 g (85%) of example 16A as a foam. MS: 535 (M+H, 100%); NMR ($CDCl_3$, 300 Hz): δ 7.1–7.3 (m, 20H), 5.15 (d, 2H), 3.9 (d, 2H), 3.5 (bs, 2H), 3.3–3.4 (m, 2H), 2.7–2.8 (m, 2H), 2.5–2.6 (m, 2H), 2.0–2.1 (m, 6H).

Alternate Route to XXVIf:

Ester Hydrolysis: Synthesis of Diacid LIVa

To a solution of 100.7 g (458.0 mmol) of (4R,5R)-(-)-dimethyl-2,3-O-isopropylidine-L-tartrate in 450 mL of ethanol was added 450 ml of 15% sodium hydroxide in water. After stirring 5 h the solvent was partially removed under reduced pressure and the residue was diluted with water and extracted with EtOAc. The aqueous layer was then acidified with conc. HCl, saturated with NaCl, and extracted with EtOAc. The combined organic layers were washed with brine and dried over $MgSO_4$. The solvent was removed under reduced pressure and the solid residue was triturated with $CH_2Cl_2$ and hexanes to give 72.2 g (83%) of the diacid LIVa as a white solid. mp 98–100° C. $^1$H NMR (300 Hz, $CD_3OD$) δ 4.83 (s, 2H, CH), 1.54 (s, 6H, $CH_3$).

Preparation of Weinreb Amide: Synthesis of LIVb

To a solution of 30 g (157.8 mmol) of LIVa in 1 L of methylene chloride was added 60 g (370.0 mmol) of 1,1'-carbonyldiimidazole. After stirring 6 h, 34.0 g (350 mmol) of N,O-dimethylhydroxylamine hydrochloride was added and the resulting solution was stirred overnight. The solvent was partially removed under reduced pressure and the residue was diluted with ethyl acetate, The solution was then acidified with 4N HCl, saturated with NaCl, and extracted with EtOAc. The combined organic layers were washed with brine and dried over $MgSO_4$. The solvent was removed under reduced pressure and the residue was triturated with ethyl acetate and hexanes to give 35.6 g (82%) of the bis-Weinreb amide LIVb as a tan solid. mp. 78–80° C. $^1$H NMR (300 Hz, $CDCl_3$): δ 5.16 (s, 2H, CH), 3.70 (s, 6H, $OCH_3$), 3.22 (s, 6H, $CH_3$), 1.52 (s, 6H, $CH_3$); MS (CI, $NH_3$) m/e 277 (M+1).

Addition of Grignard Reagent: Synthesis of Diketone LIVc

To a solution of 4.0 g (14.5 mmol) of the LIVb in 100 mL of THF was added 20 mL (40 mmol) of 2M octylmagnesium bromide in THF dropwise. After stirring 3.5 h, the solution was quenched with saturated $NH_4Cl$, acidified with 1N HCl, and was extracted with EtOAc. The combined organic layers were washed with brine and dried over $MgSO_4$. The solvent was removed under reduced pressure and the residue was chromatographed on silica gel. Elution with 7.5% ethyl acetate in hexanes gave 4.86 g (88%) of the bis-octyl ketone LIVc as an oil. $^1$H NMR (300 Hz, $CDCl_3$): δ 4.55 (s, 2H, CH), 2.64 (dt, 4H, $CH_2$), 1.62 (m, 4H, $CH_2$), 1.42 (s, 6H, $CH_3$), 1.27 (broad s, 20H, $CH_2$), 0.88 (t, 6H, $CH_3$); MS (CI, $NH_3$) m/e 383 (M+1).

Oxime Formation: Synthesis of LIVd

To a solution of 4.65 g (12.2 mmol) of LIVc in 140 mL of ethanol and 35 ml of water was added 2.22 g (32.2 mmol) of hydroxylamine hydrochloride. After stirring overnight the solvent was partially removed under reduced pressure and the residue was diluted with water and extracted with EtOAc. The combined organic layers were washed with brine and dried over $MgSO_4$. The solvent was removed under reduced pressure and the residue was chromatographed on silica gel. Elution with 15% ethyl acetate in hexanes gave 3.76 g (75%) of the bis-octyl oxime LIVd as a mix of isomers. MS (CI, $NH_3$) m/e 413 (M+1).

Reduction of Oxime: Synthesis of Diamine LIVe

To a solution of 3.68 g (8.9 mmol) of LIVd in 70 mL of toluene at 0° C. was added 53 mL (80 mmol) of 1.5M diisobutylaluminum hydride in toluene over 15 min. and the solution was allowed to warm to room temperature. After stirring overnight the solution was quenched with saturated Rochelle's salt and gently stirred at room temperature. After stirring overnight the solution was extracted with EtOAc and dried over $MgSO_4$. The solvent was removed under reduced pressure and the residue was chromatographed on silica gel. Elution with 10% methanol in methylene chloride gave 2.33 g (68%) of the diamine LIVe as an oil. $^1$H NMR (300 Hz, $CDCl_3$): δ 3.80 (s, 2H, CH), 2.68 (m, 2H, CH), 1.43 (m, 4H, $CH_2$), 1.41 (s, 6H, $CH_3$), 1.27 (broad s, 24H, $CH_2$), 0.88 (t, 6H, $CH_3$).

Cyclization of the Diamine: Formation of Cyclic Urea (XXVIf):

To a solution of 1.35 g (3.5 mmol) of LIVe in 50 mL of 1,1,2,2-tetrachloroethane was added 620 mg (3.8 mmol) of 1,1'-carbonyldiimidazole. After stirring 10 min the solution was added dropwise over 30 min to 150 mL of refluxing 1,1,2,2-tetrachloroethane. The solution was cooled and was washed with dilute HCl, water, brine, and was dried over $MgSO_4$ The solvent was removed under reduced pressure and the residue was chromatographed on silica gel. Elution with 33% ethyl acetate in hexanes increasing to 50% ethyl acetate in hexanes gave 379 mg (27%) of the cyclic urea XXVIf. $^1$H NMR (300 Hz, $CDCl_3$) δ 5.24 (d, 2H, NH), 4.07 (s, 2H, CH), 3.33 (m, 2H, CH), 1.60 (m, 4H, $CH_2$), 1.43 (s, 6H, $CH_3$), 1.26 (broad s, 24H, $CH_2$), 0.88 (t, 6H, $CH_3$); MS (CI, $NH_3$) m/e 411 (M+1).

EXAMPLE 15AJ

Alkylation of the cyclic urea XXVIf and removal of the acetonide protecting group was carried out using the procedures described above to give compound 15AJ in a 68% yield. mp. 66–70° C. $^1$H NMR (300 Hz, CDCl$_3$): δ 7.32 (m, 10H, aromatic), 5.15 (d, 2H, CH$_2$), 3.87 (d, 2H, CH$_2$), 3.46 (s, 2H, CH), 3.26 (br d, 2H, CH), 1.96 (s, 2H, OH), 1.60 (m, 4H, CH$_2$), 1.26 (m, 24H, CH$_2$), 0.89 (t, 6H, CH$_3$); MS (CI, NH$_3$) m/e 551 (M+1).

TABLE 2e

| Ex. No. | Stereo 2:3:4:5 | R$^{22}$ | R$^{23}$ | R$^4$ = R$^7$ | K$_i$ HPLC | Note |
|---|---|---|---|---|---|---|
| 16A | RSSR | benzyl | benzyl | phenethyl | ++ | 1 |
| 16B | RSSR | allyl | allyl | phenethyl | + | 1 |
| 16C | RSSR | allyl | allyl | isopropyl | ++ | 2 |
| 16D | RSSR | cyclopropyl methyl | cyclopropyl methyl | isopropyl | ++ | 2 |
| 16E | RSSR | allyl | allyl | methyl | + | 2 |
| 16F | RSSR | allyl | n-butyl | methyl | + | 2 |
| 16G | RSSR | benzyl | benzyl | methyl | + | 2 |
| 16H | RSSR | 2-naphthyl-methyl | 2-naphthyl-methyl | methyl | + | 2 |
| 16I | RSSR | allyl | allyl | isobutyl | +++ | 2 |
| 16J | RSSR | cyclopropyl methyl | cyclopropyl methyl | isobutyl | +++ | 2 |
| 16K | RSSR | benzyl | benzyl | 2-naphthyl methyl | +++ | 1 |
| 16L | RSSR | cyclopropyl methyl | cyclopropyl methyl | 2-naphthyl methyl | +++ | 1 |
| 16M | RSSR | 3-cyanobenzyl | 3-cyanobenzyl | 2-naphthyl methyl | | 1 |
| 16N | RSSR | 3,4-dihydroxy benzyl | 3,4-dihydroxy benzyl | 2-naphthyl methyl | | 1 |
| 16O | RSSR | cyclopropyl methyl | cyclopropyl methyl | 2-thienyl methyl | +++ | 2 |
| 16P | RSSR | 3-(H$_2$NC(=NOH))-benzyl | 3-(H$_2$NC(=NOH))-benzyl | 2-thienyl methyl | +++ | 2 |
| 16Q | RSSR | benzyl | benzyl | 4-methylthio benzyl | +++ | 1 |
| 16R | RSSR | 3-methoxybenzyl | 3-methoxybenzyl | 2-methoxy benzyl | ++ | 1 |
| 16S | RSSR | cyclopropyl methyl | cyclopropyl methyl | 2-methoxy benzyl | ++ | 1 |
| 16T | RSSR | benzyl | benzyl | 2-methoxy benzyl | ++ | 1 |
| 16U | RSSR | benzyl | benzyl | 4-methylsulfo nylbenzyl | | 1 |
| 16V | RSSR | benzyl | benzyl | 3-aminobenzyl | | 1 |
| 16W | RSSR | benzyl | benzyl | 4-aminobenzyl | | 1 |
| 16X | RSSR | n-hexyl | n-hexyl | isopropyl | +++ | 2 |
| 16Y | RSSR | benzyl | benzyl | 3-indolylmethyl | ++ | 2 |
| 16Z | RSSR | benzyl | benzyl | isobutyl | ++ | 2 |
| 16AA | RSSR | benzyl | benzyl | 2-methylthio ethyl | + | 2 |
| 16AB | RSSR | cyclopropyl methyl | cyclopropyl methyl | 2-methylthio ethyl | + | 2 |
| 16AC | RSSR | benzyl | benzyl | 1-benzyl-3-indolyl | ++ | 2 |
| 16AD | RSSR | benzyl | benzyl | isobutyl | +++ | 2 |
| 16AE | RSSR | n-butyl | n-butyl | isobutyl | ++ | 2 |
| 16AF | RSSR | 4-hydroxymethyl benzyl | 4-hydroxymethyl benzyl | 2-methylthio ethyl | + | 2 |
| 16AG | RSSR | benzyl | benzyl | n-butyl | + | 3 |
| 16AH | RSSR | benzyl | benzyl | n-pentyl | ++ | 3 |

TABLE 2e-continued

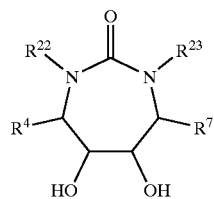

| Ex. No. | Stereo 2:3:4:5 | R²² | R²³ | R⁴ = R⁷ | $K_i$ HPLC | Note |
|---|---|---|---|---|---|---|
| 16AI | RSSR | benzyl | benzyl | n-hexyl | ++ | 3 |
| 16AJ | RSSR | benzyl | benzyl | n-octyl | + | 3 |
| 16AK | RSSR | benzyl | benzyl | 3-butenyl | + | 3 |
| 16AL | RSSR | benzyl | benzyl | 4-pentenyl | + | 3 |
| 16AM | RSSR | benzyl | benzyl | 2-ethylbutyl | ++ | 3 |
| 16AN | RSSR | benzyl | benzyl | 5-hydroxy pentyl | + | 3,4 |
| 16AO | RSSR | benzyl | benzyl | 4-hydroxy butyl | + | 3,4 |
| 16AP | RSSR | allyl | allyl | n-octyl | ++ | 3 |
| 16AQ | RSSR | allyl | allyl | n-hexyl | + | 3 |
| 16AR | RSSR | allyl | allyl | 4-pentenyl | + | 3 |
| 16AS | RSSR | allyl | allyl | 3-butenyl | + | 3 |
| 16AT | RSSR | 4-hydroxymethyl benzyl | 4-hydroxymethyl benzyl | n-butyl | ++ | 3 |

Note 1: Prepared as in Scheme 4.
Note 2: Prepared as compounds in Table 1A.
Note 3: Prepared as in Scheme 28.
Note 4: Prepared by hydroboration of the corresponding alkene.

Listed below are physical data for representative compounds of the invention.

Example 16A: MS: 535 (M+1, 100%); NMR (CDCl₃, 300 Hz): δ 7.1–7.3 (m, 20H), 5.15 (d, 2H), 3.9 (d, 2H), 3.5 (bs, 2H), 3.3–3.4 (m, 2H), 2.7–2.8 (m, 2H), 2.5–2.6 (m, 2H), 2.0–2.1 (m, 6H).

Example 16B: MS: 435 (M+1, 100%); NMR (CDCl₃, 300 Hz): δ 7.1–7.3 (m, 10H), 5.8 (m, 2H), 5.15 (s, 2H), 5.1 (d, 2H), 4.5–4.6 (m, 2H), 3.8 (s, 2H), 3.3–3.5 (m, 4H), 2.5–2.9 (m, 4H), 2.2 (m, 2H), 2.0 (m, 4H).

Example 16C: MS: 312 (22, M+2), 311 (100, M+1), 267 (1). HRMS: Calc. 311.2334. Found: 311.2330. NMR (CDCl₃): δ 5.81 (m, 2H), 5.2 (m, 4H), 4.4 (m, 2H), 4.0 (br s, 2H), 3.4 (m, 2H), 3.1 (br s, 2H), 3.0 (m, 2H), 2.4 (m, 2H), 1.2 (d, 6H), 0.9 (d, 6H).

Example 16D: MS: 341 (4), 340 (25), 339 (100, M+1), 321 (1), 295 (2), 256 (2). HRMS: Calc. 339.2647. Found: 339.2652. NMR (CDCl₃): δ 4.2 (brs, 2H), 3.65 (m, 2H), 3.20 (m, 4H), 2.6 (m, 4H), 1.2 (d, 6H), 1.0 (m, 2H), 0.9 (d, 6H), 0.5 (m, 4H), 0.2 (m, 4H).

Example 16E: MS: 256 (15, M+2), 255 (100, M+1). HRMS: Calc. 255.1706. Found: 255.1708. NMR (CDCl₃) δ 5.8 (m, 2H), 5.2 (m, 4H), 4.0 (m, 2H), 3.8 (br s, 2H), 3.65 (m, 2H), 3.4 (m, 2H), 2.8 (m, 2H), 1.2 (d, 6H).

Example 16F: MS: 272 (16, M+2), 271 (100, M+1). HRMS: Calc. 271.2021. Found: 271.2036. NMR (CDCl₃): δ 5.8 (m, 1H), 5.2 (m, 2H), 4.0 (m, 2H), 3.8 (br s, 2H), 3.6–3.3 (3H), 3.0 (m, 2H), 2.45 (m, 2H), 1.35 (m, 2H), 1.2 (d, 6H), 0.9 (m, 4H).

Example 16G: MS: 356 (23, M+2), 355 (100, M+1). HRMS: Calc. 355.2021. Found: 355.2012. NMR (CDCl₃): δ 7.4–7.2 (m, 10H), 4.9 (d, 2H), 4.2 (d, 2H), 3.6 (br s, 2H), 3.3 (m, 2H), 2.2 (m, 2H), 1.2 (d, 6H).

Example 16H: mp 236–238° C. MS: 456 (29, M+2), 455 (100, M+1), 315 (10), 158 (5). HRMS: 455.2334. Found: 455.2333. NMR (CDCl₃): δ 7.9–7.8 (m, 8H), 7.6–7.45 (m, 6H), 5.0 (d, 2H), 4.4 (m, 2H), 3.6 (br s, 2H), 3.4 (m, 2H), 1.9 (m, 2H), 1.2 (m, 2H).

Example 16I: MS 339 (100, M+1), 311 (4). HRMS 339.265377 (calc. mass=339.264768). NMR (CDCl₃): δ 5.91–5.79 (m), 5.29–5.18 (m, 4H), 4.53–4.46 (m, 2H), 3.76 (s, 2H), 3.41–3.33 (m, 4H), 2.13 (s, 2H), 1.81–1.71 (m, 2H), 1.71–1.62 (m, 2H), 1.45–1.35 (m, 2H), 0.90 (t, 12H).

Example 16J: m.p. 137–139° C. MS 367 (100, M+1). HRMS 367.295357 (calc. mass=367.296068). NMR (CDCl₃): δ 3.94 (s, 2H), 3.82 (d, 2H), 3.77 (d, 2H), 3.48 (d, 2H), 2.91 (bs, 2H), 2.63 (d, 2H), 2.61 (d, 2H), 1.99 (m, 2H), 1.70–1.61 (m, 2H), 1.43 (m, 2H), 1.26 (s, 2H), 1.07–0.98 (m, 2H), 0.91 (t, 12H), 0.52 (m, 2H), 0.22 (m, 2H).

Example 16Q: mp 214° C.
Example 16R: mp 192–193° C.
Example 16S: mp 155–156° C.
Example 16T: mp 194–195° C.
Example 16U: mp 244° C.
Example 16X: mp 112–113° C. MS 427 (100, M+1)
Example 16Y: MS: 585.2 (100, M+H). NMR (CDCl₃) δ 8.02 (s, 2H), 7.55 (d, 2H), 7.4 (d, 2H), 7.01 (m, 4H), 6.79 (s, 2H), 4.84 (d, 2H), 3.78 (s, 4H), 3.2 (m, 6H).

Example 16Z: MS: 475.2 (100, M+H). NMR (CDCl₃) δ 7.48–7.22 (m, 10H), 4.76–4.4 (dd, 4H), 3.8 (s, 2H), 3.62 (m, 2H), 2.23 (s, 2H), 1.73 (m, 2H), 1.59 (m, 4H), 1.36 (m, 4H), 0.76 (d, 6H), 0.61 (d, 6H)

Example 16AA: MS: 475.0 (100, M+H). NMR (CDCl₃) δ 7.41–7.18 (m, 10H), 5.01 (d, 2H), 4.01 (d, 2H), 3.65–3.41 (m, 5H), 3.01 (dd, 1H), 2.6–2.3 (m, 6H), 2.0 (m, 6H), 1.25 (m, 2H).

Example 16AB: MS: 403.2 (100, M+H). NMR (CDCl₃): δ 3.97 (s, 2H), 3.8–3.6 (m, 4H), 2.8–2.4 (m, 8H), 2.24 (m, 2H), 1.62 (s, 2H), 1.03 (m, 2H), 0.52 (m, 4H), 0.32–0.14 (m, 4H).

Example 16AC: MS: 765.5 (59, M+H) 382.1 (100), 274 (97). NMR (CDCl$_3$) δ 7.53 (d, 2H), 7.35–7.0 (m, 26H), 6.63 (s, 2H), 5.24 (s, 2H), 5.23 (s, 2H), 4.82 (d, 2H), 3.8 (s, 4H), 3.3–3.08 (m, 6H), 2.37 (s, 2H).

Example 16AD: MS: 439.2 (M+H) NMR (CDCl$_3$): δ 7.39–7.28 (m, 10H), 5.19 (d, 4H), 3.85 (d, 4H), 3.50 (s, 2H), 3.38 (d, 2H), 1.95 (s, 2H), 1.75 (m, 4H), 1.38 (m, 2H), 0.92 (d, 6H), 0.85 (d, 6H).

Example 16AD: MS: 439.2 (M+H). NMR (CDCl$_3$): δ 7.39–7.28 (m, 10H), 5.19 (d, 4H), 3.85 (d, 4H), 3.50 (s, 2H), 3.38 (d, 2H), 1.95 (s, 2H), 1.75 (m, 4H), 1.38 (m, 2H), 0.92 (d, 6H), 0.85 (d, 6H). MS: (M+H)+=439.2.

Example 16AE: MS: 371 (M+H). NMR (CDCl$_3$): δ 4.0 (m, 2H), 3.85 (s, 2H), 3.35 (d, 2H), 2.65 (m, 2H), 2.35 (s, 2H), 1.82 (m, 2H), 1.75–1.24 (m, 12H), 0.91 (m, 18H).

Example 16AF: MS: 552 (100, M+NH$_4$), 535 (61, M+H), 516 (81). NMR (CDCl$_3$): δ 7.38 (d, 8H), 5.05 (d, 2H), 4.68 (s, 4H), 3.98 (d, 2H), 3.65 (s, 2H), 3.52 (m, 2H), 3.43 (s, 2H), 2.57 (m, 2H), 2.42 (m, 2H), 2.03 (s, 6H), 1.97 (m, 4H), 0.84 (m, 4H).

Example 16AG: mp 109–114° C. MS m/e 439 (M+H).
Example 16AH: mp 94–97° C. MS m/e 467 (M+H).
Example 16AI: mp 79–82° C. MS m/e 495 (M+H).
Example 16AJ: mp 66–70° C. MS m/e 551 (M+H).
Example 16AK: mp 123–126° C. MS m/e 435 (M+H).
Example 16AL: MS m/e 463 (M+H).
Example 16AM: mp 91–94° C. MS m/e 495 (M+H).
Example 16AN: mp 111–116° C. MS m/e 499 (M+H).
Example 16AO: MS m/e 483 (M+H).
Example 16AP: mp 73–74° C. MS m/e 451 (M+H).
Example 16AQ: mp 73–75° C. MS m/e 395 (M+H).
Example 16AR: mp 108–111° C. MS m/e 363 (M+H).
Example 16AS: mp 110–114° C. MS m/e 335 (M+H).
Example 16AT: mp 114–116° C. MS m/e 499 (M+H).

The structures of the Examples below are shown in Table 2f–h.

Synthesis of Thiourea (XXVIIa):

Diaminodimem Compound (XXIc) (22.45 g, 47.1 mmol) was dissolved in 200 mL of tetrahydrofuran and to this solution was added 9.23 g (51.8 mmol) of thiocarbonyl diimidazole. After stirring the mixture for 18 hours at room temperature TLC (10:1:10 ethyl acetate:ethanol:hexane) indicated complete reaction. The reaction mixture was taken to dryness and the solid residue purified by flash chrmatography (silica gel, 250 g, 1:1 ethyl acetate: hexane) to provide solid which was triturated with hexane to provide 17.8 g (73% yield) of XXVIIa as a white solid.

Synthesis of Compound (XXVIIb):

Compound (XXVIIa) (3.108 g, 6 mmol) was dissolved in 15 ml acetonitrile and to this solution was added methyl iodide 1.5 ml (24 mmol) via syringe and stirred at room temperature for one hour. The contents were then taken to dryness. The residue was dissolved in 30 ml dimethylformamide and to this solution, cooled in a 0° C. ice bath, was added NaH (60% in oil) 720 mg (18 mmol) slowly (EVOLUTION!). The contents were stirred at room temperature for 30 minutes. The mixture was cooled in a 0° C. ice bath and benzyl bromide (2.052 g, 12 mmol) was added via syringe and stirred at room temperature for 18 hours. TLC (2:3 EtOAc:Hexane R$_f$=0.25) indicated a complete reaction. The reaction was worked up by diluting with water (300 ml) and extracting with diethyl ether (3×50 ml). The organic layer was dried over magnesium sulfate and the filtrate taken to dryness. The residue was purified on SiO$_2$ gel (200 g; 2:3 EtOAc:Hexane) to provide 2.923 g (78.2% yield) of XXVIIb as a colorless oil.

Synthesis of Compounds (XXVIIc) and (XXVIId):

Compound (XXVIIb) (2.900 g, 4.65 mmol) was dissolved in 25 ml pyridine and to this solution was added 742 mg (4.65 mmol) benzylhydroxylamine hydrochloride. The contents were refluxed in a 125° C. oil bath for 18 hours. (Caution: Methyl mercaptan is a by-product and the reaction should be vented to a Clorox scrubber). TLC indicated a complete reaction. The reaction was diluted with 150 ml dichloromethane. The organic layer was washed with 1N HCl (2×300 ml) followed by sat. sodium bicarbonate solution (100 ml). It was separated and dried over magnesium sulfate and the filtrate taken to dryness. The residue was purified on SiO$_2$ gel (130 g; using 1:3 EtOAc:Hexane) to provide 584 mg (18.0% yield) of Compound (XXVIIc) as a colorless oil. 1:2 EtOAc:Hexane was used to provide 2.113 g of a side product thiourea (XXVIId).

Synthesis of Oxime (XXVIIe):

Compound (XXVIIc) (584 mg, 0.84 mmmol) was dissolved in 5 ml dimethylformamide and to this solution, cooled in a 0° C. ice bath, was added NaH (60% in oil) 80 mg (2 mmol) slowly (EVOLUTION!) The contents were stirred at room temperature for 30 minutes. The mixture was cooled in a 0° C. ice bath and benzyl bromide (0.24 ml, 2 mmol) was added via syringe and stirred at room temperature for 18 hours. TLC (1:3 EtOAc:Hexane R$_f$=0.26) indicated a complete reaction. The reaction was worked up by diluting with water (50 ml) and extracting with diethyl ether (2×25 ml). The organic layer was dried over magnesium sulfate and the filtrate taken to dryness. The residue was purified on SiO$_2$ gel (33 g; 1:3 EtOAc:Hexane) to provide 491 mg (74.2% yield) of a colorless oil.

EXAMPLE 18A

Compound (XXVIId) (450 mg, 0.57 mmol) was placed in a 25 ml R.B. Flask and cooled in a 0° C. ice bath. To this flask was added 4M HCl in dioxane (5 ml, 20 mmol) and the mixture stirred at room temperature for 18 hours. TLC (2:3 EtOAc:Hexane Rf=0.29) indicated a complete reaction. The mixture was worked up by quenching in sat.sodium bicarbonate solution (50 ml) and extracting with dichloromethane (2×50 ml). The organic extracts were dried over magnesium sulfate and the filtrate taken to dryness. The residue was purified on SiO$_2$ gel(33 g; 2:3 EtOAc:Hexane) to provide 246 mg (70.5% yield) of Example 18A as a waxy solid.

EXAMPLE 17A

Example 18A (160 mg, 0.26 mmol) was dissolved in 5 ml ethanol. To this mixture was added 50 mg of 10% palladium hydroxide on Carbon and the suspension stirred for 18 hours under hydrogen (1 atm). TLC (10:1:10 EtOAc:EtOH: Hexane R$_f$=0.3) indicated a complete reaction. The suspension was filtered through a celite pad and the filtrate taken to dryness. The residue was purified on SiO$_2$ gel (33 g; 10:1:10 EtOAc:EtOH:Hexane) to provide 97 mg of Example 17A (69.5% yield) as a white solid.

EXAMPLE 19A

Compound (XXVIId) (500 mg, 0.82 mmol) was placed in a 25 ml R.B. Flask and cooled in a 0° C. ice bath. To this flask was added 4M HCl in dioxane (7.5 ml, 30 mmol) and the mixture stirred at room temperature for 18 hours. TLC (1:2 EtOAc:Hexane R$_f$=0.29) indicated a complete reaction. The mixture was worked up by quenching in sat.sodium bicarbonate solution (50 ml) and extracting with dichloromethane (2×50 ml). The organic extracts were dried over magnesium sulfate and the filtrate taken to dryness. The residue was purified on $SiO_2$ gel (33 g; 1:2 EtOAc:Hexane) to provide 181 mg (51.1% yield) of Example 19A as a white solid.

TABLE 2f

| Ex. No. | R | HPLC Ki | $IC_{90}$ | m. p. °C. | MS M + H |
|---|---|---|---|---|---|
| 17A | $CH_2C_6H_5$ | ++ | | 120.1 | 522.275 |

TABLE 2g

| Ex. No. | R | HPLC Ki | $IC_{90}$ | m. p. °C. | MS M + H |
|---|---|---|---|---|---|
| 18A | $CH_2C_6H_5$ | + | | 59.5 | 612.322 |

TABLE 2h

| Ex. No. | R | HPLC Ki | $IC_{90}$ | m. p. °C. | MS M + H |
|---|---|---|---|---|---|
| 19A | $CH_2Ph$ | +++ | +++ | 74.0 | |

The structures of the Examples below are shown in Table 2i.

Acetylation of Diol: Compound (XXVIIIa):

Example 1X (3.517 g, 7.58 mmol) was dissolved in 25 ml pyridine and to this solution, cooled in a 0° C. ice bath, was added 350 mg 4-Dimethylaminopyridine and 7.16 ml (75.85 mmol) acetic anhydride. The contents were stirred at room temperature for 18 hours. TLC (1:4 EtOAc:Hexane $R_f$=0.3) indicated a complete reaction. The reaction was diluted with 250 ml dichloromethane. The organic layer was washed with 1N HCl (2×300 ml) followed by sat. sodium bicarbonate solution (100 ml). It was separated and dried over magnesium sulfate and the filtrate taken to dryness. The residue was purified on $SiO_2$ gel (200 g; 1:5 EtOAc:Hexane) to provide 2.632 g (67.0%) of XXVIIIa as a white solid.

Nitration of Benzyl Group: Compound (XXVIIIb) and (XXVIIIc):

Compound (XXVIIIa) (518 mg, 1 mmol) was dissolved in 4 ml acetonitrile and to this solution, cooled in a −40° C. dry ice-acetone bath, was added 4.4 ml (2.2 mmol) 0.5M Nitronium tetrafluoroborate in sulfolane. The contents were stored in a −40° C. freezer for 18 hours. TLC indicated a complete reaction. The reaction was diluted with 100 ml ether and washed with water (2×50 ml). The organic layer was dried over magnesium sulfate and the filtrate taken to dryness. The residue was purified on $SiO_2$ gel (75 g; 1:3 EtOAC:Hexane for XXVIIIb, 1:2 EtOAc:Hexane for XXVIIIc) to provide 106 mg (17.4% yield) of XXVIIIb as a white solid and 159 mg (26.2% yield) of XXVIIIc as a white solid.

EXAMPLE 20A

Compound (XXVIIIb) (106 mg, 0.174 mmol) was dissolved in 5 ml methanol and to this solution was added 0.5 ml 0.5M sodium methoxide in methanol via syringe. The contents were stirred at room temperature for 30 minutes. TLC indicated a complete reaction. The mixture was quenched by adding 500 mg of AG50W-X8 acid resin and stirring the suspension at room temperature for 5 minutes. The filtrate was taken to dryness and the residue purified on $SiO_2$ gel (33 g; 1:2 EtOAc:Hexane) to provide 43 mg (47.1% yield) of Example 20A as a white solid.

EXAMPLE 20B

Compound (XXVIIIc) (159 mg, 0.261 mmol) was dissolved in 5 ml methanol and to this solution was added 0.5 ml 0.5M sodium methoxide in methanol via syringe. The contents were stirred at room temperature for 30 minutes. A white precipitate started forming after 15 minutes. TLC indicated a complete reaction. The mixture was quenched by adding 500 mg of AG50W-X8 acid resin and stirring the suspension at room temperature for 5 minutes. 10 ml dichloromethane was then added to solubilize the solid. The filtrate was taken to dryness and the residue provided 111mg (81.1% yield) of Example 20B as a white solid.

EXAMPLE 20E

Example 20A (100 mg, 0.191 mmol) was dissolved in 5 ml ethanol. To this mixture was added 50 mg of 5% palladium on Carbon and the suspension stirred for 18 hours under hydrogen (1 atm). TLC indicated a complete reaction. The suspension was filtered through a celite pad and the filtrate taken to dryness. The residue provided 47 mg (53.0% yield) of Example 20E as a white solid.

EXAMPLE 20F

Example 20B (100 mg, 0.191 mmol) was suspended in 5 ml ethanol. To this mixture was added 50 mg of 5% palladium on Carbon and the suspension stirred for 18 hours under hydrogen (1 atm). The starting material went into solution as the reaction progressed. TLC indicated a complete reaction. The suspension was filtered through a celite pad and the filtrate taken to dryness. The residue provided 49 mg (55.2% yield) of example 20F as a white solid.

EXAMPLE 20G

A. Synthesis of 4-Fluorobenzyl Cyclic Urea (XXXI)

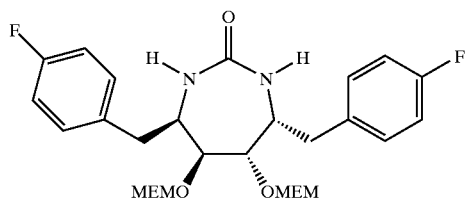

(XXXI)

The synthesis of 4-fluorobenzyl cyclic urea is outlined in Scheme 7. N-acetyl-D-4-fluorophenylalanine methyl ester (23.9 g, 0.1 mol), obtained using the procedure of M. J. Burk (J. Am. Chem. Soc. 1991, 113, 8518), was dissolved in 40 mL of acetic acid and treated with 100 mL of concentrated HCl, 40 mL of water and heated to reflux for 5 hrs. The solution was cooled to room temperature and then made basic (pH=10) with 50% NaOH while cooling in an ice bath. Benzyl chloroformate (25 mL, 29 g, 0.17 mol) and NaOH are added in four portions and the solution is maintained alkaline by the addition of NaOH. The mixture is then stirred at rt for 30 min. The alkaline solution is extracted with ether (2×500 mL) and the solution acidified with conc HCl to pH 1. The precipitate is extracted into methylene chloride and dried over $MgSO_4$. The solution is filtered and concentrated to give 20 g of the N-Cbz-D-4-fluorophenylalanine as a white solid that is used without further purification.

A solution of N,O-dimethylhydroxylamine hydrochloride (8.0 g, 0.082 mol) in DMF is prepared by gentle warming. The solution is allowed to cool slightly and treated with N-methylmorpholine (8.2 g, 0.082 mol) and diluted with THF to facilitate transfering of the resulting thick suspension.

A solution of N-Cbz-D-4-fluorophenylalanine (20 g, 0.063 mol) in THF is treated with N-methylmorpholine (9.0 g 0.09 mol) and cooled to 0° C. in an ice bath. To the stirred cold solution is added isobutyl chloroformate (8.6 g, 0.063 mol) in small portions over a period of 10 mins. Then the solution of N,O-dimethylhydroxylamine in DMF prepared above is added and the reaction mixture is stirred for 20 mins. Most of the solvent is removed on a rotorary evaporator and the residue is partitioned between water and methylene chloride. The organic layer is washed successively with 1 N HCl, 1 N NaOH, water, brine and then dried over $MgSO_4$. The solution is then filtered and concentrated and the residue chromatographed on silica gel (50% EtOAc/Hex) to give 16 g of the amide.

Using the procedure of by J-A. Fehrentz and B. Castro (Synthesis, 1983, 676) 11 g (0.031 mol) of N-Cbz-D-4-fluorophenyl-alanine N,O-dimethylhydroxylamide was converted to 9.0 g of N-Cbz-D-4-fluorophenylalaninal obtained as a thick oil that was used without further purification.

N-Cbz-D-4-fluorophenylalaninal (9.0 g , 0.031 mol) was converted, using procedure 1, to (2R,3S,4S,5R)-2.5-bis(N-Cbz-amino)-3,4-dihydroxy-1,6-di(4-fluorophenyl)hexane (4 g) obtained as a white solid. MS: (CI, $NH_3$) $(M+H)^+=605$.

The (2R,3S,4S,5R)-2,5-bis(N-Cbz-amino)-3,4-dihydroxy-1,6-di(4-fluorophenyl)hexane (4.0 g, 0.0066 mol) was converted, as described in procedure 4, to 1.3 g of the 4-fluorobenzyl cyclic urea (XXXI) obtained as a white solid. MS: (CI, $NH_3$) $(M+H)^+=539.3$ B. The 4-fluorobenzyl cyclic urea (XXXI) (270 mg, 0.5 mmol) was alkylated with 3-benzoxybenzyl chloride (350 mg, 1.5 mmol) according to general procedure 5. The resulting intermediate was dissolved in THF and hydrogenated for 12 hours (200 mg 10% Pd/C, 55 psi) to remove the benzyl protecting groups. The MEM group was then removed, according to general procedure 5, to give, after chromatography on HPLC (silica gel, 10% $MeOH/CHCl_3$), 140 mg of Example 20G as a white foam. MS: (CI, $NH_3$) $(M+H)^+=575.2$ (100%).

EXAMPLE 20W

By variation of the above-described methods, the title compound was prepared. NMR ($CDCl_3$): δ 7.12–7.32 (m, 12H) 6.61–6.83 (m, 6H) 4.91 (d, 2H) 3.80 (s, 6H) 3.64 (m, 2H) 3.55 (m, 2H) 3.10 (d, 2H) 3.00 (m, 4H) 2.11 (s, 2H).

TABLE 2i

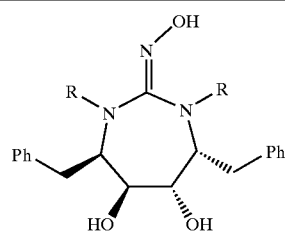

| Ex. No. | $R^{22},R^{23}$ | $R^4$ | $R^7$ | HPLC Ki | $IC_{90}$ | m. p. ° C. | Mass Spec M + H (M + $NH_4$) |
|---|---|---|---|---|---|---|---|
| 20A | cyclopropyl-methyl | 4-nitro-benzyl | 2-nitro-benzyl | +++ | +++ | 209.8 | 525.234 |
| 20B | cyclopropyl-methyl | 4-nitro-benzyl | 4-nitro-benzyl | +++ | +++ | 227.5 | 525.234 |
| 20C | n-butyl | 4-nitro-benzyl | 2-nitro-benzyl | +++ | +++ | 165.0 | 529.266 |
| 20D | n-butyl | 4-nitro-benzyl | 4-nitro-benzyl | | | 245.0 (dec) | 529.266 |

TABLE 2i-continued

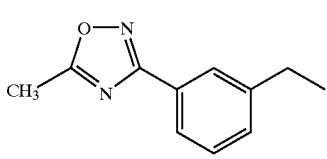

| Ex. No. | $R^{22}, R^{23}$ | $R^4$ | $R^7$ | HPLC Ki | $IC_{90}$ | m. p. °C. | Mass Spec M + H (M + NH$_4$) |
|---|---|---|---|---|---|---|---|
| 20E | cyclopropyl-methyl | 4-amino-benzyl | 2-amino-benzyl | +++ | +++ | | 465.286 |
| 20F | cyclopropyl-methyl | 4-amino-benzyl | 4-amino-benzyl | ++ | +++ | | 465.286 |
| 20G | 3-hydroxy benzyl | 4-fluoro benzyl | 4-fluoro benzyl | +++ | | | 575.2 |
| 20H | cyclopropyl-methyl | 4-fluoro benzyl | 4-fluoro benzyl | +++ | | | 471.2 |
| 20I | 4-hydroxy methylbenzyl | 4-fluoro benzyl | 4-fluoro benzyl | +++ | | | 603.2 |
| 20J | 4-acetyl benzyl | benzyl | benzyl | ++ | | | (608) |
| 20K | 4-fluoro methylbenzyl | benzyl | benzyl | +++ | +++ | | 571 |
| 20L | 3-(H$_2$NC(O))-benzyl | 4-fluoro benzyl | 4-fluoro benzyl | +++ | +++ | | (646.4) |
| 20M | 4-(CH$_3$CH(OH))-benzyl | benzyl | benzyl | +++ | +++ | | 595.2 |
| 20N | 3-(CH$_3$C(O))-benzyl | 4-fluoro benzyl | 4-fluoro benzyl | +++ | +++ | | (644.4) |
| 20O | 3-cyano-benzyl | 4-fluoro benzyl | 4-fluoro benzyl | ++ | +++ | | (610.2) |
| 20P | 3-(CH$_3$CH$_2$CH$_2$—C(O))-benzyl | 4-fluoro benzyl | 4-fluoro benzyl | +++ | +++ | | (700.5) |
| 20Q | 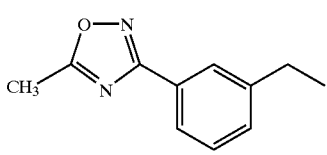 | benzyl | benzyl | +++ | +++ | | 671.4 |
| 20R | 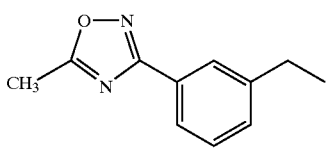 | benzyl | benzyl | ++ | +++ | | 779.4 |
| 20S | 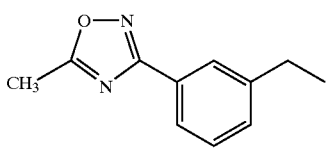 | 4-fluoro benzyl | 4-fluoro benzyl | ++ | ++ | | 815.5 |
| 20T | 3-(HOCH2)-benzyl | 4-fluoro benzyl | 4-fluoro benzyl | +++ | +++ | | 603.3 |
| 20U | 3-(CH$_3$C(NOH))-benzyl | 4-fluoro benzyl | 4-fluoro benzyl | +++ | +++ | | 657.5 |
| 20V | 3-(H$_2$NC(=NOH))-benzyl | benzyl | benzyl | +++ | +++ | | 623.3 |
| 20W | benzyl | 3-methoxy-benzyl | 3-methoxy-benzyl | +++ | +++ | | |
| 20X | 3-(H$_2$NC(=NOH))-benzyl | 4-fluoro benzyl | 4-fluoro benzyl | +++ | +++ | | 659.3 |
| 20Y | 3-carbo methoxybenzyl | 3,4-difluoro benzyl | 3,4-difluoro benzyl | +++ | +++ | | 695.4 |

TABLE 2i-continued

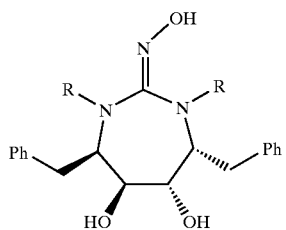

| Ex. No. | $R^{22}, R^{23}$ | $R^4$ | $R^7$ | HPLC Ki | $IC_{90}$ | m. p. °C. | Mass Spec M + H (M + NH₄) |
|---|---|---|---|---|---|---|---|
| 20Z | 4-carbomethoxybenzyl | 3,4-difluorobenzyl | 3,4-difluorobenzyl | ++ | +++ | | (712.4) |
| 20AA | 3-hydroxymethyl benzyl | 3,4-difluorobenzyl | 3,4-difluorobenzyl | +++ | +++ | | 639.4 |
| 20AB | 4-hydroxymethyl benzyl | 3,4-difluorobenzyl | 3,4-difluorobenzyl | +++ | +++ | | 639.4 |
| 20AC | 3-(H₂NC(O))-benzyl | 3,4-difluorobenzyl | 3,4-difluorobenzyl | +++ | +++ | | 665.2 |
| 20AD | 3-(H₂NC(=NOH))-benzyl | 3,4-difluorobenzyl | 3,4-difluorobenzyl | +++ | +++ | | 695. |
| 20AE | $R^{22}$ = cyclopropyl methy $R^{23}$ = 3-(3-pyrazolyl benzyl | 4-fluoro benzyl | 4-fluoro benzyl | +++ | +++ | 123–126 | 573.2 |
| 20AF | cyclopropyl methyl | 4-methoxy benzyl | 4-methoxy benzyl | +++ | | 145–147 | 495 |
| 20AG | benzyl | 4-methoxy benzyl | 4-methoxy benzyl | +++ | | | 567 |
| 20AH | 2-naphthyl methyl | 4-methoxy benzyl | 4-methoxy benzyl | +++ | | | 667 |
| 20AI | 4-carbomethoxy benzyl | 4-methoxy benzyl | 4-methoxy benzyl | + | | | 700 |
| 20AJ | 4-hydroxymethyl benzyl | 4-methoxy benzyl | 4-methoxy benzyl | +++ | | | 644 |
| 20AK | benzyl | 4-hydroxy benzyl | 4-hydroxy benzyl | +++ | | 179–180 | 539 |
| 20AL | allyl | 4-methoxy benzyl | 4-methoxy benzyl | +++ | | | 467 |
| 20AM | benzyl | 4-(2-hydroxy ethoxy) benzyl | 4-(2-hydroxy ethoxy) benzyl | +++ | | 129–131 | 627 (644) |
| 20AN | benzyl | 4-(2-morpholin ylethoxy) benzyl | 4-(2-hydroxy ethoxy) benzyl | +++ | | 101–103 | 765 |
| 20AO | H | 3-methoxy benzyl | 3-methoxy benzyl | ++ | ++ | 205.4 | 387 |
| 20AP | n-butyl | 3-hydroxy benzyl | 3-hydroxy benzyl | ++ | + | 182.1 | 541 |
| 20AQ | 3-hydroxy benzyl | 3-hydroxy benzyl | 3-hydroxy benzyl | +++ | +++ | 161.2 | 571 |
| 20AR | n-butyl | 3-(H₂NC(O)CH₂O) benzyl | 3-(H₂NC(O)CH₂O) benzyl | +++ | | 101.3 | 581 |
| 20AS | cyclopropyl methyl | 3-methoxy benzyl | 3-methoxy benzyl | +++ | +++ | | 495 |
| 20AT | 4-hydroxy methylbenzyl | 3-methoxy benzyl | 3-methoxy benzyl | +++ | +++ | | 627 |
| 20AU | 3-methoxy benzyl | 3-methoxy benzyl | 3-methoxy benzyl | +++ | +++ | | 627 |
| 20AV | cyclopropyl methyl | 3-(EtOC(O)CH₂O) | 3-(EtOC(O)CH₂O) | ++ | | | 639 |

TABLE 2i-continued

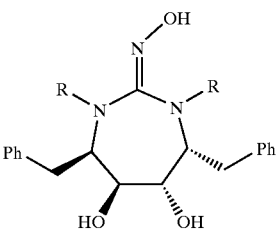

| Ex. No. | $R^{22}, R^{23}$ | $R^4$ | $R^7$ | HPLC Ki | $IC_{90}$ | m. p. °C. | Mass Spec M + H (M + NH$_4$) |
|---|---|---|---|---|---|---|---|
| | | benzyl | benzyl | | | | |

The structures of the Examples below are shown in Table 2j.

EXAMPLE 21A

A. Synthesis of Aziridine Urea (XXXIIa)

A solution of Example 1A (5.3 g, 0.016 mol) in pyridine was treated with acetic anhydride (3.3 g, 0.033 mol) and stirred at room temperature for 3 hrs. 10 mL of MeOH was added and the mixture was evaporated to dryness. The residue was extracted into methylene chloride and washed sequentially with water, 1 N HCl, brine, and dried over MgSO$_4$. The solution was filtered, concentrated and the residue chromatographed on silica gel (5% MeOH/CHCl$_3$) to give 2.0 g of the corresponding monoacetate product as a white solid. The solid obtained was dissolved in methylene chloride and cooled in an ice bath under nitrogen. To this was added DAST (0.875 g, 0.005 mol) via syringe and the solution stirred for 10 mins. The mixture was quenched with sat'd NaHCO$_3$ and the organic layer washed with water and brine. The solution is dried over MgSO$_4$ then filtered and concentrated to give 1.9 g of the acetate aziridine (XXXIIa) which is used without further purification.

B. The acetate aziridine (XXXIIa) (100 mg. 0.29 mmol) is dissolved in MeOH (2 mL) and treated with 1 N NaOH (0.5 ml) and stirred at rt for 30 min. The mixture is diluted with water (20 mL) and extracted into CH$_2$Cl$_2$. The extract is washed with water and brine, dried over MgSO$_4$ then filtered and concentrated to give 30 mg of Example 21A as a white solid. MS: (CI, NH$_3$) (M+H)$^+$=309.0.

EXAMPLES 21B AND 21C

The acetate aziridine (XXXIIa) (200 mg, 0.57 mmol) is alkylated with benzyl bromide (120 mg, 0.69 mmol) according to Procedure 5 to give a mixture of products. This was HPLC chromatographed on silica gel (50% EtOAc/Hex) to give first 50 mg of Example 21B as a white solid. MS: (CI, NH$_3$) (M+H)$^+$=309.0. This was followed by 30 mg of Example 21C, obtained as a colorless oil. MS: (CI, NH$_3$) (M+H)$^+$489.2.

TABLE 2j

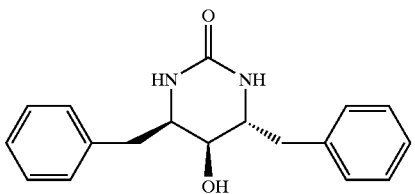

| Ex No. | $R^{22}$ | R | $K_i$ | $IC_{90}$ | MS M+H (M +NH$_4$) |
|---|---|---|---|---|---|
| 21A | H | H | + | ++/+ | 309.0 |
| 21B | benzyl | Ac | + | ++/+ | 441.0 |
| 21C | benzyl | benzyl | ++ | | 489.2 |
| 21D | benzyl | H | + | ++/+ | 399.1 |
| 21E | 3-benzyloxy benzyl | H | + | ++/+ | 505.2 |
| 21F | 3-cyanobenzyl | H | + | + | 424.2 |
| 21G | 3-(H$_2$NC(O))benzyl | H | ++ | ++ | 442.0 |
| 21H | 3-H$_2$NC(=NOH)benzyl | H | ++ | +++ | (474) |

The structures of the Examples below are shown in Table 2k.

Preparation of the Cyclic Urea (XXXIIIa):

A. Preparation of 4-Amino-2-(t-butoxycarbonylamino)-1,5-diphenyl-3-(2-methoxyethoxymethyl)pentane A mixture of 595 mg (1.50 mmole) of 4-azido-2-(t-butoxycarbonylamino-1,5-diphenyl-3-hydroxypentane (EP 0 402 646 A1), 10 ml of dioxane, 0.2 ml (1.75 mmole) of MEM chloride, and 0.32 ml (1.83 mmole) of diisopropylethylamine was heated at 80° C. for 16 hrs. Evaporated the solvent and purified the residue by flash chromatography on silica gel with 85:15 hexane-ethyl acetate to give 0.64 g (88%) of an oil. Mass spec (M+H)$^+$=485.2. This was reduced to the title compound with hydrogen using 100 mg of 10% Pd on carbon in 60 ml of ethyl acetate and 0.6 ml of acetic acid in 49% yield.

B. Preparation of 2,4-Diamino-1,5-diphenyl-3-hydroxypentane

The product from Part A (218 mg) was dissolved in 2 ml of ice cold 1:1 trifluoroacetic acid—dichloromethane. After 1 hr the solution was poured into a mixture of sodium bicarbonate solution and ethyl acetate. The ethyl acetate extract yielded 163 mg of the desired diamino compound.

C. Cyclization of the Diamine

The product from Part B (146 mg), 75 mg of carbonyl diimidazole, and 0.15 ml of diisopropylethylamine were dissolved in 2.5 ml of anydrous THF and stirred at room temperature for 16 hrs. The solvent was evaporated. The residue was purified by preparative TLC on silica gel with 90:10 dichloromethane—methanol to give 108 mg (69%) of the cyclic urea. Mass spec $(M+H)^+$=385.1.

N-Alkylation of the Cyclic Urea (XXXIIIa):

D. The product from Part C (93 mg) was dissolved in 2.5 ml of anhydrous DMF, and 100 mg of 60% NaH in mineral oil was added. The mixture was stirred for one hr. m-Benzyloxybenzyl chloride (350 mg) was added, and the mixture was stirred for 16 hrs at room temperature. Water and ethyl acetate were added. The ethyl acetate extract was washed with water, dried and evaporated. The residue was purified by prep TLC on silica gel with 60:40 hexane-ethyl acetate to give 105 mg (54%) of the desired bis-alkylated product. Mass spec $(M+H)^+$=777.5.

Deprotection of Protecting Groups (Example 22A):

The product from part δ (103 mg) was dissolved in 4N HCl/dioxane for 16 hrs. The solution was evaporated and purified by prep TLC on silica gel with 60:40 hexane-ethyl acetate. Mass spec $(M+H)^+$=689.4. The purified material was hydrogenated for 16 hrs in the presence of 3 ml ethanol. 0.2 ml of acetic acid, and 35 mg of 10% Pd on carbon to give Example 22A. Mass spec $(M+H)^+$=509.25; calculated, 509.24.

TABLE 2k

| Ex No. | $R^{22}$ | $R^{23}$ | $K_i$ | $IC_{90}$ | MS M + H |
|---|---|---|---|---|---|
| 22A | m-(HO)—C$_6$H$_4$CH$_2$— | m-(HO)—C$_6$H$_4$CH$_2$— | ++ | | 509.25 |

The structures of the Examples below are shown in Table 2m.

EXAMPLE 23F

Synthesis of Intermediate (XXXIVa): Compound XXIC (2.846 g, 5.95 mmol) was dissolved in pyridine (37.5 mL) and to this solution was added sulfamide (572 mg, 5.95 mmol). The contents were refluxed in a 125° C. oil bath for 18 hours. (Caution: Ammonia is a by-product and the reaction should be well vented). TLC (1:1 EtOAc:Hexane Rf=0.2) indicated a complete reaction. The reaction was diluted with 200 ml diethyl ether and the organic layer was washed with water (300 ml), followed by 1N HCL (2×100 ml) and sat. sodium bicarbonate solution (25 ml). The organic layer was dried over magnesium sulfate and the filtrate taken to dryness. The residue was purified on Silica gel (130 g; using 1:1 EtOAc:Hexane followed by 20:1:20 EtOAc:EtOH:Hexane) to provide 2.412 g (75.3% yield) of the desired intermediate (XXXIVa) as a white solid.

Intermediate (XXXIVa) (269 mg, 0.5 mmol) was dissolved in dimethylformamide (3 mL) and to this solution, cooled in a 0° C. ice bath, was slowly added sodium hydride (60% in oil, 80 mg, 2 mmol) (EVOLUTION!). The contents were stirred at room temperature for 30 minutes. The mixture was cooled in a 0° C. ice bath and (bromomethyl) cyclopropane (0.19 mL, 2 mmol) was added via syringe and stirred at room temperature for 18 hours. TLC (1:1 EtOAc:Hexane Rf=0.3) indicated a complete reaction. The reaction was worked up by diluting with water (50 mL) and extracting with diethyl ether (2×25 mL). The organic layer was dried over magnesium sulfate and the filtrate taken to dryness. The residue was placed in a 50 ml R.B. flask and dissolved in methanol (3 mL) and to the flask was added 4M HCl in dioxane (3 mL, 12 mmol) and the mixture stirred at room temperature for 18 hours. TLC (2:3 EtOAc:Hexane Rf=0.3) indicated a complete reaction. The mixture was worked up by quenching in sat. sodium bicarbonate (25 ml) and extracting with dichloromethane (2×25 mL). The organic extracts were dried over magnesium sulfate and the filtrate taken to dryness. The residue was purified on silica gel (55 g; 1:2 EtOAc:Hexane followed by 1:1) to provide 129 mg (54.8% yield) of the title compound as a white solid. m.p. 71–72° C.

EXAMPLE 23C

Intermediate (XXXIVa) from Example 23F (538 mg, 1.0 mmol) was dissolved in N,N-dimethylformamide (5 mL) and to this solution, cooled in a 0° C. ice bath, was slowly added sodium hydride (60% in oil, 160 mg, 4 mmol) (EVOLUTION!). The contents were stirred at room temperature for 30 minutes. The mixture was cooled in a 0° C. ice bath and m-benzyloxybenzyl chloride (931 mg, 4 mmol) was added as a solid and the mixture stirred at room temperature for 18 hours. TLC (1:2 EtOAc:Hexane Rf=0.25) indicated a complete reaction. The reaction was worked up by diluting with water (100 mL) and extracting with diethyl ether (2×50 mL). The organic layer was dried over magnesium sulfate and the filtrate taken to dryness. The residue was purified on silica gel (75 g; 1:2 followed by 1:1 EtOAc:Hexane) to provide 785 mg (84.3% yield) of the intermediate (XXXIVb) (where $R^{22}$=$R^{23}$=m-benzyloxybenzyl) as a colorless foam.

Intermediate (XXXIVb) (700 mg, 0.75 mmol) was dissolved in methanol (3.5 mL) and to this solution cooled in a 0° C. ice bath, was added 4M HCl in dioxane (3.5 mL, 14 mmol) and the mixture stirred at room temperature for 18 hours. TLC (1:2 EtOAc:Hexane Rf=0.26) indicated a complete reaction. The mixture was worked up by quenching in sat.sodium bicarbonate (50 mL) and extracting with dichloromethane (2×50 mL). The organic extracts were dried over magnesium sulfate and the filtrate taken to dryness. The residue was purified on silica gel (75 g; 1:2 followed by 2:3 EtOAc:Hexane) to provide 357 mg (63.1% yield) of the title compound as a white solid. m.p.194–195° C.

EXAMPLE 23D

Example 23C (257 mg, 0.34 mmol) was dissolved in a mixture of ethanol (5 mL) and dioxane (5 mL). To the mixture was added palladium hydroxide on Carbon (20%, 100 mg) and the suspension stirred for 18 hours under hydrogen (1 atm). TLC (10:1:10 EtOAc:EtOH:Hexane Rf=0.3) indicated a complete reaction. The suspension was filtered through a celite pad and the filtrate taken to dryness. The residue was purified on silica gel (33 g; 1:1 EtOAc:Hexane followed by 20:1:20 EtOAc:EtOH:Hexane) to provide 162 mg (82.9% yield) of the desired compound as a white solid. m.p.123–124° C.

5% NaOH and $CH_2Cl_2$. The organic phase was then washed with saturated NaCl, dried ($Na_2SO_4$) and evaporated leaving 100 mg of Intermediate (XXXIXb) as a yellow oil (95% yield).

EXAMPLES 24B AND 24C

To a suspension of 60% NaH (160 mg, 4.0 mmol; washed twice with hexane) in DMF (3 mL) was added a solution of Intermediate (XXXIVb) (100 mg, 0.20 mmol.) in DMF (7

TABLE 2m

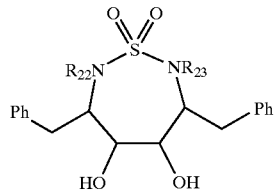

| Ex. No. | Stereo 2,3,4,5 | $R^{22}$ | $R^{23}$ | HPLC $K_i$ | $IC_{90}$ | mp, ° C. | Mass Spec M + H (M + $NH_4$) |
|---|---|---|---|---|---|---|---|
| 23A | RSSR | H | H | + | ++ | 253–255 | 363.1387 |
| 23B | RSSR | p-($HOCH_2$)—$C_6H_4CH_2$— | p-($HOCH_2$)—$C_6H_4CH_2$— | +++ | +++ | 189–190 | 603.2528 |
| 23C | RSSR | m-($C_6H_5CH_2O$)—$C_6H_4CH_2$— | m-($C_6H_5CH_2O$)—$C_6H_4CH_2$— | ++ | ++ | 194–195 | 755.3155 |
| 23D | RSSR | m-(HO)—$C_6H_4CH_2$— | m-(HO)—$C_6H_4CH_2$— | +++ | +++ | 123–124 | 575.2216 |
| 23E | RSSR | allyl | allyl | ++ | +++ | 112–113 | 443.2005 |
| 23F | RSSR | cyclopropylmethyl | cyclopropylmethyl | +++ | +++ | 71–72 | 471.2318 |
| 23G | RSSR | n-butyl | n-butyl | +++ | +++ | oil | 475.2631 |
| 23H | RSSR | 2-naphthylmethyl | 2-naphthylmethyl | +++ | +++ | 211–212 | 643.2631 |
| 23I | RSSR | benzyl | benzyl | ++ | +++ | 159–161 | 543.2306 |
| 23J | RSSR | p-($C_6H_5CH_2O$)—$C_6H_4CH_2$— | p-($C_6H_5CH_2O$)—$C_6H_4CH_2$— | + | ++ | | 755.3147 |
| 23K | RSSR | p-(HO)—$C_6H_4CH_2$— | p-(HO)—$C_6H_4CH_2$— | +++ | +++ | 223–225 | (592.2486) |
| 23L | RSSR | m-nitrobenzyl | m-nitrobenzyl | ++ | +++ | 196–198 | 633.2014 |
| 23M | RSSR | m-aminobenzyl | m-aminobenzyl | +++ | +++ | 212–214 | 573.2535 |
| 23N | RSSR | m-($HOCH_2$)—$C_6H_4CH_2$— | m-($HOCH_2$)—$C_6H_4CH_2$— | +++ | +++ | | 603.2540 |
| 23O | RSSR | m-(($CH_3$)$_2NCH_2CO$)—$C_6H_4CH_2$— | m-(($CH_3$)$_2NCH_2CO$)—$C_6H_4CH_2$— | +++ | +++ | 137–139 | 743.3596 |
| 23P | RSSR | m-($CH_3OCH_2$)—$C_6H_4CH_2$— | m-($CH_3OCH_2$)—$C_6H_4CH_2$— | ++ | ++ | 152–154 | 631.2832 |
| 23Q | RSSR | m-(CHO)—$C_6H_4CH_2$— | m-(CHO)—$C_6H_4CH_2$— | +++ | +++ | 91–93 | 599.2211 |
| 23R | RSSR | $CH_2$-tetrahydrofuran-3-yl | $CH_2$-tetrahydrofuran-3-yl | ++ | +++ | 97–99 | 531.2533 |
| 23S | RSSR | m-(HON=CH)—$C_6H_4CH_2$— | m-(HON=CH)—$C_6H_4CH_2$— | +++ | +++ | 105–107 | (646.2708) |
| 23T | RSSR | m-($CH_3CO$)—$C_6H_4CH_2$— | m-($CH_3CO$)—$C_6H_4CH_2$— | +++ | +++ | 96–99 | 627.2523 |
| 23U | RSSR | m-(HON=C($CH_3$))—$C_6H_4CH_2$— | m-(HON=C($CH_3$))—$C_6H_4CH_2$— | +++ | +++ | 110–113 | 657.2739 |
| 23V | RSSR | $CH_3$ | $CH_3$ | + | ++/+ | 200–203 | 391.1696 |
| 23W | RSSR | $CH_2CH_3$ | $CH_2CH_3$ | ++ | ++ | 182–185 | 419.2007 |
| 23X | RSSR | $CH_2CH_2CH_3$ | $CH_2CH_2CH_3$ | +++ | +++ | 145–148 | 447.2316 |
| 23Y | RSSR | m-(CN)—$C_6H_4CH_2$— | m-(CN)—$C_6H_4CH_2$— | ++ | +++ | 146–149 | 593.2227 |
| 23Z | RSSR | m-(2-(4-morpholino)-ethylNHC(=O))$C_6H_4CH_2$— | m-(2-(4-morpholino)-ethylNHC(=O))$C_6H_4CH_2$— | ++ | +/++ | 119–122 | 855.4111 |
| 23AA | RSSR | m-(2-(N,N-dimethylamino)-ethylNHC(=O))—$C_6H_4CH_2$— | m-(2-(N,N-dimethylamino)-ethylNHC(=O))—$C_6H_4CH_2$— | ++ | ++ | 127–130 | 771.3903 |
| 23AB | RSSR | m-(2-amino-4-thienyl)-$C_6H_4CH_2$— | m-(2-amino-4-thienyl)-$C_6H_4CH_2$— | +++ | +++ | 185–190 | 739 |
| 23AC | RSSR | 5-hydroxypentyl | 5-hydroxypentyl | +++ | +++ | | (552) |
| 23AD | RSSR | 6-hydroxypentyl | 6-hydroxypentyl | +++ | +++ | | (580) |
| 23AE | RSSR | 5-hydroxypentyl | H | ++ | ++/+ | | (466) |
| 23AF | RSSR | 5-hydroxypentyl | 2-naphthylmethyl | +++ | +++ | | (606) |
| 23AG | RSSR | 5-hydroxypentyl | p-($HOCH_2$)—$C_6H_4CH_2$— | +++ | +++ | | (586) |
| 23AH | RSSR | 5-hydroxypentyl | m-($HOCH_2$)—$C_6H_4CH_2$— | +++ | +++ | | (586) |

The structures of the Examples below are shown in Table 2n.

Intermediate (XXXIVb): To a solution of diamine (XXIC) (100 mg, 0.21 mmol.) in ethanol (3 mL), was added p-toluenesulfonic acid monohydrate (39 mg, 0.21 mmol.). After stirring for 10 min., dimethylacetamide dimethyl acetal (0.034 mL, 0.21 mmol.) was added. The reaction was then stirred at room temperature for 25 min. and then refluxed for 2 h. After cooling to room temperature, the reaction was evaporated in vacuo and partitioned between mL). After stirring for 35 min., a solution of 4-tetrahydropyranyloxymethylbenzyl chloride (XXXIVC) (0.53 g, 2.20 mmol.) in DMF (2 mL) was added followed by addition of potassium iodide (0.33 g, 2.0 mmol.). After stirring overnight, additional chloride (XXXIVC) (0.53 g, 2.20 mmol.) was added and the reaction was heated to 50° C. and stirred overnight. The reaction was quenched by addition of acetic acid (1 mL) in $Et_2O$ (100 mL). After basification with 5% NaOH, the organic phase was washed with water (2×), brine (2×), dried ($Na_2SO_4$), and evaporated leaving 2.1 g of a yellow oil. This material was taken up in methanol (10 mL) and 4N HCl in dioxane (5 mL) was added. After stirring overnight, the reaction was evaporated in vacuo and partitioned between 5% NaOH and $CH_2Cl_2$. The organic phase was dried and evaporated leaving 1.1 g of an orange oil. Column chromatography (flash silica gel; 5% MeOH/$CH_2Cl_2$ and 0.1% $NH_4O$) gave 182 mg of Example 24B and 300 mg of Example 24C, both as white solids.

Example 24B: Mass spec. $MH^+$=445.2; mp=105–110° C. (HCl salt).

Example 24C: Mass spec. $M^+$=565.5; mp=72–75° C. (Note: The mass spec is $M^+$ since this is already a charged species.).

EXAMPLE 24A

By an analogous process reported above, and instead using benzyl chloride, the desired product was obtained. The acid deprotection step was not performed in this instance.

Example 24A: $^1H$ NMR (300 Hz, $CDCl_3$): δ 6.90–7.35 (m, 15 H), 4.09–4.14 (m, 2H), 3.56 (dd, 2H), 3.13 (dd, 1H), 2.50–2.95 (m, 5H), 1.97 (s, 3H). Mass spec. $MH^+$=415.1, mp=130–137° C.

TABLE 2n

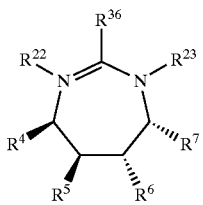

| Ex No | $R^{22}$ | $R^{23}$ | $R^4 = R^7$ | $R^5 = R^6$ | $K_i$ | MS (M + H)$^+$ |
|---|---|---|---|---|---|---|
| 24A | . . . | benzyl | benzyl | OMEM | | 415.1 |
| 24B | HCl | m-(HO)—$C_6H_4CH_2$— | benzyl | OH | | 445.2 |
| 24C | m-(HO)—$C_6H_4CH_2$— | m-(HO)—$C_6H_4CH_2$— | benzyl | OH | | (565.2) |

The structures of the Examples below are shown in Table 2o.

EXAMPLE 25A

Intermediate (XLVa), (3S,5R)-5-[(1'R)-1'-[(t-Butyloxycarbonyl)amino]-2'-phenethyl]-3-phenylmethyltetrahydrofuran-2-one, can be prepared from N-Boc-phenylalanine following the 8-step procedure of G. B. Dreyer, et al [*Biochem.* 1992, 31, 6646–6659]. This is converted to the acid (XLVb) using the procedure of B. E. Evans, et al [*J. Org. Chem.* 1985, 50, 4615–4625], wherein a solution of (3S,5R)-5-[(1'R)-1'-[(t-Butyloxycarbonyl)amino]-2'-phenethyl]-3-phenylmethyltetrahydrofuran-2-one (XLVa) (11.0 g, 2.5 mmol) in 15 mL of dioxane/7.5 mL of water was treated with 2.7 mL of 1 N NaOH dropwise. The mixture was stirred at room temperature for 30 min. and then concentrated at rt on a rotary evaporator. The residue was acidified with 10% citric acid and extracted into ether. The ether extract was washed with water, brine and dried over $MgSO_4$. The solution was filtered and concentrated to give the hydroxy acid as white solid.

The hydroxy acid was immediately dissolved in dry DMF and treated with t-butyldimethylsilyl chloride (2.6 g, 17.5 mmol) and imidazole (2.2 g). The mixture was stirred overnight at room temperature. Analysis by TLC (50:50 EtOAc/Hex) showed no starting material remained, at which time the solution was concentrated in vacuo and the residue acidified to pH 4 with 10% citric acid and extracted into ether. The ether extract was washed with water, brine and dried over $MgSO_4$. The solution was filtered and concentrated to give 1.7 g of the silyl ether-silyl ester as a colorless syrup.

A solution of the silyl ether-silyl ester in tetrahydrofuran (THF, 10 mL) was treated with 10 mL of glacial acid and water (3 mL). The solution was stirred at room temperature for 2.5 hrs until analysis by TLC showed complete conversion to silyl ether-acid (XLVb). The solution was concentrated in vacuo and the resulting residue diluted with water and extracted into ether. The ether extract was washed with water, brine and dried over $MgSO_4$. The solution was filtered and concentrated to give the acid (XLVb) as a solid.

A solution of the acid (XLVb) in dioxane was treated with N-hydroxy succinimide (290 mg, 2.5 mmol) and 1,3-dicyclohexylcarbodiimide (DCC, 500 mg, 2.5 mmol) and stirred overnight. The solution was cooled in an ice bath and the solids were filtered off. The filtrate was concentrated to give the activated ester (XLVc) as a sticky foam. MS (M+H)+=625.5 (41%); (M+H-BOC)+=525.4 (100%).

The above activated ester (XLVc) was dissolved in ether, cooled in an ice bath and treated with HCl (g) for 15 minutes and stirred at 0° C. for an additional hour. The solution was concentrated in vacuo at RT to give a white foam. This was dissolved in THF (100 mL) and made basic with triethyamine (3 mL). The resulting suspension was stirred at room temperature overnight. The solution was concentrated and the residue was chromatographed on silica gel (medium pressure LC, ethyl acetate). This was further purified by HPLC chromatography on silica gel (50:50 EtOAc/Hex) to give 170 mg (17% overall yield/6 steps) of the lactam (XLVd) as a colorless oil. MS (M+H)+=410.2 (100%).

A solution of (XLVd) (170 mg, 0.42 mmol) in DMF was cooled to 0° C. and treated with 60% NaH in oil dispersion (25 mg, 0.62 mmol) and stirred at 0° C. for 30 minutess. Benzyl bromide (105 mg, 0.44 mmol) was added and stirred for 1 hour and the reaction was allowed to warm to room temperature. The mixture was cooled to 0° C. and quenched with 1 N HCl and diluted with water. The suspension was extracted into ethyl acetate, washed with water, brine, dried over $MgSO_4$ and concentrated. The residue was HPLC chromatographed on silica gel (30% EtOAc/Hex) to give 130 mg of (XLVf) as a colorless film. MS (M+H)+=500.2 (100%).

The silyl ether-lactam (XLVf) (130 mg, 0.26 mmol) was dissolved in tetrabutylammonium fluoride (TBAF, 1 M in THF, 5 mL) solution and stirred at room temperature for 30 minutes. The solution was diluted with water and extracted into ethyl acetate. The extracts were washed with water, brine, dried over $MgSO_4$ and concentrated. The residue was HPLC chromatographed on silica gel (65% EtOAc/Hex) to give 79 mg of Example 25A (XLVg) as a white foam. MS (M+H)+=386.2 (100%).

TABLE 2o

| Ex No | $R^{22}$ | $R^{23}$ | $R^4$ | $K_i$ | MS $(M+H)^+$ |
|---|---|---|---|---|---|
| 25A | benzyl | benzyl | benzyl | + | 386.2 |

The structures of the Examples below are shown in Table 2p.

EXAMPLE 26A

5H-Dibenzo [A,D] Cyclohepten-5-one-10,11-dihydro-10,11-diol

A mixture of 5H-dibenzo [A,D] cyclohepten-5-one-10,11-dihydro-10,11-diolacetate (ester) (100 mg, 0.31 mmol) and sodium hydroxide 50% aqueous solution (5 drops) was disolved in methanol (10 ml). The mixture was stirred at room temperature for 5 minutes, neutralized with concentrated hydrochloric acid and extracted with ethyl acetate twice. The organic layer was washed with water, brine, dried with magnesium sulfate and then concentrated in vacuo. The concentrate was dissolved with a minimum amount of methylene chloride and hexane was added to the cloudy point. The resulting precipitate was filtered to give opaque fine needle crystals (47 mg, 64%). mp 107.5–107.9° C., Mass Spec 241.1 (M+H)$^+$; Analysis Calc. for $C_{15}H_{12}O_3$: C, 74.99; H, 5.03; Found: C, 74.70; H, 5.01. $^1$H NMR (CDCl$_3$/TMS) δ 7.85 (2H, m), 7.67 (2H, m), 7.57 (2H, m), 7.44 (2H, m), 5.02 (2H, m), 3.03 (2H, m).

TABLE 2p

| Ex No | $R^{22}$—$R^4$ | $R^{23}$—$R^7$ | $K_i$ | mp, ° C. | MS $(M+H)^+$ |
|---|---|---|---|---|---|
| 26A | fused aromatic | fused aromatic | + | 107.5–108 | 241 |

The structures of the Examples below are shown in Table 2q.

EXAMPLE 27A

Compound XXIIb (3.0 g, 4.8 mmol) was dissolved in of anhydrous acetonitrile (40 ml) and to this solution was added benzyl bromide (820 mg) and tetrabutylammonium iodide (20 mg). The contents were heated at reflux under a nitrogen atmosphere for 14 h and the solvent was removed under reduced pressure. The crude residue was chromatographed on silica gel using ethyl acetate-hexane (1:1) as the eluent. The major fraction contained 2.5 g (76% yield) of Intermediate (LIIIa) as a white solid. MS: (M+H)$^+$699.4, (100%); $^1$H NMR (CDCl$_3$): δ 7.25 (m, 12H), 6.99 (m, 3H), 4.95 (d, 1H), 4.82 (d, 1H), 4.65 (d, 1H), 4.50 (d, 1H), 4.15 (m, 1H), 3.85 (m, 1H), 3.62 (m, 1H), 3.60 (m, 1H), 3.56 (m, 1H), 3.4 (s, 3H), 3.39 (m, 1H), 3.35 (s, 3H), 3.12 (m, 1H), 2.92 (m, 1H), 2.10 (s, 3H).

Intermediate (LIIIa) (300 mg, 0.48 mmol) was dissolved in methanol (5 ml) and a solution of hydrochloric acid in dioxane (4M, 5 ml) was added. This mixture was stirred at room temperature for 4 h and then the solvent was removed under reduced pressure (the excess HCl can be removed by extensive washing with methanol followed by evaporation). The crude residue was chromatographed on silica gel using a 10% ethyl acetate in methylene chloride as the eluent. The major product contained 175 mg (81%) of Example 27A. mp: 91–93° C. MS: (M+H)$^+$523.2, (100%). IR (KBr, cm$^{-1}$): δ 3416, 3086, 1584 and 1282. $^1$H NMR (CDCl$_3$): δ 7.25 (m, 10H), 5.85 (d, 1H), 3.80 (m, 1H), 3.65 (d, 1H), 3.38 (s, 1H), 3.12–2.90 (m, 2H), 2.21 (s, 1H). $^{13}$C NMR (CDCl$_3$, ppm) 193.6, 139.9, 137.6, 130.2, 130.1, 129.1, 128.8, 128.3, 127.0, 72.0, 67.7, 62.2, 32.8.

The above reaction (removal of the MEM protecting group) can also be done by dissolving the starting material in methanol followed by bubbling HCl gas into the solution for 5 min at –10° C. and then stirring at room temperature for 20 min. Similar work up of the first procedure leads to the desired Example 27A.

EXAMPLE 27B

By substituting cyclopropylmethyl bromide into procedure of Example 27A and using the appropriate monoalkylated cyclic thiourea, Example 27B was prepared in good yield. mp: 84–86° C.; MS: (M+H)$^+$451.1; $^1$H NMR (CDCl$_3$): δ 7.35–7.20 (m, 5H), 5.0 (d, 1H), 4.85 (d, 1H), 4.10 (m, 2H), 3.95 (m, 1H), 3.75 (m, 1H), 3.45 (m, 2H), 3.38 (s, 3H), 3.2 (m, 1H), 3.0 (m, 1H), 2.78 (m, 1H), 1.20 (m, 1H), 0.21 (m, 2H), 0.17 (m, 2H).

EXAMPLE 27C

Using an analogous procedure to that described for Example 27B, Example 27C was prepared in good yield. mp: 257–259° C.; MS: (M+H)$^+$583.2; $^1$H NMR (CDCl$_3$): δ 7.25–7.15 (m, 9H), 5.80 (m, 2H), 4.75 (s, 2H), 3.82 (m, 1H), 3.42 (m, 1H), 3,35 (m, 2H), 2.95 (m, 2H).

EXAMPLE 27D

Using an analogous procedure to that described for Example 27A, Example 27D was prepared in good yield (m-MEMOCH$_2$C$_6$H$_5$CH$_2$Br was the alkylating agent). mp: 253–255° C.; MS (CDI): m/e 583.3 (100%, M+H); $^1$H NMR (CD$_3$OD, 300 Hz) δ 2.95 (m, 2H), 3.20 (m, 1H), 3.40 (m, 1H), 3.78 (m, 1H), 5.82 (m, 1H) and 7.15–7.30 (m, 9H).

EXAMPLE 27E

By using the appropriate alkylating agent (m-cyanobenzylbromide), Example 27E was prepared in an anologous procedure to Example 27A; mp: 154–155° C.; MS (CDI): m/e 548.2 (100%, M+H); $^1$H NMR (CD$_3$OD, 300 Hz) δ 2.81 (m, 1H), 2.95 (m, 2H), 3.20 (m, 1H), 3.25 (m, 2H), 3.85 (m, 1H), 3.90 (m, 1H), 5.25 (m, 1H), 5.80 (m, 1H), 7.10 (m, 5H), 7.15 (m, 10H) and 7.25 (m, 4H).

EXAMPLE 27F

Example 27F was made by using p-MEMOC$_6$H$_5$CH$_2$Br as the alkylating agent in the procedure of Example 27A.

mp: 162° C.; MS (CDI): m/e 555.2 (100%, M+H); ¹H NMR (CD₃OD) δ 2.85 (m, 2H), 3.12 (m, 2H), 3.8 (m, 1H), 5.80 (m, 1H), 6.75 (m, 2H), 6.95 (m, 2H) and 7.15 (m, 5H).

EXAMPLE 27G

Example 27G was prepared according to the procedure described for Example 27A, using m-MEMOC₆H₅CH₂Br as the alkylating agent. mp: 82° C.; MS (CDI): m/e 583.2 (100%, M+H); ¹H NMR (CD₃OD, 300 Hz) 62.85 (m, 2H), 3.25 (m, 2H), 3.62 (s, 3H), 3.90 (m, 1H), 5.80 (m, 1H), 6.80 (m, 3H) and 7.10–7.20 (m, 6H).

EXAMPLE 27H

Example 27H was prepared using an analogous procedure to that described for Example 27A by employing m-NCC₆H₅CH₂Br as the alkylating agent. mp: 110° C.; MS (CDI): m/e 577.2 (M+H); ¹H NMR (CD₃OD, 300 Hz) δ 2.8 (m, 2H), 3.15 (m, 2H), 3.45 (m, 2H), 3.65 (m, 1H), 3.70 (m, 1H), 3.82 (m, 1H), 4.15 (m, 1H), 5.28 (m, 1H), 5.82 (m, 1H), 7.25 (m, 4H), 7.40 (m, 10H) and 7.80 (m, 4H).

EXAMPLE 27I

Example 27K was prepared by treating Example 27H with hydroxylamine HCl, using an analogous procedure to that described for Example 27N. mp: 130–132° C.; MS (CDI) m/e 611.2 (100%, M+H); ¹H NMR (CD₃OD, 300 Hz) δ 2.81 (m, 2H), 3.21 (m, 2H), 3.45 (m, 2H), 3.8 (m, 2H), 4.72 (m, 2H), 5.85 (m, 2H) and 7.25 (m, 18H).

EXAMPLE 27J

Example 27L was synthesized in a similar fashion to that described for Example 27F by using m-MEMOC₆H₅CH₂Br as the alkylating agent. mp: 125° C.; MS (CDI): m/e 555.3 (100%, M+H); ¹H NMR (CD₃OD, 300 Hz) δ 3.05–3.20 (m, 2H), 3.41–3.60 (m, 2H), 3.95 (m, 1H), 5.82 (m, 1H), 6.80 (m, 3H) and 7.20–7.45 (m, 6H).

EXAMPLE 27K

Example 27M was prepared using an analogous procedure to that described for Example 27A by using m-NCC₆H₅CH₂Br as the alkylating agent. mp: 102° C.; MS (CDI) m/e 573.3 (100%, M+H); ¹H NMR (CD₃OD, 300 Hz) 52.80 (m, 1H), 3.05 (m, 1H), 3.20 (m, 1H), 3.42 (m, 1H), 3.78 (m, 1H), 5.15 (m, 1H), 7.15 (m, 2H), 7.25 (m, 3H), 7.45 (m, 1H) and 7.60 (m, 3H).

EXAMPLE 27L

To a solution containing 200 mg (0.34 mmol) of Example 27M in 10 mL of anhydrous ethanol was added 60 mg (0.87 mmol) of hydroxylamine.HCl and 87 mg (0.87 mmol) of triethylamine. The reaction mixture was heated at reflux until the starting material could not be detected by TLC), and then the solvent was removed under reduced pressure. The residue was chromatographed on a C₁₈ silica column using a 20% solution of water in methanol as the eluent. The major fraction isolated contained 97 mg (45% yield) of thiourea, Example 27N. mp: 150° C.; MS (DCI): m/e 639.2 (100%, M+H); ¹H NMR (CD₃OD, 300 Hz) 82.85 (m, 2H), 3.15 (m, 1H), 3.25 (m, 1H), 3.80 (m, 1H), 5.82 (m, 1H), 7.15 (m, 5H) and 7.45 (m, 4H).

EXAMPLE 27M

To a solution of containing 5.0 g (10.5 mmol) of Di-amine-Di-MEM compound III in 75 ml of THF was added 2.20 g (22.0 mmol) of K₂CO₃ and 4.48 g (23.0 mmol) of 4-fluoro-3-cyanobenzyl bromide. The reaction mixture was stirred at room temperature for 18 h and then 100 mL of water was added. The mixture was extracted with CH₂Cl₂ and the organic layer was dried over MgSO₄ and filtered. The filtrate was treated with 1.73 g (15.0 mmol) of thiophosgene and 2.0 g (20.0 mmol) of triethylamine. The reaction was stirred at room temperature overnight and then washed with 100 mL of 10% citric acid. The organic layer was washed with brine, dried over MgSO₄ and filtered. The solvent was removed under reduced pressure and the residue was chromatographed on silica gel using a 50% solution of ethyl acetate in hexane as the eluent to give 2.45 g (30% yield) of the alkylated intermediate. Removal of the the MEM groups was done by using analogous procedure to that described for intermediate LIIIa. The thiourea compound obtained from the previous step was converted to example 27P by applying the same porcedure described for Example 27N. mp 154° C.; MS (DCI): m/e 675.2 (100%, M+H); ¹H NMR (CD₃OD, 300 Hz) 2.85 (m, 2H), 3.35 (m, 1H), 3.52 (m, 1H), 3.78 (m, 1H), 5.61 (m, 1H), 7.10 (m, 1H) and 7.25 (m, 8H).

TABLE 2q

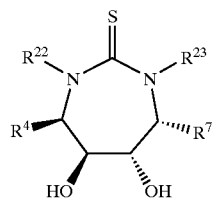

| Ex. No | Stereo 2,3,4,5 | $R^{22} = R^{23}$ | $R^4 = R^7$ | HPLC $K_i$ | $IC_{90}$ | mp, ° C. | Mass Spec (M + H) |
|---|---|---|---|---|---|---|---|
| 27A | RSSR | C₆H₅CH₂— | C₆H₅CH₂— | +++ | +++ | 92–94 | 523.2 |
| 27B | RSSR | (C₃H₅)CH₂— | C₆H₅CH₂— | +++ | +++ | 84–86 | 451.1 |
| 27C | RSSR | p-HOC₆H₄CH₂— | C₆H₅CH₂— | +++ | +++ | 257–258 | 583.2 |
| 27D | RSSR | m-HOCH₂—C₆H₄CH₂— | m-HOCH₂—C₆H#CH₂— | +++ | +++ | 253–355 | 583.3 |
| 27E | RSSR | m-cyano-C₆H₄CH₂— | C₆H₄CH₂— | +++ | +++ | 154–155 | 548.2 |
| 27F | RSSR | p-HOC₆H₄CH₂— | p-HO—C₆H₄CH₂— | +++ | +++ | 162 | 555.2 |

TABLE 2q-continued

| | | | | | | | |
|---|---|---|---|---|---|---|---|
| 27G | RSSR | m-CH3O—C$_6$H$_4$CH$_2$— | m-CH3O—C$_6$H$_4$CH$_2$— | +++ | +++ | 82 | 583.2 |
| 27H | RSSR | m-cyano-C$_6$H$_4$CH$_2$— | p-HOCH$_2$—C$_6$H$_4$CH$_2$— | +++ | +++ | 110 | 577.2 |
| 27I | RSSR | m-HONNH$_2$—C$_6$H$_4$CH$_2$— | p-HOCH$_2$—C$_6$H$_4$CH$_2$— | +++ | +++ | 130–132 | 611.2 |
| 27J | RSSR | m-HO—C$_6$H$_4$CH$_2$— | m-HO—C$_6$H$_4$CH$_2$— | +++ | +++ | 125 | 555.3 |
| 27K | RSSR | m-cyano-C$_6$H$_4$CH$_2$— | m-cyano-C$_6$H$_4$CH$_2$— | +++ | +++ | 102 | 573.3 |
| 27L | RSSR | m-(H$_2$NC(=NOH))C$_6$H$_4$CH$_2$— | m-(H$_2$NC(=NOH))C$_6$H$_4$CH$_2$— | +++ | +++ | 150 | 639.2 |
| 27M | RSSR | m-(H$_2$NC(=NOH))-p-fluoro-C$_6$H$_4$CH$_2$— | m-(H$_2$NC(=NOH))-p-fluoro-C$_6$H$_4$CH$_2$— | +++ | +++ | 152–153 | 675.2 |

The structures of the Examples below are shown in Table 2r. Compounds in Table 2r were prepared as shown 5 in Scheme 28.

EXAMPLE 28D

Preparation of Diamine (La):

To a suspension of 10 g of (2R,3S,4S,5R)-2,5-bis-(N-Cbz-amino)-3,4-(dihydroxy)-1,6-diphenylhexane in 200 mL of methylene chloride was added 10.8 mL of 2,2-dimethoxypropane and 0.41 g of camphorsulfonic acid. The mixture was stirred at room temperature for 48 hr, then washed successively with saturated sodium hydrogen carbonate solution and saturated sodium chloride solution. The organic phase was dried over anhydrous magnesium sulfate and concentrated on a rotary evaporator. The residue was crystallized from ether/hexane (1/10 v/v) to give 6.6 g (60% yield) acetonide as white needles, mp 76–77° C.

To a solution of 6.6 g of this acetonide in 100 mL of tetrahydrofuran/ethanol (1/1 v/v) was added 0.7 g of 10% Pd/C. The mixture was stirred vigorously under 1 atmosphere of hydrogen gas for 18 hr. The catalyst was isolated by filtration and washed with tetrahydrofuran. The combined filtrate and washings were concentrated on a rotary evaporator. The residue consisted of 3.6 g (100% yield) of diamine, La, which was used without further purification.

To a solution of 2 g of compound La in 15 mL of anhydrous tetrahydrofuran, maintained at 0–10° C. under a nitrogen atmosphere with efficient stirring, was added 1.8 mL (2.2 eq) of triethylamine followed by dropwise addition of a solution of 0.9 mL (1 eq) of phenyldichlorophosphate in 4 mL of tetrahydrofuran. The mixture was stirred for 16 hr at room temperature. The resulting triethylamine hydrochloride was isolated by filtration and washed with tetrahydrofuran. The combined filtrate and washings were concentrated on a rotary evaporator, taken up in methylene chloride/ethyl ether (1/1 v/v), and washed successively with water (2×), and saturated sodium chloride solution (1×). After drying over anhydrous magnesium sulfate, the organic layer was concentrated on a rotary evaporator. Purification of the residue by column chromatography using a short pad of silica gel eluting with hexane/ethyl acetate (1/1 v/v) gave 1.8 g (64% yield) of the cyclic phosphoramide, Lb, as a sticky white foam.

To a solution of 0.1 g of compound Lb in 3 mL of anhydrous N,N-dimethylformamide, maintained under a nitrogen atmosphere at room temperature, was added 35 mg of 60% NaH (by weight, dispersed in oil). The mixture was stirred for 10–15 min followed by addition of 0.16 mL bromomethylcyclopropane. The mixture was stirred for 48 hr at room temperature, then quenched by water addition. The product was extracted with ethyl acetate (3×). The combined extracts were washed successively with water (2×) and saturated sodium chloride solution (1×), dried over anhydrous magnesium sulfate, and concentrated on a rotary evaporator. The residue was purified using rotary preparative tlc eluting with hexane/ethyl acetate (4/1 v/v) to give 97 mg (79% yield) of the bisalkylated product as an amber oil. To a solution of 97 mg of this bisalkylated product in 2 mL of anhydrous methylene chloride, maintained under an argon atmosphere at −78° C., was added 0.5 mL of a 2.0 M solution of dimethylboron bromide in methylene chloride by dropwise addition. The addition was completed in 10–15 min, and the mixture was thereafter stirred for 1 hr at −78° C. The mixture was then transferred via syringe to a rapidly stirring mixture of 1 mL tetrahydrofuran and 0.5 mL aqueous saturated sodium hydrogen carbonate solution. After stirring for 5 min, the mixture was extracted with ethyl acetate (3×). The combined extracts were washed successively with 10% aqueous potassium hydrogen sulfate solution and saturated sodium chloride solution. After drying over anhydrous magnesium sulfate, the organic layer was concentrated by rotary evaporation. The residue was purified by rotary preparative tlc eluting with hexane/ethyl acetate (4/1 v/v) to give 70 mg (78% yield) of compound 28D as an amorphous white solid. MS 547 (M+H)$^+$453 (100%, M+H—C$_6$H$_5$OH)$^+$. $^1$H NMR (CDCl$_3$): δ 0.24 (4H, m) 0.44 (4H, m) 0.95 (2H, m) 2.22 (1H, d) 2.52 (1H, m) 3.18 (4H, m) 3.38 (2H, m) 3.63 (1H, m) 3.90 (1H, t) 4.03 (2H, m) 7.00 (1H, m) 7.06 (2H, m) 7.24 (10H, m) 7.50 (2H, m).

EXAMPLE 28M

Compound of example 28M was prepared from compound Lb using the alkylation procedure described for example 28D by replacing the bromomethylcyclopropane with 3-(N-methyl-N-trifluoroacetamido)benzyl bromide. A solution of 0.27 g of the bisalkylation product, thus prepared, in 7 mL of methanol was treated with 4 eq of solid potassium carbonate. The mixture was stirred for 48 hr at room temperature, diluted with water, and extracted with methylene chloride. The extract was washed successively with saturated sodium hydrogen carbonate solution and saturated sodium chloride solution, then dried over anhydrous magnesium sulfate. Concentration by rotary evaporation and purification of the residue by column chromatography using silica gel eluting with hexane/ethyl acetate (1/1 v/v) gave the free amino compound in 57% yield.

To a solution of this diamine in 3 mL of methanol was added 0.01 g p-toluenesulfonic acid monohydrate. The solution was stirred for 1 hr at room temperature, then concentrated by rotary evaporation. The residue was taken up in ethyl acetate, washed with saturated sodium hydrogen carbonate solution, and dried over anhydrous magnesium sulfate. Concentration by rotary evaporation and purification by column chromatography on silica gel using methylene chloride/ethyl acetate/ethanol (10/10/0.5 volume ratios) gave a 19% yield of compound 28M. MS: 583 (M+H–$C_6H_5OH$) $^1H$ NMR ($CDCl_3$): δ 2.58–2.77 (m, 2H); 2.70 (s, 3): 2.78 (s, 3H); 3.02 (d, 2H); 3.20–3.39 (m, 2H); 3.42 (d of d, 2H); 3.50–3.73 (m, 2H); 3.88 (s, 2H); 4.30–4.59 (m, 4H); 6.42–6.52 (m, 4H); 6.55–6.62 (m, 3H); 6.95 (d, 2H); 7.00–7.37 (m, 10H); 7.52 (d, 2H).

sition on the column support. $^1H$ NMR (300 Hz) ($CDCl_3$): δ 1.441 (36H, d, J=4 Hz), 2.974 (6H, m), 3.353 (2H, s), 3.49 (4H, m), 4.865 (2H, d, J=8 Hz), 4.919 (4H, d, J=14 Hz), 7.111 (10H, t, J=8 Hz), 7.293 (8H, m); $^{31}P$ NMR (121 Hz) ($CDCl_3$) δ −9.8 (s, decoupled).

This diester intermediate (36 g, 37.85 mmol) was dissolved in 200 ml methanol and to this solution was added 3.6 g of Amberlyst 15 ion exchange resin. The contents were stirred at reflux for 5 hours. The mixture was filtered through a celite pad and concentrated to afford 27 g (98.2%) of Compound 29A as a white solid. $^1H$ NMR (DMSO-$d_6$) δ

TABLE 2r

| Ex. No. | $R^{22} = R^{23}$ | $R^4 = R^7$ | $R^{24A}$ | $K_i$ HPLC | $IC_{90}$ | mp, °C. | Mass spec (M + H) |
|---|---|---|---|---|---|---|---|
| 28A | H | benzyl | phenyloxy | + | ++ | | 456 (M + $NH_4$) |
| 28B | 2-naphthyl methyl | benzyl | phenyloxy | ++ | +++ | | |
| 2BC | cyclopropyl methyl | benzyl | phenyloxy | ++ | +++ | | 547 |
| 28D | n-butyl | benzyl | phenyloxy | ++ | +++ | | 551 |
| 28E | 4-($HOCH_2$)-benzyl | benzyl | phenyloxy | ++ | +++ | | |
| 28F | H | benzyl | ethoxy | + | ++/+ | 245–246 | 408 (M + $NH_4$) 391 |
| 28G | cyclopropyl methyl | benzyl | dimethyl amino | + | ++ | | 498 |
| 28H | 4-($HOCH_2$)-benzyl | benzyl | methoxy | ++ | ++ | | 617 |
| 28I | 4-($HOCH_2$)-benzyl | benzyl | dimethyl amino | ++ | ++ | 159–160 | 630 |
| 28J | 3-($HOCH_2$)-benzyl | benzyl | phenoxy | ++ | ++ | 109–110 | |
| 28K | benzyl | benzyl | methyl | ++ | | | 541 |
| 28L | 3-($CH_3NH$)-benzyl | benzyl | phenoxy | ++ | ++ | | |

The examples below are representative procedures for the preparation of the compounds shown in Table 2s below.

EXAMPLE 29A

Compound of example 5U (11.340 g, 20 mmol) was dissolved in 60 ml tetrahydrofuran and cooled to 0° C. di-t-butyl-N,N-diethylphosphoramidite 13.000 g(52 mmol) in 40 ml tetrahydrofuran was added followed by additon of 7.28 g (104 mmol) of tetrazole. The contents were stirred for 5 minutes in the 0° C. ice bath and then for 15 minutes in a water bath at approximately 23° C. The contents were cooled in a −40° C. bath and 21.5 g (62.4 mmol) of 50% m-chloroperoxybenzoic acid in 100 ml dichloromethane added over a 10 minute period and stirred for 5 minutes in the same bath and then 15 minutes in a water bath at approximately 23° C. The reaction was quenched with 250 ml of 10% aqueous sodium bisulfite at 0° C. The aqueous layer was extracted with ether (100 ml). The organic extracts were combined and washed with sat. sodium bicarbonate (100 ml), 10% aqueous sodium bisulfite (250 ml) and then sat. sodium bicarbonate (100 ml). The organic layer was separated and dried over magnesium sulfate and the filtrate taken to dryness. The residue was purified on $SiO_2$ gel [750 g; using chloroform (500 ml) followed by 1% Methanol:Chloroform (4 liters) followed by 1.5% (4 liters)] to provide 14.410 g (75.8% yield) of the bisphosphate ester as a white solid. Caution! The "flash chromatography" column should be done as fast as possible to avoid any decompo- 2.842 (4H, m), 2.955 (2H, m), 3.336 (2H, s), 3.420 (2H, d, J=11 Hz), 4.662 (2H, d, J=4.2 Hz), 4.822 (4H, d, J=6.9 Hz), 7.016 (4H, d, J=6.9 Hz), 7.084 (4H, d, J=7.7 Hz), 7.266 (10H, m); $^{31}P$ NMR (DMSO-$d_6$) δ −0.48 (s, decoupled)

EXAMPLE 29B

Compound 29A (2.178 g, 3 mmol) was treatd slowly with 11.71 ml (12 mmol) of 1.024N Potassium bicarbonate solution. After the addition was complete the solution was filtered through a sintered glass filter funnel and lyophilized to afford 2.433 g (92.3% yield) of desired tetrapotassium salt as a white solid.

EXAMPLE 29D

Compound 5U (8.2 g, 14.4 mmol) was dissolved in methylene chloride (170 ml) under a nitrogen atmosphere. N,N-Dimethylglycine (1.78 g, 17.3 mmol, 1.2 equiv.) was added followed by the reagents, 1-(3-dimethylaminopropyl)-3-ethylcarbodiimide hydrochloride (3.32 g, 17.3 mmol, 1.2 equiv.) and 4-dimethylaminopyridine (2.11 g, 17.3 mmol, 1.2 equiv.). After stirring overnight, silica gel (40 g, 230–400 mesh) was added and the solvent removed on a rotary evaporator. The residue was applied to the top of flash silica gel column and eluted with 20% methanol-80% ether to give partially purified D. Further chromatography using 15% isopropanol-85% methylene chloride gave the desired monoester (2.54 g, 27%). $^1$H NMR (300 Hz, CDCl$_3$) δ 7.35–7.02 (18H, m), 5.06 (2H, s), 4.85 (1H, d), 4.80 (1H, d), 4.50 (2H, s), 3.46 (6H, m), 3.07 (2H, s), 2.96 (7H, m), 2.22 (6H, s). $^{13}$C NMR (75.4 Hz, CDCl$_3$) δ 170.2, 162.1, 140.2, 139.6, 138.4, 137.3, 134.8, 129.5, 129.4, 128.9, 128.5, 128.5, 128.1, 127.1, 126.4, 71.1, 71.0, 66.0, 64.3, 63.8, 60.1, 55.3, 55.1, 45.1, 32.6.

This mono-ester (1.39 g, 2.14 mmol) was dissolved in a mixed solvent system (88 ml, 9% isopropanol-91% ether). A solution of hydrochloric acid (0.59 ml, 2.35 mmol, 1.1 equiv., 4.0 M in dioxane) was added dropwise. After stirring for 1.5 hours, the reaction was filtered under nitrogen. The filtrate was rinsed into a flask with water and frozen. The frozen solution was lyophilized to give 29D as its mono-hydrochloride-monohydrate (1.39 g, 92% for the monohydrate). $^1$H NMR (300 Hz, CD$_3$OD) δ 7.38–7.01 (18H, m), 5.26 (2H, s), 4.82 (1H, d), 4.78 (1H, d), 4.56 (2H, s), 4.12 (2H, dd), 3.58 (4H, m), 3.09–2.78 (6H, m), 2.91 (6H, s). $^{13}$C NMR (100.6 Hz, CD$_3$OD) δ 166.89, 163.83, 142.37, 141.30, 141.24, 140.17, 138.14, 135.64, 130.86, 130.65, 130.48, 129.93, 129.67, 129.57, 128.24, 127.48, 72.05, 71.90, 68.81, 67.81, 66.93, 64.79, 57.99, 57.07, 56.72, 44.49, 33.64, 33.58. MS (NH$_3$ CI) m/e 652 (M+H−HCl).

EXAMPLE 29E

Compound 5U (5.0 g, 8.82 mmol) was dissolved in methylene chloride (50 ml) under a nitrogen atmosphere. An excess of 2,2-dimethoxypropane (10 ml) and a catalytic amount of p-toluenesulfonic acid monohydrate (250 mg) were then added. After stirring for one hour, water (25 ml) was added and stirring continued for ten minutes. The reaction was then transferred to a separatory funnel where the layers were separated. The organic phase was was successively with a saturated aqueous solution of sodium bicarbonate and brine. After drying over anhydrous magnesium sulfate, the crude product was isolated by filtration and evaporation. Purification was accomplished by flash silica gel column chromatography (5% methanol-95% methylene chloride). The acetonide was obtained in 90% yield (4.75 g). $^1$H NMR (300 Hz, CDCl$_3$) δ 7.37–7.23 (10H, m), 7.09 (8H, d), 4.88 (2H, d), 4.65 (4H, d), 3.82 (2H, s), 3.76 (2H, b), 3.04 (2H, d), 2.92 (4H, m), 1.94 (2H, t), 1.34 (6H, s). $^{13}$C NMR (75.4 Hz, CDCl$_3$) δ 161.7, 140.2, 138.8, 137.6, 129.4, 129.3, 129.2, 128.7, 127.2, 126.6, 110.2, 75.5, 65.0, 60.8, 56.0, 33.5, 26.7.

This acetonide (999 mg, 1.67 mmol) was dissolved in methylene chloride (10.0 ml) under a nitrogen atmosphere. N,N-Dimethylglycine (431 mg, 4.18 mmol, 2.5 equiv.) and the reagents 1-(3-dimethylaminopropyl)-3-ethylcarbodiimide hydrochloride (802 mg, 4.18 mmol, 2.5 equiv.) and 4-dimethylaminopyridine (511 mg, 4.18 mmol, 2.5 equiv.) were added and stirring continued overnight. The reaction was applied directly to a flash silica gel column and eluted with 10% methanol-90% ether. The desired bis-ester was obtained in 73% yield (0.95 g). $^1$H NMR (300 Hz, CDCl$_3$) δ 7.36–7.04 (18H, m), 5.14 (4H, s), 4.92 (2H, d), 3.86 (2H, s), 3.77 (2H, d), 3.18 (4H, s), 3.08 (2H, d), 2.92 (4H, m), 2.33 (12H, s), 1.37 (6H, s). MS (NH$_3$ CI) m/e 777 (M+H).

This bis-ester (402 mg, 0.518 mmol) was dissolved in methanol (5.0 ml) and hydrochloric acid (1.0 ml, 1.0 N solution) was added. After stirring for 0.5 hour the solvent was removed by rotary evaporation and the residue azeotropically dried with toluene. Further drying in vacuo gave 29E (383 mg).

TABLE 2s

| Ex. No. | $R^{42} = R^{43}$ | K$_i$ (HPLC) | IC$_{90}$ | mp, °C. | Mass Spec (M + H) |
|---|---|---|---|---|---|
| 29A | PO$_3$H$_2$ | | | | |
| 29B | PO$_3^-$ (K$^+$) | | | | |
| 29C | Me$_2$NCH$_2$C(O)— | | | | |
| 29D | $R^{22}$ = H, $R^{23}$ = Me$_2$NCH$_2$C(O)—.HCl | | | | 652 |
| 29E | Me$_2$NCH$_2$C(O)—.HCl | | | | 737 |
| 29F | (3-pyridinyl)-CH$_2$C(O)— | | | | 805 |
| 29G | (4-pyridinyl)-CH$_2$C(O)— | | | | 777 |
| 29H | (1-morpholinyl)-CH$_2$C(O)— | | | | 821 |
| 29I | (3-pyridinyl)-CH=CHC(O)— | | | | 829 |
| 29J | (1-morpholinyl)-(CH$_2$)$_3$C(O)— | | | | 877 |
| 29K | (4-methyl-1-piperazinyl)-(CH$_2$)$_3$C(O)— | | | | 903 |
| 29L | (1-piperidinyl)-(CH$_2$)$_3$C(O)— | | | | 837 |
| 29M | (4-methyl-1-piperazinyl)-CH$_2$C(O)— | | | | 847 |
| 29N | (1-piperidinyl)-CH$_2$C(O)— | | | | 817 |
| 29O | (4-phenyl-1-piperazinyl)-CH$_2$C(O)— | | | | 971 |
| 29P | (1-morpholinyl)-(CH$_2$)$_2$C(O)— | | | | 849 |
| 29Q | (CH$_3$)$_2$C(NH$_2$)C(O)— | | | | 737 |
| 29R | CH$_3$CH(NH$_2$)C(O)— | | | | 709 |
| 29S | 3-(1-morpholinyl methyl)C$_6$H$_4$C(O)—.HCl | + | +++ | 167–168 | |
| 29T | 4-(1-morpholinyl methyl)C$_6$H$_4$C(O)—.HCl | + | +++ | 165–167 | |
| 29U | 3-(EtNHCH$_2$)—C$_6$H$_4$C(O)—.HCl | + | +++ | 124–126 | |
| 29V | 4-(EtNHCH$_2$)—C$_6$H$_4$C(O)—.HCl | + | +++ | 134–136 | |
| 29W | 4-(2-HOCH$_2$CH$_2$NHCH$_2$)—C$_6$H$_4$C(O)—.HCl | ++ | +++ | 169–170 | |
| 29X | 4-(4-methyl-1-piperazinyl methyl)-C$_6$H$_4$C(O)—.2HCl | ++ | +++ | 224–225 | |
| 29Y | 3-(4-methyl-1-piperazinyl methyl)-C$_6$H$_4$C(O)—.2HCl | ++ | +++ | 195–196 | |

The examples shown in Table 2t were prepared according to Scheme 34.

TABLE 2t

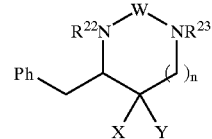

| Ex. No. | W | $R^{22} = R^{23}$ | n | X, Y | $K_i$ | mp, °C. |
|---|---|---|---|---|---|---|
| 30A | C=O | benzyl | 1 | H, OH (±) | + | 52–56 |
| 30B | C=O | 4-(HOCH$_2$)-benzyl | 1 | H, OH | + | 70–76 |
| 30C | C=O | 3-cyanobenzyl | 1 | H, OH | + | 56–65 |
| 30D | C=O | 4-hydroxybenzyl | 1 | H, OH | + | 78–85 |
| 30E | C=O | cyclopropyl methyl | 1 | H, OH | + | |
| 30F | C=O | 2-naphthylmethyl | 1 | H, OH | + | 59–66 |
| 30G | C=O | 6-hydroxyhexyl | 1 | H, OH | + | |
| 30H | SO$_2$ | benzyl | 1 | H, OH | | 123–125 |
| 30I | SO$_2$ | 2-naphthylmethyl | 1 | H, OH | ++ | 188.5–190 |
| 30J | SO$_2$ | cyclopropyl methyl | 1 | H, OH | + | |
| 30K | SO$_2$ | 4-hydroxymethyl | 1 | H, OH | + | |
| 30L | C=O | benzyl | 2 | H, OH | + | 134–136 |
| 30M | C=O | 2-naphthylmethyl | 2 | H, OH | + | 179–181 |
| 30N | C=O | 4-(HOCH$_2$)-benzyl | 2 | H, OH | ++ | 72–75 |
| 30O | C=O | cyclopropyl methyl | 2 | H, OH | + | |
| 30P | C=O | 3-cyanobenzyl | 2 | H, OH | + | 142.5–144 |
| 30Q | SO$_2$ | benzyl | 2 | H, OH | + | 118.120 |

TABLE 2t-continued

| Ex. No. | W | $R^{22} = R^{23}$ | n | X, Y | $K_i$ | mp, °C. |
|---|---|---|---|---|---|---|
| 30R | C=O | 3-(H$_2$NC(=NOH))-benzyl | 2 | H, OH | +++ | |
| 30S | C=O | benzyl | 2 | =O | + | |
| 30T | C=O | benzyl | 2 | =NOH | + | |
| 30U | C=O | benzyl | 1 | H, OH (R) | + | |
| 30V | C=O | benzyl | 1 | H, OH (S) | + | |

The examples in Table 2u were prepared using the procedures outlined in Example 23f above. Compounds where $R^4=R^7=$4-fluorobenzyl were prepared from (2R,2S,4S,4R)-2,5-bis(N-Cbzamino)-3,4-dimethoxyethoxymethoxy-1,6-di-(4-fluorophenyl)hexane. Further manipulations to X and Y were carried out using methods well known to one of ordinary skill in organic chemistry.

TABLE 2u

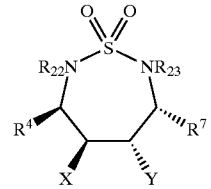

| Ex. No. | stereo 2,3,4,5 | $R^{22} = R^{23}$ | $R^4 = R^7$ | X, Y | $K_i$ (HPLC) | IC$_{90}$ | Mass Spec (M + H) |
|---|---|---|---|---|---|---|---|
| 31A | RSSR | 3-carbomethoxy benzyl | 4-fluoro benzyl | OH, OH | ++ | +++ | 712.4 (M + NH$_4$) |
| 31B | RSSR | 4-carbomethoxy benzyl | 4-fluoro benzyl | OH, OH | ++ | +++ | 695.4 |
| 31C | RSSR | 3-hydroxymethyl benzyl | 4-fluoro benzyl | OH, OH | +++ | +++ | 639.4 |
| 31D | RSSR | 4-hydroxymethyl benzyl | 4-fluoro benzyl | OH, OH | +++ | +++ | 656.2 (M + NH$_4$) |
| 31E | RSSR | benzyl | 4-fluoro benzyl | OH, H | ++ | +++ | 527.2 |
| 31F | RSRR | benzyl | benzyl | epoxy | + | ++/+ | 525.2 |

What is claimed is:

1. A method of treatment of viral infections which comprises administering to a host in need of such treatment a therapeutically effective amount of a compound of formula (IIa):

(IIa)
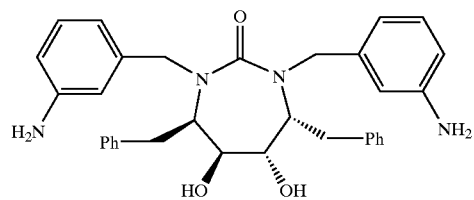
or a pharmaceutically acceptable salt form thereof.
2. A method of treatment of HIV infection which comprises administering to a host in need of such treatment a therapeutically effective amount of a compound of formula (IIa):
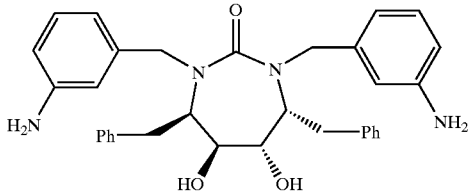
or a pharmaceutically acceptable salt form thereof.
* * * * *